US012186278B2

(12) United States Patent
Brogdon et al.

(10) Patent No.: US 12,186,278 B2
(45) Date of Patent: Jan. 7, 2025

(54) MESOTHELIN CHIMERIC ANTIGEN RECEPTOR (CAR) AND ANTIBODY AGAINST PD-L1 INHIBITOR FOR COMBINED USE IN ANTICANCER THERAPY

(71) Applicants: Novartis AG, Basel (CH); The Trustees of the University of Pennsylvania, Philadelphia, PA (US); Dana-Farber Cancer Institute, Inc., Boston, MA (US); President and Fellows of Harvard College, Cambridge, MA (US)

(72) Inventors: Jennifer Brogdon, Sudbury, MA (US); Hwai Wen Chang, San Marcos, CA (US); Boris Engels, Arlington, MA (US); Gordon James Freeman, Brookline, MA (US); Gerhard Johann Frey, San Diego, CA (US); Jennifer Marie Mataraza, Cambridge, MA (US); Reshma Singh, Cambridge, MA (US); Arlene Helen Sharpe, Brookline, MA (US)

(73) Assignees: Novartis AG, Basel (CH); The Trustees of the University of Pennsylvania, Philadelphia, PA (US); Dana Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 353 days.

(21) Appl. No.: 17/811,606

(22) Filed: Jul. 11, 2022

(65) Prior Publication Data

US 2023/0000964 A1 Jan. 5, 2023

Related U.S. Application Data

(62) Division of application No. 16/065,387, filed as application No. PCT/US2016/067957 on Dec. 21, 2016, now Pat. No. 11,413,340.

(60) Provisional application No. 62/270,780, filed on Dec. 22, 2015.

(51) Int. Cl.

| | |
|---|---|
| ***C07K 16/00*** | (2006.01) |
| ***A61K 39/00*** | (2006.01) |
| ***A61K 39/395*** | (2006.01) |
| ***A61K 45/06*** | (2006.01) |
| ***A61P 35/00*** | (2006.01) |

(52) U.S. Cl.

CPC ...... *A61K 39/4636* (2023.05); *A61K 39/3955* (2013.01); *A61K 39/4611* (2023.05); *A61K 39/4631* (2023.05); *A61K 39/464468* (2023.05); *A61K 45/06* (2013.01); *A61P 35/00* (2018.01); *A61K 2039/505* (2013.01); *A61K 2039/545* (2013.01); *A61K 2239/31* (2023.05); *A61K 2239/38* (2023.05)

(58) Field of Classification Search

None

See application file for complete search history.

(56) References Cited

U.S. PATENT DOCUMENTS

| | | | |
|---|---|---|---|
| 5,359,046 | A | 10/1994 | Capon |
| 5,686,281 | A | 11/1997 | Roberts |
| 5,712,149 | A | 1/1998 | Roberts |
| 5,874,240 | A | 2/1999 | Ni |
| 5,906,936 | A | 5/1999 | Eshhar |
| 6,103,521 | A | 8/2000 | Capon |
| 6,319,494 | B1 | 11/2001 | Capon |
| 6,355,779 | B1 | 3/2002 | Goodwin |
| 6,410,319 | B1 | 6/2002 | Raubitschek |
| 6,569,997 | B1 | 5/2003 | Kwon |
| 7,049,136 | B2 | 5/2006 | Seed |
| 7,052,906 | B1 | 5/2006 | Lawson |
| 7,070,995 | B2 | 7/2006 | Jensen |
| 7,265,209 | B2 | 9/2007 | Jensen |
| 7,319,143 | B2 | 1/2008 | Gross |
| 7,320,787 | B2 | 1/2008 | Seed |
| 7,446,190 | B2 | 11/2008 | Sadelain |
| 7,446,191 | B2 | 11/2008 | Jensen |
| 7,514,537 | B2 | 4/2009 | Jensen |
| 7,638,326 | B2 | 12/2009 | June |
| 7,741,465 | B1 | 6/2010 | Eshhar |
| 7,745,140 | B2 | 6/2010 | June |
| 7,754,482 | B2 | 7/2010 | Riley |
| 7,994,298 | B2 | 8/2011 | Zhang |
| 8,211,422 | B2 | 7/2012 | Eshhar |
| 8,252,914 | B2 | 8/2012 | Zhang |

(Continued)

FOREIGN PATENT DOCUMENTS

| | | |
|---|---|---|
| CN | 103347897 | 10/2013 |
| EP | 0574512 A1 | 12/1993 |

(Continued)

OTHER PUBLICATIONS

Almagro, Juan C., and Johan Fransson. “Humanization of antibodies.” Frontiers in Bioscience-Landmark 13.5 (2008):1619-1633.

(Continued)

*Primary Examiner* — Meera Natarajan

(74) *Attorney, Agent, or Firm* — Saul Ewing LLP; Kathryn Doyle

(57) ABSTRACT

Provided are compositions and methods for treating diseases associated with expression of mesothelin comprising administering a cell that expresses a chimeric antigen receptor (CAR) specific to mesothelin in combination with a PD-L1 inhibitor.

27 Claims, 10 Drawing Sheets

Specification includes a Sequence Listing.

(56) References Cited

U.S. PATENT DOCUMENTS

| | | | |
|---|---|---|---|
| 8,268,970 | B2 | 9/2012 | Terrett |
| 8,389,282 | B2 | 3/2013 | Sadelain |
| 8,399,645 | B2 | 3/2013 | Campana |
| 8,465,743 | B2 | 6/2013 | Rosenberg |
| 8,637,307 | B2 | 1/2014 | June |
| 8,722,400 | B2 | 5/2014 | Riley |
| 8,906,682 | B2 | 12/2014 | June |
| 8,911,993 | B2 | 12/2014 | June |
| 8,916,381 | B1 | 12/2014 | June |
| 8,975,071 | B1 | 3/2015 | June |
| 9,101,584 | B2 | 8/2015 | June |
| 9,102,760 | B2 | 8/2015 | June |
| 9,102,761 | B2 | 8/2015 | June |
| 9,394,368 | B2 | 7/2016 | Brogdon |
| 9,573,988 | B2 | 2/2017 | Brogdon |
| 9,745,368 | B2 | 8/2017 | Milone |
| 9,777,061 | B2 | 10/2017 | Ebersbach |
| 9,815,901 | B2 | 11/2017 | Brogdon |
| 2003/0060444 | A1 | 3/2003 | Finney |
| 2003/0077249 | A1 | 4/2003 | Bebbington |
| 2003/0148982 | A1 | 8/2003 | Brenner |
| 2003/0224520 | A1 | 12/2003 | June |
| 2004/0038886 | A1 | 2/2004 | Finney |
| 2004/0043401 | A1 | 3/2004 | Sadelain |
| 2005/0113564 | A1 | 5/2005 | Campana |
| 2005/0129671 | A1 | 6/2005 | Cooper |
| 2007/0036773 | A1 | 2/2007 | Cooper |
| 2008/0131415 | A1 | 6/2008 | Riddell |
| 2009/0257994 | A1 | 10/2009 | Jensen |
| 2011/0052554 | A1 | 3/2011 | Zakrzewski |
| 2012/0107933 | A1 | 5/2012 | Ho |
| 2012/0148552 | A1 | 6/2012 | Jensen |
| 2012/0321667 | A1 | 12/2012 | Sentman |
| 2013/0071409 | A1 | 3/2013 | Riley |
| 2013/0071414 | A1 | 3/2013 | Dotti |
| 2013/0149337 | A1 | 6/2013 | Cooper |
| 2013/0155909 | A1 | 6/2013 | Jackson |
| 2013/0287748 | A1 | 10/2013 | June |
| 2014/0050708 | A1 | 2/2014 | Powell |
| 2014/0099309 | A1 | 4/2014 | Powell, Jr. |
| 2014/0099340 | A1 | 4/2014 | June |
| 2014/0106449 | A1 | 4/2014 | June |
| 2014/0186947 | A1 | 7/2014 | June |
| 2014/0212446 | A1 | 7/2014 | Riley |
| 2014/0219975 | A1 | 8/2014 | June |
| 2014/0227237 | A1 | 8/2014 | June |
| 2014/0271635 | A1 | 9/2014 | Brogdon |
| 2014/0322169 | A1 | 10/2014 | Harper |
| 2014/0322183 | A1 | 10/2014 | Milone |
| 2014/0322212 | A1 | 10/2014 | Brogdon |
| 2014/0322275 | A1 | 10/2014 | Brogdon |
| 2014/0370045 | A1 | 12/2014 | June |
| 2015/0017141 | A1 | 1/2015 | June |
| 2015/0140019 | A1 | 5/2015 | June |
| 2015/0190428 | A1 | 7/2015 | June |
| 2015/0202286 | A1 | 7/2015 | June |
| 2015/0283178 | A1 | 10/2015 | June |
| 2015/0290244 | A1 | 10/2015 | June |
| 2015/0342994 | A1 | 12/2015 | Riley |
| 2016/0046724 | A1 | 2/2016 | Brogdon |
| 2016/0051651 | A1 | 2/2016 | Brogdon |
| 2016/0068601 | A1 | 3/2016 | Brogdon |
| 2016/0096892 | A1 | 4/2016 | Brogdon |
| 2016/0185861 | A1 | 6/2016 | Bedoya |
| 2016/0311907 | A1 | 10/2016 | Brogdon |
| 2016/0311917 | A1 | 10/2016 | Beatty |
| 2016/0340406 | A1 | 11/2016 | Zhao |
| 2016/0362472 | A1 | 12/2016 | Bitter |
| 2017/0008963 | A1 | 1/2017 | Brogdon |
| 2017/0081411 | A1 | 3/2017 | Engels |
| 2017/0137783 | A1 | 5/2017 | Bedoya |
| 2017/0183415 | A1 | 6/2017 | Brogdon |
| 2017/0209492 | A1 | 7/2017 | June |
| 2017/0211055 | A1 | 7/2017 | Brogdon |
| 2017/0226495 | A1 | 8/2017 | Guimaraes |
| 2017/0239294 | A1 | 8/2017 | Thomas-Tikhonenko |
| 2017/0260268 | A1 | 9/2017 | Beatty |
| 2017/0274014 | A1 | 9/2017 | Brogdon |
| 2017/0306416 | A1 | 10/2017 | Bedoya |
| 2017/0335281 | A1 | 11/2017 | Loew |
| 2018/0022795 | A1 | 1/2018 | Milone |
| 2018/0044423 | A1 | 2/2018 | Ebersbach |
| 2018/0044424 | A1 | 2/2018 | June |
| 2018/0118834 | A1 | 5/2018 | Brogdon |
| 2018/0125892 | A1 | 5/2018 | Brannetti |
| 2018/0133296 | A1 | 5/2018 | Barrett |
| 2018/0140602 | A1 | 5/2018 | Angst |
| 2018/0230193 | A1 | 8/2018 | Loew |
| 2018/0252727 | A1 | 9/2018 | Garfall |
| 2018/0258149 | A1 | 9/2018 | Motz |
| 2018/0298068 | A1 | 10/2018 | Albelda |
| 2018/0312595 | A1 | 11/2018 | Brogdon |

FOREIGN PATENT DOCUMENTS

| | | | |
|---|---|---|---|
| EP | 0871495 | A1 | 10/1998 |
| EP | 1226244 | A2 | 7/2002 |
| WO | 1992015322 | A1 | 9/1992 |
| WO | 9530014 | A1 | 11/1995 |
| WO | 9623814 | A1 | 8/1996 |
| WO | 9624671 | A1 | 8/1996 |
| WO | 1997015669 | A1 | 5/1997 |
| WO | 9723613 | A2 | 7/1997 |
| WO | 9818809 | A1 | 5/1998 |
| WO | 9900494 | A2 | 1/1999 |
| WO | 9957268 | A1 | 11/1999 |
| WO | 0014257 | A1 | 3/2000 |
| WO | 0233101 | A1 | 4/2002 |
| WO | 02077029 | A2 | 10/2002 |
| WO | 02088334 | A1 | 11/2002 |
| WO | 03057171 | A2 | 7/2003 |
| WO | 2005019429 | A2 | 3/2005 |
| WO | 2005044996 | A2 | 5/2005 |
| WO | 2005118788 | A2 | 12/2005 |
| WO | 2006060878 | A1 | 6/2006 |
| WO | 2008045437 | A2 | 4/2008 |
| WO | 2009045957 | | 4/2009 |
| WO | 2010085660 | A2 | 7/2010 |
| WO | 2010111282 | | 9/2010 |
| WO | 2011059836 | A2 | 5/2011 |
| WO | 2011097477 | A1 | 8/2011 |
| WO | 2012058460 | A2 | 5/2012 |
| WO | 2012079000 | A1 | 6/2012 |
| WO | 2012082841 | A2 | 6/2012 |
| WO | 2012099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138858 | A1 | 10/2012 |
| WO | 2013019615 | A2 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013063419 | A2 | 5/2013 |
| WO | 2013074916 | A1 | 5/2013 |
| WO | 2013126712 | A1 | 8/2013 |
| WO | 2013126729 | A1 | 8/2013 |
| WO | 2013126733 | A1 | 8/2013 |
| WO | 2013142034 | | 9/2013 |
| WO | 2014011984 | A1 | 1/2014 |
| WO | 2014011987 | A1 | 1/2014 |
| WO | 2014011988 | A2 | 1/2014 |
| WO | 2014011993 | A2 | 1/2014 |
| WO | 2014011996 | A1 | 1/2014 |
| WO | 2014012001 | A2 | 1/2014 |
| WO | 2014031687 | A1 | 2/2014 |
| WO | 2014039513 | A2 | 3/2014 |
| WO | 2014052064 | | 4/2014 |
| WO | 2014055442 | A2 | 4/2014 |
| WO | 2014055657 | A1 | 4/2014 |
| WO | 2014130635 | A1 | 8/2014 |
| WO | 2014145252 | A2 | 9/2014 |
| WO | 2015090229 | A1 | 6/2015 |

(56) References Cited

FOREIGN PATENT DOCUMENTS

| | | | |
|---|---|---|---|
| WO | 2015090230 | A1 | 6/2015 |
| WO | 2015112626 | A1 | 7/2015 |
| WO | 2015142661 | A1 | 9/2015 |
| WO | 2015142675 | A2 | 9/2015 |
| WO | 2015157252 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |
| WO | 2017112741 | | 6/2017 |

OTHER PUBLICATIONS

Baeksgaard & Sorensen, "Acute tumor lysis syndrome in solid tumors—a case report and review of the literature" Cancer Chemotherapy Pharmacology (2003) vol. 51 pp. 187-192.
Berglund et al, "The epitope space of the human proteome," Protein Science, 2008, 17:606-613 (Year: 2008).
Bondanza et al. "Suicide gene therapy of graft-versus-host disease induced by central memory human T lymphocytes" Blood (2006) vol. 107 No. 5 pp. 1828-1836.
Brentjens , et al., "Safety and persistence of adoptively transferred autologous CD19-targeted T cells in patients with relapsed or chemotherapy refractory B-cell leukemias.", 2011, Blood 118:4817-4828.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. I8 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138, pp. 1-9 (Mar. 20, 2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito, et al., "Control of large, established tumor xenografts with genetically retargeted human T cells containing CD28 and CD137 domains", 2009, PNAS 106(9):3360-3365.
Corada, et al., "Monoclonal antibodies directed to different regions of vascular endothelial cadherin extracellular domain affect adhesion and clustering of the protein and modulate endothelial permeability", Blood, 97:1679-84, 2001.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dotti et al."Design and development of therapies using chimeric antigen receptor-expressing T cells" Immunological Reviews (2013) vol. 257, No. 1, pp. 107-126.
Dropulic, et al., "Gene-based immunotherapy for human immunodeficiency virus infection and acquired immunodeficiency syndrome.", Human Gene Therapy, 17:, 2006, 577-88.
Dull et al., "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724(1993).
Finney et al., "Chimeric receptors providing both primary and costimulatory signaling in T cells from a single gene product," J. Immunol. 161: 2791-2797 (1998).
Finney, et al., Activation of Resting Human Primary T cells with Chimeric Receptors: Costimulation from CD28, Indcible Costimulatory, CD134 and CD137 in Series with Signals from the TCRz Chain, J Immunol 2004, 174: 104-113.
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski, et al., "Redirected primary T cells harboring a chimeric receptor require costimulation for their antigen-specific activation.", 2005, Blood 105:3087-3093.
Geiger , et al., "Integrated src kinase and costimulatory activity enhances signal transduction through single-chain Chimeric receptors in T lymphocytes.", 2001, Blood 98:2364-2371.
Geiger & Jyothi, "Development and Application of Receptor-Modified T Lymphocytes for Adoptive Immunotherapy" Transfusion Medicine Reviews (2001) vol. 15 No. 1 pp. 21-34.
GenBank Accession No. NP_000725.1 accessed on Jan. 7, 2016 from http://www.ncbi.nlm.nih.gov/protein/NP_000725.
GenBank Accession No. NP 932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:—Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Hornback et al., "The Recombinant T Cell Receptor Strategy: Insights into Structure and Function of Recombinant Immunorecep-

(56) References Cited

OTHER PUBLICATIONS tors on the Way Towards an Optimal Receptor Design for Cellular Immunotherapy," Current Gene Therapy 2: 211-226 (2002).
Imai et al., "Genetic modification of primary natural killer cells overcomes inhibitory signals and induces specific killing of leukemic cells" Blood (2005) vol. 106 No. 1 pp. 376-383.
Imai, et al., "Chimeric receptors with 4-1BB signaling capacity provoke potent cytotoxicity against acute lymphoblastic leukemia", Leukemia 18(4): 2004, 676-684.
International Search Report and Written Opinion for International application No. PCT/CN2014/094393, dated Mar. 30, 2015.
International Search Report and Written Opinion for International Application No. PCT/US2016/067957 dated Apr. 7, 2017.
International Search Report for International Application No. PCT/CN2013/089979 dated Sep. 26, 2014.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No 9 pp. 1245-1256.
John et al. "Blockade of PD-1 immunosuppression boosts CAR T-cell therapy" OncoImmunology (2013) vol. 2, No. 10, e26286, pp. 1-3.
Johnson et al., "Gene therapy with human and mouse T-cell receptors mediates cancer regression and targets normal tissues expressing cognate antigen" Blood (2009) vol. 114 No. 3 pp. 535-545.
Singapore Search Report and Written Opinion for Singapore Application No. 11201604815R dated Jul. 26, 2018.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Supplementary European Search Report for European Application No. EP14871351.4 dated May 23, 2017.
Tanyi Janos L et al., "Abstract CT105: Safety and feasibility of chimeric antigen receptor modified T cells directed against mesothelin (CART-meso) in patients with mesothelin expressing cancers", & 106th Annual Meeting of the American-Association-For-Cancer-Research (AACR); Philadelphia, PA, USA; Apr. 18-22, 2015, vol. 75, No. 15, Suppl., doi: 10.1158/1538-7445.AM2015-CT105, Issn 0008-5472, (201508), Cancer Research, Url: http://cancerres.aacrjournals.org/content/75/15_Supplement/CT105, (Mar. 16, 2017), XP002768566.
Tchou et al."Mesothelin, a novel immunotherapy target for triple negative breast cancer" Breast Cancer Research and Treatment (2012) vol. 133, Iss 2, pp. 799-804.
Till et al., "Adoptive immunotherapy for indolent non-Hodgkin lymphoma and mantle cell lymphoma using genetically modified autologous CD20-specific T cells" Blood (2008) vol. 112 No 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology 2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
June et al., "Engineering lymphocyte subsets: tools, trials and tribulations" Nat Rev Immunol (2009) vol. 9 No. 10 pp. 704-716.
Kalos Michael et al., "T Cells with Chimeric Antigen Receptors Have Potent Antitumor Effects and Can Establish Memory in Patients with Advanced Leukemia", Aug. 10, 2011, (Aug. 10, 2011), vol. 3, No. 95, p. 95ra73.1, XP002667262.
Kaneko et al. "A Binding Domain on Mesothelin for CA125/MUC16" The Journal of Biological Chemistry (2009) vol. 284, No. 6, pp. 3739-3749.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al., "A Phase I Clinical Trial of Treatment of B-Cell Malignancies with Autologous Anti-Cd19-CAR-Transduced T Cells" Blood (2010) vol. 116 No 21 pp. 1179-1180 & 52nd Annual Meeting of the American-Society-of-Hematology (ASH); Orlando, FL, USA; Dec. 4-7, 2010 abstract.
Kochenderfer et al., "Construction and Preclinical Evaluation of an anti-CD19 Chimeric Antigen Receptor", J. Immunotherapy, 32(7): 689-702 (2009).
Kochenderfer et al., "Eradication of B-lineage cells and regression of lymphoma in a patient treated with autologous T cells genetically-engineered to recognize CD19," Blood 116: 4099-4102 (2010).
Krause et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kulkarni-Kale, Urmila, Shriram Bhosle, and Ashok S. Kolaskar. "CEP: a conformational epitope prediction server." Nucleic acids research 33.suppl_2 (2005): W168-W171.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2006) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lanitis et al., "Redirected Antitumor Activity of Primary Human Lymphocytes Transduced With a Fully Human Anti-mesothelin Chimeric Receptor", Molecular Therapy, (Mar. 31, 2012), vol. 20, No. 3, pp. 633-643, XP055066976.
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A. 88: 8905-8909 (1991).
Levine et al., "Gene transfer in humans using a conditionally replicating lentiviral vector" PNAS (2006) vol. 103 No. 46 pp. 17372-17377.
MaCallan et al., "Measurement and modeling of human T cell kinetics" European Journal of Immunology (2003) vol. 33 pp. 2316-2326.
Maher, J., et al., "Human T-lymphocyte cytotoxicity and proliferation directed by a single chimeric TCRζ/CD28 receptor", Nature Biotechnology, vol. 20, pp. 70-75 (2002).

(56) References Cited

OTHER PUBLICATIONS

Maus et al., "T cells expressing chimeric antigen receptors can cause anaphylaxis in humans" Cancel Immunol Res, 1:26-31 (2013).
McGuinness et al., "Anti-tumor activity of human T cells expressing the CC49-zeta chimeric immune receptor," Hum. Gene Ther. 10: 165-173 (1999).
Milone et al., "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Moon et al., "Multifactorial T-cell Hypofunction That is Reversible Can Limit the Efficacy of Chimeric Antigen Receptor-Transduced Human T cells in Solid Tumors", Clin Cancer Res, 20(16), 4262-73, 2014.
Morello, A et al., "Mesothelin-Targeted CARs: Driving T Cells to Solid Tumors", Cancer Discovery, 6(2): 133-46 (2016) (Epublication: Oct. 26, 2015).
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science 1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Padlan, EA, "X-ray crystallography of antibodies," Advances in Protein Chemistry, 49:57-133 (1996).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy 1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No 5 pp. 1822-1826.
Sebestyen et al., Human TCR That Incorporate CD3 Induce Highly Preferred Pairing between TCR and Chains following Gene Transfer Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," Anticancer Res. 32: 2377-2384 (2012).

MESOTHELIN CHIMERIC ANTIGEN RECEPTOR (CAR) AND ANTIBODY AGAINST PD-L1 INHIBITOR FOR COMBINED USE IN ANTICANCER THERAPY

RELATED APPLICATIONS

This application is a divisional of U.S. patent application Ser. No. 16/065,387, filed Jun. 22, 2018, which is a U.S. national phase application and claims the benefit of priority under 35 U.S.C. § 371 of International Application No. PCT/US2016/067957, filed Dec. 21, 2016, which claims priority to U.S. Ser. No. 62/270,780 filed Dec. 22, 2015, the contents of each of which are incorporated herein by reference in its their entirety.

REFERENCE TO AN ELECTRONIC SEQUENCE LISTING

The contents of the electronic sequence listing (sequencelisting.xml; Size: 732,091 bytes; and Date of Creation: Jul. 8, 2022) is herein incorporated by reference in its entirety.

FIELD OF THE INVENTION

The present invention relates generally to the use of cells, e.g., immune effector cells, engineered to express a Chimeric Antigen Receptor (CAR) that targets mesothelin in combination with PD-L1 inhibitors to treat a disease.

BACKGROUND OF THE INVENTION

Mesothelin was originally identified by Pastan and colleagues as a tumor associated antigen due to its limited expression by normal tissues and overexpression on tumors. Chang K, et al., *Cancer Res.* 1992; 52(1):181-186 and Chang K, et al. *Proc Natl Acad Sci USA.* 1996; 93(1):136-140. The mesothelin gene encodes a precursor 71-kDa protein that is processed to yield the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. A soluble splice variant of the 40-kDa carboxyl-terminal fragment called "soluble mesothelin/MPF-related" has been found in the sera of patients with pancreatic ductal adenocarcinoma (PDA). Johnston, F, et al. *Clinical Cancer Research.* 2009; 15(21):6511. Mesothelin is currently being explored both as a therapeutic target as well as a bio-marker for disease activity and therapeutic response. Argani P, et al. *Clin Cancer Res.* 2001; 7(12):3862-3868.

Mesothelin is a differentiation antigen that is also present on normal tissues. Using the mouse anti-human mesothelin antibody K1 that was developed by the Pastan group, strong K1 reactivity has been demonstrated within mesothelial cells that line the peritoneal, pleural, and pericardial cavities, although at lower levels than usually seen for malignant tissues. Chang K, et al., *Cancer Res.* 1992; 52(1):181-186. Weak K1 reactivity has been detected within the Fallopian tube epithelium, tracheal basal epithelium and tonsils epithelium. Mesothelin has also been found on all layers of the cornea. Jirsova K, et al. *Experimental eye research.* 2010; 91(5):623-629. However, K1 reactivity has not been detected in the majority of normal tissues including the liver, kidneys, spleen, bone marrow, lymph nodes, thymus, cardiac muscle, tongue, skeletal muscle, skin, cerebral cortex, cerebellum, spinal cord, peripheral nerve, pituitary, adrenal, salivary gland, mammary gland, thyroid, parathyroid, testis, prostate, epididymis, cervical epithelium, lung parenchyma, esophagus, small-bowel epithelium, colon epithelium, bladder epithelium, gall-bladder epithelium. Chang K, et al., *Cancer Res.* 1992; 52(1):181-186.

Mesothelin is overexpressed in the vast majority of primary pancreatic adenocarcinomas with rare and weak expression seen in benign pancreatic tissue. Argani P, et al. *Clin Cancer Res.* 2001; 7(12):3862-3868. Epithelial malignant pleural mesothelioma (MPM) universally expresses mesothelin while sarcomatoid MPM does not express mesothelin. Most serous epithelial ovarian carcinomas, and the related primary peritoneal carcinomas, express mesothelin.

Mesothelin is a target of a natural immune response in ovarian cancer, and has been proposed to be a target for cancer immunotherapy. Bracci L, et al. *Clin Cancer Res.* 2007; 13(2 Pt 1):644-653; Moschella F, et al. *Cancer Res.* 2011; 71(10):3528-3539; Gross G, et al. *FASEB J.* 1992; 6(15):3370-3378; Sadelain M, et al. *Nat Rev Cancer.* 2003; 3(1):35-45; Muul L M, et al. *Blood.* 2003; 101(7):2563-2569; Yee C, et al. *Proc Natl Acad Sci USA.* 2002; 99(25):16168-16173. The presence of mesothelin-specific CTLs in patients with pancreatic cancer correlates with overall survival. Thomas A M, et al. *J Exp Med.* 2004; 200:297-306. In addition, Pastan and coworkers have used soluble antibody fragments of an anti-mesothelin antibody conjugated to immunotoxins to treat cancer patients with mesothelin-positive tumors. This approach has demonstrated adequate safety and some clinical activity in pancreatic cancer. Hassan R, et al. *Cancer Immun.* 2007; 7:20 and Hassan R, et al. *Clin Cancer Res.* 2007; 13(17):5144-5149. In ovarian cancer, this therapeutic strategy produced one minor response by RECIST criteria and stable disease in a second patient who also had complete resolution of their ascites.

SUMMARY OF THE INVENTION

The present disclosure features, at least in part, methods and compositions for treating a disease associated with the expression of mesothelin, e.g., a cancer, in a subject by using a combination therapy that includes a cell, e.g., an immune effector cell, expressing a chimeric antigen receptor (CAR) that specifically binds to mesothelin (also referred to herein as a "mesothelin CAR-expressing cell") and an inhibitor of Programmed Death-Ligand 1 (also referred to herein as a "PD-L1 inhibitor"). In some embodiments, the CAR that specifically binds to mesothelin includes an antigen binding domain, e.g., a mesothelin binding domain, a transmembrane domain, and an intracellular signaling domain, e.g., as described herein. In some embodiments, the PD-L1 inhibitor is an antibody molecule, a polypeptide, a small molecule, or a polynucleotide, e.g., an inhibitory nucleic acid. In one embodiment, the PD-L1 inhibitor is an antibody molecule, e.g., an antibody molecule described herein. Without wishing to be bound by theory, treating a subject having a disease associated with mesothelin expression, e.g., a cancer described herein, with a combination therapy that includes a mesothelin CAR-expressing cell and a PD-L1 inhibitor is believed to result in improved inhibition or reduction of tumor progression in the subject, e.g., as compared to treating a subject having the disease with a mesothelin CAR-expressing cell or a PD-L1 inhibitor alone.

Accordingly, in one aspect, the disclosure features a method of treating a subject having a disease associated with expression of mesothelin e.g., a cancer as described herein. The method includes administering to the subject a cell, e.g., a population of cells, comprising, e.g., expressing a CAR that specifically binds to mesothelin, and a PD-L1 inhibitor. In one embodiment, the CAR-expressing cell and the PD-L1 inhibitor is administered sequentially. In one embodiment, the PD-L1 inhibitor is administered prior to administration of the mesothelin CAR-expressing cell. In one embodiment, the PD-L1 inhibitor is administered after the administration of the mesothelin CAR-expressing cell. In one embodiment, the PD-L1 inhibitor and mesothelin CAR-expressing cell are administered simultaneously or concurrently.

In embodiments, the CAR-expressing cell e.g., mesothelin CAR-expressing cell described herein, and the PD-L1 inhibitor is administered in a treatment interval. In one embodiment, the treatment interval comprises a single dose of the PD-L1 inhibitor and a single dose of the CAR-expressing cell. In another embodiment, the treatment interval comprises a first and second dose of the PD-L1 inhibitor and a dose of the CAR-expressing cell.

In embodiments where the treatment interval comprises a single dose of the PD-L1 inhibitor and a single dose of the CAR-expressing cell, the dose of PD-L1 inhibitor is administered prior to the dose of the CAR-expressing cell, and the treatment interval is initiated upon administration of the dose of the PD-L1 inhibitor and completed upon administration of the dose of the CAR-expressing cell. In one embodiment, the treatment interval further comprises one or more, e.g., 1, 2, 3, 4, or 5 or more, subsequent doses of the PD-L1 inhibitor. In such embodiments, the treatment interval comprises two, three, four, five, six, or more, doses of PD-L1 inhibitor and one dose of the CAR-expressing cell. In one embodiment, the dose of the CAR-expressing cell is administered at least 2 days, 3 days, 4 days, 5 days, 6 days, 7 days, or 2 weeks after a dose of PD-L1 inhibitor is administered. In embodiments where more than one dose of PD-L1 inhibitor is administered, the dose of the CAR-expressing cell is administered at least 2 days, 3 days, 4 days, 5, days, 6 days, 7 days, or 2 weeks after the first dose of PD-L1 inhibitor is administered or after the initiation of the treatment interval. In one embodiment, the dose of the CAR-expressing cell is administered about 2 days after the dose of the PD-L1 inhibitor is administered.

In embodiments where the treatment interval comprises a first and second dose of a PD-L1 inhibitor and a dose of a CAR-expressing cell, the dose of the CAR-expressing cell is administered after administration of the first dose of the PD-L1 inhibitor but before the administration of the second dose of the PD-L1 inhibitor. In such embodiments, the treatment interval is initiated upon administration of the first dose of the PD-L1 inhibitor and completed upon administration of the second dose of the PD-L1 inhibitor. In one embodiment, the second dose of the PD-L1 inhibitor is administered at least 5 days, 7 days, 1 week, 2 weeks, 3 weeks, or 4 weeks after administration of the first dose of the PD-L1 inhibitor. In one embodiment, the dose of the CAR-expressing cell is administered at least 2 days, 3 days, 4 days, 5 days, 6 days, 7 days, or 2 weeks after administration of the first dose of the PD-L1 inhibitor. In one embodiment, the second dose of the PD-L1 inhibitor is administered at least 2 days, 3 days, 4 days, 5 days, 6 days, 7 days, 2 weeks, or 3 weeks after administration of the dose of the CAR-expressing cell.

In one embodiment, any of the treatment intervals described herein can be repeated one or more times, e.g., 1, 2, 3, 4, or 5 more times. In one embodiment, the treatment interval is repeated once, resulting in a treatment regimen comprising two treatment intervals. In an embodiment, the repeated treatment interval is administered at least 1 day, e.g., 1 day, 2 days, 3 days, 4 days, 5 days, 6 days, 7 days, or 2 weeks, after the completion of the first or previous treatment interval. In an embodiment, the repeated treatment interval is administered at least 3 days after the completion of the first or previous treatment interval.

In one embodiment, any of the treatment intervals described herein can be followed by one or more, e.g., 1, 2, 3, 4, or 5, subsequent treatment intervals. The one or more subsequent treatment interval is different from the first or previous treatment interval. By way of example, a first treatment interval consisting of a single dose of a PD-L1 inhibitor and a single dose of a CAR-expressing cell is followed by a second treatment interval consisting of two doses of a PD-L1 inhibitor and a single dose of a CAR-expressing cell. In one embodiment, the one or more subsequent treatment intervals is administered at least 1 day, e.g., 1 day, 2 days, 3 days, 4 days, 5 days, 6 days, 7 days, or 2 weeks, after the completion of the first or previous treatment interval.

In any of the methods described herein, one or more subsequent doses, e.g., 1, 2, 3, 4, or 5 or more doses, of the PD-L1 inhibitor is administered after the completion of one or more treatment intervals. In embodiments where the treatment intervals are repeated or two or more treatment intervals are administered, one or more subsequent doses, e.g., 1, 2, 3, 4, or 5, of the PD-L1 inhibitor is administered after the completion of one treatment interval and before the initiation of another treatment interval. In one embodiment, a dose of the PD-L1 inhibitor is administered every 5 days, 7 days, 2 weeks, 3 weeks, or 4 days after the completion of one or more, or each, treatment intervals.

In any of the methods described herein, one or more, e.g., 1, 2, 3, 4, or 5 or more, subsequent doses of the CAR-expressing cell are administered after the completion of one or more treatment intervals. In embodiments where the treatment intervals are repeated or two or more treatment intervals are administered, one or more subsequent doses, e.g., 1, 2, 3, 4, or 5, or more doses, of the CAR-expressing cell is administered after the completion of one treatment interval and before the initiation of another treatment interval. In one embodiment, a dose of the CAR-expressing cell is administered every 2 days, 3 days, 4 days, 5 days, 7 days, 2 weeks, 3 weeks, or 4 days after the completion of one or more, or each, treatment intervals.

In one embodiment, the treatment interval comprises a single dose of a PD-L1 inhibitor that is administered prior to a single dose of a CAR-expressing cell. In this embodiment, the dose of the CAR-expressing cell is administered 2 days after the administration of the dose of the PD-L1 inhibitor. The treatment interval is repeated one time, and the second treatment interval is initiated 3 days after the completion of the first treatment interval, e.g., after the administration of the single dose of the CAR-expressing cell. In one embodiment, the PD-L1 inhibitor is administered every 5 days after the completion of the second treatment interval, e.g., one or more doses of the PD-L1 inhibitor is administered every 5 days, 7 days, 2 weeks, 3 weeks, or 4 weeks, after the second treatment interval.

In any of the methods described herein, the subject is administered a single dose of a CAR-expressing cell and a single dose of a PD-L1 inhibitor. In one embodiment, the single dose of the CAR-expressing cell is administered at least 2 days, e.g., 2, 3, 4, 5, 6, 7 days, or 2 weeks, after administration of the single dose of the PD-L1 inhibitor.

In one embodiment, one or more, e.g., 1, 2, 3, 4, or 5, subsequent doses of a CAR-expressing cell are administered to the subject after the initial dose of the CAR-expressing cell.

In one embodiment, the one or more subsequent doses of the CAR-expressing cell are administered at least 2 days, e.g., 2, 3, 4, 5, 6, 7 days or 2 weeks, after the previous dose of the CAR-expressing cell. In one embodiment, the one or more subsequent doses of the CAR-expressing cell are administered at least 5 days after the previous dose of the CAR-expressing cell. In one embodiment, the subject is administered three doses of the CAR-expressing cell per week or one dose every 2 days.

In one embodiment, one or more, e.g., 1, 2, 3, 4, or 5, subsequent doses of PD-L1 inhibitor are administered after administration of the single dose of the PD-L1 inhibitor. In one embodiment, the one or more subsequent doses of the PD-L1 inhibitor are administered at least 5 days, 7 days, 2 weeks, 3 weeks or 4 weeks, after the previous dose of PD-L1 inhibitor.

In one embodiment, the one or more subsequent doses of the PD-L1 inhibitor are administered at least 1, 2, 3, 4, 5, 6, or 7 days, after a dose of the CAR-expressing cell, e.g., the initial dose of the CAR-expressing cell.

In one embodiment, one or more, e.g., 1, 2, 3, 4, or 5, doses of the PD-L1 inhibitor is administered prior to the first dose of the CAR-expressing cell.

In one embodiment, the administration of the one or more doses of the CAR-expressing cell and the one or more doses of PD-L1 inhibitor is repeated, e.g., 1, 2, 3, 4, or 5 more times.

In any of the administration regimens or treatment intervals described herein, a dose of mesothelin CAR-expressing cells comprises at least about $1\times10^7$, $1.5\times10^7$, $2\times10^7$, $2.5\times10^7$, $3\times10^7$, $3.5\times10^7$, $4\times10^7$, $5\times10^7$, $1\times10^8$, $1.5\times10^8$, $2\times10^8$, $2.5\times10^8$, $3\times10^8$, $3.5\times10^8$, $4\times10^8$, $5\times10^8$, $1\times10^9$, $2\times10^9$, or $5\times10^9$ cells. In some embodiments, a dose of mesothelin CAR-expressing cells comprises at least about $1\text{-}3\times10^7$ to $1\text{-}3\times10^8$. In some embodiments, the subject is administered about $1\text{-}3\times10^7$ mesothelin CAR-expressing cells. In other embodiments, the subject is administered about $1\text{-}3\times10^8$ mesothelin CAR-expressing cells.

In any of the administration regimens described herein, a dose of a PD-L1 inhibitor, e.g., an anti-PD-L1 antibody molecule described herein, comprises about 1 to 30 mg/kg, e.g., about 5 to 25 mg/kg, about 10 to 20 mg/kg, about 1 to 5 mg/kg, or about 3 mg/kg. In one embodiment, the dose is about 10 to 20 mg/kg. In one embodiment, the dose is about 1 to 5 mg/kg. In one embodiment, the dose is less than 5 mg/kg, less than 4 mg/kg, less than 3 mg/kg, less than 2 mg/kg, or less than 1 mg/kg.

In another aspect, the disclosure features a composition (e.g., one or more dosage formulations, combinations, or one or more pharmaceutical compositions) comprising a cell expressing a mesothelin CAR described herein and a PD-L1 inhibitor described herein. In one embodiment, the mesothelin CAR comprises a mesothelin antigen binding domain, a transmembrane domain, and an intracellular signaling domain, as described herein. In one embodiment, the mesothelin CAR comprises a mesothelin antigen binding domain listed in Table 2. In one embodiment, the PD-L1 inhibitor comprises an antibody molecule, a small molecule, a polypeptide, e.g., a fusion protein, or an inhibitory nucleic acid, e.g., a siRNA or shRNA. In one embodiment, the PD-L1 inhibitor comprises an antibody molecule, e.g., an antibody molecule listed in Table 6. The CAR-expressing cell and the PD-L1 inhibitor can be in the same or different formulation or pharmaceutical composition.

In another aspect, the disclosure features a composition (e.g., one or more dosage formulations, combinations, or one or more pharmaceutical compositions) comprising a cell expressing a mesothelin CAR described herein and a PD-L1 inhibitor described herein, for use in a method of treating a disease associated with expression of mesothelin, e.g., a cancer described herein. In one embodiment, the mesothelin CAR comprises a mesothelin antigen binding domain, a transmembrane domain, and an intracellular signaling domain, as described herein. In one embodiment, the mesothelin CAR comprises a mesothelin antigen binding domain listed in Table 2. In one embodiment, the PD-L1 inhibitor comprises an antibody molecule, a small molecule, a polypeptide, e.g., a fusion protein, or an inhibitory nucleic acid, e.g., a siRNA or shRNA. In one embodiment, the PD-L1 inhibitor comprises an antibody molecule, e.g., an antibody molecule listed in Table 6. The CAR-expressing cell and the PD-L1 inhibitor can be in the same or different formulation or pharmaceutical composition.

PD-L1 Inhibitors

Provided herein are PD-L1 inhibitors for use in any of the methods or compositions described herein. In any of the methods or compositions described herein, the PD-L1 inhibitor comprises an antibody molecule, a small molecule, a polypeptide, e.g., a fusion protein, or an inhibitory nucleic acid, e.g., a siRNA or shRNA.

In one embodiment, the PD-L1 inhibitor is characterized by one or more of the following: inhibits or reduces PD-L1 expression, e.g., transcription or translation of PD-L1; inhibits or reduces PD-L1 activity, e.g., inhibits or reduces binding of PD-L1 to its receptor, e.g., PD-1 or CD80 (B7-1) or both; or binds to PD-L1 or its receptor, e.g., PD-1.

In one embodiment, the PD-L1 inhibitor is an antibody molecule. In one embodiment, the PD-L1 inhibitor is selected from the group consisting of YW243.55.S70, MPDL3280A (atezolizumab), MEDI-4736, MSB-0010718C (avelumab), MDX-1105, and any anti-PD-L1 antibody molecules listed in Table 6.

In one embodiment, the PD-L1 inhibitor comprises an anti-PD-L1 antibody molecule comprising a heavy chain complementary determining region 1 (HC CDR1), a heavy chain complementary determining region 2 (HC CDR2), and a heavy chain complementary determining region 3 (HC CDR3) of any PD-L1 antibody molecule amino acid sequence listed in Table 6; and a light chain complementary determining region 1 (LC CDR1), a light chain complementary determining region 2 (LC CDR2), and a light chain complementary determining region 3 (LC CDR3) of any PD-L1 antibody molecule amino acid sequence listed in Table 6. In one embodiment, the anti-PD-L1 antibody molecule comprises a HC CDR1 amino acid sequence chosen from SEQ ID NO: 287, 290, or 195, a HC CDR2 amino acid sequence of SEQ ID NO: 288, and a HC CDR3 amino acid sequence of SEQ ID NO: 289; and a LC CDR1 amino acid sequence of SEQ ID NO: 295, a LC CDR2 amino acid sequence of SEQ ID NO: 296, and a LC CDR3 amino acid sequence of SEQ ID NO: 297. In one embodiment, the anti-PD-L1 antibody comprises a HC CDR1 amino acid sequence chosen from SEQ ID NO: 287, 290, or 195, a HC CDR2 amino acid sequence of SEQ ID NO: 291, and a HC CDR3 amino acid sequence of SEQ ID NO: 292; and a LC CDR1 amino acid sequence of SEQ ID NO: 298, a LC CDR2 amino acid sequence of SEQ ID NO: 299, and a LC CDR3 amino acid sequence of SEQ ID NO: 300.

In one embodiment, the anti-PD-L1 antibody molecule comprises a heavy chain variable region comprising the amino acid sequence of any heavy chain variable region listed in Table 6, e.g., SEQ ID NOs: 304, 316, 324, 332, 336, 340, 348, 356, or 364. In one embodiment, the anti-PD-L1 antibody molecule comprises a heavy chain variable region comprising the amino acid sequence having at least one, two or three modifications but not more than 30, 20 or 10 modifications to the amino acid sequence of any heavy chain variable region provided in Table 6, e.g., SEQ ID NOs: 304, 316, 324, 332, 336, 340, 348, 356, or 364. In one embodiment, the anti-PD-L1 antibody molecule comprises a heavy chain variable region comprising an amino acid sequence with 95-99% identity to the amino acid sequence of any heavy chain variable region provided in Table 6, e.g., SEQ ID NOs: 304, 316, 324, 332, 336, 340, 348, 356, or 364.

In one embodiment, the anti-PD-L1 antibody molecule comprises a heavy chain comprising the amino acid sequence of any heavy chain listed in Table 6, e.g., SEQ ID NOs: 306, 318, 326, 334, 338, 342, 350, 358, 366, 393, 377, or 382. In one embodiment, the anti-PD-L1 antibody molecule comprises a heavy chain comprising the amino acid sequence having at least one, two or three modifications but not more than 30, 20 or 10 modifications to any heavy chain listed in Table 6, e.g., SEQ ID NOs: 306, 318, 326, 334, 338, 342, 350, 358, 366, 393, 377, or 382. In one embodiment, the anti-PD-L1 antibody molecule comprises a heavy chain comprising an amino acid sequence with 95-99% identity to the amino acid sequence of any heavy chain listed in Table 6, e.g., SEQ ID NOs: 306, 318, 326, 334, 338, 342, 350, 358, 366, 393, 377, or 382.

In one embodiment, the anti-PD-L1 antibody molecule comprises a light chain variable region comprising the amino acid sequence of any light chain variable region listed in Table 6, e.g., SEQ ID NOs: 308, 312, 320, 328, 344, 352, 360, 368, or 372. In one embodiment, the anti-PD-L1 antibody molecule comprises a light chain variable region comprising the amino acid sequence having at least one, two or three modifications but not more than 30, 20 or 10 modifications to the amino acid sequence of any light chain variable region provided in Table 6, e.g., SEQ ID NOs: 308, 312, 320, 328, 344, 352, 360, 368, or 372. In one embodiment, the anti-PD-L1 antibody molecule comprises a light chain variable region comprising an amino acid sequence with 95-99% identity to the amino acid sequence of any light chain variable region provided in Table 6, e.g., SEQ ID NOs: 308, 312, 320, 328, 344, 352, 360, 368, or 372.

In one embodiment, the anti-PD-L1 antibody molecule comprises a light chain comprising the amino acid sequence of any light chain listed in Table 6, e.g., SEQ ID NOs: 310, 314, 322, 330, 346, 354, 362, 370, or 374. In one embodiment, the anti-PD-L1 antibody molecule comprises a light chain comprising the amino acid sequence having at least one, two or three modifications but not more than 30, 20 or 10 modifications to any light chain listed in Table 6, e.g., SEQ ID NOs: 310, 314, 322, 330, 346, 354, 362, 370, or 374. In one embodiment, the anti-PD-L1 antibody molecule comprises a light chain comprising an amino acid sequence with 95-99% identity to the amino acid sequence to any light chain listed in Table 6, e.g., SEQ ID NOs: 310, 314, 322, 330, 346, 354, 362, 370, or 374.

In one embodiment, the anti-PD-L1 antibody molecule comprises:

i) a heavy chain variable domain comprising the amino acid sequence of SEQ ID NO: 304 and a light chain variable domain comprising the amino acid sequence of SEQ ID NO: 308;

ii) a heavy chain variable domain comprising the amino acid sequence of SEQ ID NO: 304 and a light chain variable domain comprising the amino acid sequence of SEQ ID NO: 312;

iii) a heavy chain variable domain comprising the amino acid sequence of SEQ ID NO: 304 and a light chain variable domain comprising the amino acid sequence of SEQ ID NO: 372.

iv) a heavy chain variable domain comprising the amino acid sequence of SEQ ID NO: 316 and a light chain variable domain comprising the amino acid sequence of SEQ ID NO: 320;

v) a heavy chain variable domain comprising the amino acid sequence of SEQ ID NO: 316 and a light chain variable domain comprising the amino acid sequence of SEQ ID NO: 352;

vi) a heavy chain variable domain comprising the amino acid sequence of SEQ ID NO: 324 and a light chain variable domain comprising the amino acid sequence of SEQ ID NO: 328;

vii) a heavy chain variable domain comprising the amino acid sequence of SEQ ID NO: 324 and a light chain variable domain comprising the amino acid sequence of SEQ ID NO: 360;

viii) a heavy chain variable domain comprising the amino acid sequence of SEQ ID NO: 332 and a light chain variable domain comprising the amino acid sequence of SEQ ID NO: 328;

ix) a heavy chain variable domain comprising the amino acid sequence of SEQ ID NO: 336 and a light chain variable domain comprising the amino acid sequence of SEQ ID NO: 328;

x) a heavy chain variable domain comprising the amino acid sequence of SEQ ID NO: 336 and a light chain variable domain comprising the amino acid sequence of SEQ ID NO: 308;

xi) a heavy chain variable domain comprising the amino acid sequence of SEQ ID NO: 336 and a light chain variable domain comprising the amino acid sequence of SEQ ID NO: 372;

xii) a heavy chain variable domain comprising the amino acid sequence of SEQ ID NO: 340 and a light chain variable domain comprising the amino acid sequence of SEQ ID NO: 344;

xiii) a heavy chain variable domain comprising the amino acid sequence of SEQ ID NO: 340 and a light chain variable domain comprising the amino acid sequence of SEQ ID NO: 372;

xiv) a heavy chain variable domain comprising the amino acid sequence of SEQ ID NO: 348 and a light chain variable domain comprising the amino acid sequence of SEQ ID NO: 352;

xv) a heavy chain variable domain comprising the amino acid sequence of SEQ ID NO: 348 and a light chain variable domain comprising the amino acid sequence of SEQ ID NO: 386;

xvi) a heavy chain variable domain comprising the amino acid sequence of SEQ ID NO: 356 and a light chain variable domain comprising the amino acid sequence of SEQ ID NO: 352; or xvii) a heavy chain variable domain comprising the amino acid sequence of SEQ ID NO: 78 and a light chain variable domain comprising the amino acid sequence of SEQ ID NO: 368.

In one embodiment, the anti-PD-L1 antibody molecule comprises:

i) a heavy chain comprising the amino acid sequence of SEQ ID NO: 306 and a light chain comprising the amino acid sequence of SEQ ID NO: 310;
ii) a heavy chain comprising the amino acid sequence of SEQ ID NO: 306 and a light chain comprising the amino acid sequence of SEQ ID NO: 214;
iii) a heavy chain comprising the amino acid sequence of SEQ ID NO: 306 and a light chain comprising the amino acid sequence of SEQ ID NO: 374;
iv) a heavy chain comprising the amino acid sequence of SEQ ID NO: 318 and a light chain comprising the amino acid sequence of SEQ ID NO: 322;
v) a heavy chain comprising the amino acid sequence of SEQ ID NO: 318 and a light chain comprising the amino acid sequence of SEQ ID NO: 354;
vi) a heavy chain comprising the amino acid sequence of SEQ ID NO: 326 and a light chain comprising the amino acid sequence of SEQ ID NO: 330;
vii) a heavy chain comprising the amino acid sequence of SEQ ID NO: 326 and a light chain comprising the amino acid sequence of SEQ ID NO: 362;
viii) a heavy chain comprising the amino acid sequence of SEQ ID NO: 334 and a light chain comprising the amino acid sequence of SEQ ID NO: 330;
ix) a heavy chain comprising the amino acid sequence of SEQ ID NO: 338 and a light chain comprising the amino acid sequence of SEQ ID NO: 330;
x) a heavy chain comprising the amino acid sequence of SEQ ID NO: 338 and a light chain comprising the amino acid sequence of SEQ ID NO: 310;
xi) a heavy chain comprising the amino acid sequence of SEQ ID NO: 338 and a light chain comprising the amino acid sequence of SEQ ID NO: 374;
xii) a heavy chain comprising the amino acid sequence of SEQ ID NO: 342 and a light chain comprising the amino acid sequence of SEQ ID NO: 346;
xiii) a heavy chain comprising the amino acid sequence of SEQ ID NO: 342 and a light chain comprising the amino acid sequence of SEQ ID NO: 374;
xiv) a heavy chain comprising the amino acid sequence of SEQ ID NO: 350 and a light chain comprising the amino acid sequence of SEQ ID NO: 354;
xv) a heavy chain comprising the amino acid sequence of SEQ ID NO: 350 and a light chain comprising the amino acid sequence of SEQ ID NO: 374;
xvi) a heavy chain comprising the amino acid sequence of SEQ ID NO: 358 and a light chain comprising the amino acid sequence of SEQ ID NO: 354;
xvii) a heavy chain comprising the amino acid sequence of SEQ ID NO: 366 and a light chain comprising the amino acid sequence of SEQ ID NO: 370;
xviii) a heavy chain comprising the amino acid sequence of SEQ ID NO: 393 and a light chain comprising the amino acid sequence of SEQ ID NO: 322;
xix) a heavy chain comprising the amino acid sequence of SEQ ID NO: 91 and a light chain comprising the amino acid sequence of SEQ ID NO: 330; or
xx) a heavy chain comprising the amino acid sequence of SEQ ID NO: 382 and a light chain comprising the amino acid sequence of SEQ ID NO: 354.

Mesothelin CAR-Expressing Cells

Provided herein are cells, e.g., immune effector cells, that express a chimeric antigen receptor (CAR) that targets, e.g., specifically binds to, mesothelin for use in any of the methods or compositions described herein. The CAR that specifically binds to mesothelin also referred to herein as "a mesothelin CAR or a mesoCAR". The mesothelin CAR expressed by the mesothelin CAR-expressing cell described herein includes a mesothelin binding domain, a transmembrane domain, and an intracellular signaling domain. In one embodiment, the intracellular signaling domain comprises a costimulatory domain and/or a primary signaling domain.

In one embodiment, the mesothelin binding domain comprises a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2. In one embodiment, the mesothelin binding domain comprises a HC CDR1, a HC CDR2, and a HC CDR3 according to the HC CDR amino acid sequences in Table 4, and a LC CDR1, a LC CDR2, and a LC CDR3 according to the LC CDR amino acid sequences in Table 5.

In one embodiment, the mesothelin binding domain comprises (e.g., consists of) the amino acid sequence selected from the group consisting of SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62. In one embodiment, the mesothelin binding domain comprises (e.g., consists of) an amino acid sequence having at least one, two or three modifications but not more than 30, 20 or 10 modifications (e.g., substitutions, e.g., conservative substitutions) to any of SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62. In one embodiment, the mesothelin binding domain comprises (e.g., consists of) an amino acid sequence with 95-99% identity to the amino acid sequence to any of SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62.

In one embodiment, the mesothelin CAR includes a transmembrane domain that comprises a transmembrane domain of a protein, e.g., a protein described herein, e.g., selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises the sequence of SEQ ID NO: 6. In one embodiment, the transmembrane domain comprises an amino acid sequence comprising at least one, two or three modifications but not more than 20, 10 or 5 modifications of the amino acid sequence of SEQ ID NO:6, or a sequence with 95-99% identity to an amino acid sequence of SEQ ID NO:6. In one embodiment, the nucleic acid sequence encoding the transmembrane domain comprises a nucleotide sequence of SEQ ID NO: 17, or a sequence with 95-99% identity thereof.

In one embodiment, the mesothelin binding domain is connected to the transmembrane domain by a hinge region, e.g., a hinge region described herein. In one embodiment, the encoded hinge region comprises SEQ ID NO:2, or a sequence with 95-99% identity thereof. In one embodiment, the nucleic acid sequence encoding the hinge region comprises a nucleotide sequence of SEQ ID NO: 13, or a sequence with 95-99% identity thereof.

In one embodiment, the isolated nucleic acid molecule further comprises a sequence encoding a costimulatory domain, e.g., a costimulatory domain described herein. In embodiments, the intracellular signaling domain comprises a costimulatory domain. In embodiments, the intracellular signaling domain comprises a primary signaling domain. In embodiments, the intracellular signaling domain comprises a costimulatory domain and a primary signaling domain.

In one embodiment, the costimulatory domain is a functional signaling domain from a protein, e.g., described herein, e.g., selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one embodiment, the costimulatory domain of 4-1BB comprises the amino acid sequence of SEQ ID NO:7. In one embodiment, the encoded costimulatory domain comprises an amino acid sequence having at least one, two or three modifications but not more than 20, 10 or 5 modifications of an amino acid sequence of SEQ ID NO:7, or a sequence with 95-99% identity to the amino acid sequence of SEQ ID NO:7. In one embodiment, the nucleic acid sequence encoding the costimulatory domain comprises the nucleotide sequence of SEQ ID NO:18, or a sequence with 95-99% identity thereof. In another embodiment, the costimulatory domain of CD28 comprises the amino acid sequence of SEQ ID NO:43. In one embodiment, the costimulatory domain comprises an amino acid sequence having at least one, two or three modifications but not more than 20, 10 or 5 modifications of an amino acid sequence of SEQ ID NO:43, or a sequence with 95-99% identity to an amino acid sequence of SEQ ID NO:43. In one embodiment, the nucleic acid sequence encoding the costimulatory domain of CD28 comprises the nucleotide sequence of SEQ ID NO:44, or a sequence with 95-99% identity thereof. In another embodiment, the costimulatory domain of CD27 comprises the amino acid sequence of SEQ ID NO:8. In one embodiment, the costimulatory domain comprises an amino acid sequence having at least one, two or three modifications but not more than 20, 10 or 5 modifications of an amino acid sequence of SEQ ID NO:8, or a sequence with 95-99% identity to an amino acid sequence of SEQ ID NO:8. In one embodiment, the nucleic acid sequence encoding the costimulatory domain of CD27 comprises the nucleotide sequence of SEQ ID NO:19, or a sequence with 95-99% identity thereof. In another embodiment, the costimulatory domain of ICOS comprises the amino acid sequence of SEQ ID NO:45. In one embodiment, the costimulatory domain of ICOS comprises an amino acid sequence having at least one, two or three modifications but not more than 20, 10 or 5 modifications of an amino acid sequence of SEQ ID NO:45, or a sequence with 95-99% identity to an amino acid sequence of SEQ ID NO:45. In one embodiment, the nucleic acid sequence encoding the costimulatory domain of ICOS comprises the nucleotide sequence of SEQ ID NO:46, or a sequence with 95-99% identity thereof.

In some embodiments, the primary signaling domain comprises a functional signaling domain of CD3 zeta. In embodiments, the functional signaling domain of CD3 zeta comprises the amino acid sequence of SEQ ID NO:9 (mutant CD3 zeta) or SEQ ID NO:10 (wild type human CD3 zeta), or a sequence with 95-99% identity thereof.

In one embodiment, the intracellular signaling domain comprises a functional signaling domain of 4-1BB and/or a functional signaling domain of CD3 zeta. In one embodiment, the intracellular signaling domain of 4-1BB comprises the sequence of SEQ ID NO: 7 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:7 and/or an amino acid sequence of SEQ ID NO:9 or SEQ ID NO:10, or a sequence with 95-99% identity to an amino acid sequence of SEQ ID NO:7 and/or an amino acid sequence of SEQ ID NO:9 or SEQ ID NO:10. In one embodiment, the intracellular signaling domain comprises the sequence of SEQ ID NO:7 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain comprises the nucleotide sequence of SEQ ID NO:18, or a sequence with 95-99% identity thereof, and/or the CD3 zeta nucleotide sequence of SEQ ID NO:20 or SEQ ID NO:21, or a sequence with 95-99% identity thereof.

In one embodiment, the intracellular signaling domain comprises a functional signaling domain of CD27 and/or a functional signaling domain of CD3 zeta. In one embodiment, the encoded intracellular signaling domain of CD27 comprises the amino acid sequence of SEQ ID NO:8 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:8 and/or an amino acid sequence of SEQ ID NO:9 or SEQ ID NO:10, or a sequence with 95-99% identity to an amino acid sequence of SEQ ID NO:8 and/or an amino acid sequence of SEQ ID NO:9 or SEQ ID NO:10. In one embodiment, the intracellular signaling domain comprises the sequence of SEQ ID NO:8 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of CD27 comprises the nucleotide sequence of SEQ ID NO:19, or a sequence with 95-99% identity thereof, and/or the CD3 zeta nucleotide sequence of SEQ ID NO:20 or SEQ ID NO:21, or a sequence with 95-99% identity thereof.

In one embodiment, the intracellular signaling domain comprises a functional signaling domain of CD28 and/or a functional signaling domain of CD3 zeta. In one embodiment, the intracellular signaling domain of CD28 comprises the amino acid sequence of SEQ ID NO:43 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:43 and/or an amino acid sequence of SEQ ID NO:9 or SEQ ID NO:10, or a sequence with 95-99% identity to an amino acid sequence of SEQ ID NO:43 and/or an amino acid sequence of SEQ ID NO:9 or SEQ ID NO:10. In one embodiment, the intracellular signaling domain comprises the sequence of SEQ ID NO:43 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of CD28 comprises the nucleotide sequence of SEQ ID NO:44, or a sequence with 95-99% identity thereof, and/or the CD3 zeta nucleotide sequence of SEQ ID NO:20 or SEQ ID NO:21, or a sequence with 95-99% identity thereof.

In one embodiment, the intracellular signaling domain comprises a functional signaling domain of ICOS and/or a functional signaling domain of CD3 zeta. In one embodiment, the intracellular signaling domain of ICOS comprises the amino acid sequence of SEQ ID NO:45 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:45 and/or an amino acid sequence of SEQ ID NO:9 or SEQ ID NO:10, or a sequence with 95-99% identity to an amino acid sequence of SEQ ID NO:45 and/or an amino acid sequence of SEQ ID NO:9 or SEQ ID NO:10. In one embodiment, the intracellular signaling domain comprises the sequence of SEQ ID NO:45 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of ICOS comprises the nucleotide sequence of SEQ ID NO:46, or a sequence with 95-99% identity thereof, and/or the CD3 zeta nucleotide sequence of SEQ ID NO:20 or SEQ ID NO:21, or a sequence with 95-99% identity thereof.

In one embodiment, the mesothelin CAR further comprises a leader sequence comprising the amino acid sequence of SEQ ID NO:1.

In one embodiment, the mesothelin CAR comprises the amino acid sequence of any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86. In one embodiment, the mesothelin CAR comprises an amino acid sequence having at least one, two or three modifications but not more than 30, 20 or 10 modifications to any of SEQ ID NO: 67, SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86. In one embodiment, the mesothelin CAR comprises an amino acid sequence with 95-99% identity to any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86.

In embodiments of any of the methods and compositions described herein, the cell comprising a CAR comprises a nucleic acid encoding the CAR.

In one embodiment, the nucleic acid encoding the CAR is a lentiviral vector. In one embodiment, the nucleic acid encoding the CAR is introduced into the cells by lentiviral transduction. In one embodiment, the nucleic acid encoding the CAR is an RNA, e.g., an in vitro transcribed RNA. In one embodiment, the nucleic acid encoding the CAR is introduced into the cells by electroporation.

In embodiments of any of the methods and compositions described herein, the cell is a T cell or an NK cell. In one embodiment, the T cell is an autologous or allogeneic T cell.

In one embodiment, the method further comprises administering an additional therapeutic agent for treating a disease described herein, e.g., an anti-cancer therapeutic agent.

In embodiments of any of the methods and compositions described herein, the disease associated with mesothelin expression is a cancer. In one embodiment, the cancer is chosen from one or more of mesothelioma, malignant pleural mesothelioma, non-small cell lung cancer, small cell lung cancer, squamous cell lung cancer, or large cell lung cancer, pancreatic cancer, pancreatic ductal adenocarcinoma, pancreatic metastatic, ovarian cancer, or colorectal cancer and bladder cancer, or a metastasis thereof.

In embodiments of any of the methods and compositions described herein, the subject is a mammal, e.g., a human. In one embodiment, the subject expresses PD-L1 and/or PD-L2. In one embodiment, the cancer cell or a cell in close proximity to a cancer cell, e.g., a cancer-associated cell, in the subject expresses PD-L1 and/or PD-L2. In an embodiment, the cancer-associated cell is a anti-tumor immune cell, e.g., a tumor infiltrating lymphocyte (TIL).

In one embodiment, the cell expressing a CAR, e.g., a mesothelin CAR-expressing cell described herein, expresses PD-1 and/or PD-L1.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIG. 8, comprising FIG. 8A shows day 0 PK following the first dose of RAD001. FIG. 8B shows Day 14 PK following the final RAD001 dose. Diamonds denote the 10 mg/kg dose of RAD001; squares denote the 1 mg/kg dose of RAD001; triangles denote the 3 mg/kg dose of RAD001; and x's denote the 10 mg/kg dose of RAD001.

FIG. 9, comprising FIG. 9A shows $CD4^+$ CAR T cells; FIG. 9B shows $CD8^+$ CAR T cells. Circles denote PBS; squares denote huCTL019; triangles denote huCTL019 with 3 mg/kg RAD001; inverted triangles denote huCTL019 with 0.3 mg/kg RAD001; diamonds denote huCTL019 with 0.03 mg/kg RAD001; and circles denote huCTL019 with 0.003 mg/kg RAD001.

DETAILED DESCRIPTION

Definitions

Figure 1A:
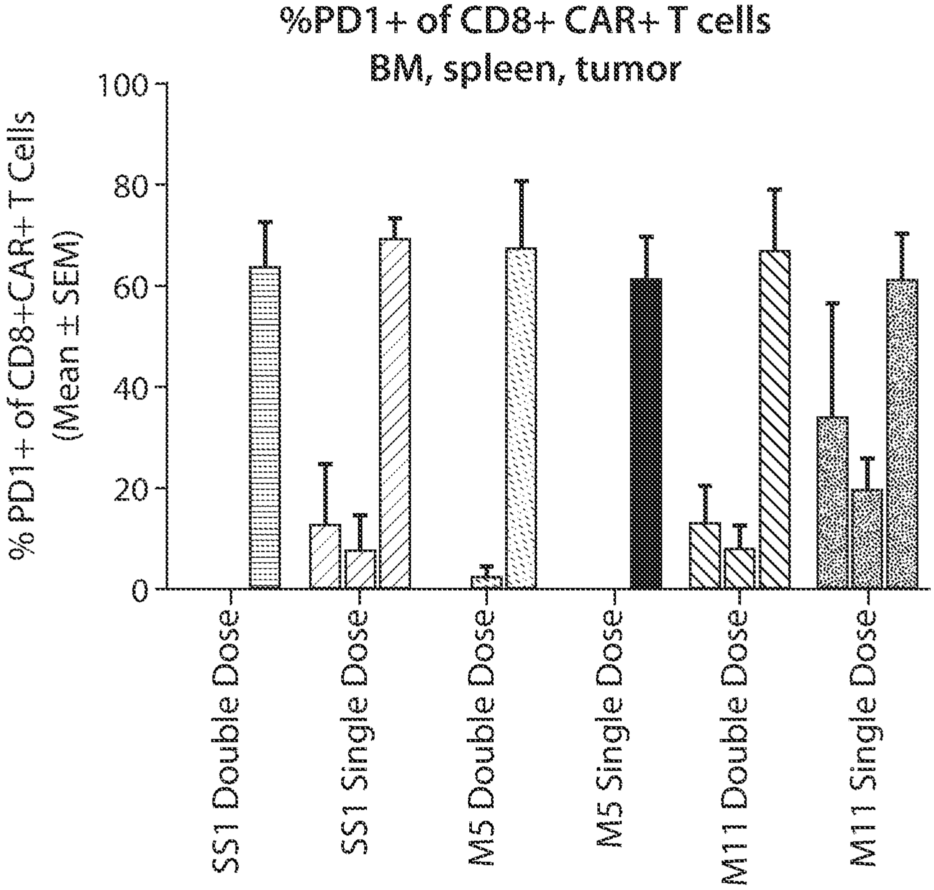
FIG. 1A shows flow cytometric analysis of the expression of PD1 on CAR T cells. Shown is the percentage of CD8+ CAR+ cells expressing PD1. Bone marrow, spleen and tumor were analyzed 30 days after adoptive transfer into Panc02.03 tumor bearing NSG mice. CAR T cells taken from the tumors, but not the other organs were largely positive for PD1 expression (more than 60%). CARTs were stained with anti-CD8a (BioLegend, RPAT8), anti-PD1 (BD Bioscience, EH12.1), anti-PDL1 (BD Bioscience, M1H1), ProteinL-Biotin, and Streptavidin-PE.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the stimulatory molecule is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen recognition domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers. In some aspects, the signaling domain of the CAR described herein is derived from a stimulatory molecule or co-stimulatory molecule described herein, or is a synthesized or engineered signaling domain.

As used herein, the term "mesothelin" refers to the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. The term also refers to a soluble splice variant of the 40-kDa carboxyl-terminal fragment also called "soluble mesothelin/MPF-related". Preferably, the term refers to a human mesothelin of GenBank accession number AAH03512.1, and naturally cleaved portions thereof, e.g., as expressed on a cell membrane, e.g., a cancer cell membrane.

The term "antibody" or "antibody molecule" as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules. In one embodiment, the antibody or antibody molecule comprises, e.g., consists of, an antibody fragment.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), A1-Lazikani et al., (1997) JMB 273,927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR of the invention comprising an antibody or antibody fragment thereof may exist in a variety of forms where the antigen binding domain is expressed as part of a contiguous polypeptide chain including, for example, scFv antibody fragments, linear antibodies, single domain antibodies such as sdAb (either VL or VH), camelid VHH domains, a humanized antibody, a bispecific antibody, an antibody conjugate (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR of the invention comprises an antibody fragment. In a further aspect, the CAR comprises an antibody fragment that comprises a scFv.

As used herein, the term "antibody molecule" refers to a protein, e.g., an immunoglobulin chain or fragment thereof, comprising at least one immunoglobulin variable domain sequence. The term antibody molecule encompasses antibodies and antibody fragments. In one embodiment, an antibody molecule encompasses a "binding domain" (also referred to herein as "anti-target (e.g., mesothelin) binding domain"). In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the uncontrolled growth of aberrant cells. Cancer includes all types of cancerous growths or oncogenic processes, metastatic tissues or malignantly transformed cells, tissues or organs irrespective of the histopathologic type or stage of invasiveness. Cancer cells can spread locally or through the bloodstream and lymphatic system to other parts of the body.

Examples of various cancers are described herein and include, but are not limited to, mesothelioma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of mesothelin" includes, but is not limited to, a disease associated with expression of mesothelin or condition associated with cells which express mesothelin including, e.g., proliferative diseases such as a cancer or malignancy or a precancerous condition such as a mesothelial hyperplasia; or a noncancer related indication associated with cells which express mesothelin. Examples of various cancers that express mesothelin include but are not limited to, mesothelioma, lung cancer, ovarian cancer, pancreatic cancer, and the like.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested, e.g., for the ability to bind mesothelin using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules, such as downregulation of TGF-β, and/or reorganization of cytoskeletal structures, and the like.

The term "stimulatory molecule," refers to a molecule expressed by an immune effector cell (e.g., a T cell, NK cell, B cell) that provides the cytoplasmic signaling sequence(s) that regulate activation of the immune effector cell in a stimulatory way for at least some aspect of the immune effector cell signaling pathway, e.g., the T cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from CD3 zeta, common FcR gamma (FCER1G), Fc gamma RIIa, FcR beta (Fc epsilon Rib), CD3 gamma, CD3 delta, CD3 epsilon, CD5, CD22, CD79a, CD79b, CD278 (also known as "ICOS"), FεRI, DAP10, DAP12, and CD66d. In a specific CAR of the invention, the intracellular signaling domain in any one or more CARs of the invention comprises an intracellular signaling sequence, e.g., a primary signaling sequence of CD3-zeta. In a specific CAR of the invention, the primary signaling sequence of CD3-zeta is the sequence provided as SEQ ID NO:18, or the equivalent residues from a non-human species, e.g., mouse, rodent, monkey, ape and the like. In a specific CAR of the invention, the primary signaling sequence of CD3-zeta is the sequence as provided in SEQ ID NO:20, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR-expressing cell, e.g., a CART cell or CAR-expressing NK cell. Examples of immune effector function, e.g., in a CART cell or CAR-expressing NK cell, include cytolytic activity and helper activity, including the secretion of cytokines. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. In an embodiment, the intracellular signaling domain is synthesized or engineered. For example, in the case of a CAR-expressing immune effector cell, e.g., CART cell or CAR-expressing NK cell, a primary intracellular signaling domain can comprise a cytoplasmic sequence of a T cell receptor, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta, CD3 gamma, CD3 delta, CD3 epsilon, CD5, CD22, CD79a, CD79b, CD278 ("ICOS"), FcεRI CD66d, DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:18. In one aspect, the "zeta stimulatory domain" or a "CD3-zeta stimulatory domain" is the sequence provided as SEQ ID NO:20. Also encompassed herein are CD3 zeta domains comprising one or more mutations to the amino acid sequences described herein, e.g., SEQ ID NO: 20.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:14 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" is used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by its promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "humanized" refers to those forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise a significant portion of at least one, and typically two, variable domains, in which all or substantially all of the CDR regions correspond to those of a non-human immunoglobulin and all or substantially all of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms “peptide,” “polypeptide,” and “protein” are used interchangeably, and refer to a compound comprised of amino acid residues covalently linked by peptide bonds. A protein or peptide must contain at least two amino acids, and no limitation is placed on the maximum number of amino acids that can comprise a protein’s or peptide’s sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. “Polypeptides” include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, a recombinant peptide, or a combination thereof.

The term “promoter” refers to a DNA sequence recognized by the synthetic machinery of the cell, or introduced synthetic machinery, required to initiate the specific transcription of a polynucleotide sequence.

The term “promoter/regulatory sequence” refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term “constitutive” promoter refers to a nucleotide sequence which, when operably linked with a polynucleotide which encodes or specifies a gene product, causes the gene product to be produced in a cell under most or all physiological conditions of the cell.

The term “inducible” promoter refers to a nucleotide sequence which, when operably linked with a polynucleotide which encodes or specifies a gene product, causes the gene product to be produced in a cell substantially only when an inducer which corresponds to the promoter is present in the cell.

The term “tissue-specific” promoter refers to a nucleotide sequence which, when operably linked with a polynucleotide encodes or specified by a gene, causes the gene product to be produced in a cell substantially only if the cell is a cell of the tissue type corresponding to the promoter.

The term “flexible polypeptide linker” or “linker” as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly\text{-}Gly\text{-}Gly\text{-}Ser)_n$, where n is a positive integer equal to or greater than 1 (SEQ ID NO: 609). For example, n=1, n=2, n=3, n=4, n=5 and n=6, n=7, n=8, n=9 and n=10 (SEQ ID NO: 606). In one embodiment, the flexible polypeptide linkers include, but are not limited to, $(Gly_4\ Ser)_4$ (SEQ ID NO: 27) or $(Gly_4\ Ser)_3$ (SEQ ID NO: 28). In another embodiment, the linkers include multiple repeats of $(Gly_2Ser)$, (GlySer) or $(Gly_3Ser)$ (SEQ ID NO: 29). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the “front” or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, “in vitro transcribed RNA” refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a “poly(A)” is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, “polyadenylation” refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, “transient” refers to expression of a non-integrated transgene for a period of hours, days or weeks, wherein the period of time of expression is less than the period of time for expression of the gene if integrated into the genome or contained within a stable plasmid replicon in the host cell.

As used herein, the terms “treat”, “treatment” and “treating” refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a binding partner (e.g., tumor antigen) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with regulatable intracellular signal generation. In some embodiments, an RCAR comprises at least an extracellular antigen binding domain, a transmembrane and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$ $CD127^{high}$, $CD27_{+}$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$ increased $CD127^{high}$ increased $CD27^{+}$, decreased KLRG1, and increased BCL2;

wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or "relapse" as used herein refers to the return or reappearance of a disease (e.g., cancer) or the signs and symptoms of a disease such as cancer after a period of improvement or responsiveness, e.g., after prior treatment of a therapy, e.g., cancer therapy. The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

DESCRIPTION

Provided herein are compositions and methods for treating a disease such as cancer, by administering a cell comprising a chimeric antigen receptor that targets mesothelin, e.g., mesothelin CAR, in combination with a PD-L1 inhibitor. Exemplary components to generate a mesothelin CAR and a mesothelin CAR-expressing cell are disclosure herein. Exemplary PD-L1 inhibitors are also described herein.

In embodiments, the combination therapy of a mesothelin CAR-expressing cell described herein and a PD-L1 inhibitor described herein results in one or more of the following: improved or increased anti-tumor activity of the mesothelin CAR-expressing cell; increased proliferation or persistence of the mesothelin CAR-expressing cell; improved or increased infiltration of the mesothelin CAR-expressing cell; improved inhibition of tumor progression; delay of tumor progression; inhibition or reduction in cancer cell proliferation; and/or reduction in tumor burden, e.g., tumor volume, or size.

As demonstrated in the examples provided herein, in some embodiments, administration of the PD-L1 inhibitor prior to administration of a mesothelin CAR-expressing cell results in increased therapeutic efficacy, e.g., increased inhibition of tumor progression and/or tumor growth, in some cancers, e.g., as compared to administration of the PD-L1 inhibitor after administration of a mesothelin CAR-expressing cell or administration of the PD-L1 inhibitor or mesothelin CAR-expressing cell alone.

PD-L1 is known to downregulate the immune response, e.g., anti-tumor immune response. PD-L1 can also be expressed by cancer cells or cancer associated cells, e.g., tumor infiltrating lymphocytes (TILs). Without wishing to be bound by theory, in some embodiments, a subject that is administered the combination therapy described herein, e.g., a mesothelin CAR-expressing cell and a PD-L1 inhibitor, is more likely to have increased anti-tumor activity if the subject has one or more of: a cancer that expresses, e.g., highly expresses, PD-L1; a cancer that is infiltrated by anti-tumor immune cells, e.g., tumor infiltrating lymphocytes (TILs); and/or cancer-associated cells that express, e.g., highly express, PD-L1, as compared to a subject that is not administered the combination therapy, or is administered a mesothelin CAR-expressing cell or PD-L1 inhibitor alone. For example, without wishing to be bound by theory, treatment with a PD-L1 inhibitor prevents or reduces the down-regulation of the anti-tumor immune response, e.g., exhaustion of anti-tumor immune cells, e.g., TILs or mesothelin CAR expressing immune cells, thereby increasing the anti-tumor efficacy.

Mesothelin Chimeric Antigen Receptor (CAR)

The present disclosure encompasses immune effector cells (e.g., T cells or NK cells) comprising a CAR molecule that targets, e.g., specifically binds, to mesothelin (mesothelin CAR). In one embodiment, the immune effector cells are engineered to express the mesothelin CAR. In one embodiment, the immune effector cells comprise a recombinant nucleic acid construct comprising nucleic acid sequences encoding the mesothelin CAR.

In embodiments, the mesothelin CAR comprises an antigen binding domain that specifically binds to mesothelin, e.g., mesothelin binding domain, a transmembrane domain, and an intracellular signaling domain. In one embodiment, the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

Sequences of non-limiting examples of various components that can be part of a mesothelin CAR molecule described herein, are listed in Table 1, where "aa" stands for amino acids, and "na" stands for nucleic acids that encode the corresponding peptide.

TABLE 1

Sequences of various components of CAR (aa-amino acid sequence, na-nucleic acid sequence)

| SEQ ID NO | Descrip. | Sequence |
|---|---|---|
| 11 | EF-1 promoter (na) | CGTGAGGCTCCGGTGCCCGTCAGTGGGCAGAGCGCACATCGCCCAC<br>AGTCCCCGAGAAGTTGGGGGGAGGGGTCGGCAATTGAACCGGTGCC<br>TAGAGAAGGTGGCGCGGGGTAAACTGGGAAAGTGATGTCGTGTACT<br>GGCTCCGCCTTTTTCCCGAGGGTGGGGGAGAACCGTATATAAGTGCA<br>GTAGTCGCCGTGAACGTTCTTTTTCGCAACGGGTTTGCCGCCAGAAC<br>ACAGGTAAGTGCCGTGTGTGGTTCCCGCGGGCCTGGCCTCTTTACGG<br>GTTATGGCCCTTGCGTGCCTTGAATTACTTCCACCTGGCTGCAGTACG<br>TGATTCTTGATCCCGAGCTTCGGGTTGGAAGTGGGTGGGAGAGTTCG<br>AGGCCTTGCGCTTAAGGAGCCCCTTCGCCTCGTGCTTGAGTTGAGGC<br>CTGGCCTGGGCGCTGGGGCCGCCGCGTGCGAATCTGGTGGCACCTTC<br>GCGCCTGTCTCGCTGCTTTCGATAAGTCTCTAGCCATTTAAAATTTTT<br>GATGACCTGCTGCGACGCTTTTTTTCTGGCAAGATAGTCTTGTAAAT<br>GCGGGCCAAGATCTGCACACTGGTATTTCGGTTTTTGGGGCCGCGGG<br>CGGCGACGGGGCCCGTGCGTCCCAGCGCACATGTTCGGCGAGGCGG<br>GGCCTGCGAGCGCGGCCACCGAGAATCGGACGGGGGTAGTCTCAAG<br>CTGGCCGGCCTGCTCTGGTGCCTGGCCTCGCGCCGCCGTGTATCGCC<br>CCGCCCTGGGCGGCAAGGCTGGCCCGGTCGGCACCAGTTGCGTGAG<br>CGGAAAGATGGCCGCTTCCCGGCCCTGCTGCAGGGAGCTCAAAATG<br>GAGGACGCGGCGCTCGGGAGAGCGGGCGGGTGAGTCACCCACACAA<br>AGGAAAAGGGCCTTTCCGTCCTCAGCCGTCGCTTCATGTGACTCCAC<br>GGAGTACCGGGCGCCGTCCAGGCACCTCGATTAGTTCTCGAGCTTTT<br>GGAGTACGTCGTCTTTAGGTTGGGGGGAGGGGTTTTATGCGATGGAG<br>TTTCCCCACACTGAGTGGGTGGAGACTGAAGTTAGGCCAGCTTGGCA<br>CTTGATGTAATTCTCCTTGGAATTTGCCCTTTTTGAGTTTGGATCTTG<br>GTTCATTCTCAAGCCTCAGACAGTGGTTCAAAGTTTTTTTCTTCCATT |

TABLE 1-continued

Sequences of various components of CAR (aa-amino acid sequence, na-nucleic acid sequence)

| SEQ ID NO | Descrip. | Sequence |
|---|---|---|
| | | TCAGGTGTCGTGA |
| 1 | Leader (aa) | MALPVTALLLPLALLLHAARP |
| 12 | Leader (na) | ATGGCCCTGCCTGTGACAGCCCTGCTGCTGCCTCTGGCTCTGCTGCTG<br>CATGCCGCTAGACCC |
| 2 | CD 8 hinge (aa) | TTTPAPRPPTPAPTIASQPLSLRPEACRPAAGGAVHTRGLDFACD |
| 13 | CD 8 hinge (na) | ACCACGACGCCAGCGCCGCGACCACCAACACCGGCGCCCACCATCG<br>CGTCGCAGCCCCTGTCCCTGCGCCCAGAGGCGTGCCGGCCAGCGGCG<br>GGGGGCGCAGTGCACACGAGGGGGCTGGACTTCGCCTGTGAT |
| 3 | Ig4 hinge (aa) | ESKYGPPCPPCPAPEFLGGPSVFLFPPKPKDTLMISRTPEVTCVVVDVSQ<br>EDPEVQFNWYVDGVEVHNAKTKPREEQFNSTYRVVSVLTVLHQDWLN<br>GKEYKCKVSNKGLPSSIEKTISKAKGQPREPQVYTLPPSQEEMTKNQVS<br>LTCLVKGFYPSDIAVEWESNGQPENNYKTTPPVLDSDGSFFLYSRLTVD<br>KSRWQEGNVFSCSVMHEALHNHYTQKSLSLSLGKM |
| 14 | Ig4 hinge (na) | GAGAGCAAGTACGGCCCTCCCTGCCCCCCTTGCCCTGCCCCCGAGTT<br>CCTGGGCGGACCCAGCGTGTTCCTGTTCCCCCCCAAGCCCAAGGACA<br>CCCTGATGATCAGCCGGACCCCCGAGGTGACCTGTGTGGTGGTGGAC<br>GTGTCCCAGGAGGACCCCGAGGTCCAGTTCAACTGGTACGTGGACG<br>GCGTGGAGGTGCACAACGCCAAGACCAAGCCCCGGGAGGAGCAGTT<br>CAATAGCACCTACCGGGTGGTGTCCGTGCTGACCGTGCTGCACCAGG<br>ACTGGCTGAACGGCAAGGAATACAAGTGTAAGGTGTCCAACAAGGG<br>CCTGCCCAGCAGCATCGAGAAAACCATCAGCAAGGCCAAGGGCCAG<br>CCTCGGGAGCCCCAGGTGTACACCCTGCCCCCTAGCCAAGAGGAGA<br>TGACCAAGAACCAGGTGTCCCTGACCTGCCTGGTGAAGGGCTTCTAC<br>CCCAGCGACATCGCCGTGGAGTGGGAGAGCAACGGCCAGCCCGAGA<br>ACAACTACAAGACCACCCCCCCTGTGCTGGACAGCGACGGCAGCTTC<br>TTCCTGTACAGCCGGCTGACCGTGGACAAGAGCCGGTGGCAGGAGG<br>GCAACGTCTTTAGCTGCTCCGTGATGCACGAGGCCCTGCACAACCAC<br>TACACCCAGAAGAGCCTGAGCCTGTCCCTGGGCAAGATG |
| 4 | IgD hinge (aa) | RWPESPKAQASSVPTAQPQAEGSLAKATTAPATTRNTGRGGEEKKKEK<br>EKEEQEERETKTPECPSHTQPLGVYLLTPAVQDLWLRDKATFTCFVVGS<br>DLKDAHLTWEVAGKVPTGGVEEGLLERHSNGSQSQHSRLTLPRSLWNA<br>GTSVTCTLNHPSLPPQRLMALREPAAQAPVKLSLNLLASSDPPEAASWL<br>LCEVSGFSPPNILLMWLEDQREVNTSGFAPARPPPQPGSTTFWAWSVLR<br>VPAPPSPQPATYTCVVSHEDSRTLLNASRSLEVSYVTDH |
| 15 | IgD hinge (na) | AGGTGGCCCGAAAGTCCCAAGGCCCAGGCATCTAGTGTTCCTACTGC<br>ACAGCCCCAGGCAGAAGGCAGCCTAGCCAAAGCTACTACTGCACCT<br>GCCACTACGCGCAATACTGGCCGTGGCGGGGAGGAGAAGAAAAAGG<br>AGAAAGAGAAAGAAGAACAGGAAGAGAGGGAGACCAAGACCCCTG<br>AATGTCCATCCCATACCCAGCCGCTGGGCGTCTATCTCTTGACTCCC<br>GCAGTACAGGACTTGTGGCTTAGAGATAAGGCCACCTTTACATGTTT<br>CGTCGTGGGCTCTGACCTGAAGGATGCCCATTTGACTTGGGAGGTTG<br>CCGGAAAGGTACCCACAGGGGGGGTTGAGGAAGGGTTGCTGGAGCG<br>CCATTCCAATGGCTCTCAGAGCCAGCACTCAAGACTCACCCTTCCGA<br>GATCCCTGTGGAACGCCGGGACCTCTGTCACATGTACTCTAAATCAT<br>CCTAGCCTGCCCCCACAGCGTCTGATGGCCCTTAGAGAGCCAGCCGC<br>CCAGGCACCAGTTAAGCTTAGCCTGAATCTGCTCGCCAGTAGTGATC<br>CCCCAGAGGCCGCCAGCTGGCTCTTATGCGAAGTGTCCGGCTTTAGC<br>CCGCCCAACATCTTGCTCATGTGGCTGGAGGACCAGCGAGAAGTGA<br>ACACCAGCGGCTTCGCTCCAGCCCGGCCCCCACCCCAGCCGGGTTCT<br>ACCACATTCTGGGCCTGGAGTGTCTTAAGGGTCCCAGCACCACCTAG<br>CCCCCAGCCAGCCACATACACCTGTGTTGTGTCCCATGAAGATAGCA<br>GGACCCTGCTAAATGCTTCTAGGAGTCTGGAGGTTTCCTACGTGACT<br>GACCATT |
| 6 | CD8 Transmembrane (aa) | IYIWAPLAGTCGVLLLSLVITLYC |
| 17 | CD8 Transmembrane (na) | ATCTACATCTGGGCGCCCTTGGCCGGGACTTGTGGGGTCCTTCTCCT<br>GTCACTGGTTATCACCCTTTACTGC |
| 7 | 4-1BB intracellular domain (aa) | KRGRKKLLYIFKQPFMRPVQTTQEEDGCSCRFPEEEEGGCEL |

TABLE 1-continued

| Sequences of various components of CAR (aa-amino acid sequence, na-nucleic acid sequence) | | |
|---|---|---|
| SEQ ID NO | Descrip. | Sequence |
| 18 | 4-IBB intracellular domain (na) | AAACGGGGCAGAAAGAAACTCCTGTATATATTCAAACAACCATTTAT<br>GAGACCAGTACAAACTACTCAAGAGGAAGATGGCTGTAGCTGCCGA<br>TTTCCAGAAGAAGAAGAAGGAGGATGTGAACTG |
| 8 | CD27 (aa) | QRRKYRSNKGESPVEPAEPCRYSCPREEEGSTIPIQEDYRKPEPACSP |
| 19 | CD27 (na) | AGGAGTAAGAGGAGCAGGCTCCTGCACAGTGACTACATGAACATGA<br>CTCCCCGCCGCCCCGGGCCCACCCGCAAGCATTACCAGCCCTATGCC<br>CCACCACGCGACTTCGCAGCCTATCGCTCC |
| 9 | CD3-zeta (aa) (Q/K mutant) | RVKFSRSADAPAYKQGQNQLYNELNLGRREEYDVLDKRRGRDPEMGG<br>KPRRKNPQEGLYNELQKDKMAEAYSEIGMKGERRRGKGHDGLYQGLS<br>TATKDTYDALHMQALPPR |
| 20 | CD3-zeta (na) (Q/K mutant) | AGAGTGAAGTTCAGCAGGAGCGCAGACGCCCCCGCGTACAAGCAGG<br>GCCAGAACCAGCTCTATAACGAGCTCAATCTAGGACGAAGAGAGGA<br>GTACGATGTTTTGGACAAGAGACGTGGCCGGGACCCTGAGATGGGG<br>GGAAAGCCGAGAAGGAAGAACCCTCAGGAAGGCCTGTACAATGAAC<br>TGCAGAAAGATAAGATGGCGGAGGCCTACAGTGAGATTGGGATGAA<br>AGGCGAGCGCCGGAGGGGCAAGGGGCACGATGGCCTTTACCAGGGT<br>CTCAGTACAGCCACCAAGGACACCTACGACGCCCTTCACATGCAGGC<br>CCTGCCCCCTCGC |
| 10 | CD3-zeta (aa) (NCBI Reference Sequence NM_000734.3) | RVKFSRSADAPAYQQGQNQLYNELNLGRREEYDVLDKRRGRDPEMGG<br>KPRRKNPQEGLYNELQKDKMAEAYSEIGMKGERRRGKGHDGLYQGLS<br>TATKDTYDALHMQALPPR |
| 21 | CD3-zeta (na) (NCBI Reference Sequence NM_000734.3) | AGAGTGAAGTTCAGCAGGAGCGCAGACGCCCCCGCGTACCAGCAGG<br>GCCAGAACCAGCTCTATAACGAGCTCAATCTAGGACGAAGAGAGGA<br>GTACGATGTTTTGGACAAGAGACGTGGCCGGGACCCTGAGATGGGG<br>GGAAAGCCGAGAAGGAAGAACCCTCAGGAAGGCCTGTACAATGAAC<br>TGCAGAAAGATAAGATGGCGGAGGCCTACAGTGAGATTGGGATGAA<br>AGGCGAGCGCCGGAGGGGCAAGGGGCACGATGGCCTTTACCAGGGT<br>CTCAGTACAGCCACCAAGGACACCTACGACGCCCTTCACATGCAGGC<br>CCTGCCCCCTCGC |
| 36 | CD28 Intracellular domain (amino acid sequence) | RSKRSRLLHSDYMNMTPRRPGPTRKHYQPYAPPRDFAAYRS |
| 37 | CD28 Intracellular domain (nucleotide sequence) | AGGAGTAAGAGGAGCAGGCTCCTGCACAGTGACTACATGAACATGA<br>CTCCCCGCCGCCCCGGGCCCACCCGCAAGCATTACCAGCCCTATGCC<br>CCACCACGCGACTTCGCAGCCTATCGCTCC |
| 38 | ICOS Intracellular domain (amino acid sequence) | T K K K Y S S S V H D P N G E Y M F M R A V N T A K K S R L T D V T L |
| 607 | ICOS Intracellular domain (nucleotide sequence) | ACAAAAAAGAAGTATTCATCCAGTGTGCACGACCCTAACGGTGAAT<br>ACATGTTCATGAGAGCAGTGAACACAGCCAAAAAATCCAGACTCAC<br>AGATGTGACCCTA |
| 5 | GS hinge/linker (aa) | GGGGSGGGGS |
| 16 | GS hinge/linker (na) | GGTGGCGGAGGTTCTGGAGGTGGAGGTTCC |

TABLE 1-continued

Sequences of various components of CAR (aa-amino acid sequence, na-nucleic acid sequence)

| SEQ ID NO | Descrip. | Sequence |
|---|---|---|
| 608 | GS hinge/linker (na) | GGTGGCGGAGGTTCTGGAGGTGGGGGTTCC |
| 25 | linker | GGGGS |
| 26 | linker | (Gly-Gly-Gly-Gly-Ser)n, where n = 1-6, e.g., GGGGSGGGGS GGGGSGGGGS GGGGSGGGGS |
| 27 | linker | (Gly4 Ser)4 |
| 28 | linker | (Gly4 Ser)3 |
| 29 | linker | (Gly3Ser) |
| 609 | linker | (Gly-Gly-Gly-Ser)n where n is a positive integer equal to or greater than 1 |
| 606 | linker | (Gly-Gly-Gly-Ser)n, where n = 1-10, e.g., GGGSGGGSGG GSGGGSGGGS GGGSGGGSGG GSGGGSGGGS |
| 610 | linker | GSTSGSGKPGSGEGSTKG |
| 30 | polyA | $(A)_{5000}$<br>This sequence may encompass 50-5000 adenines. |
| 31 | polyT | $(T)_{100}$ |
| 32 | polyT | $(T)_{5000}$<br>This sequence may encompass 50-5000 thymines. |
| 33 | polyA | $(A)_{5000}$<br>This sequence may encompass 100-5000 adenines. |
| 34 | polyA | $(A)_{400}$<br>This sequence may encompass 100-400 adenines. |
| 35 | polyA | $(A)_{2000}$<br>This sequence may encompass 50-2000 adenines. |
| 22 | PD1 CAR (aa) | pgwfldspdrpwnpptfspallvvtegdnatftcsfsntsesfvlnwyrmspsngtdklaafpedrsapga<br>dcrfrvtqlpngrdfhmsvvrarrndsgtylcgaislapkaqikeslraelrvterraevptahpspsprp<br>agqfqtlvtttpaprpptpaptiasqplslrpeacrpaaggavhtrgldfacdiyiwaplagtcgvlllsl<br>vitlyckrgrkkllyifkqpfmrpvqttqeedgcscrfpeeeeggcelrvkfsrsadapaykqgqnqlyne<br>lnlgrreeydvldkrrgrdpemggkprrknpqeglynelqkdkmaeayseigmkgerrrgkghdglyqgls<br>tatkdtydalhmqalppr |
| 23 | PD-1 CAR (na) (PD1 ECD underlined) | atggccctccctgtcactgccctgcttctccccctcgcactcctgctccacgccgctagaccacccggatg<br>gtttctggactctccggatcgcccgtggaatcccccaaccttctcaccggcactcttggttgtgactgagg<br>gcgataatgcgaccttcacgtgctcgttctccaacacctccgaatcattcgtgctgaactggtaccgcatg<br>agcccgtcaaaccagaccgacaagctcgccgcgtttccggaagatcggtcgcaaccgggacaggattgtcg<br>gttccgcgtgactcaactgccgaatggcagagacttccacatgagcgtggtccgcgctaggcgaaacgact<br>ccgggacctacctgtgcggagccatctcgctggcgcctaaggcccaaatcaaagagagcttgagggccgaa<br>ctgagagtgaccgagcgcagagctgaggtgccaactgcacatccatccccatcgcctcggcctgcggggca<br>gtttcagaccctggtcacgaccactccggcgccgcgcccaccgactccggccccaactatcgcgagccagc<br>ccctgtcgctgaggccggaagcatgccgccctgccgccggaggtgctgtgcatacccggggattggacttc<br>gcatgcgacatctacatttgggctcctctcgccggaacttgtggcgtgctccttctgtccctggtcatcac<br>cctgtactgcaagcggggtcggaaaaagcttctgtacattttcaagcagcccttcatgaggcccgtgcaaa<br>ccacccaggaggaggacggttgctcctgccggttccccgaagaggaagaaggaggttgcgagctgcgcgtg<br>aagttctcccggagcgccgacgcccccgcctataagcagggccagaaccagctgtacaacgaactgaacct<br>gggacggcgggaagagtacgatgtgctggacaagcggcgcggccgggaccccgaaatgggcgggaagccta<br>gaagaaagaaccctcaggaaggcctgtataacgagctgcagaaggacaagatggccgaggcctactccgaa<br>attgggatgaagggagagcggcggaggggaaaggggcacgacggcctgtaccaaggactgtccaccgccac<br>caaggacacatacgatgccctgcacatgcaggcccttccccctcgc |
| 24 | PD-1 CAR (aa) with signal (PD1 ECD underlined) | Malpvtalllplalllhaarppgwfldspdrpwnpptfspallvvtegdnatftcsfsntsesfvlnwvrm<br>spsnqtdklaafpedrsqpgqdcrfrvtqlpngrdfhmsvvrarrndsgtylcgaislapkaqikeslrae<br>lrvterraevptahpspsprpagqfqtlvtttpaprpptpaptiasqplslrpeacrpaaggavhtrgldf<br>acdiyiwaplagtcgvlllslvitlyckrgrkkllyifkqpfmrpvqttqeedgcscrfpeeeeggcelrv<br>kfsrsadapaykqgqnqlynelnlgrreeydvldkrrgrdpemggkprrknpqeglynelqkdkmaeayse<br>igmkgerrrgkghdglyqglstatkdtydalhmqalppr |

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

In one aspect, the mesothelin CARs of the invention comprise at least one intracellular signaling domain selected from the group of a CD137 (4-1BB) signaling domain, a CD28 signaling domain, a CD27 signaling domain, an ICOS signaling domain, a CD3zeta signal domain, and any combination thereof. In one aspect, the CARs of the invention comprise at least one intracellular signaling domain is from one or more costimulatory molecule(s) selected from CD137 (4-1BB), CD28, CD27, or ICOS.

Antigen Binding Domain

In one aspect, the CAR of the invention comprises a target-specific binding element otherwise referred to as an antigen binding domain. In one embodiment, the portion of the CAR comprising the antigen binding domain comprises an antigen binding domain that targets, e.g., specifically binds to, mesothelin. In one embodiment, the antigen binding domain targets, e.g., specifically binds to, human mesothelin.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as an antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. Thus, in one aspect, the antigen binding domain comprises a human antibody or an antibody fragment.

In one embodiment, the mesothelin binding domain comprises one or more (e.g., all three) light chain complementary determining region 1 (LC CDR1), light chain complementary determining region 2 (LC CDR2), and light chain complementary determining region 3 (LC CDR3) of a mesothelin binding domain selected from SEQ ID NOS: 39-62 and one or more (e.g., all three) heavy chain complementary determining region 1 (HC CDR1), heavy chain complementary determining region 2 (HC CDR2), and heavy chain complementary determining region 3 (HC CDR3) of a mesothelin binding domain selected from SEQ ID NOS: 39-62. In one embodiment, the mesothelin binding domain comprises a light chain variable region described herein (e.g., in Table 2) and/or a heavy chain variable region described herein (e.g., in Table 2). In one embodiment, the mesothelin binding domain is a scFv comprising a light chain variable region and a heavy chain variable region of an amino acid sequence of Table 2. In an embodiment, the mesothelin binding domain (e.g., an scFV) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2, or a sequence with 95-99% identity to an amino acid sequence of Table 2; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 2, or a sequence with 95-99% identity to an amino acid sequence of Table 2.

In one embodiment, the mesothelin binding domain comprises a light chain variable region comprising an amino acid sequence described herein, e.g., in Table 2 or 3, is attached to a heavy chain variable region comprising an amino acid sequence described herein, e.g., in Table 2 or 3, via a linker, e.g., a linker described herein. In one embodiment, the humanized anti-mesothelin binding domain includes a (Gly4-Ser)n linker (SEQ ID NO: 26), wherein n is 1, 2, 3, 4, 5, or 6, preferably 3 or 4. The light chain variable region and heavy chain variable region of a scFv can be, e.g., in any of the following orientations: light chain variable region-linker-heavy chain variable region or heavy chain variable region-linker-light chain variable region.

In another embodiment, the mesothelin binding domain comprises any antibody or antibody fragment thereof known in the art that binds to mesothelin. Examples of other anti-mesothelin antibodies or antibody fragment thereof known in the art include those described in WO2009/120769 (e.g., antibody m912, whose light and heavy chain amino acid sequences are SEQ ID NO: 1 and SEQ ID NO: 2 of WO2009/120769); U.S. Pat. No. 6,083,502, US Patent Publication No. US2008/0261245, WO2009/068204, WO2010/111282, WO2014/004549, and U.S. Patent Publication No. US2015/0274836.

In one aspect, the antibodies of the invention may exist in a variety of other forms including, for example, Fab, Fab', $F(ab')_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide brudge at the hinge region, and an isolated CDR or other epitope binding fragments of an antibody. In one aspect, the antibody fragment provided herein is a scFv. In some instances, a human scFv may also be derived from a yeast display library.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together, e.g., using flexible polypeptide linkers. The scFv molecules can comprise a linker (e.g., a Ser-Gly linker) with an optimized length and/or amino acid composition. The linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_1$, where n is a positive integer equal to or greater than 1. (SEQ ID NO: 135) In one embodiment, the linker can be $(Gly_4Ser)_4$ (SEQ ID NO: 27) or $(Gly_4Ser)_3$ (SEQ ID NO: 28). Variation in the linker length may retain or enhance activity, giving rise to superior efficacy in activity studies.

Exemplary Mesothelin Antigen Binding Domains and CAR Constructs

Exemplary mesothelin CAR constructs disclosed herein comprise a scFv (e.g., a human scFv) as disclosed in Table 2 or 3 herein, optionally preceded with an optional leader sequence (e.g., SEQ ID NO:1 and SEQ ID NO:12 for exemplary leader amino acid and nucleotide sequences, respectively). The sequences of the scFv fragments (amino acid sequences of SEQ ID NOs: 39-62) are provided herein in Table 2. The mesothelin CAR construct can further include an optional hinge domain, e.g., a CD8 hinge domain (e.g., including the amino acid sequence of SEQ ID NO: 2 or encoded by a nucleic acid sequence of SEQ ID NO:13); a transmembrane domain, e.g., a CD8 transmembrane domain (e.g., including the amino acid sequence of SEQ ID NO: 6 or encoded by the nucleotide sequence of SEQ ID NO: 17); an intracellular domain, e.g., a 4-1BB intracellular domain (e.g., including the amino acid sequence of SEQ ID NO: 7 or encoded by the nucleotide sequence of SEQ ID NO: 18; and a functional signaling domain, e.g., a CD3 zeta domain (e.g., including amino acid sequence of SEQ ID NO: 9 or 10, or encoded by the nucleotide sequence of SEQ ID NO: 20 or 21). In certain embodiments, the domains are contiguous with and in the same reading frame to form a single fusion protein. In other embodiments, the domain are in separate polypeptides, e.g., as in an RCAR molecule as described herein.

In certain embodiments, the full length mesothelin CAR molecule includes the amino acid sequence of, or is encoded by the nucleotide sequence of, M1, M2, M3, M4, M5, M6, M7, M8, M9, M10, M11, M12, M13, M14, M15, M16, M17, M18, M19, M20, M21, M22, M23, M24, or ss1, provided in Table 2 or 3, or a sequence substantially identical (e.g., 95-99% identical thereto, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes the scFv amino acid sequence of, or is encoded by the nucleotide sequence of, M1, M2, M3, M4, M5, M6, M7, M8, M9, M10, M11, M12, M13, M14, M15, M16, M17, M18, M19, M20, M21, M22, M23, M24, or ss1, provided in Table 2 or 3, or a sequence substantially identical (e.g., 95-99% identical thereto, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes the heavy chain variable region and/or the light chain variable region of M1, M2, M3, M4, M5, M6, M7, M8, M9, M10, M11, M12, M13, M14, M15, M16, M17, M18, M19, M20, M21, M22, M23, M24, or ss1, provided in Table 2, or a sequence substantially identical (e.g., 95-99% identical, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes one, two or three CDRs from the heavy chain variable region (e.g., HCDR1, HCDR2 and/or HCDR3) of M1, M2, M3, M4, M5, M6, M7, M8, M9, M10, M11, M12, M13, M14, M15, M16, M17, M18, M19, M20, M21, M22, M23, M24, or ss1, provided in Table 4; and/or one, two or three CDRs from the light chain variable region (e.g., LCDR1, LCDR2 and/or LCDR3) of M1, M2, M3, M4, M5, M6, M7, M8, M9, M10, M11, M12, M13, M14, M15, M16, M17, M18, M19, M20, M21, M22, M23, M24, or ss1, provided in Table 5; or a sequence substantially identical (e.g., 95-99% identical, or up to 5, 4, 3, 2, or 1 amino acid changes) to any of the aforesaid sequences.

The sequences of CDR sequences of the scFv domains are shown in Table 4 for the heavy chain variable domains and in Table 5 for the light chain variable domains.

TABLE 4

Amino acid sequences for the heavy chain (HC) CDR1, CDR2, and CDR3 regions of human anti-mesothelin scFvs

| Descrip. | HC-CDR1 | SEQ ID NO: | HC-CDR2 | SEQ ID NO | HC-CDR3 | SEQ ID NO |
|---|---|---|---|---|---|---|
| M1 | GYTFTGYYMH | 136 | RINPNSGGTNYAQKFQG | 155 | GRYYGMDV | 175 |
| M2 | GYTFTGYYMH | 136 | WINPNSGGTNYAQKFQG | 156 | DLRRTVVTPRAYYG MDV | 176 |
| M3 | GYTFTGYYMH | 136 | WINPNSGGTNYAQKFQG | 156 | GEWDGSYYYDY | 177 |
| M4 | GFTFSSYWMH | 137 | RINTDGSTTTYADSVEG | 157 | GHWAV | 178 |
| M5 | GYTFTDYYMH | 138 | WINPNSGGTNYAQKFQG | 156 | GWDFDY | 179 |
| M6 | GYTFTSYYMH | 139 | IINPSGGSTSYAQKFQ | 158 | YRLIAVAGDYYYYG MDV | 180 |
| M7 | GFTFSSYAMH | 140 | VISYDGSNKYYADSVKG | 274 | WKVSSSSPAFDY | 181 |

TABLE 4-continued

Amino acid sequences for the heavy chain (HC) CDR1, CDR2, and CDR3 regions of human anti-mesothelin scFvs

| Descrip. | HC-CDR1 | SEQ ID NO: | HC-CDR2 | SEQ ID NO | HC-CDR3 | SEQ ID NO |
|---|---|---|---|---|---|---|
| M8 | GYPFTGYSLH | 141 | WINPNSGGTNYAQKFQG | 159 | DHYGGNSLFY | 182 |
| M9 | GYTFTSYYMH | 142 | IINPSGGSTGYAQKFQG | 160 | GGYSSSSDAFDI | 183 |
| M10 | GYTFTSYGIS | 143 | WISAYNGNTNYAQKLQ | 161 | VAGGIYYYYGMDV | 184 |
| M11 | GYTFTGYYMH | 144 | WINPNSGGTNYAQNFQG | 162 | GWDFDY | 185 |
| M12 | GYTFTGYYMH | 144 | RINPNSGGTNYAQKFQG | 163 | TTTSYAFDI | 186 |
| M13 | GFIFSDYYMG | 145 | YIGRSGSSMYYADSVKG | 164 | SPWAATEDFQH | 187 |
| M14 | GFTFRGYYIH | 146 | IINPSGGSRAYAQKFQG | 165 | TASCGGDCYYLDY | 188 |
| M15 | GFTFDDYAMH | 147 | GISWNSGSIGYADSVK | 166 | DGSSSWSWGYFDY | 189 |
| M16 | GFTFDDYAMH | 147 | GISWNSGSTGYADSVKG | 167 | DSSSWYGGGSAFDI | 190 |
| M17 | GFTFDDYAMH | 147 | GISWNSGSTGYADSVKG | 167 | DSSSWYGGGSAFDI | 191 |
| M18 | GFTFSSYWMH | 148 | RINSDGSSTSYADSVKG | 168 | TGWVGSYYYYMDV | 192 |
| M19 | GFTFSSYGMH | 149 | VISYDGSNKYYADSVKG | 169 | GYSRYYYYGMDV | 193 |
| M20 | GFTFSSYAMS | 150 | AISGSGGSTYYADSVKG | 170 | REAAAGHDWYFDL | 194 |
| M21 | GYTFTSYYMH | 151 | IINPSGGSTSYAQKFQG | 171 | SPRVTTGYFDY | 195 |
| M22 | GDTSTRHYIH | 152 | VINPTTGPATGSPAYAQMLQ G | 172 | SWGRSAPYYFDY | 196 |
| M23 | GYTFTNYYMH | 153 | IINPSGGYTTYAQKFQG | 173 | IRSCGGDCYYFDN | 197 |
| M24 | GFSLSTAGVHVG | 154 | LISWADDKRYRPSLRS | 174 | QGFDGYEAN | 198 |
| Ss1 | GYSFTGYTMN | 281 | LITPYNGASSYNQKFRG | 282 | GGYDGRGFDY | 283 |

TABLE 5

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M1 | RASQSVSSNFA | 199 | DASNRAT | 223 | HQRSNWLYT | 247 |
| M2 | QASQDISNSLN | 200 | DASTLET | 224 | QQHDNLPLT | 248 |
| M3 | RASQSINTYLN | 201 | AASSLQS | 225 | QQSFSPLT | 249 |
| M4 | RASQSISDRLA | 202 | KASSLES | 226 | QQYGHLPMYT | 250 |
| M5 | RASQSIRYYLS | 203 | TASILQN | 227 | LQTYTTPD | 251 |
| M6 | RASQGVGRWLA | 204 | AASTLQS | 228 | QQANSFPLT | 252 |
| M7 | RASQSVYTKYLG | 205 | DASTRAT | 229 | QHYGGSPLIT | 253 |
| M8 | RASQDSGTWLA | 206 | DASTLED | 230 | QQYNSYPLT | 254 |
| M9 | RASQDISSALA | 207 | DASSLES | 231 | QQFSSYPLT | 255 |
| M10 | KSSHSVLYNRNNKNYLA | 208 | WASTRKS | 232 | QQTQTFPLT | 256 |
| M11 | RASQSIRYYLS | 209 | TASILQN | 233 | LQTYTTPD | 257 |
| M12 | RASQSISTWLA | 210 | KASTLES | 234 | QQYNTYSPYT | 258 |

TABLE 5-continued

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M13 | RASQSVTSNYLA | 211 | GASTRAT | 235 | QQYGSAPVT | 259 |
| M14 | RASENVNIWLA | 212 | KSSSLAS | 236 | QQYQSYPLT | 260 |
| M15 | QGDALRSYYAS | 213 | GKNNRPS | 237 | NSRDSSGYPV | 261 |
| M16 | QGDSLRSYYAS | 214 | GRSRRPS | 238 | NSRDNTANHYV | 262 |
| M17 | QGDSLRSYYAS | 215 | GKNNRPS | 239 | NSRGSSGNHYV | 263 |
| M18 | RASQSVSSNYLA | 216 | DVSTRAT | 240 | QQRSNWPPWT | 264 |
| M19 | RASQSVYTKYLG | 217 | DASTRAT | 241 | QHYGGSPLIT | 265 |
| M20 | RASQSISSYLN | 218 | AASSLQS | 242 | QQSYSIPLT | 266 |
| M21 | RASQSISSWLA | 219 | KASSLES | 243 | QQYSSYPLT | 267 |
| M22 | RASQGISDYS | 220 | AASTLQS | 244 | QQYYSYPLT | 268 |
| M23 | RASENVNIWLA | 221 | KSSSLAS | 245 | QQYQSYPLT | 269 |
| M24 | RASRGISSALA | 222 | DASSLES | 246 | QQSYSTPWT | 270 |
| Ss1 | SASSSVSYMH | 284 | DTSKLAS | 285 | QQWSGYPLT | 286 |

The amino acid and nucleic acid sequences of the mesothelin scFv domains and mesothelin CAR molecules are provided in Table 2 (amino acid sequences) and Table 3 (nucleic acid sequences). In one embodiment, the mesothelin CAR molecule includes a leader sequence described herein, e.g., as underlined in the sequences provided in Table 2. In one embodiment, the mesothelin CAR molecule does not include a leader sequence.

TABLE 2

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| 39 | M1 (ScFv domain) | QVQLQQSGAEVKKPGASVKVSCKASGYTFTGYYMHWVRQ<br>APGQGLEWMGRINPNSGGTNYAQKFQGRVTMTRDTSISTAYMELSRLRSEDTAVYYCARG<br>RYYGMDVWGQGTMVTVSSGGGGSGGGGSGGGGSGGGGSEIVLTQSPATLSLSPGERATIS<br>CRASQSVSSNFAWYQQRPGQAPRLLIYDASNRATGIPPRFSGSGSGTDFTLTISSLEPED<br>FAAYYCHQRSNWLYTFGQGTKVDIK |
| 63 | M1 (full) >ZA53-27BC (M1 ZA53-27BC R001-A11 126161) | **MALPVTALLLPLALLLHAARP**QVQLQQSGAEVKKPGASVKVSCKASGYTFTGYYMHWVRQ<br>APGQGLEWMGRINPNSGGTNYAQKFQGRVTMTRDTSISTAYMELSRLRSEDTAVYYCARG<br>RYYGMDVWGQGTMVTVSSGGGGSGGGGSGGGGSGGGGSEIVLTQSPATLSLSPGERATIS<br>CRASQSVSSNFAWYQQRPGQAPRLLIYDASNRATGIPPRFSGSGSGTDFTLTISSLEPED<br>FAAYYCHQRSNWLYTFGQGTKVDIKTTTPAPRPPTPAPTIASQPLSLRPEACRPAAGGAV<br>HTRGLDFACDIYIWAPLAGTCGVLLLSLVITLYCKRGRKKLLYIFKQPFMRPVQTTQEED<br>GCSCRFPEEEEGGCELRVKFSRSADAPAYKQGQNQLYNELNLGRREEYDVLDKRRGRDPE<br>MGGKPRRKNPQEGLYNELQKDKMAEAYSEIGMKGERRRGKGHDGLYQGLSTATKDTYDAL<br>HMQALPPR |
| 40 | M2 (ScFv domain) | QVQLVQSGAEVKKPGASVKVSCKASGYTFTGYYMHWVRQ<br>APGQGLEWMGWINPNSGGTNYAQKFQGRVTMTRDTSISTAYMELSRLRSDDTAVYYCARD<br>LRRTVVTPRAYYGMDVWGQGTTVTVSSGGGGSGGGGSGGGGSGGGGSDIQLTQSPSTLSA<br>SVGDRVTITCQASQDISNSLNWYQQKAGKAPKLLIYDASTLETGVPSRFSGSGSGTDFSF<br>TISSLQPEDIATYYCQQHDNLPLTFGQGTKVEIK |
| 64 | M2 (full) >FA56-26RC (M2 | **MALPVTALLLPLALLLHAARP**QVQLVQSGAEVKKPGASVKVSCKASGYTFTGYYMHWVRQ<br>APGQGLEWMGWINPNSGGTNYAQKFQGRVTMTRDTSISTAYMELSRLRSDDTAVYYCARD<br>LRRTVVTPRAYYGMDVWGQGTTVTVSSGGGGSGGGGSGGGGSGGGGSDIQLTQSPSTLSA |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| | FA56-26RC R001-A10 126162) | SVGDRVTITCQASQDISNSLNWYQQKAGKAPKLLIYDASTLETGVPSRFSGSGSGTDFSFTISSLQPEDIATYYCQQHDNLPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 41 | M3 (ScFv domain) | QVQLVQSGAEVKKPGAPVKVSCKASGYTFTGYYMHWVRQAPGQGLEWMGWINPNSGGTNYAQKFQGRVTMTRDTSISTAYMELSRLRSDDTAVYYCARGEWDGSYYYDYWGQGTLVTVSSGGGGSGGGGSGGGGSGGGGSDIVLTQTPSSLSASVGDRVTITCRASQSINTYLNWYQHKPGKAPKLLIYAASSLQSGVPSRFSGSGSGTDFTLTISSLQPEDFATYYCQQSFSPLTFGGGTKLEIK |
| 65 | M3 >VA58-21LC (M3 VA58-21LC R001-A1 126163) | **MALPVTALLLPLALLLHAARP**QVQLVQSGAEVKKPGAPVKVSCKASGYTFTGYYMHWVRQAPGQGLEWMGWINPNSGGTNYAQKFQGRVTMTRDTSISTAYMELSRLRSDDTAVYYCARGEWDGSYYYDYWGQGTLVTVSSGGGGSGGGGSGGGGSGGGGSDIVLTQTPSSLSASVGDRVTITCRASQSINTYLNWYQHKPGKAPKLLIYAASSLQSGVPSRFSGSGSGTDFTLTISSLQPEDFATYYCQQSFSPLTFGGGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 42 | M4 (ScFv domain) | QVQLVESGGGLVQPGGSLRLSCAASGFTFSSYWMHWVRQVPGKGLVWVSRINTDGSTTTYADSVEGRFTISRDNAKNTLYLQMNSLRDDDTAVYYCVGGHWAVWGQGTTVTVSSGGGGSGGGGSGGGGSGGGGSDIQMTQSPSTLSASVGDRVTITCRASQSISDRLAWYQQKPGKAPKLLIYKASSLESGVPSRFSGSGSGTEFTLTISSLQPDDFAVYYCQQYGHLPMYTFGQGTKVEIK |
| 66 | M4 >DP37-07IC (M4 DP37-07IC R001-C6 126164) | **MALPVTALLLPLALLLHAARP**QVQLVESGGGLVQPGGSLRLSCAASGFTFSSYWMHWVRQVPGKGLVWVSRINTDGSTTTYADSVEGRFTISRDNAKNTLYLQMNSLRDDDTAVYYCVGGHWAVWGQGTTVTVSSGGGGSGGGGSGGGGSGGGGSDIQMTQSPSTLSASVGDRVTITCRASQSISDRLAWYQQKPGKAPKLLIYKASSLESGVPSRFSGSGSGTEFTLTISSLQPDDFAVYYCQQYGHLPMYTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 43 | M5 (ScFv domain) | QVQLVQSGAEVEKPGASVKVSCKASGYTFTDYYMHWVRQAPGQGLEWMGWINPNSGGTNYAQKFQGRVTMTRDTSISTAYMELSRLRSDDTAVYYCASGWDFDYWGQGTLVTVSSGGGGSGGGGSGGGGSGGGGSDIVMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIK |
| 67 | M5 >XP31-20LC (M5 XP31-20LC R001-B4 126165) | **MALPVTALLLPLALLLHAARP**QVQLVQSGAEVEKPGASVKVSCKASGYTFTDYYMHWVRQAPGQGLEWMGWINPNSGGTNYAQKFQGRVTMTRDTSISTAYMELSRLRSDDTAVYYCASGWDFDYWGQGTLVTVSSGGGGSGGGGSGGGGSGGGGSDIVMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 44 | M6 (ScFv domain) | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARYRLIAVAGDYYYYGMDVWGQGTMVTVSSGGGGSGGGGSGGGGSGGGGSDIQMTQSPSSVSASVGDRVTITCRASQGVGRWLAWYQQKPGTAPKLLIYAASTLQSGVPSRFSGSGSGTDFTLTINNLQPEDFATYYCQQANSFPLTFGGGTRLEIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| 68 | M6<br>>FE10-06ID<br>(M6<br>46FE10-<br>06ID<br>R001-A4<br>126166) | **MALPVTALLLPLALLLHAARP**QVQLVQSGAEVKKPGASVKVSCKASGYTFTSYYMHWVRQ<br>APGQGLEWMGIINPSGGSTSYAQKFQGRVTMTRDTSTSTVYMELSSLRSEDTAVYYCARY<br>RLIAVAGDYYYYGMDVWGQGTMVTVSSGGGGSGGGGSGGGGSGGGGSDIQMTQSPSSVSA<br>SVGDRVTITCRASQGVGRWLAWYQQKPGTAPKLLIYAASTLQSGVPSRFSGSGSGTDFTL<br>TINNLQPEDFATYYCQQANSFPLTFGGGTRLEIKTTTPAPRPPTPAPTIASQPLSLRPEA<br>CRPAAGGAVHTRGLDFACDIYIWAPLAGTCGVLLLSLVITLYCKRGRKKLLYIFKQPFMR<br>PVQTTQEEDGCSCRFPEEEEGGCELRVKFSRSADAPAYKQGQNQLYNELNLGRREEYDVL<br>DKRRGRDPEMGGKPRRKNPQEGLYNELQKDKMAEAYSEIGMKGERRRGKGHDGLYQGLST<br>ATKDTYDALHMQALPPR |
| 45 | M7 (ScFv<br>domain) | QVQLVQSGGGVVQPGRSLRLSCAASGFTFSSYAMHWVRQ<br>APGKGLEWVAVISYDGSNKYYADSVKGRFTISRDNSKNTLYLQMNSLRAEDTAVYYCARW<br>KVSSSSPAFDYWGQGTLVTVSSGGGGSGGGGSGGGGSGGGGSEIVLTQSPATLSLSPGER<br>AILSCRASQSVYTKYLGWYQQKPGQAPRLLIYDASTRATGIPDRFSGSGSGTDFTLTINR<br>LEPEDFAVYYCQHYGGSPLITFGQGTRLEIK |
| 69 | M7<br>>VE12-01CD<br>(M7<br>VE12-01CD<br>R001-A5<br>126167) | **MALPVTALLLPLALLLHAARP**QVQLVQSGGGVVQPGRSLRLSCAASGFTFSSYAMHWVRQ<br>APGKGLEWVAVISYDGSNKYYADSVKGRFTISRDNSKNTLYLQMNSLRAEDTAVYYCARW<br>KVSSSSPAFDYWGQGTLVTVSSGGGGSGGGGSGGGGSGGGGSEIVLTQSPATLSLSPGER<br>AILSCRASQSVYTKYLGWYQQKPGQAPRLLIYDASTRATGIPDRFSGSGSGTDFTLTINR<br>LEPEDFAVYYCQHYGGSPLITFGQGTRLEIKTTTPAPRPPTPAPTIASQPLSLRPEACRP<br>AAGGAVHTRGLDFACDIYIWAPLAGTCGVLLLSLVITLYCKRGRKKLLYIFKQPFMRPVQ<br>TTQEEDGCSCRFPEEEEGGCELRVKFSRSADAPAYKQGQNQLYNELNLGRREEYDVLDKR<br>RGRDPEMGGKPRRKNPQEGLYNELQKDKMAEAYSEIGMKGERRRGKGHDGLYQGLSTATK<br>DTYDALHMQALPPR |
| 46 | M8 (ScFv<br>domain) | QVQLQQSGAEVKKPGASVKVSCKTSGYPFTGYSLHWVRQ<br>APGQGLEWMGWINPNSGGTNYAQKFQGRVTMTRDTSISTAYMELSRLRSDDTAVYYCARD<br>HYGGNSLFYWGQGTLVTVSSGGGGSGGGGSGGGGSGGGGSDIQLTQSPSSISASVGDTVS<br>ITCRASQDSGTWLAWYQQKPGKAPNLLMYDASTLEDGVPSRFSGSASGTEFTLTVNRLQP<br>EDSATYYCQQYNSYPLTFGGGTKVDIK |
| 70 | M8<br>>LE13-05XD<br>(M8<br>LE13-05XD<br>R001-E5<br>126168) | **MALPVTALLLPLALLLHAARP**QVQLQQSGAEVKKPGASVKVSCKTSGYPFTGYSLHWVRQ<br>APGQGLEWMGWINPNSGGTNYAQKFQGRVTMTRDTSISTAYMELSRLRSDDTAVYYCARD<br>HYGGNSLFYWGQGTLVTVSSGGGGSGGGGSGGGGSGGGGSDIQLTQSPSSISASVGDTVS<br>ITCRASQDSGTWLAWYQQKPGKAPNLLMYDASTLEDGVPSRFSGSASGTEFTLTVNRLQP<br>EDSATYYCQQYNSYPLTFGGGTKVDIKTTTPAPRPPTPAPTIASQPLSLRPEACRPAAGG<br>AVHTRGLDFACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYDVLDKRRGRD<br>PEMGGKPRRKNPQEGLYNELQKDKMAEAYSEIGMKGERRRGKGHDGLYQGLSTATKDTYD<br>ALHMQALPPR |
| 47 | M9 (ScFv<br>domain) | QVQLVQSGAEVKKPGASVEVSCKASGYTFTSYYMHWVRQ<br>APGQGLEWMGIINPSGGSTGYAQKFQGRVTMTRDTSTSTVHMELSSLRSEDTAVYYCARG<br>GYSSSSDAFDIWGQGTMVTVSSGGGGSGGGGSGGGGSGGGGSDIQMTQSPPSLSASVGDR<br>VTITCRASQDISSALAWYQQKPGTPPKLLIYDASSLESGVPSRFSGSGSGTDFTLTISSL<br>QPEDFATYYCQQFSSYPLTFGGGTRLEIK |
| 71 | M9<br>>BE15-00SD<br>(M9<br>BE15-00SD<br>R001-A3<br>126169) | **MALPVTALLLPLALLLHAARP**QVQLVQSGAEVKKPGASVEVSCKASGYTFTSYYMHWVRQ<br>APGQGLEWMGIINPSGGSTGYAQKFQGRVTMTRDTSTSTVHMELSSLRSEDTAVYYCARG<br>GYSSSSDAFDIWGQGTMVTVSSGGGGSGGGGSGGGGSGGGGSDIQMTQSPPSLSASVGDR<br>VTITCRASQDISSALAWYQQKPGTPPKLLIYDASSLESGVPSRFSGSGSGTDFTLTISSL<br>QPEDFATYYCQQFSSYPLTFGGGTRLEIKTTTPAPRPPTPAPTIASQPLSLRPEACRPAA<br>GGAVHTRGLDFACDIYIWAPLAGTCGVLLLSLVITLYCKRGRKKLLYIFKQPFMRPVQTT<br>QEEDGCSCRFPEEEEGGCELRVKFSRSADAPAYKQGQNQLYNELNLGRREEYDVLDKRRG<br>RDPEMGGKPRRKNPQEGLYNELQKDKMAEAYSEIGMKGERRRGKGHDGLYQGLSTATKDT<br>YDALHMQALPPR |
| 48 | M10 (ScFv<br>domain) | QVQLVQSGAEVKKPGASVKVSCKASGYTFTSYGISWVRQ<br>APGQGLEWMGWISAYNGNTNYAQKLQGRVTMTTDTSTSTAYMELRSLRSDDTAVYYCARV<br>AGGIYYYYGMDVWGQGTTITVSSGGGGSGGGGSGGGGSGGGGSDIVMTQTPDSLAVSLGE<br>RATISCKSSHSVLYNRNNKNYLAWYQQKPGQPPKLLFYWASTRKSGVPDRFSGSGSGTDF<br>TLTISSLQPEDFATYFCQQTQTFPLTFGQGTRLEIN |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| 72 | M10<br>>RE16-05MD<br>(M10<br>RE16-05MD<br>R001-D10<br>126170) | **MALPVTALLLPLALLLHAARP**QVQLVQSGAEVKKPGASVKVSCKASGYTFTSYGISWVRQ<br>APGQGLEWMGWISAYNGNTNYAQKLQGRVTMTTDTSTSTAYMELRSLRSDDTAVYYCARV<br>AGGIYYYYGMDVWGQGTTITVSSGGGGSGGGGSGGGGSGGGGSDIVMTQTPDSLAVSLGE<br>RATISCKSSHSVLYNRNNKNYLAWYQQKPGQPPKLLFYWASTRKSGVPDRFSGSGSGTDF<br>TLTISSLQPEDFATYFCQQTQTFPLTFGQGTRLEINTTTPAPRPPTPAPTIASQPLSLRP<br>EACRPAAGGAVHTRGLDFACDIYIWAPLAGTCGVLLLSLVITLYCKRGRKKLLYIFKQPF<br>MRPVQTTQEEDGCSCRFPEEEEGGCELRVKFSRSADAPAYKQGQNQLYNELNLGRREEYD<br>VLDKRRGRDPEMGGKPRRKNPQEGLYNELQKDKMAEAYSEIGMKGERRRGKGHDGLYQGL<br>STATKDTYDALHMQALPPR |
| 49 | M11 (ScFv domain) | QVQLQQSGAEVKKPGASVKVSCKASGYTFTGYYMHWVRQ<br>APGQGLEWMGWINPNSGGTNYAQNFQGRVTMTRDTSISTAYMELRRLRSDDTAVYYCASG<br>WDFDYWGQGTLVTVSSGGGGSGGGGSGGGGSGGGGSDIRMTQSPSSLSASVGDRVTITCR<br>ASQSIRYYLSWYQQKPGKAPKLLIYTASILQNGVPSRFSGSGSGTDFTLTISSLQPEDFA<br>TYYCLQTYTTPDFGPGTKVEIK |
| 73 | M11<br>>NE10-19WD<br>(M11<br>NE10-19WD<br>R001-G2<br>126171) | **MALPVTALLLPLALLLHAARP**QVQLQQSGAEVKKPGASVKVSCKASGYTFTGYYMHWVRQ<br>APGQGLEWMGWINPNSGGTNYAQNFQGRVTMTRDTSISTAYMELRRLRSDDTAVYYCASG<br>WDFDYWGQGTLVTVSSGGGGSGGGGSGGGGSGGGGSDIRMTQSPSSLSASVGDRVTITCR<br>ASQSIRYYLSWYQQKPGKAPKLLIYTASILQNGVPSRFSGSGSGTDFTLTISSLQPEDFA<br>TYYCLQTYTTPDFGPGTKVEIKTTTPAPRPPTPAPTIASQPLSLRPEACRPAAGGAVHTR<br>GLDFACDIYIWAPLAGTCGVLLLSLVITLYCKRGRKKLLYIFKQPFMRPVQTTQEEDGCS<br>CRFPEEEEGGCELRVKFSRSADAPAYKQGQNQLYNELNLGRREEYDVLDKRRGRDPEMGG<br>KPRRKNPQEGLYNELQKDKMAEAYSEIGMKGERRRGKGHDGLYQGLSTATKDTYDALHMQ<br>ALPPR |
| 50 | M12 (ScFv domain) | QVQLVQSGAEVKKPGASVKVSCKASGYTFTGYYMHWVRQ<br>APGQGLEWMGRINPNSGGTNYAQKFQGRVTMTTDTSTSTAYMELRSLRSDDTAVYYCART<br>TTSYAFDIWGQGTMVTVSSGGGGSGGGGSGGGGSGGGGSDIQLTQSPSTLSASVGDRVTI<br>TCRASQSISTWLAWYQQKPGKAPNLLIYKASTLESGVPSRFSGSGSGTEFTLTISSLQPD<br>DFATYYCQQYNTYSPYTFGQGTKLEIK |
| 74 | M12<br>>DE12-14RD<br>(M12<br>DE12-14RD<br>R001-G9<br>126172) | **MALPVTALLLPLALLLHAARP**QVQLVQSGAEVKKPGASVKVSCKASGYTFTGYYMHWVRQ<br>APGQGLEWMGRINPNSGGTNYAQKFQGRVTMTTDTSTSTAYMELRSLRSDDTAVYYCART<br>TTSYAFDIWGQGTMVTVSSGGGGSGGGGSGGGGSGGGGSDIQLTQSPSTLSASVGDRVTI<br>TCRASQSISTWLAWYQQKPGKAPNLLIYKASTLESGVPSRFSGSGSGTEFTLTISSLQPD<br>DFATYYCQQYNTYSPYTFGQGTKLEIKTTTPAPRPPTPAPTIASQPLSLRPEACRPAAGG<br>AVHTRGLDFACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYDVLDKRRGRD<br>PEMGGKPRRKNPQEGLYNELQKDKMAEAYSEIGMKGERRRGKGHDGLYQGLSTATKDTYD<br>ALHMQALPPR |
| 51 | M13 (ScFv domain) | QVQLVQSGGGLVKPGGSLRLSCEASGFIFSDYYMGWIRQ<br>APGKGLEWVSYIGRSGSSMYYADSVKGRFTFSRDNAKNSLYLQMNSLRAEDTAVYYCAAS<br>PVVAATEDFQHWGQGTLVTVSSGGGGSGGGGSGGGGSGGGGSDIVMTQTPATLSLSPGER<br>ATLSCRASQSVTSNYLAWYQQKPGQAPRLLLFGASTRATGIPDRFSGSGSGTDFTLTINR<br>LEPEDFAMYYCQQYGSAPVTFGQGTKLEIK |
| 75 | M13<br>>TE13-19LD<br>(M13<br>TE13-19LD<br>R002-C3<br>126173) | **MALPVTALLLPLALLLHAARP**QVQLVQSGGGLVKPGGSLRLSCEASGFIFSDYYMGWIRQ<br>APGKGLEWVSYIGRSGSSMYYADSVKGRFTFSRDNAKNSLYLQMNSLRAEDTAVYYCAAS<br>PVVAATEDFQHWGQGTLVTVSSGGGGSGGGGSGGGGSGGGGSDIVMTQTPATLSLSPGER<br>ATLSCRASQSVTSNYLAWYQQKPGQAPRLLLFGASTRATGIPDRFSGSGSGTDFTLTINR<br>LEPEDFAMYYCQQYGSAPVTFGQGTKLEIKTTTPAPRPPTPAPTIASQPLSLRPEACRPA<br>AGGAVHTRGLDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRREEYDVLDKRR<br>GRDPEMGGKPRRKNPQEGLYNELQKDKMAEAYSEIGMKGERRRGKGHDGLYQGLSTATKD<br>TYDALHMQALPPR |
| 52 | M14 (ScFv domain) | QVQLVQSGAEVRAPGASVKISCKASGFTFRGYYIHWVRQ<br>APGQGLEWMGIINPSGGSRAYAQKFQGRVTMTRDTSTSTVYMELSSLRSDDTAMYYCART<br>ASCGGDCYYLDYWGQGTLVTVSSGGGGSGGGGSGGGGSGGGGSDIQMTQSPPTLSASVGD<br>RVTITCRASENVNIWLAWYQQKPGKAPKLLIYKSSSLASGVPSRFSGSGSGAEFTLTISS<br>LQPDDFATYYCQQYQSYPLTFGGGTKVDIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| 76 | M14<br>>BS83-95ID<br>(M1 4<br>BS83-95ID<br>R001-E8<br>126174) | **MALPVTALLLPLALLLHAARP**QVQLVQSGAEVRAPGASVKISCKASGFTFRGYYIHWVRQ<br>APGQGLEWMGIINPSGGSRAYAQKFQGRVTMTRDTSTSTVYMELSSLRSDDTAMYYCART<br>ASCGGDCYYLDYWGQGTLVTVSSGGGGSGGGGSGGGGSGGGGSDIQMTQSPPTLSASVGD<br>RVTITCRASENVNIWLAWYQQKPGKAPKLLIYKSSSLASGVPSRFSGSGSGAEFTLTISS<br>LQPDDFATYYCQQYQSYPLTFGGGTKVDIKTTTPAPRPPTPAPTIASQPLSLRPEACRPA<br>AGGAVHTRGLDFACDIYIWAPLAGTCGVLLLSLVITLYCKRGRKKLLYIFKQPFMRPVQT<br>TQEEDGCSCRFPEEEEGGCELRVKFSRSADAPAYKQGQNQLYNELNLGRREEYDVLDKRR<br>GRDPEMGGKPRRKNPQEGLYNELQKDKMAEAYSEIGMKGERRRGKGHDGLYQGLSTATKD<br>TYDALHMQALPPR |
| 53 | M15 (ScFv<br>domain) | QVQLVQSGGGLVQPGRSLRLSCAASGFTFDDYAMHWVRQ<br>APGKGLEWVSGISWNSGSIGYADSVKGRFTISRDNAKNSLYLQMNSLRAEDTAVYYCAKD<br>GSSSWSWGYFDYWGQGTLVTVSSGGGGSGGGGSGGGGSSSELTQDPAVSVALGQTVRTTC<br>QGDALRSYYASWYQQKPGQAPMLVIYGKNNRPSGIPDRFSGSDSGDTASLTITGAQAEDE<br>ADYYCNSRDSSGYPVFGTGTKVTVL |
| 77 | M15<br>>HS86-94XD<br>(M15<br>HS86-94XD<br>NT<br>127553) | **MALPVTALLLPLALLLHAARP**QVQLVQSGGGLVQPGRSLRLSCAASGFTFDDYAMHWVRQ<br>APGKGLEWVSGISWNSGSIGYADSVKGRFTISRDNAKNSLYLQMNSLRAEDTAVYYCAKD<br>GSSSWSWGYFDYWGQGTLVTVSSGGGGSGGGGSGGGGSSSELTQDPAVSVALGQTVRTTC<br>QGDALRSYYASWYQQKPGQAPMLVIYGKNNRPSGIPDRFSGSDSGDTASLTITGAQAEDE<br>ADYYCNSRDSSGYPVFGTGTKVTVLTTTPAPRPPTPAPTIASQPLSLRPEACRPAAGGAV<br>HTRGLDFACDIYIWAPLAGTCGVLLLSLVITLYCKRGRKKLLYIFKQPFMRPVQTTQEED<br>GCSCRFPEEEEGGCELRVKFSRSADAPAYKQGQNQLYNELNLGRREEYDVLDKRRGRDPE<br>MGGKPRRKNPQEGLYNELQKDKMAEAYSEIGMKGERRRGKGHDGLYQGLSTATKDTYDAL<br>HMQALPPR |
| 54 | M16 (ScFv<br>domain) | EVQLVESGGGLVQPGRSLRLSCAASGFTFDDYAMHWVRQ<br>APGKGLEWVSGISWNSGSTGYADSVKGRFTISRDNAKNSLYLQMNSLRAEDTALYYCAKD<br>SSSWYGGGSAFDIWGQGTMVTVSSGGGGSGGGGSGGGGSSSELTQEPAVSVALGQTVRIT<br>CQGDSLRSYYASWYQQKPGQAPVLVIFGRSRRPSGIPDRFSGSSSGNTASLIITGAQAED<br>EADYYCNSRDNTANHYVFGTGTKLTVL |
| 78 | M16<br>>XS87-99RD<br>(M16<br>XS87-99RD<br>NT<br>127554) | **MALPVTALLLPLALLLHAARP**EVQLVESGGGLVQPGRSLRLSCAASGFTFDDYAMHWVRQ<br>APGKGLEWVSGISWNSGSTGYADSVKGRFTISRDNAKNSLYLQMNSLRAEDTALYYCAKD<br>SSSWYGGGSAFDIWGQGTMVTVSSGGGGSGGGGSGGGGSSSELTQEPAVSVALGQTVRIT<br>CQGDSLRSYYASWYQQKPGQAPVLVIFGRSRRPSGIPDRFSGSSSGNTASLIITGAQAED<br>EADYYCNSRDNTANHYVFGTGTKLTVLTTTPAPRPPTPAPTIASQPLSLRPEACRPAAGG<br>AVHTRGLDFACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYDVLDKRRGRD<br>PEMGGKPRRKNPQEGLYNELQKDKMAEAYSEIGMKGERRRGKGHDGLYQGLSTATKDTYD<br>ALHMQALPPR |
| 55 | M17 (ScFv<br>domain) | EVQLVESGGGLVQPGRSLRLSCAASGFTFDDYAMHWVRQ<br>APGKGLEWVSGISWNSGSTGYADSVKGRFTISRDNAKNSLYLQMNSLRAEDTALYYCAKD<br>SSSWYGGGSAFDIWGQGTMVTVSSGGGGSGGGGSGGGGSSSELTQDPAVSVALGQTVRIT<br>CQGDSLRSYYASWYQQKPGQAPVLVIYGKNNRPSGIPDRFSGSSSGNTASLTITGAQAED<br>EADYYCNSRGSSGNHYVFGTGTKVTVL |
| 79 | M17<br>>NS89-94MD<br>(M17<br>NS89-94MD<br>NT<br>127555) | **MALPVTALLLPLALLLHAARP**EVQLVESGGGLVQPGRSLRLSCAASGFTFDDYAMHWVRQ<br>APGKGLEWVSGISWNSGSTGYADSVKGRFTISRDNAKNSLYLQMNSLRAEDTALYYCAKD<br>SSSWYGGGSAFDIWGQGTMVTVSSGGGGSGGGGSGGGGSSSELTQDPAVSVALGQTVRIT<br>CQGDSLRSYYASWYQQKPGQAPVLVIYGKNNRPSGIPDRFSGSSSGNTASLTITGAQAED<br>EADYYCNSRGSSGNHYVFGTGTKVTVLTTTPAPRPPTPAPTIASQPLSLRPEACRPAAGG<br>AVHTRGLDFACDIYIWAPLAGTCGVLLLSLVITLYCKRGRKKLLYIFKQPFMRPVQTTQE<br>EDGCSCRFPEEEEGGCELRVKFSRSADAPAYKQGQNQLYNELNLGRREEYDVLDKRRGRD<br>PEMGGKPRRKNPQEGLYNELQKDKMAEAYSEIGMKGERRRGKGHDGLYQGLSTATKDTYD<br>ALHMQALPPR |
| 56 | M18 (ScFv<br>domain) | QVQLVQSGGGLVQPGGSLRLSCAASGFTFSSYWMHWVRQ<br>APGKGLVWVSRINSDGSSTSYADSVKGRFTISRDNAKNTLYLQMNSLRAEDTAVYYCVRT<br>GWVGSYYYYMDVWGKGTTVTVSSGGGGSGGGGSGGGGSGGGGSEIVLTQSPGTLSLSPGE<br>RATLSCRASQSVSSNYLAWYQQKPGQPPRLLIYDVSTRATGIPARFSGGGSGTDFTLTIS<br>SLEPEDFAVYYCQQRSNWPPWTFGQGTKVEIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| 80 | M18 >DS90-09HD (M18 DS90-09HD R003-A05 127556) | **MALPVTALLLPLALLLHAARP**QVQLVQSGGGLVQPGGSLRLSCAASGFTFSSYWMHWVRQAPGKGLVWVSRINSDGSSTSYADSVKGRFTISRDNAKNTLYLQMNSLRAEDTAVYYCVRTGWVGSYYYYMDVWGKGTTVTVSSGGGGSGGGGSGGGGSGGGGSEIVLTQSPGTLSLSPGERATLSCRASQSVSSNYLAWYQQKPGQPPRLLIYDVSTRATGIPARFSGGGSGTDFTLTISSLEPEDFAVYYCQQRSNWPPWTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 57 | M19 (ScFv domain) | QVQLVQSGGGWQPGRSLRLSCAASGFTFSSYGMHWVRQAPGKGLEWVAVISYDGSNKYYADSVKGRFTISRDNSKNTLYLQMNSLRAEDTAVYYCAKGYSRYYYYGMDVWGQGTTVTVSSGGGGSGGGGSGGGGSGGGGSEIVMTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTKVDIK |
| 81 | M19 >TS92-04BD (M19 TS92-04BD R003-C06 127557) | **MALPVTALLLPLALLLHAARP**QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKGYSRYYYYGMDVWGQGTTVTVSSGGGGSGGGGSGGGGSGGGGSEIVMTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 58 | M20 (ScFv domain) | QVQLVQSGGGLVQPGGSLRLSCAASGFTFSSYAMSWVRQAPGKGLEWVSAISGSGGSTYYADSVKGRFTISRDNSKNTLYLQMNSLRAEDTAVYYCAKREAAAGHDWYFDLWGRGTLVTVSSGGGGSGGGGSGGGGSGGGGSDIRVTQSPSSLSASVGDRVTITCRASQSISSYLNWYQQKPGKAPKLLIYAASSLQSGVPSRFSGSGSGTDFTLTISSLQPEDFATYYCQQSYSIPLTFGQGTKVEIK |
| 82 | M20 (full) >JS93-08WD (M20 JS93-08WD R003-E07 127558) | **MALPVTALLLPLALLLHAARP**QVQLVQSGGGLVQPGGSLRLSCAASGFTFSSYAMSWVRQAPGKGLEWVSAISGSGGSTYYADSVKGRFTISRDNSKNTLYLQMNSLRAEDTAVYYCAKREAAAGHDWYFDLWGRGTLVTVSSGGGGSGGGGSGGGGSGGGGSDIRVTQSPSSLSASVGDRVTITCRASQSISSYLNWYQQKPGKAPKLLIYAASSLQSGVPSRFSGSGSGTDFTLTISSLQPEDFATYYCQQSYSIPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 59 | M21 (ScFv domain) | QVQLVQSWAEVKKPGASVKVSCKASGYTFTSYYMHWVRQAPGQGLEWMGIINPSGGSTSYAQKFQGRVTMTRDTSTSTVYMELSNLRSEDTAVYYCARSPRVTTGYFDYWGQGTLVTVSSGGGGSGGGGSGGGGSGGGGSDIQLTQSPSTLSASVGDRVTITCRASQSISSWLAWYQQKPGKAPKLLIYKASSLESGVPSRFSGSGSGTEFTLTISSLQPDDFATYYCQQYSSYPLTFGGGTRLEIK |
| 83 | M21 (full CAR) | **MALPVTALLLPLALLLHAARP**QVQLVQSWAEVKKPGASVKVSCKASGYTFTSYYMHWVRQAPGQGLEWMGIINPSGGSTSYAQKFQGRVTMTRDTSTSTVYMELSNLRSEDTAVYYCARSPRVTTGYFDYWGQGTLVTVSSGGGGSGGGGSGGGGSGGGGSDIQLTQSPSTLSASVGDRVTITCRASQSISSWLAWYQQKPGKAPKLLIYKASSLESGVPSRFSGSGSGTEFTLTISSLQPDDFATYYCQQYSSYPLTFGGGTRLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 60 | M22 (ScFv domain) | QVQLVQSGAEVRRPGASVKISCRASGDTSTRHYIHWLRQAPGQGPEWMGVINPTTGPATGSPAYAQMLQGRVTMTRDTSTRTVYMELRSLRFEDTAVYYCARSVVGRSAPYYFDYWGQGTLVTVSSGGGGSGGGGSGGGGSGGGGSDIQMTQSPSSLSASVGDRVTITCRASQGISDYSAWYQQKPGKAPKLLIYAASTLQSGVPSRFSGSGSGTDFTLTISYLQSEDFATYYCQQYYSYPLTFGGGTKVDIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO | Description | Amino Acid Sequence |
|---|---|---|
| 84 | M22 (full CAR) | **MALPVTALLLPLALLLHAARP**QVQLVQSGAEVRRPGASVKISCRASGDTSTRHYIHWLRQAPGQGPEWMGVINPTTGPATGSPAYAQMLQGRVTMTRDTSTRTVYMELRSLRFEDTAVYYCARSVVGRSAPYYFDYWGQGTLVTVSSGGGGSGGGGSGGGGSGGGGSDIQMTQSPSSLSASVGDRVTITCRASQGISDYSAWYQQKPGKAPKLLIYAASTLQSGVPSRFSGSGSGTDFTLTISYLQSEDFATYYCQQYYSYPLTFGGGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 61 | M23 (ScFv domain) | QVQLQQSGAEVKKPGASVKVSCKASGYTFTNYYMHWVRQAPGQGLEWMGIINPSGGYTTYAQKFQGRLTMTRDTSTSTVYMELSSLRSEDTAVYYCARIRSCGGDCYYFDNWGQGTLVTVSSGGGGSGGGGSGGGGSGGGGSDIQLTQSPSTLSASVGDRVTITCRASENVNIWLAWYQQKPGKAPKLLIYKSSSLASGVPSRFSGSGSGAEFTLTISSLQPDDFATYYCQQYQSYPLTFGGGTKVDIK |
| 85 | M23 (full CAR) | **MALPVTALLLPLALLLHAARP**QVQLQQSGAEVKKPGASVKVSCKASGYTFTNYYMHWVRQAPGQGLEWMGIINPSGGYTTYAQKFQGRLTMTRDTSTSTVYMELSSLRSEDTAVYYCARIRSCGGDCYYFDNWGQGTLVTVSSGGGGSGGGGSGGGGSGGGGSDIQLTQSPSTLSASVGDRVTITCRASENVNIWLAWYQQKPGKAPKLLIYKSSSLASGVPSRFSGSGSGAEFTLTISSLQPDDFATYYCQQYQSYPLTFGGGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 62 | M24 (ScFv domain) | QITLKESGPALVKPTQTLTLTCTFSGFSLSTAGVHVGWIRQPPGKALEWLALISWADDKRYRPSLRSRLDITRVTSKDQVVLSMTNMQPEDTATYYCALQGFDGYEANWGPGTLVTVSSGGGGSGGGGSGGGGSGGGGSDIVMTQSPSSLSASAGDRVTITCRASRGISSALAWYQQKPGKPPKLLIYDASSLESGVPSRFSGSGSGTDFTLTIDSLEPEDFATYYCQQSYSTPWTFGQGTKVDIK |
| 86 | M24 (full CAR) | **MALPVTALLLPLALLLHAARP**QITLKESGPALVKPTQTLTLTCTFSGFSLSTAGVHVGWIRQPPGKALEWLALISWADDKRYRPSLRSRLDITRVTSKDQVVLSMTNMQPEDTATYYCALQGFDGYEANWGPGTLVTVSSGGGGSGGGGSGGGGSGGGGSDIVMTQSPSSLSASAGDRVTITCRASRGISSALAWYQQKPGKPPKLLIYDASSLESGVPSRFSGSGSGTDFTLTIDSLEPEDFATYYCQQSYSTPWTFGQGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 275 | Ss1 (scFv domain) | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSSGGGGSGGGGSGGGGSDIELTQSPAIMSASPGEKVTMTCSASSSVSYMHWYQQKSGTSPKRWIYDTSKLASGVPGRFSGSGSGNSYSLTISSVEAEDDATYYCQQWSGYPLTFGAGTKLEI |
| 278 | Ss1 (full CAR) | **MALPVTALLLPLALLLHAARP**QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSSGGGGSGGGGSGGGGSDIELTQSPAIMSASPGEKVTMTCSASSSVSYMHWYQQKSGTSPKRWIYDTSKLASGVPGRFSGSGSGNSYSLTISSVEAEDDATYYCQQWSGYPLTFGAGTKLEITTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPA |

TABLE 3

Nucleic Acid Sequences encoding CAR molecules (the leader sequence is underlined)

| SEQ ID NO: | Desc. | Nucleic Acid Sequence |
|---|---|---|
| 87 | M1 (ScFv domain) >ZA53-27BC (M1) | CAAGTCCAACTGCAGCAGTCAGGAGCGGAAGTGAAGAAACCAGGAGCGTCAGTCAAAGTGTCGTGCAAGGCTAGCGGCTAC<br>ACCTTCACCGGCTACTA<br>CATGCACTGGGTTCGACAGGCTCCAGGGCAGGGTCTGGAGTGGATGGGCCGCATCAACCCGAATTCCGGTGGGACTAACT<br>ACGCCCAGAAGTTCCAGGGAAGAGTGACCATGACTAGGGACACGTCGATCAGCACTGCGTACATGGAACTGAGCCGCCTG<br>CGGTCCGAGGATACTGCCGTCTACTACTGCGCACGCGGAAGGTACTATGGAATGGACGTGTGGGGCCAAGGGACTATGGT<br>GACTGTGAGCTCGGGAGGGGGAGGCTCCGGTGGCGGGGGATCAGGAGGAGGAGGATCAGGGGGAGGAGGTTCCGAAATTG<br>TCCTCACCCAGAGCCCGGCAACCCTCTCACTTTCCCCGGGAGAGCGCGCAACCATCTCTTGCCGGGCTAGCCAATCCGTG<br>TCGTCCAATTTCGCCTGGTACCAGCAACGGCCGGGACAAGCCCCTAGACTCCTGATCTACGACGCCAGCAACAGAGCGAC<br>TGGAATTCCTCCACGCTTTTCGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACGTTTGGCCAGGGCACCAAGGTGGATATCAAG |
| 111 | M1 (Full) >ZA53-27BC (M1) | ATGGCCCTCCCTGTCACCGCCCTGCTGCTTCCGCTGGCTCTTCTGCTCCACGCCGCTCGGCCCCAAGTCCAACTGCAGCAG<br>TCAGGAGCGGAAGTGAAGAAACCAGGAGCGTCAGTCAAAGTGTCGTGCAAGGCTAGCGGCTACACCTTCACCGGCTACTA<br>CATGCACTGGGTTCGACAGGCTCCAGGGCAGGGTCTGGAGTGGATGGGCCGCATCAACCCGAATTCCGGTGGGACTAACT<br>ACGCCCAGAAGTTCCAGGGAAGAGTGACCATGACTAGGGACACGTCGATCAGCACTGCGTACATGGAACTGAGCCGCCTG<br>CGGTCCGAGGATACTGCCGTCTACTACTGCGCACGCGGAAGGTACTATGGAATGGACGTGTGGGGCCAAGGGACTATGGT<br>GACTGTGAGCTCGGGAGGGGGAGGCTCCGGTGGCGGGGGATCAGGAGGAGGAGGATCAGGGGGAGGAGGTTCCGAAATTG<br>TCCTCACCCAGAGCCCGGCAACCCTCTCACTTTCCCCGGGAGAGCGCGCAACCATCTCTTGCCGGGCTAGCCAATCCGTG<br>TCGTCCAATTTCGCCTGGTACCAGCAACGGCCGGGACAAGCCCCTAGACTCCTGATCTACGACGCCAGCAACAGAGCGAC<br>TGGAATTCCTCCACGCTTTTCGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACGTTTGGCCAGGGCACCAAGGTGGATATCAAGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 88 | M2 (ScFv domain) >FA56-26RC (M2) | CAAGTCCAACTCGTCCAGTCAGGAGCAGAAGTCAAGAAACCAGGTGCTAGCGTGAAAGTGTCGTGCAAGGCGTCGGGATAC<br>ACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATTATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG |
| 112 | M2 (Full) >FA56-26RC (M2) | ATGGCCCTCCCTGTCACCGCCCTGCTGCTTCCGCTGGCTCTTCTGCTCCACGCCGCTCGGCCCCAAGTCCAACTCGTCCAG<br>TCAGGAGCAGAAGTCAAGAAACCAGGTGCTAGCGTGAAAGTGTCGTGCAAGGCGTCGGGATACACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATTATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 89 | M3 (ScFv domain) >VA58-21LC (M3) | CAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGGCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG |

TABLE 3-continued

| Nucleic Acid Sequences encoding CAR molecules (the leader sequence is underlined) | | |
|---|---|---|
| SEQ ID NO: | Desc. | Nucleic Acid Sequence |
| 113 | M3<br>(Full)<br>>VA58-<br>21LC<br>(M3) | ATGGCCCTCCCTGTCACCGCCCTGCTGCTTCCGCTGGCTCTTCTGCTCCACGCCGCTCGGCCCCAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGGCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 90 | M4<br>(ScFv<br>domain)<br>>DP37-<br>07IC<br>(M4) | CAAGTGCAACTCGTTGAA<br>TCAGGTGGAGGTTTGGTGCAACCCGGAGGATCTCTCAGACTGTCGTGTGCGGCGTCCGGGTTCACCTTTTCGTCCTACTG<br>GATGCACTGGGTGCGCCAGGTGCCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGTACCTTCAGATGAATTCACTG<br>CGCGATGACGACACCGCAGTCTACTACTGCGTCGGTGGACACTGGGCGGTCTGGGGACAGGGAACTACGGTGACTGTGTC<br>CAGCGGCGGGGGAGGAAGCGGCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCAGCCAATCCATTAGCGACCGG<br>CTTGCCTGGTACCAACAGAAACCTGGAAAGGCCCCGAAGCTGCTCATCTACAAGGCCTCGTCACTGGAGTCGGGAGTCCC<br>GTCCCGCTTTTCCGGCTCGGGCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCGAAATCAAG |
| 114 | M4<br>>DP37-<br>07IC<br>(M4) | ATGGCCCTCCCTGTCACCGCCCTGCTGCTTCCGCTGGCTCTTCTGCTCCACGCCGCTCGGCCCCAAGTGCAACTCGTTGAA<br>TCAGGTGGAGGTTTGGTGCAACCCGGAGGATCTCTCAGACTGTCGTGTGCGGCGTCCGGGTTCACCTTTTCGTCCTACTG<br>GATGCACTGGGTGCGCCAGGTGCCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGTACCTTCAGATGAATTCACTG<br>CGCGATGACGACACCGCAGTCTACTACTGCGTCGGTGGACACTGGGCGGTCTGGGGACAGGGAACTACGGTGACTGTGTC<br>CAGCGGCGGGGGAGGAAGCGGCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCAGCCAATCCATTAGCGACCGG<br>CTTGCCTGGTACCAACAGAAACCTGGAAAGGCCCCGAAGCTGCTCATCTACAAGGCCTCGTCACTGGAGTCGGGAGTCCC<br>GTCCCGCTTTTCCGGCTCGGGCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCGAAATCAAG**ACCACTACC**CCA<br>GCACCGAGGCCACCCACCCCGGCTCCTACCATCGCCTCCCAGCCTCTGTCCCTGCGTCCGGAGGCATGTAGACCCGCAGC<br>TGGTGGGGCCGTGCATACCCGGGGTCTTGACTTCGCCTGCGATATCTACATTTGGGCCCCTCTGGCTGGTACTTGCGGGG<br>TCCTGCTGCTTTCACTCGTGATCACTCTTTACTGTAAGCGCGGTCGGAAGAAGCTGCTGTACATCTTTAAGCAACCCTTC<br>ATGAGGCCTGTGCAGACTACTCAAGAGGAGGACGGCTGTTCATGCCGGTTCCCAGAGGAGGAGGAAGGCGGCTGCGAACT<br>GCGCGTGAAATTCAGCCGCAGCGCAGATGCTCCAGCCTACAAGCAGGGGCAGAACCAGCTCTACAACGAACTCAATCTTG<br>GTCGGAGAGAGGAGTACGACGTGCTGGACAAGCGGAGAGGACGGGACCCAGAAATGGGCGGGAAGCCGCGCAGAAAGAAT<br>CCCCAAGAGGGCCTGTACAACGAGCTCCAAAAGGATAAGATGGCAGAAGCCTATAGCGAGATTGGTATGAAAGGGGAACG<br>CAGAAGAGGCAAAGGCCACGACGGACTGTACCAGGGACTCAGCACCGCCACCAAGGACACCTATGACGCTCTTCACATGC<br>AGGCCCTGCCGCCTCGG |
| 91 | M5<br>(ScFv<br>domain)<br>>XP31-<br>20LC<br>(M5) | CAAGTCCAACTCGTTCAATCAGGCGCAGAAGTCGAAAAGCCCGGAGCATCAGTCAAAGTCTCTTGCAAGGCTTCCGGCTAC<br>ACCTTCACGGACTACTAC<br>ATGCACTGGGTGCGCCAGGCTCCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTACATGGAGCTCAGCCGCCTCC<br>GGTCGGACGATACCGCCGTGTACTATTGTGCGTCGGGATGGGACTTCGACTACTGGGGGCAGGGCACTCTGGTCACTGTG<br>TCAAGCGGAGGAGGTGGATCAGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGCGTCCCAGTCCATTCGGTACT<br>ACCTGTCGTGGTACCAGCAGAAGCCGGGGAAAGCCCCAAAACTGCTTATCTATACTGCCTCGATCCTCCAAAACGGCGTG<br>CCATCAAGATTCAGCGGTTCGGGCAGCGGGACCGACTTTACCCTGACTATCAGCAGCCTGCAGCCGGAAGATTTCGCCAC<br>GTACTACTGCCTGCAAACCTACACCACCCCCGGACTTCGGACCTGGAACCAAGGTGGAGATCAAG |
| 115 | M5<br>(Full)<br>>XP31-<br>20LC<br>(M5) | ATGGCCCTCCCTGTCACCGCCCTGCTGCTTCCGCTGGCTCTTCTGCTCCACGCCGCTCGGCCCCAAGTCCAACTCGTTCAA<br>TCAGGCGCAGAAGTCGAAAAGCCCGGAGCATCAGTCAAAGTCTCTTGCAAGGCTTCCGGCTACACCTTCACGGACTACTAC<br>ATGCACTGGGTGCGCCAGGCTCCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTACATGGAGCTCAGCCGCCTCC<br>GGTCGGACGATACCGCCGTGTACTATTGTGCGTCGGGATGGGACTTCGACTACTGGGGGCAGGGCACTCTGGTCACTGTG<br>TCAAGCGGAGGAGGTGGATCAGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGCGTCCCAGTCCATTCGGTACT<br>ACCTGTCGTGGTACCAGCAGAAGCCGGGGAAAGCCCCAAAACTGCTTATCTATACTGCCTCGATCCTCCAAAACGGCGTG<br>CCATCAAGATTCAGCGGTTCGGGCAGCGGGACCGACTTTACCCTGACTATCAGCAGCCTGCAGCCGGAAGATTTCGCCAC<br>GTACTACTGCCTGCAAACCTACACCACCCCCGGACTTCGGACCTGGAACCAAGGTGGAGATCAAG**ACCACTACC**CCAGCAC<br>CGAGGCCACCCACCCCGGCTCCTACCATCGCCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTGGGCCCCTCTGGCTGGTACTTGCGGGGTCCT |

TABLE 3-continued

Nucleic Acid Sequences encoding CAR molecules (the leader sequence is underlined)

| SEQ ID NO: | Desc. | Nucleic Acid Sequence |
|---|---|---|
| | | GCTGCTTTCACTCGTGATCACTCTTTACTGTAAGCGCGGTCGGAAGAAGCTGCTGTACATCTTTAAGCAACCCTTCATGA<br>GGCCTGTGCAGACTACTCAAGAGGAGGACGGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAACCAGCTCTACAACGAACTCAATCTTGGTCG<br>GAGAGAGGAGTACGACGTGCTGGACAAGCGGAGAGGACGGGACCCAGAAATGGGCGGGAAGCCGCGCAGAAAGAATCCCC<br>AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 92 | M6 (ScFv domain) >FE10-06ID (M6) | CAAGTGCAACTCGTCCAGTCAGGTGCAGAAGTGAAGAAACCCGGAGCGTCAGTCAAAGTGTCATGCAAGGCGTCAGGCTAC<br>ACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG |
| 116 | M6 (Full) >FE10-06ID (M6) | ATGGCCCTCCCTGTCACCGCCCTGCTGCTTCCGCTGGCTCTTCTGCTCCACGCCGCTCGGCCCCAAGTGCAACTCGTCCAG<br>TCAGGTGCAGAAGTGAAGAAACCCGGAGCGTCAGTCAAAGTGTCATGCAAGGCGTCAGGCTACACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 93 | M7 (ScFv domain) >VE12 01CD (M7) | CAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG |
| 117 | M7 (Full) >VE12-01CD (M7) | ATGGCCCTCCCTGTCACCGCCCTGCTGCTTCCGCTGGCTCTTCTGCTCCACGCCGCTCGGCCCCAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG**ACCACTACC**CCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |

TABLE 3-continued

Nucleic Acid Sequences encoding CAR molecules (the leader sequence is underlined)

| SEQ ID NO: | Desc. | Nucleic Acid Sequence |
|---|---|---|
| 94 | M8<br>(ScFv<br>domain)<br>>LE13-<br>05XD<br>(M8) | CAAGTCCAACTCCAGCAG<br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG |
| 118 | M8<br>(Full)<br>>LE13-<br>05XD<br>(M8) | ATGGCCCTCCCTGTCACCGCCCTGCTGCTTCCGCTGGCTCTTCTGCTCCACGCCGCTCGGCCCCAAGTCCAACTCCAGCAG<br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 95 | M9<br>(ScFv<br>domain)<br>>BE15-<br>00SD<br>(M9) | CAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG |
| 119 | M9<br>(Full)<br>>BE15-<br>00SD<br>(M9) | ATGGCCCTCCCTGTCACCGCCCTGCTGCTTCCGCTGGCTCTTCTGCTCCACGCCGCTCGGCCCCAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG**ACCACTACC**CCAGCACCGAGGCCACCCACCCCGGCTCCTACCATCGCCTCCCAGCCTCTGTCCCTGCGTCCGGA<br>GGCATGTAGACCCGCAGCTGGTGGGGCCGTGCATACCCGGGGTCTTGACTTCGCCTGCGATATCTACATTTGGGCCCCTCT<br>GGCTGGTACTTGCGGGGTCCTGCTGCTTTCACTCGTGATCACTCTTTACTGTAAGCGCGGTCGGAAGAAGCTGCTGTAC<br>ATCTTTAAGCAACCCTTCATGAGGCCTGTGCAGACTACTCAAGAGGAGGACGGCTGTTCATGCCGGTTCCCAGAGGAGGA<br>GGAAGGCGGCTGCGAACTGCGCGTGAAATTCAGCCGCAGCGCAGATGCTCCAGCCTACAAGCAGGGGCAGAACCAGCTCT<br>ACAACGAACTCAATCTTGGTCGGAGAGAGGAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAGGATAAGATGGCAGAAGCCTATAGCGAGAT<br>TGGTATGAAAGGGGAACGCAGAAGAGGCAAAGGCCACGACGGACTGTACCAGGGACTCAGCACCGCCACCAAGGACACCT<br>ATGACGCTCTTCACATGCAGGCCCTGCCGCCTCGG |
| 96 | M10<br>(ScFv<br>domain)<br>>RE16-<br>05MD<br>(M10) | CAAGTGCAACTCGTCCAGAGCGGAGCAGAAGTCAAGAAGCCAGGAGCGTCAGTGAAAGTGTCATGCAAGGCCAGCGGCTAT<br>ACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATCTACTACTACTACGGCATGGACGTCTGGGGA<br>CAGGGAACCACCATTACGGTGTCGAGCGGAGGGGGAGGCTCGGGGGGAGGAGGAAGCGGAGGTGGCGGCTCCGGGGGCGG<br>CGGATCGGACATTGTGATGACCCAGACTCCTGACTCCCTGGCTGTTTCGTTGGGAGAGCGCGCGACTATCTCGTGTAAGT<br>CCAGCCACTCAGTCCTGTACAATCGCAATAACAAGAACTACCTCGCGTGGTACCAGCAAAAACCGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT |

TABLE 3-continued

Nucleic Acid Sequences encoding CAR molecules (the leader sequence is underlined)

| SEQ ID NO: | Desc. | Nucleic Acid Sequence |
|---|---|---|
| 120 | M10 (Full) >RE16-05MD (M10) | ATGGCCCTCCCTGTCACCGCCCTGCTGCTTCCGCTGGCTCTTCTGCTCCACGCCGCTCGGCCCCAAGTGCAACTCGTCCAG<br>AGCGGAGCAGAAGTCAAGAAGCCAGGAGCGTCAGTGAAAGTGTCATGCAAGGCCAGCGGCTATACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATCTACTACTACTACGGCATGGACGTCTGGGGA<br>CAGGGAACCACCATTACGGTGTCGAGCGGAGGGGGAGGCTCGGGGGGAGGAGGAAGCGGAGGTGGCGGCTCCGGGGGCGG<br>CGGATCGGACATTGTGATGACCCAGACTCCTGACTCCCTGGCTGTTTCGTTGGGAGAGCGCGCGACTATCTCGTGTAAGT<br>CCAGCCACTCAGTCCTGTACAATCGCAATAACAAGAACTACCTCGCGTGGTACCAGCAAAAACCGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT**ACCACTACC**CCAGCACCGAGGCCACCCACCCCGGCTCCTACCATCGCCTCCCAG<br>CCTCTGTCCCTGCGTCCGGAGGCATGTAGACCCGCAGCTGGTGGGGCCGTGCATACCCGGGGTCTTGACTTCGCCTGCGA<br>TATCTACATTTGGGCCCCTCTGGCTGGTACTTGCGGGGTCCTGCTGCTTTCACTCGTGATCACTCTTTACTGTAAGCGCG<br>GTCGGAAGAAGCTGCTGTACATCTTTAAGCAACCCTTCATGAGGCCTGTGCAGACTACTCAAGAGGAGGACGGCTGTTCA<br>TGCCGGTTCCCAGAGGAGGAGGAAGGCGGCTGCGAACTGCGCGTGAAATTCAGCCGCAGCGCAGATGCTCCAGCCTACAA<br>GCAGGGGCAGAACCAGCTCTACAACGAACTCAATCTTGGTCGGAGAGAGGAGTACGACGTGCTGGACAAGCGGAGAGGAC<br>GGGACCCAGAAATGGGCGGGAAGCCGCGCAGAAAGAATCCCCAAGAGGGCCTGTACAACGAGCTCCAAAAGGATAAGATG<br>GCAGAAGCCTATAGCGAGATTGGTATGAAAGGGGAACGCAGAAGAGGCAAAGGCCACGACGGACTGTACCAGGGACTCAG<br>CACCGCCACCAAGGACACCTATGACGCTCTTCACATGCAGGCCCTGCCGCCTCGG |
| 97 | M11 (ScFv domain) >NE10-19WD (M11) | CAAGTCCAATTGCAGCAGAGCGGAGCAGAAGTGAAGAAGCCAGGAGCGTCAGTCAAAGTGTCGTGTAAGGCGTCAGGATAC<br>ACCTTCACGGGATACTAC<br>ATGCACTGGGTGCGCCAGGCCCCGGGCCAAGGACTCGAGTGGATGGGCTGGATCAACCCTAACTCTGGAGGCACCAACTA<br>CGCCCAGAATTTCCAAGGCAGAGTGACCATGACCCGGGACACCTCCATCTCGACTGCCTATATGGAACTGCGGCGGCTGC<br>GCTCGGACGATACTGCTGTGTATTACTGCGCCAGCGGCTGGGACTTTGACTACTGGGGACAGGGTACTCTGGTGACTGTT<br>TCCTCGGGAGGAGGCGGATCGGGTGGAGGAGGTAGCGGGGGAGGGGGGTCGGGAGGCGGAGGCAGCGATATTCGCATGAC<br>TCAATCGCCGTCCTCCCTGAGCGCTAGCGTGGGAGATCGAGTCACCATCACTTGCAGAGCGTCACAGTCGATTCGCTACT<br>ACCTGTCCTGGTACCAGCAGAAACCGGGAAAGGCACCAAAGCTTCTGATCTACACGGCCTCCATCCTGCAAAATGGTGTC<br>CCATCAAGGTTCTCCGGGTCAGGGAGCGGCACTGACTTCACTCTCACCATCTCCTCACTCCAGCCCGAGGACTTTGCAAC<br>CTACTACTGCCTCCAGACGTACACCACCCCGGATTTCGGTCCTGGAACCAAGGTGGAAATCAAA |
| 121 | M11 (Full) >NE10-19WD (M11) | ATGGCCCTCCCTGTCACCGCCCTGCTGCTTCCGCTGGCTCTTCTGCTCCACGCCGCTCGGCCCCAAGTCCAATTGCAGCAG<br>AGCGGAGCAGAAGTGAAGAAGCCAGGAGCGTCAGTCAAAGTGTCGTGTAAGGCGTCAGGATACACCTTCACGGGATACTAC<br>ATGCACTGGGTGCGCCAGGCCCCGGGCCAAGGACTCGAGTGGATGGGCTGGATCAACCCTAACTCTGGAGGCACCAACTA<br>CGCCCAGAATTTCCAAGGCAGAGTGACCATGACCCGGGACACCTCCATCTCGACTGCCTATATGGAACTGCGGCGGCTGC<br>GCTCGGACGATACTGCTGTGTATTACTGCGCCAGCGGCTGGGACTTTGACTACTGGGGACAGGGTACTCTGGTGACTGTT<br>TCCTCGGGAGGAGGCGGATCGGGTGGAGGAGGTAGCGGGGGAGGGGGGTCGGGAGGCGGAGGCAGCGATATTCGCATGAC<br>TCAATCGCCGTCCTCCCTGAGCGCTAGCGTGGGAGATCGAGTCACCATCACTTGCAGAGCGTCACAGTCGATTCGCTACT<br>ACCTGTCCTGGTACCAGCAGAAACCGGGAAAGGCACCAAAGCTTCTGATCTACACGGCCTCCATCCTGCAAAATGGTGTC<br>CCATCAAGGTTCTCCGGGTCAGGGAGCGGCACTGACTTCACTCTCACCATCTCCTCACTCCAGCCCGAGGACTTTGCAAC<br>CTACTACTGCCTCCAGACGTACACCACCCCGGATTTCGGTCCTGGAACCAAGGTGGAAATCAAA**ACCACTACC**CCAGCAC<br>CGAGGCCACCCACCCCGGCTCCTACCATCGCCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTGGGCCCCTCTGGCTGGTACTTGCGGGGTCCT<br>GCTGCTTTCACTCGTGATCACTCTTTACTGTAAGCGCGGTCGGAAGAAGCTGCTGTACATCTTTAAGCAACCCTTCATGA<br>GGCCTGTGCAGACTACTCAAGAGGAGGACGGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAACCAGCTCTACAACGAACTCAATCTTGGTCG<br>GAGAGAGGAGTACGACGTGCTGGACAAGCGGAGAGGACGGGACCCAGAAATGGGCGGGAAGCCGCGCAGAAAGAATCCCC<br>AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 98 | M12 (ScFv domain) >DE12-14RD (M12) | CAAGTCCAACTCGTCCAA<br>AGCGGAGCAGAAGTCAAAAAGCCAGGAGCGTCGGTGAAAGTGTCTTGCAAAGCCAGCGGCTACACCTTCACGGGTTACTA<br>CATGCACTGGGTGCGCCAGGCGCCGGGCCAGGGGCTGGAGTGGATGGGCCGGATTAACCCTAACAGCGGGGGAACTAATT<br>ACGCTCAGAAGTTCCAGGGTAGAGTCACCATGACTACGGACACTTCCACTTCCACCGCCTATATGGAACTGCGCTCCCTC<br>CGCTCAGATGATACTGCCGTGTATTACTGCGCGCGGACTACCACGTCATACGCATTTGACATCTGGGGCCAGGGAACTAT<br>GGTGACCGTGAGCTCGGGCGGAGGCGGTTCAGGGGGAGGAGGAAGCGGAGGAGGAGGATCGGGAGGAGGTGGCTCCGATA<br>TCCAGCTGACTCAGTCCCCGAGCACCCTGTCGGCGTCGGTGGGGGACAGGGTTACCATCACCTGTAGAGCTTCCCAATCC<br>ATTTCGACTTGGCTGGCCTGGTACCAGCAAAAGCCGGGAAAGGCCCCTAATTTGCTTATCTACAAGGCATCGACCCTCGA<br>AAGCGGTGTGCCCTCCCGGTTTTCGGGATCAGGATCAGGGACCGAGTTCACCCTGACCATCTCATCCCTCCAGCCGGACG<br>ACTTCGCCACTTACTACTGCCAGCAGTACAACACCTACTCGCCATACACTTTCGGCCAAGGCACCAAGCTGGAGATCAAG |
| 122 | M12 (Full) >DE12-14RD (M12) | ATGGCCCTCCCTGTCACCGCCCTGCTGCTTCCGCTGGCTCTTCTGCTCCACGCCGCTCGGCCCCAAGTCCAACTCGTCCAA<br>AGCGGAGCAGAAGTCAAAAAGCCAGGAGCGTCGGTGAAAGTGTCTTGCAAAGCCAGCGGCTACACCTTCACGGGTTACTA<br>CATGCACTGGGTGCGCCAGGCGCCGGGCCAGGGGCTGGAGTGGATGGGCCGGATTAACCCTAACAGCGGGGGAACTAATT<br>ACGCTCAGAAGTTCCAGGGTAGAGTCACCATGACTACGGACACTTCCACTTCCACCGCCTATATGGAACTGCGCTCCCTC<br>CGCTCAGATGATACTGCCGTGTATTACTGCGCGCGGACTACCACGTCATACGCATTTGACATCTGGGGCCAGGGAACTAT<br>GGTGACCGTGAGCTCGGGCGGAGGCGGTTCAGGGGGAGGAGGAAGCGGAGGAGGAGGATCGGGAGGAGGTGGCTCCGATA<br>TCCAGCTGACTCAGTCCCCGAGCACCCTGTCGGCGTCGGTGGGGGACAGGGTTACCATCACCTGTAGAGCTTCCCAATCC<br>ATTTCGACTTGGCTGGCCTGGTACCAGCAAAAGCCGGGAAAGGCCCCTAATTTGCTTATCTACAAGGCATCGACCCTCGA<br>AAGCGGTGTGCCCTCCCGGTTTTCGGGATCAGGATCAGGGACCGAGTTCACCCTGACCATCTCATCCCTCCAGCCGGACG<br>ACTTCGCCACTTACTACTGCCAGCAGTACAACACCTACTCGCCATACACTTTCGGCCAAGGCACCAAGCTGGAGATCAAG<br>**ACCACTACC**CCAGCACCGAGGCCACCCACCCCGGCTCCTACCATCGCCTCCCAGCCTCTGTCCCTGCGTCCGGAGGCATG |

TABLE 3-continued

Nucleic Acid Sequences encoding CAR molecules (the leader sequence is underlined)

| SEQ ID NO: | Desc. | Nucleic Acid Sequence |
|---|---|---|
| | | TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 99 | M13 (ScFv domain) >TE13-19LD (M13) | CAAGTTCAACTCGTGCAATCAGGTGGAGGACTCGTCAAACCCGGAGGATCATTGAGACTGTCATGCGAAGCGAGCGGTTTT<br>ATCTTCTCCGATTACTAT<br>ATGGGATGGATTCGGCAGGCCCCGGGAAAGGGACTCGAATGGGTGTCATACATCGGAAGGTCAGGCTCGTCCATGTACTA<br>CGCAGACTCGGTGAAAGGCAGATTCACCTTTAGCCGGGACAACGCCAAGAATTCCCTCTACTTGCAGATGAACAGCCTGC<br>GAGCCGAGGATACTGCTGTCTACTACTGTGCCGCGTCGCCGGTGGTGGCAGCTACTGAAGATTTCCAGCACTGGGGACAG<br>GGAACTCTGGTCACGGTGTCGAGCGGTGGGGGCGGAAGCGGAGGCGGAGGATCGGGCGGCGGAGGTTCGGGGGGGGGAGG<br>GTCTGACATCGTGATGACCCAAACCCCAGCCACCCTGAGCCTCTCCCCTGGAGAGCGCGCGACTCTTTCGTGCCGCGCTT<br>CCCAGTCAGTGACCAGCAATTACTTGGCTTGGTACCAACAGAAGCCGGGACAGGCGCCACGGCTGCTGCTTTTTGGTGCC<br>AGCACTCGCGCCACCGGAATCCCGGATCGCTTCTCGGGCTCAGGGTCCGGGACGGACTTCACCCTGACTATCAACCGGCT<br>GGAACCTGAGGACTTCGCGATGTACTACTGCCAGCAGTACGGCTCCGCACCAGTCACTTTCGGACAAGGCACCAAGCTGG<br>AGATCAAG |
| 123 | M13 (Full) >TE13-19LD (M13) | ATGGCCCTCCCTGTCACCGCCCTGCTGCTTCCGCTGGCTCTTCTGCTCCACGCCGCTCGGCCCCAAGTTCAACTCGTGCAA<br>TCAGGTGGAGGACTCGTCAAACCCGGAGGATCATTGAGACTGTCATGCGAAGCGAGCGGTTTTATCTTCTCCGATTACTAT<br>ATGGGATGGATTCGGCAGGCCCCGGGAAAGGGACTCGAATGGGTGTCATACATCGGAAGGTCAGGCTCGTCCATGTACTA<br>CGCAGACTCGGTGAAAGGCAGATTCACCTTTAGCCGGGACAACGCCAAGAATTCCCTCTACTTGCAGATGAACAGCCTGC<br>GAGCCGAGGATACTGCTGTCTACTACTGTGCCGCGTCGCCGGTGGTGGCAGCTACTGAAGATTTCCAGCACTGGGGACAG<br>GGAACTCTGGTCACGGTGTCGAGCGGTGGGGGCGGAAGCGGAGGCGGAGGATCGGGCGGCGGAGGTTCGGGGGGGGGAGG<br>GTCTGACATCGTGATGACCCAAACCCCAGCCACCCTGAGCCTCTCCCCTGGAGAGCGCGCGACTCTTTCGTGCCGCGCTT<br>CCCAGTCAGTGACCAGCAATTACTTGGCTTGGTACCAACAGAAGCCGGGACAGGCGCCACGGCTGCTGCTTTTTGGTGCC<br>AGCACTCGCGCCACCGGAATCCCGGATCGCTTCTCGGGCTCAGGGTCCGGGACGGACTTCACCCTGACTATCAACCGGCT<br>GGAACCTGAGGACTTCGCGATGTACTACTGCCAGCAGTACGGCTCCGCACCAGTCACTTTCGGACAAGGCACCAAGCTGG<br>AGATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 100 | M14 (ScFv domain) >BS83-95ID (M14) | CAAGTCCAACTCGTCCAGTCGGGAGCAGAAGTTAGAGCACCAGGAGCGTCAGTGAAAATCTCATGCAAGGCCTCGGGCTTC<br>ACGTTCCGCGGATACTAC<br>ATCCACTGGGTGCGCCAAGCCCCGGGTCAGGGATTGGAGTGGATGGGAATCATTAACCCATCAGGAGGGAGCCGGGCTTA<br>CGCGCAGAAGTTCCAGGGACGCGTCACTATGACCCGAGATACTTCCACCTCGACTGTGTACATGGAACTCTCGTCCCTGA<br>GGTCCGACGACACTGCGATGTATTACTGTGCTCGGACTGCCAGCTGCGGTGGGGACTGTTACTACCTCGATTACTGGGGC<br>CAGGGAACTCTGGTGACCGTGTCCAGCGGAGGTGGCGGGTCAGGGGGTGGCGGAAGCGGAGGCGGCGGTTCAGGCGGAGG<br>AGGCTCGGACATCCAAATGACGCAATCGCCGCCTACCCTGAGCGCTTCCGTGGGAGATCGGGTGACCATTACTTGCAGAG<br>CATCCGAGAACGTCAATATCTGGCTGGCCTGGTACCAACAGAAGCCGGGGAAGGCCCCTAAACTGCTGATCTACAAGTCG<br>AGCAGCCTTGCCTCTGGAGTGCCCTCCCGCTTCTCGGGCTCGGGATCAGGAGCGGAATTCACCCTCACCATCTCCTCCCT<br>GCAGCCAGATGACTTTGCCACCTACTACTGCCAGCAGTACCAGAGCTATCCGTTGACCTTTGGGGGAGGCACTAAAGTGG<br>ACATCAAG |
| 124 | M14 (Full) >BS83-95ID (M14) | ATGGCCCTCCCTGTCACCGCCCTGCTGCTTCCGCTGGCTCTTCTGCTCCACGCCGCTCGGCCCCAAGTCCAACTCGTCCAG<br>TCGGGAGCAGAAGTTAGAGCACCAGGAGCGTCAGTGAAAATCTCATGCAAGGCCTCGGGCTTCACGTTCCGCGGATACTAC<br>ATCCACTGGGTGCGCCAAGCCCCGGGTCAGGGATTGGAGTGGATGGGAATCATTAACCCATCAGGAGGGAGCCGGGCTTA<br>CGCGCAGAAGTTCCAGGGACGCGTCACTATGACCCGAGATACTTCCACCTCGACTGTGTACATGGAACTCTCGTCCCTGA<br>GGTCCGACGACACTGCGATGTATTACTGTGCTCGGACTGCCAGCTGCGGTGGGGACTGTTACTACCTCGATTACTGGGGC<br>CAGGGAACTCTGGTGACCGTGTCCAGCGGAGGTGGCGGGTCAGGGGGTGGCGGAAGCGGAGGCGGCGGTTCAGGCGGAGG<br>AGGCTCGGACATCCAAATGACGCAATCGCCGCCTACCCTGAGCGCTTCCGTGGGAGATCGGGTGACCATTACTTGCAGAG<br>CATCCGAGAACGTCAATATCTGGCTGGCCTGGTACCAACAGAAGCCGGGGAAGGCCCCTAAACTGCTGATCTACAAGTCG<br>AGCAGCCTTGCCTCTGGAGTGCCCTCCCGCTTCTCGGGCTCGGGATCAGGAGCGGAATTCACCCTCACCATCTCCTCCCT<br>GCAGCCAGATGACTTTGCCACCTACTACTGCCAGCAGTACCAGAGCTATCCGTTGACCTTTGGGGGAGGCACTAAAGTGG<br>ACATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |

TABLE 3-continued

Nucleic Acid Sequences encoding CAR molecules (the leader sequence is underlined)

| SEQ ID NO: | Desc. | Nucleic Acid Sequence |
|---|---|---|
| 101 | M15 (ScFv domain) >HS86-94XD (M15) | CAAGTTCAACTCGTTCAA<br>TCAGGTGGAGGACTCGTGCAACCAGGAAGATCACTCAGACTCAGCTGCGCCGCGTCGGGATTCACTTTCGATGACTACGC<br>AATGCACTGGGTGCGGCAGGCCCCGGGCAAAGGACTGGAATGGGTGAGCGGAATTAGCTGGAACTCGGGGTCCATCGGGT<br>ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGGACGCGCTGCGCTCG<br>TACTACGCTTCATGGTACCAGCAGAAGCCCGGACAGGCACCTATGCTGGTCATCTACGGAAAGAATAACCGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTG |
| 125 | M15 (Full) >HS86-94XD (M15) | ATGGCCCTCCCTGTCACCGCCCTGCTGCTTCCGCTGGCTCTTCTGCTCCACGCCGCTCGGCCCCAAGTTCAACTCGTTCAA<br>TCAGGTGGAGGACTCGTGCAACCAGGAAGATCACTCAGACTCAGCTGCGCCGCGTCGGGATTCACTTTCGATGACTACGC<br>AATGCACTGGGTGCGGCAGGCCCCGGGCAAAGGACTGGAATGGGTGAGCGGAATTAGCTGGAACTCGGGGTCCATCGGGT<br>ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGGACGCGCTGCGCTCG<br>TACTACGCTTCATGGTACCAGCAGAAGCCCGGACAGGCACCTATGCTGGTCATCTACGGAAAGAATAACCGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 102 | M16 (ScFv domain) >XS87-99RD (M16) | GAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG |
| 126 | M16 (Full) >XS87-99RD (M16) | ATGGCCCTCCCTGTCACCGCCCTGCTGCTTCCGCTGGCTCTTCTGCTCCACGCCGCTCGGCCCGAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 103 | M17 (ScFv domain) >NS89-94MD (M17) | GAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG |

TABLE 3-continued

Nucleic Acid Sequences encoding CAR molecules (the leader sequence is underlined)

| SEQ ID NO: | Desc. | Nucleic Acid Sequence |
|---|---|---|
| 127 | M17 (Full) >NS89-94MD (M17) | ATGGCCCTCCCTGTCACCGCCCTGCTGCTTCCGCTGGCTCTTCTGCTCCACGCCGCTCGGCCCGAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 104 | M18 (ScFv domain) >DS90-09HD (M18) | CAAGTGCAGCTCGTTCAATCAGGCGGAGGACTCGTTCAACCAGGAGGATCATTGCGACTCTCATGTGCGGCCTCTGGATTC<br>ACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACTACATGGACGTGTGGGGC<br>AAAGGAACTACTGTCACCGTGTCAAGCGGCGGTGGAGGTTCCGGCGGGGGAGGATCGGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG |
| 128 | M18 (Full) >DS90-09HD (M18) | ATGGCCCTCCCTGTCACCGCCCTGCTGCTTCCGCTGGCTCTTCTGCTCCACGCCGCTCGGCCCCAAGTGCAGCTCGTTCAA<br>TCAGGCGGAGGACTCGTTCAACCAGGAGGATCATTGCGACTCTCATGTGCGGCCTCTGGATTCACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACTACATGGACGTGTGGGGC<br>AAAGGAACTACTGTCACCGTGTCAAGCGGCGGTGGAGGTTCCGGCGGGGGAGGATCGGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG**ACCACTACC**CCAGCACCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGGTCTTGACTTCGCCTGCGATATCTACATTTG<br>GGCCCCTCTGGCTGGTACTTGCGGGGTCCTGCTGCTTTCACTCGTGATCACTCTTTACTGTAAGCGCGGTCGGAAGAAGC<br>TGCTGTACATCTTTAAGCAACCCTTCATGAGGCCTGTGCAGACTACTCAAGAGGAGGACGGCTGTTCATGCCGGTTCCCA<br>GAGGAGGAGGAAGGCGGCTGCGAACTGCGCGTGAAATTCAGCCGCAGCGCAGATGCTCCAGCCTACAAGCAGGGGCAGAA<br>CCAGCTCTACAACGAACTCAATCTTGGTCGGAGAGAGGAGTACGACGTGCTGGACAAGCGGAGAGGACGGGACCCAGAAA<br>TGGGCGGGAAGCCGCGCAGAAAGAATCCCCAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGACTGTACCAGGGACTCAGCACCGCCACCAA<br>GGACACCTATGACGCTCTTCACATGCAGGCCCTGCCGCCTCGG |
| 105 | M19 (ScFv domain) >TS92-04BD (M19) | CAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAG |
| 129 | M19 (Full) >TS92-04BD (M19) | ATGGCCCTCCCTGTCACCGCCCTGCTGCTTCCGCTGGCTCTTCTGCTCCACGCCGCTCGGCCCCAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA |

TABLE 3-continued

Nucleic Acid Sequences encoding CAR molecules (the leader sequence is underlined)

| SEQ ID NO: | Desc. | Nucleic Acid Sequence |
|---|---|---|
| | | GTGGACATCAAG**ACCACTACC**CCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 106 | M20 (ScFv domain) >JS93-08WD (M20) | CAAGTGCAACTTGTTCAATCAGGAGGAGGACTCGTTCAACCCGGAGGATCACTGCGACTCTCATGTGCAGCGTCGGGGTTC<br>ACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTCGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG |
| 130 | M20 (Full) >JS93-08WD (M20) | ATGGCCCTCCCTGTCACCGCCCTGCTGCTTCCGCTGGCTCTTCTGCTCCACGCCGCTCGGCCCCAAGTGCAACTTGTTCAA<br>TCAGGAGGAGGACTCGTTCAACCCGGAGGATCACTGCGACTCTCATGTGCAGCGTCGGGGTTCACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTCGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 107 | M21 (ScFv domain) >ZS95-03QD (M21) | CAAGTCCAACTCGTTCAGTCATGGGCAGAAGTCAAGAAACCCGGTGCAAGCGTCAAAGTGTCGTGTAAGGCCTCCGGCTAC<br>ACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA |
| 131 | M21 (Full) >ZS95-03QD (M21) | ATGGCCCTCCCTGTCACCGCCCTGCTGCTTCCGCTGGCTCTTCTGCTCCACGCCGCTCGGCCCCAAGTCCAACTCGTTCAG<br>TCATGGGCAGAAGTCAAGAAACCCGGTGCAAGCGTCAAAGTGTCGTGTAAGGCCTCCGGCTACACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA**ACCACTACC**CCAGCACCGAGGCCACCCACCCCGGCTCCTACCATCGCCTCCCAGCCTCTGTCCCTGCGTCCGGAGGCA<br>TGTAGACCCGCAGCTGGTGGGGCCGTGCATACCCGGGGTCTTGACTTCGCCTGCGATATCTACATTTGGGCCCCTCTGGC<br>TGGTACTTGCGGGGTCCTGCTGCTTTCACTCGTGATCACTCTTTACTGTAAGCGCGGTCGGAAGAAGCTGCTGTACATCT<br>TTAAGCAACCCTTCATGAGGCCTGTGCAGACTACTCAAGAGGAGGACGGCTGTTCATGCCGGTTCCCAGAGGAGGAGGAA<br>GGCGGCTGCGAACTGCGCGTGAAATTCAGCCGCAGCGCAGATGCTCCAGCCTACAAGCAGGGGCAGAACCAGCTCTACAA<br>CGAACTCAATCTTGGTCGGAGAGAGGAGTACGACGTGCTGGACAAGCGGAGAGGACGGGACCCAGAAATGGGCGGGAAGC<br>CGCGCAGAAAGAATCCCCAAGAGGGCCTGTACAACGAGCTCCAAAAGGATAAGATGGCAGAAGCCTATAGCGAGATTGGT<br>ATGAAAGGGGAACGCAGAAGAGGCAAAGGCCACGACGGACTGTACCAGGGACTCAGCACCGCCACCAAGGACACCTATGA<br>CGCTCTTCACATGCAGGCCCTGCCGCCTCGG |

TABLE 3-continued

Nucleic Acid Sequences encoding CAR molecules (the leader sequence is underlined)

| SEQ ID NO: | Desc. | Nucleic Acid Sequence |
|---|---|---|
| 108 | M22<br>(ScFv<br>domain)<br>>PS96-<br>08LD<br>(M22) | CAAGTCCAACTCGTCCAGTCCGGTGCAGAAGTCAGAAGGCCAGGAGCAAGCGTGAAGATCTCGTGTAGAGCGTCAGGAGAC<br>ACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG |
| 132 | M22<br>(Full)<br>>PS96-<br>08LD<br>(M22) | ATGGCCCTCCCTGTCACCGCCCTGCTGCTTCCGCTGGCTCTTCTGCTCCACGCCGCTCGGCCCCAAGTCCAACTCGTCCAG<br>TCCGGTGCAGAAGTCAGAAGGCCAGGAGCAAGCGTGAAGATCTCGTGTAGAGCGTCAGGAGACACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 109 | M23<br>(ScFv<br>domain)<br>>XH66-<br>84HE<br>(M23) | CAAGTCCAACTCCAGCAATCGGGAGCAGAAGTCAAGAAACCAGGCGCATCGGTGAAAGTGTCGTGTAAGGCGTCAGGGTAC<br>ACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG |
| 133 | M23<br>(Full)<br>>XH66-<br>84HE<br>(M23) | ATGGCCCTCCCTGTCACCGCCCTGCTGCTTCCGCTGGCTCTTCTGCTCCACGCCGCTCGGCCCCAAGTCCAACTCCAGCAA<br>TCGGGAGCAGAAGTCAAGAAACCAGGCGCATCGGTGAAAGTGTCGTGTAAGGCGTCAGGGTACACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 110 | M24<br>(ScFv<br>domain)<br>>NH67-<br>89CE<br>(M24) | CAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG |

TABLE 3-continued

Nucleic Acid Sequences encoding CAR molecules (the leader sequence is underlined)

| SEQ ID NO: | Desc. | Nucleic Acid Sequence |
|---|---|---|
| 134 | M24 (Full) >NH67-89CE (M24) | ATGGCCCTCCCTGTCACCGCCCTGCTGCTTCCGCTGGCTCTTCTGCTCCACGCCGCTCGGCCCCAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 279 | Ss1 (scFv domain) | CAAGTCCAGCTCCAGCAGTCGGGCCCAGAGTTGGAGAAGCCTGGGGCGAGCGTGAAGAT<br>CTCATGCAAAGCCTCAGGCTACTCCTTTACTGGATACACGATGAATTGGGTGAAACAGT<br>CGCATGGAAAGTCACTGGAATGGATCGGTCTGATTACGCCCTACAACGGCGCCTCCAGC<br>TACAACCAGAAGTTCAGGGGAAAGGCGACCCTTACTGTCGACAAGTCGTCAAGCACCGC<br>CTACATGGACCTCCTGTCCCTGACCTCCGAAGATAGCGCGGTCTACTTTTGTGCACGCG<br>GAGGTTACGATGGACGGGGATTCGACTACTGGGGCCAGGGAACCACTGTCACCGTGTCG<br>AGCGGAGGCGGAGGGAGCGGAGGAGGAGGCAGCGGAGGTGGAGGGTCGGATATCGAACT<br>CACTCAGTCCCCAGCAATCATGTCCGCTTCACCGGGAGAAAAGGTGACCATGACTTGCT<br>CGGCCTCCTCGTCCGTGTCATACATGCACTGGTACCAACAAAAATCGGGGACCTCCCCT<br>AAGAGATGGATCTACGATACCAGCAAACTGGCTTCAGGCGTGCCGGGACGCTTCTCGGG<br>TTCGGGGAGCGGAAATTCGTATTCGTTGACCATTTCGTCCGTGGAAGCCGAGGACGACG<br>CAACTTATTACTGCCAACAGTGGTCAGGCTACCCGCTCACTTTCGGAGCCGGCACTAAG<br>CTGGAGATC |
| 280 | Ss1 (full) | ATGGCCCTCCCTGTCACCGCCCTGCTGCTTCCGCTGGCTCTTCTGCTCCACGCCGCTCG<br>GCCCCAAGTCCAGCTCCAGCAGTCGGGCCCAGAGTTGGAGAAGCCTGGGGCGAGCGTGA<br>AGATCTCATGCAAAGCCTCAGGCTACTCCTTTACTGGATACACGATGAATTGGGTGAAA<br>CAGTCGCATGGAAAGTCACTGGAATGGATCGGTCTGATTACGCCCTACAACGGCGCCTC<br>CAGCTACAACCAGAAGTTCAGGGGAAAGGCGACCCTTACTGTCGACAAGTCGTCAAGCA<br>CCGCCTACATGGACCTCCTGTCCCTGACCTCCGAAGATAGCGCGGTCTACTTTTGTGCA<br>CGCGGAGGTTACGATGGACGGGGATTCGACTACTGGGGCCAGGGAACCACTGTCACCGT<br>GTCGAGCGGAGGCGGAGGGAGCGGAGGAGGAGGCAGCGGAGGTGGAGGGTCGGATATCG<br>AACTCACTCAGTCCCCAGCAATCATGTCCGCTTCACCGGGAGAAAAGGTGACCATGACT<br>TGCTCGGCCTCCTCGTCCGTGTCATACATGCACTGGTACCAACAAAAATCGGGGACCTC<br>CCCTAAGAGATGGATCTACGATACCAGCAAACTGGCTTCAGGCGTGCCGGGACGCTTCT<br>CGGGTTCGGGGAGCGGAAATTCGTATTCGTTGACCATTTCGTCCGTGGAAGCCGAGGAC<br>GACGCAACTTATTACTGCCAACAGTGGTCAGGCTACCCGCTCACTTTCGGAGCCGGCAC<br>TAAGCTGGAGATCACCACTACCCCAGCACCGAGGCCACCCACCCCGGCTCCTACCATCG<br>CCTCCCAGCCTCTGTCCCTGCGTCCGGAGGCATGTAGACCCGCAGCTGGTGGGGCCGTG<br>CATACCCGGGGTCTTGACTTCGCCTGCGATATCTACATTTGGGCCCCTCTGGCTGGTAC<br>TTGCGGGGTCCTGCTGCTTTCACTCGTGATCACTCTTTACTGTAAGCGCGGTCGGAAGA<br>AGCTGCTGTACATCTTTAAGCAACCCTTCATGAGGCCTGTGCAGACTACTCAAGAGGAG<br>GACGGCTGTTCATGCCGGTTCCCAGAGGAGGAGGAAGGCGGCTGCGAACTGCGCGTGAA<br>ATTCAGCCGCAGCGCAGATGCTCCAGCC |

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multi-specific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH—CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with cross-linkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$—$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$—$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 26). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for mesothelin, e.g., comprises a scFv as described herein, e.g., as described in Table 2 or 3, or comprises the light chain CDRs and/or heavy chain CDRs from a mesothelin scFv described herein, and a second immunoglobulin variable domain sequence that has binding specificity for a second epitope on a different antigen. In some aspects the second immunoglobulin variable domain sequence has binding specificity for an antigen other than mesothelin, e.g., an antigen expressed by a cancer or tumor cell. In some aspects, the second immunoglobulin variable domain sequence has binding specificity for an antigen selected from a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2.

Chimeric TCR

In one aspect, the mesothelin antibodies and antibody fragments of the present invention (for example, those disclosed in Tables 2 or 3) can be grafted to one or more constant domain of a T cell receptor ("TCR") chain, for example, a TCR alpha or TCR beta chain, to create an chimeric TCR that binds specificity to mesothelin. Without being bound by theory, it is believed that chimeric TCRs will signal through the TCR complex upon antigen binding. For example, a mesothelin scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a mesothelin antibody fragment, for example a VL domain as described herein, can be grafted to the constant domain of a TCR alpha chain, and a mesothelin antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of a mesothelin antibody or antibody fragment, e.g., the CDRs of a mesothelin antibody or antibody fragment as described in Tables 4 or 5 may be grafted into a TCR alpha and/or beta chain to create a chimeric TCR that binds specifically to mesothelin. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used, e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect, the transmembrane domain is capable of signaling to the intracellular domain(s) whenever the CAR has bound to a target. A transmembrane domain of particular use in this invention may include at least the transmembrane domain(s) of, e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence SEQ ID NO:3.

In some embodiments, the hinge or spacer comprises a hinge encoded by a nucleotide sequence SEQ ID NO:14.

In one aspect, the hinge or spacer comprises an IgD hinge. For example, in one embodiment, the hinge or spacer comprises a hinge of the amino acid sequence SEQ ID NO:4.

In some embodiments, the hinge or spacer comprises a hinge encoded by a nucleotide sequence of SEQ ID NO:15.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic signaling region of the CAR. A glycine-serine doublet provides a particularly suitable linker. For example, in one aspect, the linker comprises the amino acid sequence of GGGGSGGGGS (SEQ ID NO:5). In some embodiments, the linker is encoded by a nucleotide sequence of

```
                                  (SEQ ID NO: 16)
GGTGGCGGAGGTTCTGGAGGTGGAGGTTCC.
```

In one aspect, the hinge or spacer comprises a KIR2DS2 hinge and portions thereof.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary cytoplasmic signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon Rib), CD3 gamma, CD3 delta, CD3 epsilon, CD5, CD22, CD79a, CD79b, CD278 (also known as "ICOS"), FcεRI, CD66d, DAP10, and DAP12. In one embodiment, a CAR of the invention comprises an intracellular signaling domain, e.g., a primary signaling domain of CD3-zeta, e.g., a CD3-zeta sequence described herein.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1 (also known as PD1), ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. *Blood*. 2012; 119(3):696-706). Further examples of such costimulatory molecules include an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. For example, CD27 costimulation has been demonstrated to enhance expansion, effector function, and survival of human CART cells in vitro and augments human T cell persistence and antitumor activity in vivo (Song et al. Blood. 2012; 119(3): 696-706).

The intracellular signaling domains within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling domains. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9 (mutant CD3-zeta) or SEQ ID NO: 10 (wild type human CD3-zeta).

In one aspect, the intracellular is designed to comprise the signaling domain of CD3-zeta and the signaling domain of 4-1BB. In one aspect, the signaling domain of 4-1BB comprises an amino acid sequence of SEQ ID NO: 7. In one aspect, the signaling domain of 4-1BB is encoded by a nucleic acid sequence of SEQ ID NO: 18.

In one aspect, the intracellular signaling domain is designed to comprise the signaling domain of CD3-zeta and the signaling domain of CD27. In one aspect, the signaling domain of CD27 comprises an amino acid sequence of SEQ ID NO:8. In one aspect, the signalling domain of CD27 is encoded by a nucleic acid sequence of SEQ ID NO:19.

In one aspect, the intracellular is designed to comprise the signaling domain of CD3-zeta and the signaling domain of CD28. In one aspect, the signaling domain of CD28 comprises an amino acid sequence of SEQ ID NO: 44. In one aspect, the signaling domain of CD28 is encoded by a nucleic acid sequence of SEQ ID NO: 45.

In one aspect, the intracellular is designed to comprise the signaling domain of CD3-zeta and the signaling domain of ICOS. In one aspect, the signaling domain of ICOS comprises an amino acid sequence of SEQ ID NO: 42. In one aspect, the signaling domain of ICOS is encoded by a nucleic acid sequence of SEQ ID NO: 43.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cyotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Split CAR

In some embodiments, the CAR-expressing cell described herein, uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes the tumor antigen or B cell antigen described herein, e.g., comprises an antigen binding domain described herein, and the second antigen binding domain recognizes a second antigen, e.g., a second tumor antigen or a second B cell antigen described herein.

Co-Expression of CAR with Other Molecules or Agents

Co-Expression of a Second CAR

In one aspect, the CAR-expressing cell described herein can further comprise a second CAR, e.g., a second CAR that includes a different antigen binding domain, e.g., to the same target (mesothelin) or a different target (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, e.g., 4-1BB, CD28, CD27, OX-40 or ICOS, onto the first CAR, and the primary signaling domain, e.g., CD3 zeta, on the second CAR can limit the CAR activity to cells where both targets are expressed. In one embodiment, the CAR expressing cell comprises a first mesothelin CAR that includes a mesothelin binding domain, a transmembrane domain and a costimulatory domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the CAR expressing cell comprises a first mesothelin CAR that includes a mesothelin binding domain, a transmembrane domain and a primary signaling domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the CAR-expressing cell comprises a mesothelin CAR described herein and an inhibitory CAR. In one embodiment, the inhibitory CAR comprises an antigen binding domain that binds an antigen found on normal cells but not cancer cells, e.g., normal cells that also express mesothelin. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids. In an embodiment the antigen binding domain of one of the first and the second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, e.g., a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and the second CAR comprises an scFv, and the other comprises a single VH domain, e.g., a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another 85%, 90%, 95%, 96%, 97%, 98% or 99% less than if both were scFv antigen binding domains.

Co-Expression of an Agent that Enhances CAR Activity

In another aspect, the CAR-expressing cell described herein can further express another agent, e.g., an agent that enhances the activity or fitness of a CAR-expressing cell.

For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a mesothelin CAR described herein, improves the persistence of the T cell. In one embodiment, the CAR is a PD1 CAR comprising the extracellular domain of PD1 indicated as underlined in SEQ ID NO: 24 and a signal sequence at amino acids 1-21 of SEQ ID NO:24. In one embodiment, the PD1 CAR comprises the amino acid sequence of SEQ ID NO:24.

In one embodiment, the PD1 CAR without the N-terminal signal sequence comprises the amino acid sequence provided of SEQ ID NO:22.

In one embodiment, the agent comprises a nucleic acid sequence encoding the PD1 CAR with the N-terminal signal sequence, e.g., the PD1 CAR described herein. In one embodiment, the nucleic acid sequence for the PD1 CAR is shown in Table 1, with the PD1 ECD underlined in SEQ ID NO: 23.

In another example, in one embodiment, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, e.g., as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In an embodiment, the costimulatory molecule ligand is 4-1BBL. In an embodiment, the costimulatory ligand is CD80 or CD86. In an embodiment, the costimulatory molecule ligand is CD70. In embodiments, a CAR-expressing immune effector cell described herein can be further engineered to express one or more additional costimulatory molecules or costimulatory molecule ligands.

Co-Expression of CAR with a Chemokine Receptor

In embodiments, the CAR-expressing cell described herein, e.g., mesothelin CAR-expressing cell, further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., *J Immunother.* 2010 October; 33(8):780-8 and Kershaw et al., *Hum Gene Ther.* 2002 Nov. 1; 13(16):1971-80). Thus, without wishing to be bound by theory, it is believed that chemokine receptors expressed in CAR-expressing cells that recognize chemokines secreted by tumors, e.g., solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell (e.g., CAR-Tx) described herein include a CXC chemokine receptor (e.g., CXCR1, CXCR2, CXCR3, CXCR4, CXCR5, CXCR6, or CXCR7), a CC chemokine receptor (e.g., CCR1, CCR2, CCR3, CCR4, CCR5, CCR6, CCR7, CCR8, CCR9, CCR10, or CCR11), a CX3C chemokine receptor (e.g., CX3CR1), a XC chemokine receptor (e.g., XCR1), or a chemokine-binding fragment thereof. In one embodiment, the chemokine receptor molecule to be expressed with a CAR described herein is selected based on the chemokine(s) secreted by the tumor. In one embodiment, the CAR-expressing cell described herein further comprises, e.g., expresses, a CCR2b receptor or a CXCR2 receptor. In an embodiment, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Nucleic Acid Constructs Encoding a CAR

The present invention provides CAR transgenes comprising nucleic acid sequences encoding one or more CAR constructs of the invention. In one aspect, the CAR transgene is provided as a messenger RNA transcript. In one aspect, the CAR transgene is provided as a DNA construct.

Accordingly, in one aspect, the invention pertains to an isolated nucleic acid molecule encoding a chimeric antigen receptor (CAR), wherein the CAR comprises an anti-mesothelin binding domain (e.g., a human anti-mesothelin binding domain), a transmembrane domain, and an intracellular signaling domain comprising a stimulatory domain. In one embodiment, the anti-mesothelin binding domain is an anti-mesothelin binding domain described herein, e.g., an anti-mesothelin binding domain which comprises a sequence selected from a group consisting of SEQ ID NO: 87-111, or a sequence with 95-99% identify thereof. In one embodiment, the isolated nucleic acid molecule further comprises a sequence encoding a costimulatory domain. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 6, or a sequence with 95-99% identity thereof. In one embodiment, the anti-mesothelin binding domain is connected to the transmembrane domain by a hinge region, e.g., a hinge described herein. In one embodiment, the hinge region comprises SEQ ID NO:2 or SEQ ID NO:3 or SEQ ID NO:4 or SEQ ID NO:5, or a sequence with 95-99% identity thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. In one embodiment, the costimulatory domain comprises a sequence of SEQ ID NO:7, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 7 or SEQ ID NO: 8, or a sequence with 95-99% identity thereof, and the sequence of SEQ ID NO: 9 or SEQ ID NO: 10, or a sequence with 95-99% identity thereof, wherein the sequences comprising the intracellular signaling domain are expressed in the same frame and as a single polypeptide chain. In another aspect, the invention pertains to an isolated nucleic acid molecule encoding a CAR construct comprising a leader sequence of SEQ ID NO: 1, a scFv domain having a sequence selected from the group consisting of SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, (or a sequence with 95-99% identify thereof), a hinge region of SEQ ID NO: 2 or SEQ ID NO:3 or SEQ ID NO:4 or SEQ ID NO:5 (or a sequence with 95-99% identity thereof), a transmembrane domain having a sequence of SEQ ID NO: 6 (or a sequence with 95-99% identity thereof), a 4-1BB costimulatory domain having a sequence of SEQ ID NO:7 (or a sequence with 95-99% identity thereof) or a CD27 costimulatory domain having a sequence of SEQ ID NO: 8 (or a sequence with 95-99% identity thereof), and a CD3 zeta stimulatory domain having a sequence of SEQ ID NO:9 or SEQ ID NO: 10 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO: 63; SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86, or a sequence with 95-99% identity thereof.

In another aspect, the invention pertains to an isolated nucleic acid molecule encoding a chimeric antigen receptor (CAR) molecule that comprises an anti-mesothelin binding domain, a transmembrane domain, and an intracellular signaling domain comprising a stimulatory domain, and wherein the nucleic acid encoding the anti-mesothelin binding domain comprises a sequence selected from the group consisting of SEQ ID NO: 111; SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO:134, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18) and 4-1BB (CD137). In one embodiment, the costimulatory domain comprises a sequence of SEQ ID NO:7. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:6. In one embodiment, the intracellular signaling domain comprises a functional signaling domain of 4-1BB and a functional signaling domain of zeta. In one embodiment, the intracellular signaling domain comprises the sequence of SEQ ID NO: 7 and the sequence of SEQ ID NO: 9, wherein the sequences comprising the intracellular signaling domain are expressed in the same frame and as a single polypeptide chain. In one embodiment, the anti-mesothelin binding domain is connected to the transmembrane domain by a hinge region. In one embodiment, the hinge region comprises SEQ ID NO:2. In one embodiment, the hinge region comprises SEQ ID NO: 3, SEQ ID NO: 4, or SEQ ID NO: 5.

In another aspect, the invention pertains to an isolated CAR molecule comprising a leader sequence of SEQ ID NO: 1, a scFv domain having a sequence selected from the group consisting of SEQ ID NOS: 39-62, or a sequence with 95-99% identify thereof, a hinge region of SEQ ID NO:2 or SEQ ID NO: 3 or SEQ ID NO: 4 or SEQ ID NO: 5, a transmembrane domain having a sequence of SEQ ID NO: 6, a 4-1BB costimulatory domain having a sequence of SEQ ID NO:7 or a CD27 costimulatory domain having a sequence of SEQ ID NO: 8, and a CD3 zeta stimulatory domain having a sequence of SEQ ID NO:9 or SEQ ID NO: 10. In one embodiment, the encoded CAR molecule comprises a sequence selected from the group consisting of SEQ ID NOS: 63-86, or a sequence with 95-99% identify thereof.

The present invention further provides vectors comprising CAR transgenes. In one aspect, a CAR vectors can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells or NK cells. In one aspect, the mammalian T cell is a human T cell or a human NK cell.

The present invention also includes a CAR encoding RNA construct that can be directly transfected into a cell, e.g., a T cell or a NK cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one aspect, the template includes sequences for the CAR.

In one aspect the mesothelin CAR transgene is encoded by a messenger RNA (mRNA). In one aspect the mRNA encoding the mesothelin CAR transgene is introduced into a T cell for production of a CART cell, or a NK cell.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In one embodiment, the vector comprising the nucleic acid encoding the desired CAR of the invention is a DNA, a RNA, a plasmid, an adenoviral vector, a lentivirus vector, or a retrovirus vector. A retroviral vector may also be, e.g., a gammaretroviral vector. A gammaretroviral vector may include, e.g., a promoter, a packaging signal (W), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See, e.g., June et al. 2009 *Nature Reviews Immunology* 9.10: 704-716, incorporated herein by reference in its entirety.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR transgene in a mammalian T cell is the EF1alpha promoter (EF1a or EF1α). The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:11.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

WT PGK Promoter (SEQ ID NO: 597)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT

Exemplary truncated PGK Promoters:

PGK100:

(SEQ ID NO: 598)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

-continued

PGK200:

(SEQ ID NO: 599)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:

(SEQ ID NO: 600)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK400:

(SEQ ID NO: 601)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the vector can further comprise a nucleic acid encoding a second CAR. In one embodiment, the second CAR includes an antigen binding domain to, e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2. In one embodiment, the vector comprises a nucleic acid sequence encoding a first CAR that targets a first antigen and includes an intracellular signaling domain having a costimulatory signaling domain but not a primary signaling domain, and a nucleic acid encoding a second CAR that targets a second, different, antigen and includes an intracellular signaling domain having a primary signaling domain but not a costimulatory signaling domain. In one embodiment, the vector comprises a nucleic acid encoding a first mesothelin CAR that includes a mesothelin binding domain, a transmembrane domain and a costimulatory domain and a nucleic acid encoding a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the vector comprises a nucleic acid encoding a first mesothelin CAR that includes a mesothelin binding domain, a transmembrane domain and a primary signaling domain and a nucleic acid encoding a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the vector comprises a nucleic acid encoding a mesothelin CAR described herein and a nucleic acid encoding an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta.

In embodiments, the vector may comprise two or more nucleic acid sequences, wherein one of the nucleic acid sequences encodes a CAR described herein, e.g., a mesothelin CAR described herein. In on embodiment, the other nucleic acid can encode a second CAR, e.g., an inhibitory CAR or a specifically binds to an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2), or a polypeptide that can regulate activity of the mesothelin CAR described herein. In such embodiments, the two or more nucleic acid sequences, e.g., encoding a mesothelin CAR described herein and a second CAR or other polypeptide, are encoded by a single nucleic molecule in the same frame and as a single polypeptide chain. In one embodiment, the two or more polypeptides can be separated by one or more peptide cleavage sites (e.g., an auto-cleavage site or a substrate for an intracellular protease). Examples of peptide cleavage sites include the following, wherein the GSG residues are optional:

```
T2A:
                                        (SEQ ID NO: 602)
(GSG) E G R G S L L T C G D V E E N P G P

P2A:
                                        (SEQ ID NO: 603)
(GSG) A T N F S L L K Q A G D V E E N P G P

E2A:
                                        (SEQ ID NO: 604)
(GSG) Q C T N Y A L L K L A G D V E S N P G P

F2A:
                                        (SEQ ID NO: 605)
(GSG) V K Q T L N F D L L K L A G D V E S N P G P
```

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is lipofection, e.g., using Lipofectamine (Life Technologies).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or a NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell. In one aspect, the mammalian cell is a human NK cell.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one aspect, the template includes sequences for the CAR.

In one aspect the mesothelin CAR is encoded by a messenger RNA (mRNA). In one aspect the mRNA encoding the mesothelin CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. The term "substantially complementary" refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. The term "upstream" refers to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. The term "downstream" refers to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1(2011):R14-20; Singh et al. Cancer Res. 15(2008):2961-2971; Huang et al. Mol. Ther. 16(2008):580-589; Grabundzija et al. Mol. Ther.

18(2010):1200-1209; Kebriaei et al. Blood. 122.21(2013): 166; Williams. Molecular Therapy 16.9(2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3(2013): 1829-47; and Singh et al. Cancer Res. 68.8(2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Sources of Cells

Prior to expansion and genetic modification, e.g., to express a CAR described herein, a source of cells, e.g., T cell or NK cells, can be obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present disclosure, any number of T cell lines available in the art, may be used. In certain aspects of the present disclosure, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lh1, GITR+, and FoxP3+. Alternatively, in certain aspects, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present disclosure.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present disclosure, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR Immune Effector Cells

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class I and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell. Expression systems for siRNA and shRNAs, and exemplary shRNAs, are described, e.g., in paragraphs 649 and 650 of International Publication WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein.

A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

The CRISPR/Cas system, and uses thereof, are described, e.g., in paragraphs 651-658 of International Publication WO2015/142675, filed Mar. 13, 2015, which is incorporated by reference in its entirety.

TALEN to Inhibit TCR and/or HLA

TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

TALENs, and uses thereof, are described, e.g., in paragraphs 659-665 of International Publication WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

ZFNs, and uses thereof, are described, e.g., in paragraphs 666-671 of International Publication WO2015/142675, filed Mar. 13, 2015, which is incorporated by reference in its entirety.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as set out in SEQ ID NO: 110 herein.

In an embodiment, the hTERT has a sequence at least 80%, 85%, 90%, 95%, 96^, 97%, 98%, or 99% identical to the sequence of SEQ ID NO: 110. In an embodiment, the hTERT has a sequence of SEQ ID NO: 110. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as set out in SEQ ID NO: 111 herein.

In an embodiment, the hTERT is encoded by a nucleic acid having a sequence at least 80%, 85%, 90%, 95%, 96, 97%, 98%, or 99% identical to the sequence of SEQ ID NO: 111. In an embodiment, the hTERT is encoded by a nucleic acid of SEQ ID NO: 111.

Activation and Expansion of Immune Effector Cells (e.g., T Cells)

Immune effector cells, such as T cells, may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells, e.g., T cells may be expanded by contact with a surface having attached thereto an agent that stimulates a CD3/TCR complex associated signal and a ligand that stimulates a costimulatory molecule on the surface of the immune effector cells, e.g., T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type. In one aspect, the most typical ratios for use are in the neighborhood of 1:1, 2:1 and 3:1 on the first day.

In further aspects of the present disclosure, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CAR-expressing cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CAR-expressing cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CAR-expressing cell described herein, expanded for 5 days show at least a one, two, three, four, five, tenfold or more increase in pg/ml of proinflammatory cytokine production, e.g., IFN-γ and/or GM-CSF levels, as compared to the same cells expanded in culture for 9 days under the same culture conditions.

In one aspect of the present disclosure, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

In one embodiment, the cells are cultured (e.g., expanded, simulated, and/or transduced) in media comprising serum. The serum may be, e.g., human AB serum (hAB). In some embodiments, the hAB serum is present at about 2%, about 5%, about 2-3%, about 3-4%, about 4-5%, or about 2-5%. 2% and 5% serum are each suitable levels that allow for many fold expansion of T cells. Furthermore, as shown in Smith et al., "Ex vivo expansion of human T cells for adoptive immunotherapy using the novel Xeno-free CTS Immune Cell Serum Replacement" Clinical & Translational Immunology (2015) 4, e31; doi:10.1038/cti.2014.31, medium containing 2% human AB serum is suitable for ex vivo expansion of T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some embodiments, cells transduced with a nucleic acid encoding a CAR, e.g., a CAR described herein, can be selected for administration based upon, e.g., protein expression levels of one or more of CCL20, GM-CSF, IFNγ, IL-10, IL-13, IL-17a, IL-2, IL-21, IL-4, IL-5, IL-6, IL-9, TNFα and/or combinations thereof. In some embodiments, cells transduced with a nucleic acid encoding a CAR, e.g., a CAR described herein, can be selected for administration based upon, e.g., protein expression levels of CCL20, IL-17a, IL-6 and combinations thereof.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a mesothelin CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a mesothelin CAR are described, e.g., in paragraphs [0417]-[00423] of International Publication WO2015/090230, filed Dec. 19, 2014, which is incorporated by reference in its entirety.

Populations of CAR Cells

In another aspect, the present invention provides a population of CAR-expressing cells, e.g., a population of mesothelin CAR-expressing cells. In some embodiments, the population of CAR-expressing cells comprises a mixture of cells expressing different CARs.

For example, in one embodiment, the population of CAR-expressing cells can include a first cell expressing a CAR having an anti-mesothelin binding domain described herein, and a second cell expressing a CAR having a different anti-mesothelin binding domain, e.g., an anti-mesothelin binding domain described herein that differs from the anti-mesothelin binding domain in the CAR expressed by the first cell.

As another example, the population of CAR-expressing cells can include a first cell expressing a CAR that includes an anti-mesothelin binding domain, e.g., as described herein, and a second cell expressing a CAR that includes an antigen binding domain to a target other than mesothelin (e.g., a target other than mesothelin on stroma cells, e.g., FAP; a target other than mesothelin on prostate cancer cells, e.g., androgen receptor, OR51E2, PSMA, PSCA, PDGRF-0, TARP, GloboH, MAD-CT-1, or MAD-CT-2; a target other than mesothelin on ovarian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2). In one embodiment, the population of CAR-expressing cells includes, e.g., a first cell expressing a CAR that includes a primary intracellular signaling domain, and a second cell expressing a CAR that includes a secondary signaling domain.

In one embodiment, the population of CAR-expressing cells can include a first cell expressing a CAR that includes an anti-mesothelin binding domain and a second cell expressing a CAR that includes an antigen binding domain that targets, e.g., specifically binds, an antigen expressed on B cells, or a B cell antigen. In one embodiment, the B cell antigen is CD19.

In another aspect, the present invention provides a population of cells wherein at least one cell in the population expresses a CAR having an anti-mesothelin binding domain described herein, and a second cell expressing another agent, e.g., an agent which enhances the activity or function of a CAR-expressing cell. For example, in one embodiment, the agent can be an agent which modulates or regulates, e.g., inhibits, T cell function. In some embodiments, the molecule that modulates or regulates T cell function is an inhibitory molecule, e.g., an agent described herein. Inhibitory molecules, e.g., can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells, e.g., CART cells, e.g., a mixture of cells expressing different CARs, in combination with another agent, e.g., a PD-L1 inhibitor, such as a PD-L1 inhibitor described herein. In another aspect, the present invention provides methods comprising administering a population of cells wherein at least one cell in the population expresses a CAR having an anti-mesoothelinbinding domain as described herein, and a second cell expressing another agent, e.g., an agent which enhances the activity or fitness of a CAR-expressing cell, in combination with another agent, e.g., a PD-L1 inhibitor, such as a PD-L1 inhibitor described herein.

PD-L1 Inhibitors

The immune system has the capability of recognizing and eliminating tumor cells; however, tumors can use multiple strategies to evade immunity. Blockade of immune checkpoints is one of the approaches to activating or reactivating therapeutic antitumor immunity. Programmed Death Ligand 1 (PD-L1) has been described as a ligand for the immuneinhibitory receptor Programmed Death 1 (PD-1). Binding of PD-L1 to PD-1 leads to the inhibition of T cell receptor-mediated lymphocyte proliferation and cytokine secretion (Freeman et al. (2000) *J Exp Med* 192:1027-34). Thus, blocking of PD-L1 can lead to enhancement of antitumor immunity.

Several cell types express PD-L1. For example, PD-L1 is expressed on activated T cells, dendritic cells (DCs), natural killer (NK) cells, macrophages, B cells, monocytes, and vascular endothelium cells. PD-L1 is expressed in many cancers, including human lung, ovarian and colon carcinoma and various myelomas, (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 expression strongly correlates with unfavorable prognosis in various types of cancer including kidney, ovarian, bladder, breast, gastric and pancreatic cancer.

Many tumor infiltrating T lymphocytes predominantly express PD-1 compared to T lymphocytes in normal tissues and peripheral blood T lymphocytes. This indicates that up-regulation of PD-1 on tumor-reactive T cells can contribute to impaired antitumor immune responses (Ahmadzadeh et al. (2009) *Blood* 114:1537-44). Thus, PD-L1 signaling mediated by PD-L1 expressing tumor cells interacting with PD-1 expressing T cells may lead to attenuation of T cell activation and evasion of immune surveillance (Sharpe et al. (2002) *Nat Rev Immunol.* 2:116-26; Keir et al. (2008) *Annu Rev Immunol.* 26:677-704). PD-1 blockade can inhibit hematogenous spread of poorly immunogenic tumor cells by enhanced recruitment of effector T cells (Iwai et al. (2005) *Int. Immunol.* 17:133-144).

PD-L1 inhibition can enhance T-cell immunity, e.g., through blocking both its inhibitory interactions with PD-1 and B7-1. PD-L1 inhibition can also allow for immune regulation via PD-L2/PD-1. Both PD-1 and B7-1 are expressed on T cells, B cells, DCs, and macrophages, which provides potential for bidirectional interactions between B7-1 and PD-L1 on these cell types. PD-L1 on non-hematopoietic cells may interact with B7-1 as well as PD-1 on T cells.

The term "Programmed Death Ligand 1" or "PD-L1" include isoforms, mammalian, e.g., human PD-L1, species homologs of human PD-1, and analogs comprising at least one common epitope with PD-L1. The amino acid sequence of PD-L1, e.g., human PD-1, is known in the art, e.g., Dong et al. (1999) *Nat Med.* 5(12):1365-9; Freeman et al. (2000) *J Exp Med.* 192(7):1027-34).

The present disclosure provides methods and combinations for treating a disease, e.g., associated with mesothelin expression, that include the administration of a PD-L1 inhibitor. The PD-L1 inhibitor can have one or more of the following properties: inhibits or reduces binding of PD-L1 to a receptor, e.g., PD-1 or CD80 (B7-1), or both; binds to PD-L1 or a PD-L1 binding receptor, e.g., PD-1 or CD80 (B7-1), or both; inhibits or reduces one or more activities of PD-L1, e.g., results in one or more of: an increase in tumor infiltrating lymphocytes, an increase in T-cell receptor mediated proliferation, or a decrease in immune evasion by cancerous cells; or inhibits or reduces PD-L1 expression, e.g., transcription or translation of PD-L1.

In embodiments, the PD-L1 inhibitor reduces binding of PD-L1 to a receptor, e.g., to PD-1 or CD80 (B7-1), or both. For example, the PD-L1 binding to a receptor, e.g., to PD-1 or CD80 (B7-1), or both, is reduced in the presence of the PD-L1 inhibitor by at least 1%, 5%, 10%, 20%, 30%, 40%, 50%, 60%, 70%, 80%, or 90% as compared to binding in the absence of the PD-L1 inhibitor. In one embodiment, PD-L1 binding to a receptor, e.g., to PD-1 or CD80 (B7-1), or both, is negligible, e.g., undetectable, by the standard binding assays known in the art. Ligand-receptor binding assays are well known in the art, and include immunoprecipitation and western blotting assays.

In embodiments, the PD-L1 inhibitor reduces one or more activities of PD-L1. For example, PD-L1 activity is reduced by at least 1%, 5%, 10%, 20%, 30%, 40%, 50%, 60%, 70%, 80%, or 90% as compared to PD-L1 activity in the absence of the PD-L1 inhibitor.

In embodiments, the PD-L1 inhibitor reduces PD-L1 expression, e.g., reduces transcription or translation of PD-L1. For example, PD-L1 transcription is reduced by at least 1%, 5%, 10%, 20%, 30%, 40%, 50%, 60%, 70%, 80%, or 90% as compared to PD-L1 transcription in the absence of the PD-L1 inhibitor. In another example, PD-L1 translation is reduced by at least 1%, 5%, 10%, 20%, 30%, 40%, 50%, 60%, 70%, 80%, or 90% as compared to PD-L1 translation in the absence of the PD-L1 inhibitor. Assays for determining PD-L1 RNA expression are known in the art, and include PCR amplification-based assays, e.g., QPCR, and nucleic acid hybridization-based assays, e.g., Northern blots. Assays for determining PD-L1 protein expression are known in the art, and include western blotting and immunohistochemical analysis. In such embodiments, administration of PD-L1 inhibitor results in reduced levels or amount of PD-L1 expressed in a cell, or reduced numbers of PD-L1 expressing cells.

In one embodiment, the PD-L1 inhibitor can be a small molecule; a polypeptide, e.g., a fusion protein; an antibody molecule; or an inhibitory nucleic acid; e.g., a siRNA or shRNA.

In one embodiment, the PD-L1 inhibitor is a small molecule. In one embodiment, the small molecule inhibitor binds to PD-L1. In another embodiment, the small molecule inhibitor binds to the receptor for PD-L1, e.g., PD-1 or CD80 (B7-1), or both. In yet another embodiment, the small molecule inhibitor prevents or reduces binding of PD-L1 to its receptor, e.g., PD-1 or CD80 (B7-1), or both.

In one embodiment, the PD-L1 inhibitor is a polypeptide or peptide. In one embodiment, the polypeptide or peptide inhibitor of PD-L1 binds to PD-L1 or its receptor, e.g. PD-1 or CD80 (B7-1), or both. In one embodiment, the polypeptide or peptide prevents or reduces binding of PD-L1 to its receptor, e.g., PD-1 or CD80 (B7-1), or both. In one embodiment, the polypeptide comprises a portion of PD-L1, e.g., a receptor binding portion of PD-L1, or a modified portion thereof that may exhibit increased affinity for PD-1 or CD80 (B7-1) as compared to wild-type PD-L1. In such embodiments, the polypeptide inhibits or reduces PD-L1 activity by competing for binding with the receptor.

In one embodiment, the PD-L1 inhibitor is an inhibitory nucleic acid, e.g., an RNA interfering (RNAi) agent. The inhibitory nucleic acid can be a double stranded or single stranded nucleic acid. The inhibitory nucleic acid can be a DNA, a RNA, or a hybrid comprising DNA and RNA. An inhibitory nucleic acid inhibits or reduces the expression, e.g., translation, of PD-L1. An RNA interference (RNAi) agent typically causes the destruction of target mRNA molecules to inhibit or reduce the expression, e.g., translation, of a target gene, e.g., PD-L1. Examples of RNAi agents include long dsRNA, siRNA, shRNA, and microRNAs. Inhibitory nucleic acids described herein include, but are not limited to, an aptamer, a morpholino, a ribozyme, and a nucleic acid sequences, e.g., plasmids or vectors, that comprise or encode a long dsRNA, siRNA, shRNA, or microRNA.

In one embodiment, the inhibitory nucleic acid is a RNA with at least 75%, 80%, 85%, 90%, 95%, or 99% sequence identity or complementarity to the PD-L1 gene or a fragment thereof.

In one embodiment, the inhibitory nucleic acid is a siRNA or shRNA of about 15 to about 65, about 15 to about 40, or about 15 to about 28 nucleotides in length. In embodiments where the inhibitory nucleic acid is a siRNA, the siRNA has a length of about 19 to 25 nucleotides, e.g., 19, 20, 21, or 22 nucleotides. In embodiments where the inhibitory nucleic acid is a shRNA, the shRNA has a length of about 42 to about 70 nucleotides. In one embodiment, the shRNA comprises paired antisense and sense RNA strands connected by a loop of unpaired nucleotides. In one embodiment, the duplex stem has a length of about 19 to about 29 nucleotides, either fully paired or with internal mismatches and loops. In one embodiment, the loop comprises 4, 5, 6, 7, 8, 9, or 10 nucleotides, e.g., 4 or 7 nucleotides.

The inhibitory nucleic acid can be synthesized or expressed, e.g., from a plasmid or vector. Synthetic RNAi agents can be generated using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114: 4557-4565; Masters, J. R. et al. (2001) *Proc. Natl. Acad. Sci. USA* 98:8012-8017; and Tuschl, I T. et al. (1999) *Genes & Development* 13:3191-3197). Alternatively, several commercial RNA synthesis suppliers are available including, but not limited to, Proligo (Hamburg, Germany), Dharmacon Research (Lafayette, Co., USA), Pierce Chemical (part of Perbio Science, Rockford, Ill., USA), Glen Research (Sterling, Va., USA), ChernGenes (Ashland, Mass., USA), and Cruachem (Glasgow, UK).

Assays for assessing expression, e.g., assessing RNA or protein levels, are well known in the art. For example, probes based on the PD-L1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes are used, e.g., in a PCR-based assay, to measure the level of PD-L1 mRNA. Western blotting techniques are well known in the art and are used to measure the level of PD-L1 protein.

In one embodiment, the PD-L1 inhibitor is an antibody molecule. In one embodiment, the antibody molecule binds to a mammalian, e.g., human, PD-L1. For example, the antibody molecule binds specifically to an epitope, e.g., linear or conformational epitope, (e.g., an epitope as described herein) on PD-L1.

In some embodiments, the PD-L1 inhibitor is chosen from YW243.55.S70, MPDL3280A, MEDI-4736, MSB-0010718C, or MDX-1105. MEDI4736 (Medimmune) is a human monoclonal antibody that binds to PDL1, and inhibits its interaction of the ligand with PD1.

In some embodiments, the anti-PD-L1 antibody is MSB0010718C. MSB0010718C (also referred to as A09-246-2; Merck Serono or avelumab) is a monoclonal antibody that binds to PD-L1. Other anti-PD-L1 antibodies and inhibitors are disclosed in WO2013/079174, WO2001/014557, WO2002/086083, WO2007005874, WO2010036959, WO2010077634 and WO2011066389, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain (SEQ ID NO: 24 as disclosed in WO2013/
079174)
                                    (SEQ ID NO: 611)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

Light chain (SEQ ID NO: 25 as disclosed in WO2013/
079174)
                                    (SEQ ID NO: 612)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL
```

In one embodiment, the PD-L1 inhibitor is YW243.55.S70. The YW243.55.S70 antibody is an anti-PD-L1 antibody described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche) (also known as atezolizumab). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

Exemplary PD-L1 Antibody Molecules

In one embodiment, the PD-L1 inhibitor comprises an antibody molecule (e.g., an isolated or recombinant antibody molecule) having one or more of the following properties:

(i) binds to PD-L1, e.g., human PD-L1, with high affinity, e.g., with an affinity constant of at least about $10^7$ $M^{-1}$, typically about $10^8$ $M^{-1}$, and more typically, about 10 $M^{-1}$ to $10^{10}$ $M^{-1}$ or stronger;

(ii) does not substantially bind to CD28, CTLA-4, ICOS or BTLA;

(iii) inhibits or reduces binding of PD-L1 to a receptor, e.g., PD-1 or CD80 (B7-1), or both;

(iv) binds specifically to an epitope on PD-L1, e.g., the same or similar epitope as the epitope recognized by murine monoclonal antibody BAP058 or a chimeric antibody BAP058, e.g., BAP058-chi;

(v) shows the same or similar binding affinity or specificity, or both, as any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(vi) shows the same or similar binding affinity or specificity, or both, as an antibody molecule (e.g., an heavy chain variable region and light chain variable region) described in Table 1;

(vii) shows the same or similar binding affinity or specificity, or both, as an antibody molecule (e.g., an heavy chain variable region and light chain variable region) having an amino acid sequence shown in Table 1;

(viii) shows the same or similar binding affinity or specificity, or both, as an antibody molecule (e.g., an heavy chain variable region and light chain variable region) encoded by the nucleotide sequence shown in Table 1;

(ix) inhibits, e.g., competitively inhibits, the binding of a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(x) binds the same or an overlapping epitope with a second antibody molecule to PD-1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xi) competes for binding, and/or binds the same epitope, with a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0;

(xii) has one or more biological properties of an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xiii) has one or more pharmacokinetic properties of an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0;

(xiv) inhibits one or more activities of PD-L1, e.g., results in one or more of: an increase in tumor infiltrating lymphocytes, an increase in T-cell receptor mediated proliferation, or a decrease in immune evasion by cancerous cells; or (xv) binds human PD-L1 and is cross-reactive with cynomolgus PD-L1.

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, as provided in Table 6, or encoded by the nucleotide sequence in Table 6; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 6, or encoded by the nucleotide sequence in Table 6; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 6, or encoded by a nucleotide sequence shown in Table 6. In one embodiment, one or more of the CDRs (or collectively all of the CDRs) have one, two, three, four, five, six or more changes, e.g., amino acid substitutions or deletions, relative to the amino acid sequence shown in Table 6, or encoded by a nucleotide sequence shown in Table 6.

In yet another embodiment, the anti-PD-L1 antibody molecule includes at least one, two, or three CDRs (or collectively all of the CDRs) from a light chain variable region comprising an amino acid sequence shown in Table 6, or encoded by a nucleotide sequence shown in Table 6. In one embodiment, one or more of the CDRs (or collectively all of the CDRs) have one, two, three, four, five, six or more changes, e.g., amino acid substitutions or deletions, relative to the amino acid sequence shown in Table 6, or encoded by a nucleotide sequence shown in Table 6. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 6, or encoded by a nucleotide sequence shown in Table 6. In one embodiment, one or more of the CDRs (or collectively all of the CDRs) have one, two, three, four, five, six or more changes, e.g., amino acid substitutions or deletions, relative to the amino acid sequence shown in Table 6, or encoded by a nucleotide sequence shown in Table 6.

In one embodiment, the anti-PD-L1 antibody molecule includes:

(i) a heavy chain variable region (VH) including a VHCDR1 amino acid sequence chosen from SEQ ID NO: 287, SEQ ID NO: 290 or SEQ ID NO: 195; a VHCDR2 amino acid sequence of SEQ ID NO: 288; and a VHCDR3 amino acid sequence of SEQ ID NO: 289, each disclosed in Table 6; and (ii) a light chain variable region (VL) including a VLCDR1 amino acid sequence of SEQ ID NO: 295, a VLCDR2 amino acid sequence of SEQ ID NO: 296, and a VLCDR3 amino acid sequence of SEQ ID NO: 297, each disclosed in Table 6.

In another embodiment, the anti-PD-L1 antibody molecule includes:

(i) a heavy chain variable region (VH) including a VHCDR1 amino acid sequence chosen from SEQ ID NO: 287, SEQ ID NO: 290 or SEQ ID NO: 195; a VHCDR2 amino acid sequence of SEQ ID NO: 291, and a VHCDR3 amino acid sequence of SEQ ID NO: 292, each disclosed in Table 6; and (ii) a light chain variable region (VL) including a VLCDR1 amino acid sequence of SEQ ID NO: 298, a VLCDR2 amino acid sequence of SEQ ID NO: 299, and a VLCDR3 amino acid sequence of SEQ ID NO: 300, each disclosed in Table 6.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 195.

In embodiments, the aforesaid antibody molecules have a heavy chain variable region comprising at least one framework (FW) region comprising the amino acid sequence of any of SEQ ID NOs: 124, 126, 128, 130, 132, 134, 136, 138, 140, 142, 144, 146, 148, 150, 152, or 154, or an amino acid sequence at least 90% identical thereto, or having no more than two amino acid substitutions, insertions or deletions compared to the amino acid sequence of any of SEQ ID NOs: 124, 126, 128, 130, 132, 134, 136, 138, 140, 142, 144, 146, 148, 150, 152, or 154.

In other embodiments, the aforesaid antibody molecules have a heavy chain variable region comprising at least one framework region comprising the amino acid sequence of any of SEQ ID NOs: 124, 126, 128, 130, 132, 134, 136, 138, 140, 142, 144, 146, 148, 150, 152, or 154.

In yet other embodiments, the aforesaid antibody molecules have a heavy chain variable region comprising at least two, three, or four framework regions comprising the amino acid sequences of any of SEQ ID NOs: 124, 126, 128, 130, 132, 134, 136, 138, 140, 142, 144, 146, 148, 150, 152, or 154.

In other embodiments, the aforesaid antibody molecules comprise a VHFW1 amino acid sequence of SEQ ID NO: 124, 126, 128, or 130, a VHFW2 amino acid sequence of SEQ ID NO: 132, 134, 136, 138, 140, or 142, and a VHFW3 amino acid sequence of SEQ ID NO: 144, 146, 148, 150, or 152, and, optionally, further comprising a VHFW4 amino acid sequence of SEQ ID NO: 154.

In other embodiments, the aforesaid antibody molecules have a light chain variable region comprising at least one framework region comprising the amino acid sequence of any of SEQ ID NOs: 156, 158, 160, 162, 164, 166, 168, 170, 172, 174, 176, 178, 180, 182, 184, or 186, or an amino acid sequence at least 90% identical thereto, or having no more than two amino acid substitutions, insertions or deletions compared to the amino acid sequence of any of 156, 158, 160, 162, 164, 166, 168, 170, 172, 174, 176, 178, 180, 182, 184, or 186.

In other embodiments, the aforesaid antibody molecules have a light chain variable region comprising at least one framework region comprising the amino acid sequence of any of SEQ ID NOs: 156, 158, 160, 162, 164, 166, 168, 170, 172, 174, 176, 178, 180, 182, 184, or 186.

In other embodiments, the aforesaid antibody molecules have a light chain variable region comprising at least two, three, or four framework regions comprising the amino acid sequences of any of SEQ ID NOs: 156, 158, 160, 162, 164, 166, 168, 170, 172, 174, 176, 178, 180, 182, 184, or 186.

In other embodiments, the aforesaid antibody molecules comprise a VLFW1 amino acid sequence of SEQ ID NO: 156, 158, 160, 162, 164, or 166, a VLFW2 amino acid sequence of SEQ ID NO: 168 or 170, and a VLFW3 amino acid sequence of SEQ ID NO: 172, 174, 176, 178, 180, 182, or 184, and, optionally, further comprising a VLFW4 amino acid sequence of SEQ ID NO: 186.

In other embodiments, the aforesaid antibody molecules comprise a heavy chain variable domain comprising the amino acid sequence of SEQ ID NO: 18, 30, 38, 46, 50, 54, 62, 70, or 78, or an amino acid sequence that is at least 85% identical to the amino acid sequence of SEQ ID NO: 18, 30, 38, 46, 50, 54, 62, 70, or 78.

In other embodiments, the aforesaid antibody molecules comprise a light chain variable domain comprising an amino acid sequence of SEQ ID NO: 22, 26, 34, 42, 58, 66, 74, 82, or 86 or an amino acid sequence that is at least 85% identical to any of SEQ ID NOs: 22, 26, 34, 42, 58, 66, 74, 82, or 86.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules are capable of binding to human PD-L1 with a dissociation constant ($K_D$) of less than about 0.2 nM.

In some embodiments, the aforesaid antibody molecules bind to human PD-L1 with a $K_D$ of less than about 0.2 nM, 0.15 nM, 0.1 nM, 0.05 nM, or 0.02 nM, e.g., about 0.2 nM to 0.1 nM, e.g., about 0.166 nM to 0.176 nM, e.g., about 0.171 nM, e.g., as measured by a Biacore method.

In other embodiments, the aforesaid antibody molecules are capable of reducing binding of PD-1 or B7-1 to PD-L1 or a cell that expresses PD-L1. In some embodiments, the aforesaid antibody molecules reduce (e.g., block) PD-L1 binding to a cell that expresses PD-L1 with an IC50 of less than about 1.5 nM, 1 nM, 0.8 nM, 0.6 nM, 0.4 nM, 0.2 nM, or 0.1 nM, e.g., between about 0.2 nM and about 0.1 nM, e.g., about 0.15 nM or less, e.g., about 0.145 nM. In some embodiments, the aforesaid antibodies reduce (e.g., block) B7-1 binding to a cell that expresses PD-L1 (e.g., human PD-L1-expressing 300.19 cells) with an IC50 of less than about 2 nM, 1.5 nM, 1 nM, 0.5 nM, or 0.2 nM, e.g., between about 0.5 nM and about 0.01 nM, or about 0.2 nM or less, e.g., about 0.1 nM.

In other embodiments, the aforesaid antibody molecules are capable of enhancing an antigen-specific T cell response.

In some embodiments, the aforesaid antibody molecules bind to PD-L1 with a Kd slower than $5\times10^{-4}$, $1\times10^{-4}$, $5\times10^{-5}$, or $1\times10^{-5}$ $s^{-1}$, e.g., about $6.33\times10^{-5}$ $S^{-1}$, e.g., as measured by a Biacore method. In some embodiments, the aforesaid antibody molecules bind to PD-L1 with a Ka faster than $1\times10^{4}$, $5\times10^{4}$, $1\times10^{5}$, or $5\times10^{5}$ $M^{-1}s^{-1}$, e.g., about $3.07\times10^{4}$ $M^{-1}s^{-1}$, e.g., as measured by a Biacore method.

In embodiments, the anti-PD-L1 antibody molecule is a monospecific antibody molecule or a bispecific antibody molecule. In embodiments, the anti-PD-L1 antibody molecule has a first binding specificity for PD-L1 and a second binding specifity for TIM-3, LAG-3, CEACAM (e.g., CEACAM-1, CEACAM-3, and/or CEACAM-5), PD-1 or PD-L2. In embodiments, the antibody molecule comprises an antigen binding fragment of an antibody, e.g., a half antibody or antigen binding fragment of a half antibody.

TABLE 6

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058 HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 292 | VH | QVHLQQPGAELVKPGASVKLSCKASGYTFTSYWMYWVKQGPGRGLEWIGRIDPN<br>SGSTKYNEKFKNKATLTVDKSSSTAYMQLSSLTSEDSAVYYCARDYRKGLYAMD<br>YWGQGTSVTVSS |
| SEQ ID NO: 293 | DNA VH | CAGGTCCACCTGCAGCAGCCTGGGGCTGAGCTTGTGAAGCCTGGGGCTTCAGTG<br>AAGCTGTCCTGCAAGGCTTCTGGCTACACCTTCACCAGTTACTGGATGTACTGG<br>GTGAAACAGGGGCCTGGACGAGGCCTTGAGTGGATTGGAAGGATTGATCCTAAT<br>AGTGGGAGTACTAAGTACAATGAGAAGTTCAAGAACAAGGCCACACTGACTGTA<br>GACAAATCCTCCAGCACAGCCTACATGCAGCTCAGCAGCCTGACATCTGAGGAC<br>TCTGCGGTCTATTATTGTGCAAGGGACTATAGAAAGGGGCTCTATGCTATGGAC<br>TACTGGGGTCAAGGAACCTCAGTCACCGTCTCCTCA |
| **BAP058 LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 294 | VL | DIVMTQSHKFMSTSVGDRVSITCKASQDVGTAVAWYQQKPGQSPKLLIYWASTR<br>HTGVPDRFTGSGSGTDFTLTISNVQSEDLADYFCQQYNSYPLTFGAGSKLELK |
| SEQ ID NO: 301 | DNA VL | GACATTGTGATGACCCAGTCTCACAAATTCATGTCCACATCAGTAGGAGACAGG |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | GTCAGCATCACCTGCAAGGCCAGTCAGGATGTGGGTACTGCTGTAGCCTGGTAT CAACAGAAACCAGGGCAATCTCCTAAACTACTGATTTACTGGGCATCCACCCGG CACACTGGAGTCCCTGATCGCTTCACAGGCAGTGGATCTGGGACAGATTTCACT CTCACCATTAGCAATGTGCAGTCTGAAGACTTGGCAGATTATTTCTGTCAGCAG TATAACAGCTATCCTCTCACGTTCGGTGCTGGGTCCAAGCTGGAGCTGAAA |
| **BAP058-chi HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 302 | VH | EVQLQQSGAELVKPGASVKLSCKASGYTFTSYWMYWVKQGPGRGLEWIGRIDPN SGSTKYNEKFKNKATLTVDKSSSTAYMQLSSLTSEDSAVYYCARDYRKGLYAMD YWGQGTTVTVSS |
| **BAP058-chi LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 303 | VL | DIMMTQSHKFMSTSVGDRVSITCKASQDVGTAVAWYQQKPGQSPKLLIYWASTR HTGVPDRFTGSGSGTDFTLTISNVQSEDLADYFCQQYNSYPLTFGQGTKVEIK |
| **BAP058-hum01-HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 289 (Chothia) | HCDR3 | DYRKGLYAMDY |
| SEQ ID NO: 304 | VH | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSS |
| SEQ ID NO: 305 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 306 | Heavy Chain | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 307 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum01-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 308 | VL | DIVMTQTPLSLPVTPGEPASISCKASQDVGTAVAWYLQKPGQSPQLLIYWASTR HTGIPARFSGSGSGTEFTLTISSLQSEDFAVYYCQQYNSYPLTFGQGTKVEIK |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 309 | DNA VL | GATATTGTGATGACCCAGACTCCACTCTCCCTGCCCGTCACCCCTGGAGAGCCG GCCTCCATCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCAGCCAGGTTCAGTGGCAGTGGGTCTGGGACAGAGTTCACT CTCACCATCAGCAGCCTGCAGTCTGAAGATTTTGCAGTTTATTACTGTCAGCAG TATAACAGCTATCCTCTCACGTTCGGCCAAGGGACCAAGGTGGAAATCAAA |
| SEQ ID NO: 310 | Light Chain | DIVMTQTPLSLPVTPGEPASISCKASQDVGTAVAWYLQKPGQSPQLLIYWASTR HTGIPARFSGSGSGTEFTLTISSLQSEDFAVYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 311 | DNA Light Chain | GATATTGTGATGACCCAGACTCCACTCTCCCTGCCCGTCACCCCTGGAGAGCCG GCCTCCATCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCAGCCAGGTTCAGTGGCAGTGGGTCTGGGACAGAGTTCACT CTCACCATCAGCAGCCTGCAGTCTGAAGATTTTGCAGTTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |
| | | BAP058-hum02-HC |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 304 | VH | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSS |
| SEQ ID NO: 305 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 306 | Heavy Chain | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 307 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| BAP058-hum02-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 312 | VL | DIQMTQSPSSLSASVGDRVTITCKASQDVGTAVAWYLQKPGQSPQLLIYWASTR<br>HTGVPSRFSGSGSGTDFTLTISSLQPEDFATYYCQQYNSYPLTFGQGTKVEIK |
| SEQ ID NO: 313 | DNA VL | GACATCCAGATGACCCAGTCTCCATCCTCCCTGTCTGCATCTGTAGGAGACAGA<br>GTCACCATCACTTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGCGGCAGTGGATCTGGGACAGATTTCACT<br>CTCACCATCAGCAGCCTGCAGCCTGAAGATTTTGCAACTTATTACTGTCAGCAG<br>TATAACAGCTATCCTCTCACGTTCGGCCAAGGGACCAAGGTGGAAATCAAA |
| SEQ ID NO: 314 | Light Chain | DIQMTQSPSSLSASVGDRVTITCKASQDVGTAVAWYLQKPGQSPQLLIYWASTR<br>HTGVPSRFSGSGSGTDFTLTISSLQPEDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 315 | DNA Light Chain | GACATCCAGATGACCCAGTCTCCATCCTCCCTGTCTGCATCTGTAGGAGACAGA<br>GTCACCATCACTTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGCGGCAGTGGATCTGGGACAGATTTCACT<br>CTCACCATCAGCAGCCTGCAGCCTGAAGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| BAP058-hum03-HC | | |
| SEQ ID NO: 287 (Kabat) | HCDR1 | SYWMY |
| SEQ ID NO: 288 (Kabat) | HCDR2 | RIDPNSGSTKYNEKFKN |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN<br>SGSTKYNEKFKNRVTITADKSTSTAYMELSSLRSEDTAVYYCARDYRKGLYAMD<br>YWGQGTTVTVSS |
| SEQ ID NO: 317 | DNA VH | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>GTGCGACAGGCCACTGGACAAGGGCTTGAGTGGATGGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 318 | Heavy Chain | EVQLVQSGAEVKKPGATVKISCKVSGYTFTSYWMYWVRQATGQGLEWMGRIDPN<br>SGSTKYNEKFKNRVTITADKSTSTAYMELSSLRSEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 319 | DNA Heavy Chain | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>GTGCGACAGGCCACTGGACAAGGGCTTGAGTGGATGGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| | BAP058-hum03-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 299 (Chothia) | LCDR2 | WAS |
| SEQ ID NO: 300 (Chothia) | LCDR3 | YNSYPL |
| SEQ ID NO: 320 | VL | EIVLTQSPDFQSVTPKEKVTITCKASQDVGTAVAWYLQKPGQSPQLLIYWASTR<br>HTGVPDRFSGSGSGTDFTLKISRVEAEDVGVYYCQQYNSYPLTFGQGTKVEIK |
| SEQ ID NO: 321 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCAGACAGGTTCAGTGGCAGTGGGTCAGGCACTGATTTCACA<br>CTGAAAATCAGCAGGGTGGAGGCTGAGGATGTTGGAGTTTATTACTGTCAGCAG<br>TATAACAGCTATCCTCTCACGTTCGGCCAAGGGACCAAGGTGGAAATCAAA |
| SEQ ID NO: 322 | Light Chain | EIVLTQSPDFQSVTPKEKVTITCKASQDVGTAVAWYLQKPGQSPQLLIYWASTR<br>HTGVPDRFSGSGSGTDFTLKISRVEAEDVGVYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 323 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCAGACAGGTTCAGTGGCAGTGGGTCAGGCACTGATTTCACA<br>CTGAAAATCAGCAGGGTGGAGGCTGAGGATGTTGGAGTTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| | | BAP058-hum04-HC |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 324 | VH | EVQLVQSGAEVKKPGESLRISCKGSGYTFTSYWMYWVRQAPGQGLEWMGRIDPN<br>SGSTKYNEKFKNRVTISVDTSKNQFSLKLSSVTAADTAVYYCARDYRKGLYAMD<br>YWGQGTTVTVSS |
| SEQ ID NO: 325 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCCCCTGGACAAGGGCTTGAGTGGATGGGTAGGATTGATCCTAAT<br>AGTGGGAGTACTAAGTACAATGAGAAGTTCAAGAACAGAGTCACCATATCAGTA<br>GACACGTCCAAGAACCAGTTCTCCCTGAAGCTGAGCTCTGTGACCGCCGCGGAC<br>ACGGCTGTGTATTACTGTGCAAGGGACTATAGAAAGGGGCTCTATGCTATGGAC<br>TACTGGGGCCAGGGCACCACCGTGACCGTGTCCTCC |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 326 | Heavy Chain | EVQLVQSGAEVKKPGESLRISCKGSGYTFTSYWMYWVRQAPGQGLEWMGRIDPN<br>SGSTKYNEKFKNRVTISVDTSKNQFSLKLSSVTAADTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 327 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCCCCTGGACAAGGGCTTGAGTGGATGGGTAGGATTGATCCTAAT<br>AGTGGGAGTACTAAGTACAATGAGAAGTTCAAGAACAGAGTCACCATATCAGTA<br>GACACGTCCAAGAACCAGTTCTCCCTGAAGCTGAGCTCTGTGACCGCCGCGGAC<br>ACGGCTGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |

BAP058-hum04-LC

| | | |
|---|---|---|
| SEQ ID NO: 295 (Kabat) +00 | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIK |
| SEQ ID NO: 329 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAA |
| SEQ ID NO: 330 | Light Chain | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 331 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| BAP058-hum05-HC | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 332 | VH | EVQLVQSGAEVKKPGATVKISCKVSGYTFTSYWMYWIRQSPSRGLEWLGRIDPN<br>SGSTKYNEKFKNRLTISKDTSKNQVVLTMTNMDPVDTATYYCARDYRKGLYAMD<br>YWGQGTTVTVSS |
| SEQ ID NO: 333 | DNA VH | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCC |
| SEQ ID NO: 334 | Heavy Chain | EVQLVQSGAEVKKPGATVKISCKVSGYTFTSYWMYWIRQSPSRGLEWLGRIDPN<br>SGSTKYNEKFKNRLTISKDTSKNQVVLTMTNMDPVDTATYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 335 | DNA Heavy Chain | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| | | **BAP058-hum05-LC** |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIK |
| SEQ ID NO: 329 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAA |
| SEQ ID NO: 330 | Light Chain | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 331 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| | | **BAP058-hum06-HC** |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSS |
| SEQ ID NO: 337 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG ATCCGCCAGCCCCCAGGGAAGGGGCTGGAGTGGATTGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 338 | Heavy Chain | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 339 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG ATCCGCCAGCCCCCAGGGAAGGGGCTGGAGTGGATTGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum06-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 328 | VL | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIK |
| +00<br>SEQ ID NO: 329 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAA |
| SEQ ID NO: 330 | Light Chain | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 331 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

BAP058-hum07-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 340 | VH | QVQLVQSGAEVKKPGASVKVSCKASGYTFTSYWMYWIRQSPSRGLEWLGRIDPN<br>SGSTKYNEKFKNRFTISRDDSKNTAYLQMNSLKTEDTAVYYCARDYRKGLYAMD<br>YWGQGTTVTVSS |
| SEQ ID NO: 341 | DNA VH | CAGGTTCAGCTGGTGCAGTCTGGAGCTGAGGTGAAGAAGCCTGGGGCCTCAGTG<br>AAGGTCTCCTGCAAGGCTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGATTCACCATCTCCAGA<br>GATGATTCAAAGAACACGGCGTATCTGCAAATGAACAGCCTGAAAACCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 342 | Heavy Chain | QVQLVQSGAEVKKPGASVKVSCKASGYTFTSYWMYWIRQSPSRGLEWLGRIDPN<br>SGSTKYNEKFKNRFTISRDDSKNTAYLQMNSLKTEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| +00<br>SEQ ID NO: 343 | DNA Heavy Chain | CAGGTTCAGCTGGTGCAGTCTGGAGCTGAGGTGAAGAAGCCTGGGGCCTCAGTG<br>AAGGTCTCCTGCAAGGCTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGATTCACCATCTCCAGA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | GATGATTCAAAGAACACGGCGTATCTGCAAATGAACAGCCTGAAAACCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |

BAP058-hum07-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 344 | VL | EIVLTQSPATLSLSPGERATLSCKASQDVGTAVAWYLQKPGQSPQLLIYWASTR<br>HTGIPPRFSGSGYGTDFTLTINNIESEDAAYYFCQQYNSYPLTFGQGTKVEIK |
| SEQ ID NO: 345 | DNA VL | GAAATTGTGTTGACACAGTCTCCAGCCACCCTGTCTTTGTCTCCAGGGGAAAGA<br>GCCACCCTCTCCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGATCCCACCTCGATTCAGTGGCAGCGGGTATGGAACAGATTTTACC<br>CTCACAATTAATAACATAGAATCTGAGGATGCTGCATATTACTTCTGTCAGCAG<br>TATAACAGCTATCCTCTCACGTTCGGCCAAGGGACCAAGGTGGAAATCAAA |
| SEQ ID NO: 346 | Light Chain | EIVLTQSPATLSLSPGERATLSCKASQDVGTAVAWYLQKPGQSPQLLIYWASTR<br>HTGIPPRFSGSGYGTDFTLTINNIESEDAAYYFCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 347 | DNA Light Chain | GAAATTGTGTTGACACAGTCTCCAGCCACCCTGTCTTTGTCTCCAGGGGAAAGA<br>GCCACCCTCTCCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGATCCCACCTCGATTCAGTGGCAGCGGGTATGGAACAGATTTTACC<br>CTCACAATTAATAACATAGAATCTGAGGATGCTGCATATTACTTCTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| BAP058-hum08-HC | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 348 | VH | EVQLVQSGAEVKKPGESLRISCKGSGYTFTSYWMYWVRQARGQRLEWIGRIDPN<br>SGSTKYNEKFKNRLTISKDTSKNQVVLTMTNMDPVDTATYYCARDYRKGLYAMD<br>YWGQGTTVTVSS |
| SEQ ID NO: 349 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCTCGTGGACAACGCCTTGAGTGGATAGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCC |
| SEQ ID NO: 350 | Heavy Chain | EVQLVQSGAEVKKPGESLRISCKGSGYTFTSYWMYWVRQARGQRLEWIGRIDPN<br>SGSTKYNEKFKNRLTISKDTSKNQVVLTMTNMDPVDTATYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 351 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCTCGTGGACAACGCCTTGAGTGGATAGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058-hum08-LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 352 | VL | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 353 | DNA VL | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 354 | Light Chain | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 355 | DNA Light Chain | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| **BAP058-hum09-HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSS |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 337 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG ATCCGCCAGCCCCCAGGGAAGGGGCTGGAGTGGATTGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 338 | Heavy Chain | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 339 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG ATCCGCCAGCCCCCAGGGAAGGGGCTGGAGTGGATTGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum09-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 308 | VL | DIVMTQTPLSLPVTPGEPASISCKASQDVGTAVAWYLQKPGQSPQLLIYWASTR HTGIPARFSGSGSGTEFTLTISSLQSEDFAVYYCQQYNSYPLTFGQGTKVEIK |
| SEQ ID NO: 309 | DNA VL | GATATTGTGATGACCCAGACTCCACTCTCCCTGCCCGTCACCCCTGGAGAGCCG GCCTCCATCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCAGCCAGGTTCAGTGGCAGTGGGTCTGGGACAGAGTTCACT CTCACCATCAGCAGCCTGCAGTCTGAAGATTTTGCAGTTTATTACTGTCAGCAG TATAACAGCTATCCTCTCACGTTCGGCCAAGGGACCAAGGTGGAAATCAAA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 310 | Light Chain | DIVMTQTPLSLPVTPGEPASISCKASQDVGTAVAWYLQKPGQSPQLLIYWASTR HTGIPARFSGSGSGTEFTLTISSLQSEDFAVYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 311 | DNA Light Chain | GATATTGTGATGACCCAGACTCCACTCTCCCTGCCCGTCACCCCTGGAGAGCCG GCCTCCATCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCAGCCAGGTTCAGTGGCAGTGGGTCTGGGACAGAGTTCACT CTCACCATCAGCAGCCTGCAGTCTGAAGATTTTGCAGTTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |
| | BAP058-hum10-HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 356 | VH | QITLKESGPTLVKPTQTLTLTCTFSGYTFTSYWMYWVRQAPGKGLEWVSRIDPN SGSTKYNEKFKNRVTITADKSTSTAYMELSSLRSEDTAVYYCARDYRKGLYAMD YWGQGTTVTVSS |
| SEQ ID NO: 357 | DNA VH | CAGATCACCTTGAAGGAGTCTGGTCCTACGCTGGTGAAACCCACACAGACCCTC ACGCTGACCTGCACCTTCTCTGGCTACACCTTCACCAGTTACTGGATGTACTGG GTCCGCCAGGCTCCAGGGAAGGGGCTGGAGTGGGTCAGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 358 | Heavy Chain | QITLKESGPTLVKPTQTLTLTCTFSGYTFTSYWMYWVRQAPGKGLEWVSRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 359 | DNA Heavy Chain | CAGATCACCTTGAAGGAGTCTGGTCCTACGCTGGTGAAACCCACACAGACCCTC ACGCTGACCTGCACCTTCTCTGGCTACACCTTCACCAGTTACTGGATGTACTGG GTCCGCCAGGCTCCAGGGAAGGGGCTGGAGTGGGTCAGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| BAP058-hum10-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 352 | VL | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 353 | DNA VL | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 354 | Light Chain | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 355 | DNA Light Chain | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| BAP058-hum11-HC | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO: 317 | DNA VH | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 318 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 319 | DNA Heavy Chain | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| | BAP058-hum11-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 352 | VL | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 353 | DNA VL | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 354 | Light Chain | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 355 | DNA Light Chain | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

BAP058-hum12-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 324 | VH | EVQLVQSGAEVKKPGESLRISCKGSGYTFTSYWMYWVRQAPGQGLEWMGRIDPN<br>SGSTKYNEKFKNRVTISVDTSKNQFSLKLSSVTAADTAVYYCARDYRKGLYAMD<br>YWGQGTTVTVSS |
| SEQ ID NO: 325 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCCCCTGGACAAGGGCTTGAGTGGATGGGTAGGATTGATCCTAAT<br>AGTGGGAGTACTAAGTACAATGAGAAGTTCAAGAACAGAGTCACCATATCAGTA<br>GACACGTCCAAGAACCAGTTCTCCCTGAAGCTGAGCTCTGTGACCGCCGCGGAC<br>ACGGCTGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 326 | Heavy Chain | EVQLVQSGAEVKKPGESLRISCKGSGYTFTSYWMYWVRQAPGQGLEWMGRIDPN<br>SGSTKYNEKFKNRVTISVDTSKNQFSLKLSSVTAADTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 327 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCCCCTGGACAAGGGCTTGAGTGGATGGGTAGGATTGATCCTAAT<br>AGTGGGAGTACTAAGTACAATGAGAAGTTCAAGAACAGAGTCACCATATCAGTA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | GACACGTCCAAGAACCAGTTCTCCCTGAAGCTGAGCTCTGTGACCGCCGCGGAC<br>ACGGCTGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| BAP058-hum12-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 360 | VL | DIQMTQSPSSLSASVGDRVTITCKASQDVGTAVAWYQQKPGQAPRLLIYWASTR<br>HTGVPSRFSGSGSGTDFTFTISSLQPEDIATYYCQQYNSYPLTFGQGTKVEIK |
| SEQ ID NO: 361 | DNA VL | GACATCCAGATGACCCAGTCTCCATCCTCCCTGTCTGCATCTGTAGGAGACAGA<br>GTCACCATCACTTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAA |
| SEQ ID NO: 362 | Light Chain | DIQMTQSPSSLSASVGDRVTITCKASQDVGTAVAWYQQKPGQAPRLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 363 | DNA Light Chain | GACATCCAGATGACCCAGTCTCCATCCTCCCTGTCTGCATCTGTAGGAGACAGA<br>GTCACCATCACTTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| BAP058-hum13-HC | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 364 | VH | EVQLVQSGAEVKKPGATVKISCKVSGYTFTSYWMYWVRQARGQRLEWIGRIDPN<br>SGSTKYNEKFKNRFTISRDNSKNTLYLQMNSLRAEDTAVYYCARDYRKGLYAMD<br>YWGQGTTVTVSS |
| SEQ ID NO: 365 | DNA VH | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>GTGCGACAGGCTCGTGGACAACGCCTTGAGTGGATAGGTAGGATTGATCCTAAT<br>AGTGGGAGTACTAAGTACAATGAGAAGTTCAAGAACAGATTCACCATCTCCAGA<br>GACAATTCCAAGAACACGCTGTATCTTCAAATGAACAGCCTGAGAGCCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 391 | Heavy Chain | EVQLVQSGAEVKKPGATVKISCKVSGYTFTSYWMYWVRQARGQRLEWIGRIDPN<br>SGSTKYNEKFKNRFTISRDNSKNTLYLQMNSLRAEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 367 | DNA Heavy Chain | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>GTGCGACAGGCTCGTGGACAACGCCTTGAGTGGATAGGTAGGATTGATCCTAAT<br>AGTGGGAGTACTAAGTACAATGAGAAGTTCAAGAACAGATTCACCATCTCCAGA<br>GACAATTCCAAGAACACGCTGTATCTTCAAATGAACAGCCTGAGAGCCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058-hum13-LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 368 | VL | AIQLTQSPSSLSASVGDRVTITCKASQDVGTAVAWYLQKPGQSPQLLIYWASTR HTGVPSRFSGSGSGTDFTFTISSLEAEDAATYYCQQYNSYPLTFGQGTKVEIK |
| SEQ ID NO: 369 | DNA VL | GCCATCCAGTTGACCCAGTCTCCATCCTCCCTGTCTGCATCTGTAGGAGACAGA GTCACCATCACTTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCCTCGAGGTTCAGTGGCAGTGGATCTGGGACAGATTTCACC TTTACCATCAGTAGCCTGGAAGCTGAAGATGCTGCAACATATTACTGTCAGCAG TATAACAGCTATCCTCTCACGTTCGGCCAAGGGACCAAGGTGGAAATCAAA |
| SEQ ID NO: 370 | Light Chain | AIQLTQSPSSLSASVGDRVTITCKASQDVGTAVAWYLQKPGQSPQLLIYWASTR HTGVPSRFSGSGSGTDFTFTISSLEAEDAATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 371 | DNA Light Chain | GCCATCCAGTTGACCCAGTCTCCATCCTCCCTGTCTGCATCTGTAGGAGACAGA GTCACCATCACTTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCCTCGAGGTTCAGTGGCAGTGGATCTGGGACAGATTTCACC TTTACCATCAGTAGCCTGGAAGCTGAAGATGCTGCAACATATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |
| **BAP058-hum14-HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 304 | VH | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSS |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 305 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 306 | Heavy Chain | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 307 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| BAP058-hum14-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 372 | VL | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 374 | Light Chain | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

BAP058-hum15-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSS |
| SEQ ID NO: 337 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>ATCCGCCAGCCCCCAGGGAAGGGGCTGGAGTGGATTGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 338 | Heavy Chain | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 339 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>ATCCGCCAGCCCCCAGGGAAGGGGCTGGAGTGGATTGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| | | BAP058-hum15-LC |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 372 | VL | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| | | BAP058-hum16-HC |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 291 (Chothia) | HCDR2 | DPNSGS |
| SEQ ID NO: 289 (Chothia) | HCDR3 | DYRKGLYAMDY |
| SEQ ID NO: 340 | VH | QVQLVQSGAEVKKPGASVKVSCKASGYTFTSYWMYWIRQSPSRGLEWLGRIDPN SGSTKYNEKFKNRFTISRDDSKNTAYLQMNSLKTEDTAVYYCARDYRKGLYAMD YWGQGTTVTVSS |
| SEQ ID NO: 341 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG ATCAGGCAGTCCCCATCGAGAGGCCTTGAGTGGCTGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 342 | Heavy Chain | QVQLVQSGAEVKKPGASVKVSCKASGYTFTSYWMYWIRQSPSRGLEWLGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 343 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG ATCAGGCAGTCCCCATCGAGAGGCCTTGAGTGGCTGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| | BAP058-hum16-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 372 | VL | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| | | BAP058-hum17-HC |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 348 | VH | EVQLVQSGAEVKKPGESLRISCKGSGYTFTSYWMYWVRQARGQRLEWIGRIDPN<br>SGSTKYNEKFKNRLTISKDTSKNQVVLTMTNMDPVDTATYYCARDYRKGLYAMD<br>YWGQGTTVTVSS |
| SEQ ID NO: 349 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCTCGTGGACAACGCCTTGAGTGGATAGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCC |
| SEQ ID NO: 350 | Heavy Chain | EVQLVQSGAEVKKPGESLRISCKGSGYTFTSYWMYWVRQARGQRLEWIGRIDPN<br>SGSTKYNEKFKNRLTISKDTSKNQVVLTMTNMDPVDTATYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 351 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>GTGCGACAGGCTCGTGGACAACGCCTTGAGTGGATAGGTAGGATTGATCCTAAT<br>AGTGGGAGTACTAAGTACAATGAGAAGTTCAAGAACAGACTCACCATCTCCAAG |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |

BAP058-hum17-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 372 | VL | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| BAP058-Clone K HC | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO:392 | DNA VH | GAAGTGCAGCTGGTGCAGTCTGGCGCCGAAGTGAAGAAACCCGGCGCTACCGTG AAGATCTCCTGCAAGGTGTCCGGCTACACCTTCACCAGCTACTGGATGTACTGG GTGCGACAGGCTACCGGCCAGGGCCTGGAATGGATGGGCAGAATCGACCCCAAC TCCGGCTCCACCAAGTACAACGAGAAGTTCAAGAACCGCGTGACCATCACCGCC GACAAGTCCACCTCCACCGCCTACATGGAACTGTCCTCCCTGCGGAGCGAGGAC ACCGCCGTGTACTACTGCGCCAGAGACTACCGGAAGGGCCTGTACGCCATGGAC TATTGGGGCCAGGGCACCACCGTGACCGTGTCCTCT |
| SEQ ID NO:393 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO:394 | DNA Heavy Chain | GAAGTGCAGCTGGTGCAGTCTGGCGCCGAAGTGAAGAAACCCGGCGCTACCGTG AAGATCTCCTGCAAGGTGTCCGGCTACACCTTCACCAGCTACTGGATGTACTGG GTGCGACAGGCTACCGGCCAGGGCCTGGAATGGATGGGCAGAATCGACCCCAAC TCCGGCTCCACCAAGTACAACGAGAAGTTCAAGAACCGCGTGACCATCACCGCC GACAAGTCCACCTCCACCGCCTACATGGAACTGTCCTCCCTGCGGAGCGAGGAC ACCGCCGTGTACTACTGCGCCAGAGACTACCGGAAGGGCCTGTACGCCATGGAC TATTGGGGCCAGGGCACCACCGTGACCGTGTCCTCTGCTTCCACCAAGGGCCCA AGCGTGTTCCCCCTGGCCCCCTGCTCCAGAAGCACCAGCGAGAGCACAGCCGCC CTGGGCTGCCTGGTGAAGGACTACTTCCCCGAGCCCGTGACCGTGTCCTGGAAC AGCGGAGCCCTGACCAGCGGCGTGCACACCTTCCCCGCCGTGCTGCAGAGCAGC GGCCTGTACAGCCTGAGCAGCGTGGTGACCGTGCCCAGCAGCAGCCTGGGCACC AAGACCTACACCTGTAACGTGGACCACAAGCCCAGCAACACCAAGGTGGACAAG AGGGTGGAGAGCAAGTACGGCCCACCCTGCCCCCCCTGCCCAGCCCCCGAGTTC CTGGGCGGACCCAGCGTGTTCCTGTTCCCCCCCAAGCCCAAGGACACCCTGATG ATCAGCAGAACCCCCGAGGTGACCTGTGTGGTGGTGGACGTGTCCCAGGAGGAC CCCGAGGTCCAGTTCAACTGGTACGTGGACGGCGTGGAGGTGCACAACGCCAAG ACCAAGCCCAGAGAGGAGCAGTTTAACAGCACCTACCGGGTGGTGTCCGTGCTG ACCGTGCTGCACCAGGACTGGCTGAACGGCAAAGAGTACAAGTGTAAGGTCTCC AACAAGGGCCTGCCAAGCAGCATCGAAAAGACCATCAGCAAGGCCAAGGGCCAG CCTAGAGAGCCCCAGGTCTACACCCTGCCACCCAGCCAAGAGGAGATGACCAAG AACCAGGTGTCCCTGACCTGTCTGGTGAAGGGCTTCTACCCAAGCGACATCGCC GTGGAGTGGGAGAGCAACGGCCAGCCCGAGAACAACTACAAGACCACCCCCCCA GTGCTGGACAGCGACGGCAGCTTCTTCCTGTACAGCAGGCTGACCGTGGACAAG TCCAGATGGCAGGAGGGCAACGTCTTTAGCTGCTCCGTGATGCACGAGGCCCTG CACAACCACTACACCCAGAAGAGCCTGAGCCTGTCCCTGGGCTGATGAATTC |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058-Clone K LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 320 | VL | EIVLTQSPDFQSVTPKEKVTITCKASQDVGTAVAWYLQKPGQSPQLLIYWASTR<br>HTGVPDRFSGSGSGTDFTLKISRVEAEDVGVYYCQQYNSYPLTFGQGTKVEIK |
| SEQ ID NO:395 | DNA VL | GAGATCGTGCTGACCCAGTCCCCCGACTTCCAGTCCGTGACCCCCAAAGAAAAA<br>GTGACCATCACATGCAAGGCCTCCCAGGACGTGGGCACCGCCGTGGCTTGGTAT<br>CTGCAGAAGCCTGGCCAGTCCCCTCAGCTGCTGATCTACTGGGCCTCTACCAGA<br>CACACCGGCGTGCCCGACAGATTCTCCGGCTCTGGCTCTGGCACCGACTTCACC<br>CTGAAGATCTCCCGGGTGGAAGCCGAGGATGTGGGCGTGTACTACTGCCAGCAG<br>TACAACTCCTACCCCCTGACCTTCGGCCAGGGCACCAAGGTGGAAATCAAG |
| SEQ ID NO:322 | Light Chain | EIVLTQSPDFQSVTPKEKVTITCKASQDVGTAVAWYLQKPGQSPQLLIYWASTR<br>HTGVPDRFSGSGSGTDFTLKISRVEAEDVGVYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO:396 | DNA Light Chain | GAGATCGTGCTGACCCAGTCCCCCGACTTCCAGTCCGTGACCCCCAAAGAAAAA<br>GTGACCATCACATGCAAGGCCTCCCAGGACGTGGGCACCGCCGTGGCTTGGTAT<br>CTGCAGAAGCCTGGCCAGTCCCCTCAGCTGCTGATCTACTGGGCCTCTACCAGA<br>CACACCGGCGTGCCCGACAGATTCTCCGGCTCTGGCTCTGGCACCGACTTCACC<br>CTGAAGATCTCCCGGGTGGAAGCCGAGGATGTGGGCGTGTACTACTGCCAGCAG<br>TACAACTCCTACCCCCTGACCTTCGGCCAGGGCACCAAGGTGGAAATCAAGCGT<br>ACGGTGGCCGCTCCCAGCGTGTTCATCTTCCCCCCAAGCGACGAGCAGCTGAAG<br>AGCGGCACCGCCAGCGTGGTGTGTCTGCTGAACAACTTCTACCCCAGGGAGGCC<br>AAGGTGCAGTGGAAGGTGGACAACGCCCTGCAGAGCGGCAACAGCCAGGAGAGC<br>GTCACCGAGCAGGACAGCAAGGACTCCACCTACAGCCTGAGCAGCACCCTGACC<br>CTGAGCAAGGCCGACTACGAGAAGCACAAGGTGTACGCCTGTGAGGTGACCCAC<br>CAGGGCCTGTCCAGCCCCGTGACCAAGAGCTTCAACAGGGGCGAGTGCTGATGA<br>ATTC |
| **BAP058-Clone L HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 324 | VH | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSS |
| SEQ ID NO: 376 | DNA VH | GAAGTGCAGCTGGTGCAGTCAGGCGCCGAAGTGAAGAAGCCCGGCGAGTCACTG AGAATTAGCTGTAAAGGTTCAGGCTACACCTTCACTAGCTACTGGATGTACTGG GTCCGACAGGCCCCAGGGCAAGGCCTGGAGTGGATGGGTAGAATCGACCCTAAT AGCGGCTCTACTAAGTATAACGAGAAGTTTAAGAATAGAGTGACTATTAGCGTG GACACCTCTAAGAATCAGTTTAGCCTGAAGCTGTCTAGCGTGACCGCCGCTGAC ACCGCCGTCTACTACTGCGCTAGAGACTATAGAAAGGGCCTGTACGCTATGGAC TACTGGGGTCAAGGCACTACCGTGACCGTGTCTTCA |
| SEQ ID NO: 377 | Heavy Chain | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 378 | DNA Heavy Chain | GAAGTGCAGCTGGTGCAGTCAGGCGCCGAAGTGAAGAAGCCCGGCGAGTCACTG AGAATTAGCTGTAAAGGTTCAGGCTACACCTTCACTAGCTACTGGATGTACTGG GTCCGACAGGCCCCAGGGCAAGGCCTGGAGTGGATGGGTAGAATCGACCCTAAT AGCGGCTCTACTAAGTATAACGAGAAGTTTAAGAATAGAGTGACTATTAGCGTG GACACCTCTAAGAATCAGTTTAGCCTGAAGCTGTCTAGCGTGACCGCCGCTGAC ACCGCCGTCTACTACTGCGCTAGAGACTATAGAAAGGGCCTGTACGCTATGGAC TACTGGGGTCAAGGCACTACCGTGACCGTGTCTTCAGCTAGCACTAAGGGCCCG TCCGTGTTCCCCCTGGCACCTTGTAGCCGGAGCACTAGCGAATCCACCGCTGCC CTCGGCTGCCTGGTCAAGGATTACTTCCCGGAGCCCGTGACCGTGTCCTGGAAC AGCGGAGCCCTGACCTCCGGAGTGCACACCTTCCCCGCTGTGCTGCAGAGCTCC GGGCTGTACTCGCTGTCGTCGGTGGTCACGGTGCCTTCATCTAGCCTGGGTACC AAGACCTACACTTGCAACGTGGACCACAAGCCTTCCAACACTAAGGTGGACAAG CGCGTCGAATCGAAGTACGGCCCACCGTGCCCGCCTTGTCCCGCGCCGGAGTTC CTCGGCGGTCCCTCGGTCTTTCTGTTCCCACCGAAGCCCAAGGACACTTTGATG ATTTCCCGCACCCCTGAAGTGACATGCGTGGTCGTGGACGTGTCACAGGAAGAT CCGGAGGTGCAGTTCAATTGGTACGTGGATGGCGTCGAGGTGCACAACGCCAAA ACCAAGCCGAGGGAGGAGCAGTTCAACTCCACTTACCGCGTCGTGTCCGTGCTG ACGGTGCTGCATCAGGACTGGCTGAACGGGAAGGAGTACAAGTGCAAAGTGTCC AACAAGGGACTTCCTAGCTCAATCGAAAAGACCATCTCGAAAGCCAAGGGACAG CCCCGGGAACCCCAAGTGTATACCCTGCCACCGAGCCAGGAAGAAATGACTAAG AACCAAGTCTCATTGACTTGCCTTGTGAAGGGCTTCTACCCATCGGATATCGCC GTGGAATGGGAGTCCAACGGCCAGCCGGAAAACAACTACAAGACCACCCCTCCG GTGCTGGACTCAGACGGATCCTTCTTCCTCTACTCGCGGCTGACCGTGGATAAG AGCAGATGGCAGGAGGGAAATGTGTTCAGCTGTTCTGTGATGCATGAAGCCCTG CACAACCACTACACTCAGAAGTCCCTGTCCCTCTCCCTGGGA |

BAP058-Clone L LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIK |
| SEQ ID NO: 379 | DNA VL | GAGATCGTCCTGACTCAGTCACCCGACTTTCAGTCAGTGACCCCTAAAGAGAAA GTCACTATCACCTGTAAAGCCTCTCAGGACGTGGGCACCGCCGTGGCCTGGTAT CTGCAGAAGCCTGGTCAATCACCTCAGCTGCTGATCTACTGGGCCTCTACTAGA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | CACACCGGCGTGCCCTCTAGGTTTAGCGGTAGCGGTAGTGGCACCGACTTCACC<br>TTCACTATCTCTTCACTGCAGCCCGAGGATATCGCTACCTACTACTGTCAGCAG<br>TATAATAGCTACCCCCTGACCTTCGGTCAAGGCACTAAGGTCGAGATTAAG |
| SEQ ID NO: 330 | Light Chain | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 380 | DNA Light Chain | GAGATCGTCCTGACTCAGTCACCCGACTTTCAGTCAGTGACCCCTAAAGAGAAA<br>GTCACTATCACCTGTAAAGCCTCTCAGGACGTGGGCACCGCCGTGGCCTGGTAT<br>CTGCAGAAGCCTGGTCAATCACCTCAGCTGCTGATCTACTGGGCCTCTACTAGA<br>CACACCGGCGTGCCCTCTAGGTTTAGCGGTAGCGGTAGTGGCACCGACTTCACC<br>TTCACTATCTCTTCACTGCAGCCCGAGGATATCGCTACCTACTACTGTCAGCAG<br>TATAATAGCTACCCCCTGACCTTCGGTCAAGGCACTAAGGTCGAGATTAAGCGT<br>ACGGTGGCCGCTCCCAGCGTGTTCATCTTCCCCCCCAGCGACGAGCAGCTGAAG<br>AGCGGCACCGCCAGCGTGGTGTGCCTGCTGAACAACTTCTACCCCCGGGAGGCC<br>AAGGTGCAGTGGAAGGTGGACAACGCCCTGCAGAGCGGCAACAGCCAGGAGAGC<br>GTCACCGAGCAGGACAGCAAGGACTCCACCTACAGCCTGAGCAGCACCCTGACC<br>CTGAGCAAGGCCGACTACGAGAAGCATAAGGTGTACGCCTGCGAGGTGACCCAC<br>CAGGGCCTGTCCAGCCCCGTGACCAAGAGCTTCAACAGGGGCGAGTGC |
| | | BAP058-Clone M HC |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSS |
| SEQ ID NO:397 | DNA VH | GAAGTGCAGCTGGTGCAGTCTGGCGCCGAAGTGAAGAAGCCTGGCGAGTCCCTG<br>CGGATCTCCTGCAAGGGCTCCGGCTACACCTTCACCAGCTACTGGATGTACTGG<br>ATCCGGCAGCCCCCTGGCAAGGGCCTGGAATGGATCGGCAGAATCGACCCCAAC<br>TCCGGCTCCACCAAGTACAACGAGAAGTTCAAGAACCGCGTGACCATCACCGCC<br>GACAAGTCCACCTCCACCGCCTACATGGAACTGTCCTCCCTGAGATCCGAGGAC<br>ACCGCCGTGTACTACTGCGCCAGAGACTACCGGAAGGGCCTGTACGCCATGGAC<br>TATTGGGGCCAGGGCACCACCGTGACCGTGTCCTCT |
| SEQ ID NO:398 | Heavy Chain | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLG |
| SEQ ID NO:399 | DNA Heavy Chain | GAAGTGCAGCTGGTGCAGTCTGGCGCCGAAGTGAAGAAGCCTGGCGAGTCCCTG<br>CGGATCTCCTGCAAGGGCTCCGGCTACACCTTCACCAGCTACTGGATGTACTGG<br>ATCCGGCAGCCCCCTGGCAAGGGCCTGGAATGGATCGGCAGAATCGACCCCAAC<br>TCCGGCTCCACCAAGTACAACGAGAAGTTCAAGAACCGCGTGACCATCACCGCC<br>GACAAGTCCACCTCCACCGCCTACATGGAACTGTCCTCCCTGAGATCCGAGGAC<br>ACCGCCGTGTACTACTGCGCCAGAGACTACCGGAAGGGCCTGTACGCCATGGAC<br>TATTGGGGCCAGGGCACCACCGTGACCGTGTCCTCTGCTTCTACCAAGGGCCCA<br>AGCGTGTTCCCCCTGGCCCCCTGCTCCAGAAGCACCAGCGAGAGCACAGCCGCC<br>CTGGGCTGCCTGGTGAAGGACTACTTCCCCGAGCCCGTGACCGTGTCCTGGAAC<br>AGCGGAGCCCTGACCAGCGGCGTGCACACCTTCCCCGCCGTGCTGCAGAGCAGC |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | GGCCTGTACAGCCTGAGCAGCGTGGTGACCGTGCCCAGCAGCAGCCTGGGCACC<br>AAGACCTACACCTGTAACGTGGACCACAAGCCCAGCAACACCAAGGTGGACAAG<br>AGGGTGGAGAGCAAGTACGGCCCACCCTGCCCCCCCTGCCCAGCCCCCGAGTTC<br>CTGGGCGGACCCAGCGTGTTCCTGTTCCCCCCCAAGCCCAAGGACACCCTGATG<br>ATCAGCAGAACCCCCGAGGTGACCTGTGTGGTGGTGGACGTGTCCCAGGAGGAC<br>CCCGAGGTCCAGTTCAACTGGTACGTGGACGGCGTGGAGGTGCACAACGCCAAG<br>ACCAAGCCCAGAGAGGAGCAGTTTAACAGCACCTACCGGGTGGTGTCCGTGCTG<br>ACCGTGCTGCACCAGGACTGGCTGAACGGCAAAGAGTACAAGTGTAAGGTCTCC<br>AACAAGGGCCTGCCAAGCAGCATCGAAAAGACCATCAGCAAGGCCAAGGGCCAG<br>CCTAGAGAGCCCCAGGTCTACACCCTGCCACCCAGCCAAGAGGAGATGACCAAG<br>AACCAGGTGTCCCTGACCTGTCTGGTGAAGGGCTTCTACCCAAGCGACATCGCC<br>GTGGAGTGGGAGAGCAACGGCCAGCCCGAGAACAACTACAAGACCACCCCCCCA<br>GTGCTGGACAGCGACGGCAGCTTCTTCCTGTACAGCAGGCTGACCGTGGACAAG<br>TCCAGATGGCAGGAGGGCAACGTCTTTAGCTGCTCCGTGATGCACGAGGCCCTG<br>CACAACCACTACACCCAGAAGAGCCTGAGCCTGTCCCTGGGCTGATGAATTC |
| | BAP058-Clone M LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIK |
| SEQ ID NQ:400 | DNA VL | GAGATCGTGCTGACCCAGTCCCCCGACTTCCAGTCCGTGACCCCCAAAGAAAAA<br>GTGACCATCACATGCAAGGCCTCCCAGGACGTGGGCACCGCCGTGGCTTGGTAT<br>CTGCAGAAGCCTGGCCAGTCCCCTCAGCTGCTGATCTACTGGGCCTCTACCAGA<br>CACACCGGCGTGCCCTCCAGATTCTCCGGCTCTGGCTCTGGCACCGACTTTACC<br>TTCACCATCTCCAGCCTGCAGCCCGAGGATATCGCCACCTACTACTGCCAGCAG<br>TACAACTCCTACCCCCTGACCTTCGGCCAGGGCACCAAGGTGGAAATCAAG |
| SEQ ID NO:330 | Light Chain | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO:401 | DNA Light Chain | GAGATCGTGCTGACCCAGTCCCCCGACTTCCAGTCCGTGACCCCCAAAGAAAAA<br>GTGACCATCACATGCAAGGCCTCCCAGGACGTGGGCACCGCCGTGGCTTGGTAT<br>CTGCAGAAGCCTGGCCAGTCCCCTCAGCTGCTGATCTACTGGGCCTCTACCAGA<br>CACACCGGCGTGCCCTCCAGATTCTCCGGCTCTGGCTCTGGCACCGACTTTACC<br>TTCACCATCTCCAGCCTGCAGCCCGAGGATATCGCCACCTACTACTGCCAGCAG<br>TACAACTCCTACCCCCTGACCTTCGGCCAGGGCACCAAGGTGGAAATCAAGCGT<br>ACGGTGGCCGCTCCCAGCGTGTTCATCTTCCCCCCAAGCGACGAGCAGCTGAAG<br>AGCGGCACCGCCAGCGTGGTGTGTCTGCTGAACAACTTCTACCCCAGGGAGGCC<br>AAGGTGCAGTGGAAGGTGGACAACGCCCTGCAGAGCGGCAACAGCCAGGAGAGC<br>GTCACCGAGCAGGACAGCAAGGACTCCACCTACAGCCTGAGCAGCACCCTGACC<br>CTGAGCAAGGCCGACTACGAGAAGCACAAGGTGTACGCCTGTGAGGTGACCCAC<br>CAGGGCCTGTCCAGCCCCGTGACCAAGAGCTTCAACAGGGGCGAGTGCTGATGA<br>ATTC |
| | BAP058-Clone N HC | |
| SEQ ID NO: 287 (Kabat) | HCDR1 | SYWMY |
| SEQ ID NO: 288 (Kabat) | HCDR2 | RIDPNSGSTKYNEKFKN |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO: 381 | DNA VH | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTACCGGTCAAGGCCTGGAGTGGATGGGTAGAATCGACCCTAAT AGCGGCTCTACTAAGTATAACGAGAAGTTTAAGAATAGAGTGACTATCACCGCC GATAAGTCTACTAGCACCGCCTATATGGAACTGTCTAGCCTGAGATCAGAGGAC ACCGCCGTCTACTACTGCGCTAGAGACTATAGAAAGGGCCTGTACGCTATGGAC TACTGGGGTCAAGGCACTACCGTGACCGTGTCTTCA |
| SEQ ID NO: 382 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 383 | DNA Heavy Chain | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTACCGGTCAAGGCCTGGAGTGGATGGGTAGAATCGACCCTAAT AGCGGCTCTACTAAGTATAACGAGAAGTTTAAGAATAGAGTGACTATCACCGCC GATAAGTCTACTAGCACCGCCTATATGGAACTGTCTAGCCTGAGATCAGAGGAC ACCGCCGTCTACTACTGCGCTAGAGACTATAGAAAGGGCCTGTACGCTATGGAC TACTGGGGTCAAGGCACTACCGTGACCGTGTCTTCAGCTAGCACTAAGGGCCCG TCCGTGTTCCCCCTGGCACCTTGTAGCCGGAGCACTAGCGAATCCACCGCTGCC CTCGGCTGCCTGGTCAAGGATTACTTCCCGGAGCCCGTGACCGTGTCCTGGAAC AGCGGAGCCCTGACCTCCGGAGTGCACACCTTCCCCGCTGTGCTGCAGAGCTCC GGGCTGTACTCGCTGTCGTCGGTGGTCACGGTGCCTTCATCTAGCCTGGGTACC AAGACCTACACTTGCAACGTGGACCACAAGCCTTCCAACACTAAGGTGGACAAG CGCGTCGAATCGAAGTACGGCCCACCGTGCCCGCCTTGTCCCGCGCCGGAGTTC CTCGGCGGTCCCTCGGTCTTTCTGTTCCCACCGAAGCCCAAGGACACTTTGATG ATTTCCCGCACCCCTGAAGTGACATGCGTGGTCGTGGACGTGTCACAGGAAGAT CCGGAGGTGCAGTTCAATTGGTACGTGGATGGCGTCGAGGTGCACAACGCCAAA ACCAAGCCGAGGGAGGAGCAGTTCAACTCCACTTACCGCGTCGTGTCCGTGCTG ACGGTGCTGCATCAGGACTGGCTGAACGGGAAGGAGTACAAGTGCAAAGTGTCC AACAAGGGACTTCCTAGCTCAATCGAAAAGACCATCTCGAAAGCCAAGGGACAG CCCCGGGAACCCCAAGTGTATACCCTGCCACCGAGCCAGGAAGAAATGACTAAG AACCAAGTCTCATTGACTTGCCTTGTGAAGGGCTTCTACCCATCGGATATCGCC GTGGAATGGGAGTCCAACGGCCAGCCGGAAAACAACTACAAGACCACCCCTCCG GTGCTGGACTCAGACGGATCCTTCTTCCTCTACTCGCGGCTGACCGTGGATAAG AGCAGATGGCAGGAGGGAAATGTGTTCAGCTGTTCTGTGATGCATGAAGCCCTG CACAACCACTACACTCAGAAGTCCCTGTCCCTCTCCCTGGGA |

BAP058-Clone N LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 299 (Chothia) | LCDR2 | WAS |
| SEQ ID NO: 300 (Chothia) | LCDR3 | YNSYPL |
| SEQ ID NO: 352 | VL | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 384 | DNA VL | GACGTCGTGATGACTCAGTCACCCCTGAGCCTGCCCGTGACCCTGGGGCAGCCC GCCTCTATTAGCTGTAAAGCCTCTCAGGACGTGGGCACCGCCGTGGCCTGGTAT CAGCAGAAGCCAGGGCAAGCCCCTAGACTGCTGATCTACTGGGCCTCTACTAGA CACACCGGCGTGCCCTCTAGGTTTAGCGGTAGCGGTAGTGGCACCGAGTTCACC CTGACTATCTCTTCACTGCAGCCCGACGACTTCGCTACCTACTACTGTCAGCAG TATAATAGCTACCCCCTGACCTTCGGTCAAGGCACTAAGGTCGAGATTAAG |
| SEQ ID NO: 354 | Light Chain | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 385 | DNA Light Chain | GACGTCGTGATGACTCAGTCACCCCTGAGCCTGCCCGTGACCCTGGGGCAGCCC GCCTCTATTAGCTGTAAAGCCTCTCAGGACGTGGGCACCGCCGTGGCCTGGTAT CAGCAGAAGCCAGGGCAAGCCCCTAGACTGCTGATCTACTGGGCCTCTACTAGA CACACCGGCGTGCCCTCTAGGTTTAGCGGTAGCGGTAGTGGCACCGAGTTCACC CTGACTATCTCTTCACTGCAGCCCGACGACTTCGCTACCTACTACTGTCAGCAG TATAATAGCTACCCCCTGACCTTCGGTCAAGGCACTAAGGTCGAGATTAAGCGT ACGGTGGCCGCTCCCAGCGTGTTCATCTTCCCCCCCAGCGACGAGCAGCTGAAG AGCGGCACCGCCAGCGTGGTGTGCCTGCTGAACAACTTCTACCCCCGGGAGGCC AAGGTGCAGTGGAAGGTGGACAACGCCCTGCAGAGCGGCAACAGCCAGGAGAGC GTCACCGAGCAGGACAGCAAGGACTCCACCTACAGCCTGAGCAGCACCCTGACC CTGAGCAAGGCCGACTACGAGAAGCATAAGGTGTACGCCTGCGAGGTGACCCAC CAGGGCCTGTCCAGCCCCGTGACCAAGAGCTTCAACAGGGGCGAGTGC |

BAP058-Clone O HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 364 | VH | EVQLVQSGAEVKKPGATVKISCKVSGYTFTSYWMYWVRQARGQRLEWIGRIDPN SGSTKYNEKFKNRFTISRDNSKNTLYLQMNSLRAEDTAVYYCARDYRKGLYAMD YWGQGTTVTVSS |
| SEQ ID NO: 386 | DNA VH | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTAGAGGGCAAAGACTGGAGTGGATCGGTAGAATCGACCCTAAT AGCGGCTCTACTAAGTATAACGAGAAGTTTAAGAATAGGTTCACTATTAGTAGG GATAACTCTAAGAACACCCTGTACCTGCAGATGAATAGCCTGAGAGCCGAGGAC ACCGCCGTCTACTACTGCGCTAGAGACTATAGAAAGGGCCTGTACGCTATGGAC TACTGGGGTCAAGGCACTACCGTGACCGTGTCTTCA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 366 | Heavy Chain | EVQLVQSGAEVKKPGATVKISCKVSGYTFTSYWMYWVRQARGQRLEWIGRIDPN<br>SGSTKYNEKFKNRFTISRDNSKNTLYLQMNSLRAEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLG |
| SEQ ID NO: 387 | DNA Heavy Chain | GAAGTGCAGCTGGTGCAGTCAGGCGCCGAAGTGAAGAAACCCGGCGCTACCGTG<br>AAGATTAGCTGTAAAGTCTCAGGCTACACCTTCACTAGCTACTGGATGTACTGG<br>GTCCGACAGGCTAGAGGGCAAAGACTGGAGTGGATCGGTAGAATCGACCCTAAT<br>AGCGGCTCTACTAAGTATAACGAGAAGTTTAAGAATAGGTTCACTATTAGTAGG<br>GATAACTCTAAGAACACCCTGTACCTGCAGATGAATAGCCTGAGAGCCGAGGAC<br>ACCGCCGTCTACTACTGCGCTAGAGACTATAGAAAGGGCCTGTACGCTATGGAC<br>TACTGGGGTCAAGGCACTACCGTGACCGTGTCTTCAGCTAGCACTAAGGGCCCG<br>TCCGTGTTCCCCCTGGCACCTTGTAGCCGGAGCACTAGCGAATCCACCGCTGCC<br>CTCGGCTGCCTGGTCAAGGATTACTTCCCGGAGCCCGTGACCGTGTCCTGGAAC<br>AGCGGAGCCCTGACCTCCGGAGTGCACACCTTCCCCGCTGTGCTGCAGAGCTCC<br>GGGCTGTACTCGCTGTCGTCGGTGGTCACGGTGCCTTCATCTAGCCTGGGTACC<br>AAGACCTACACTTGCAACGTGGACCACAAGCCTTCCAACACTAAGGTGGACAAG<br>CGCGTCGAATCGAAGTACGGCCCACCGTGCCCGCCTTGTCCCGCGCCGGAGTTC<br>CTCGGCGGTCCCTCGGTCTTTCTGTTCCCACCGAAGCCCAAGGACACTTTGATG<br>ATTTCCCGCACCCCTGAAGTGACATGCGTGGTCGTGGACGTGTCACAGGAAGAT<br>CCGGAGGTGCAGTTCAATTGGTACGTGGATGGCGTCGAGGTGCACAACGCCAAA<br>ACCAAGCCGAGGGAGGAGCAGTTCAACTCCACTTACCGCGTCGTGTCCGTGCTG<br>ACGGTGCTGCATCAGGACTGGCTGAACGGGAAGGAGTACAAGTGCAAAGTGTCC<br>AACAAGGGACTTCCTAGCTCAATCGAAAAGACCATCTCGAAAGCCAAGGGACAG<br>CCCCGGGAACCCCAAGTGTATACCCTGCCACCGAGCCAGGAAGAAATGACTAAG<br>AACCAAGTCTCATTGACTTGCCTTGTGAAGGGCTTCTACCCATCGGATATCGCC<br>GTGGAATGGGAGTCCAACGGCCAGCCGGAAAACAACTACAAGACCACCCCTCCG<br>GTGCTGGACTCAGACGGATCCTTCTTCCTCTACTCGCGGCTGACCGTGGATAAG<br>AGCAGATGGCAGGAGGGAAATGTGTTCAGCTGTTCTGTGATGCATGAAGCCCTG<br>CACAACCACTACACTCAGAAGTCCCTGTCCCTCTCCCTGGGA |

BAP058-Clone O LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 368 | VL | AIQLTQSPSSLSASVGDRVTITCKASQDVGTAVAWYLQKPGQSPQLLIYWASTR<br>HTGVPSRFSGSGSGTDFTFTISSLEAEDAATYYCQQYNSYPLTFGQGTKVEIK |
| SEQ ID NO: 388 | DNA VL | GCTATTCAGCTGACTCAGTCACCTAGTAGCCTGAGCGCTAGTGTGGGCGATAGA<br>GTGACTATCACCTGTAAAGCCTCTCAGGACGTGGGCACCGCCGTGGCCTGGTAT<br>CTGCAGAAGCCTGGTCAATCACCTCAGCTGCTGATCTACTGGGCCTCTACTAGA<br>CACACCGGCGTGCCCTCTAGGTTTAGCGGTAGCGGTAGTGGCACCGACTTCACC<br>TTCACTATCTCTTCACTGGAAGCCGAGGACGCCGCTACCTACTACTGTCAGCAG<br>TATAATAGCTACCCCCTGACCTTCGGTCAAGGCACTAAGGTCGAGATTAAG |
| SEQ ID NO: 370 | Light Chain | AIQLTQSPSSLSASVGDRVTITCKASQDVGTAVAWYLQKPGQSPQLLIYWASTR<br>HTGVPSRFSGSGSGTDFTFTISSLEAEDAATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 389 | DNA Light Chain | GCTATTCAGCTGACTCAGTCACCTAGTAGCCTGAGCGCTAGTGTGGGCGATAGA<br>GTGACTATCACCTGTAAAGCCTCTCAGGACGTGGGCACCGCCGTGGCCTGGTAT<br>CTGCAGAAGCCTGGTCAATCACCTCAGCTGCTGATCTACTGGGCCTCTACTAGA |

TABLE 6-continued

Amino acid and nucleotide sequences for murine, chimeric and humanized antibody molecules. The antibody molecules include murine mAh BAP058, chimeric mAh BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

```
CACACCGGCGTGCCCTCTAGGTTTAGCGGTAGCGGTAGTGGCACCGACTTCACC
TTCACTATCTCTTCACTGGAAGCCGAGGACGCCGCTACCTACTACTGTCAGCAG
TATAATAGCTACCCCCTGACCTTCGGTCAAGGCACTAAGGTCGAGATTAAGCGT
ACGGTGGCCGCTCCCAGCGTGTTCATCTTCCCCCCCAGCGACGAGCAGCTGAAG
AGCGGCACCGCCAGCGTGGTGTGCCTGCTGAACAACTTCTACCCCCGGGAGGCC
AAGGTGCAGTGGAAGGTGGACAACGCCCTGCAGAGCGGCAACAGCCAGGAGAGC
GTCACCGAGCAGGACAGCAAGGACTCCACCTACAGCCTGAGCAGCACCCTGACC
CTGAGCAAGGCCGACTACGAGAAGCATAAGGTGTACGCCTGCGAGGTGACCCAC
CAGGGCCTGTCCAGCCCCGTGACCAAGAGCTTCAACAGGGGCGAGTGC
```

Therapeutic Application for Mesothelin Expressing Diseases and Disorders

The present invention provides compositions and methods for treating diseases and disorders associated with the expression of mesothelin. An example of a disease or disorder associated with mesothelin is mesothelioma.

Malignant mesothelioma is a type of cancer that occurs in the thin layer of cells lining the body's internal organs, known as the mesothelium. There are three recognized types of mesothelioma. Pleural mesothelioma (e.g., malignant pleural mesothelioma, or MPM) is the most common form of the disease, accounting for roughly 70% of cases, and occurs in the lining of the lung known as the pleura. Peritoneal mesothelioma occurs in the lining of the abdominal cavity, known as the peritoneum. Pericardial mesothelioma originates in the pericardium, which lines the heart.

A subject may be at risk to develop mesothelioma if the subject was exposed to asbestos. Exposure to asbestos and the inhalation of asbestos particles can cause mesothelioma. In most cases, mesothelioma symptoms will not appear in a subject exposed to asbestos until many years after the exposure has occurred.

Symptoms of pleural mesothelioma include, e.g., lower back pain or side chest pain, and shortness of breath. Other symptoms include difficulty swallowing, persistent cough, fever, weight loss or fatigue. Additional symptoms that some patients experience are muscle weakness, loss of sensory capability, coughing up blood, facial and arm swelling, and hoarseness. In the early stages of the disease, such as stage 1 mesothelioma, symptoms may be mild. Patients usually report pain in one area of the chest that never seems to go away, weight loss and fever.

Peritoneal mesothelioma originates in the abdomen and as a result, symptoms often include abdominal pain, weight loss, nausea, and vomiting. Fluid buildup may occur in the abdomen as well as a result of the cancer. Peritoneal mesothelioma originates in the abdomen and will frequently spread to other organs in area including the liver, spleen or bowel. Severe abdominal pain is the most common complaint that patients first experience. There may also be a discomfort level with fluid buildup in the abdomen as well. Other symptoms of peritoneal mesothelioma may include difficult bowel movements, nausea and vomiting, fever and swollen feet.

Pericardial mesothelioma is the least common form of mesothelioma. Pericardial mesothelioma, as the name suggests, involves the heart. This rare type of mesothelioma cancer invades the pericardium, the sac that surrounds the heart. As the cancer progresses, the heart is not able to deliver oxygen as efficiently to the body causing further decline in health at an increasingly rapid rate. The symptoms most commonly associated with pericardial mesothelioma mimic those of a heart attack: nausea, pain in the chest and shortness of breath.

Subjects benefiting from treatment according to the invention include subjects with a mesothelioma, or subjects suspected of having mesothelioma, e.g., as evidenced by the presence of one or more of the symptoms described herein and/or exposure to asbestos. In particular embodiments, the mesothelioma is pleural mesothelioma (e.g., malignant pleural mesothelioma). In other aspects, the subject may be treated that has a precancerous condition such as, e.g., pleural plaques, benign mesothelioma or mesothelial hyperplasia.

Another example of a disease or disorder associated with mesothelin is pancreatic cancer. Pancreatic cancers that can be treated with methods described herein include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma. Endocrine pancreatic cancers include, but are not limited to, insulinomas and glucagonomas.

In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting. In some embodiments, the pancreatic cancer is locally advanced pancreatic cancer, unresectable pancreatic cancer, or metastatic pancreatic ductal carcinoma. In some embodiments, the pancreatic cancer is resistant to the gemcitabine-based therapy. In some embodiments, the pancreatic cancer is refractory to the gemcitabine-based therapy.

In other aspects, the disorder associated with mesothelin expression is ovarian cancer. Ovarian cancer is classified according to the histology of the tumor. Surface epithelial-stromal tumor, also known as ovarian epithelial carcinoma, is the most common type of ovarian cancer. It includes serous tumor (including serous papillary cystadenocarcinoma), endometrioid tumor and mucinous cystadenocarcinoma.

The methods described herein can be used to treat various stages of ovarian cancer, e.g., stage I, stage II, stage III or stage IV. Staging can be performed, e.g., when the ovarian cancer is removed. Ovarian cancer is staged as follows:

Stage I cancer is confined to one or both ovaries. The cancer is stage II if either one or both of the ovaries is involved and has spread to the uterus and/or the fallopian tubes or other sites in the pelvis. The cancer is stage III cancer if one or both of the ovaries is involved and has spread to lymph nodes or other sites outside of the pelvis but is still within the abdominal cavity, such as the surface of the intestine or liver. The cancer is stage IV cancer if one or both ovaries are involved and the cancer has spread outside the abdomen or to the inside of the liver.

In some embodiments, the ovarian cancer is resistant to one or more chemotherapeutic agent. In some embodiments, the ovarian cancer is refractory to the one or more chemotherapeutic agent.

Other cancers that can be treated with the combination therapy described herein include, e.g., brain cancer, bladder cancer, breast cancer, cervical cancer, colorectal cancer, liver cancer, kidney cancer, lymphoma, leukemia, lung cancer (e.g., lung adenocarcinoma), melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In one aspect, the disclosure features a method of treating cancer in a subject. The method comprises administering to the subject a combination therapy that includes administering a mesothelin CAR-expressing cell and a PD-L1 inhibitor such that the cancer is treated in the subject. An example of a cancer that is treatable by the combination therapy described herein is a cancer associated with expression of mesothelin. In one aspect, the cancer associated with expression of mesothelin is selected from mesothelioma, pancreatic cancer, ovarian cancer and lung cancer, or a metastasis resulting from any of the aforesaid cancers.

In one embodiment, the combination therapy of a mesothelin CAR-expressing cell and a PD-L1 inhibitor described herein results in one or more of: improved or increased anti-tumor activity of the mesothelin CAR-expressing cell; increased proliferation or persistence of the mesothelin CAR-expressing cell; improved or increased infiltration of the mesothelin CAR-expressing cell; improved inhibition of tumor progression; delay of tumor progression; inhibition or reduction in cancer cell proliferation; and/or reduction in tumor burden, e.g., tumor volume, or size, e.g., as compared to a monotherapy of mesothelin CAR-expressing cell or PD-L1 inhibitor alone.

The present invention provides methods for inhibiting the proliferation of or reducing a mesothelin-expressing cell population. In one embodiment, the methods comprise administering a combination therapy, e.g., a combination comprising a mesothelin CAR-expressing cell, or a population of mesothelin-CAR expressing cells, and a PD-L1 inhibitor. In certain embodiments, the combination therapy described herein reduces the quantity, number, amount or percentage of cells and/or cancer cells by at least at least 5%, 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% in a subject with or animal model of mesothelioma or another cancer associated with mesothelin-expressing cells relative to the quantity, number, amount, or percentage of cells and/or cancer cells in a subject treated with a mesothelin CAR-expressing cell or a PD-L1 inhibitor alone. In one aspect, the subject is a human.

The invention also provides methods for preventing, treating and/or managing a disorder associated with mesothelin-expressing cells (e.g., mesothelioma), the methods comprising administering to a subject in need a mesothelin CAR-expressing cell, or a population of mesothelin CAR-expressing cells, and a PD-L1 inhibitor. In one aspect, the subject is a human.

Combination Therapies

Any of the methods described herein may be used in combination with other known agents and therapies.

The combination described herein, e.g., a mesothelin CAR-expressing cell and a PD-L1 inhibitor, and the at least one additional therapeutic agent can be administered simultaneously, in the same or in separate compositions, or sequentially. For sequential administration, the CAR-expressing cell and/or the PD-L1 inhibitor described herein can be administered after the additional therapeutic agent, or the order of administration can be reversed where the additional therapeutic agent can be administered after the CAR-expressing cell and/or the PD-L1 inhibitor described herein. Alternatively, the additional therapeutic agent can be administered between administration of the CAR-expressing cell and the PD-L1 inhibitor.

In further aspects, the combination described herein, e.g., a mesothelin CAR-expressing cell and a PD-L1 inhibitor, may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation, peptide vaccine, such as that described in Izumoto et al. 2008 J Neurosurg 108:963-971.

In one embodiment, the combination described herein, e.g., a mesothelin CAR-expressing cell and a PD-L1 inhibitor, can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzumab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.04'9] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 613), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, the combination described herein, e.g., a mesothelin CAR-expressing cell and a PD-L1 inhibitor, is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, the combination described herein, e.g., a mesothelin CAR-expressing cell and a PD-L1 inhibitor, is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 $mg/m^2$ (e.g., about 300-325, 325-350, 350-375, 375-400, 400-425, or 425-450 mg/m$^2$), e.g., intravenously. In embodiments, bendamustine is administered at a dosage of about 75-125 mg/m$^2$ (e.g., 75-100 or 100-125 mg/m$^2$, e.g., about 90 mg/m$^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1(2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s53111bl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 mg/m$^2$ to 750 mg/m$^2$, e.g., about 150-175 mg/m$^2$, 175-200 mg/m$^2$, 200-225 mg/m$^2$, 225-250 mg/m$^2$, 250-300 mg/m$^2$, 300-325 mg/m$^2$, 325-350 mg/m$^2$, 350-375 mg/m$^2$, 375-400 mg/m$^2$, 400-425 mg/m$^2$, 425-450 mg/m$^2$, 450-475 mg/m$^2$, 475-500 mg/m$^2$, 500-525 mg/m$^2$, 525-550 mg/m$^2$, 550-575 mg/m$^2$, 575-600 mg/m$^2$, 600-625 mg/m$^2$, 625-650 mg/m$^2$, 650-675 mg/m$^2$, or 675-700 mg/m$^2$, where m$^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NSO). See, e.g., www.accessdata.fda.gov/drugsatfda_docs/label/2009/125326lbl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378(2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or R05072759) is a humanized and glyco-engineered anti-CD20 monoclonal antibody. See, e.g., Robak. Curr. Opin. Investig. Drugs. 10.6(2009):588-96; Clinical Trial Identifier Numbers: NCT01995669, NCT01889797, NCT02229422, and NCT01414205; and www.accessdata.fda.gov/drugsatfda_docs/label/2013/125486s0001bl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1(2011):13-25; and Forero-Torres et al. Clin Cancer Res. 18.5(2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1(2011):13-25; and Casulo et al. Clin Immunol. 154.1(2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1(2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199;) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin-5-yloxy)benzamide) is shown below.

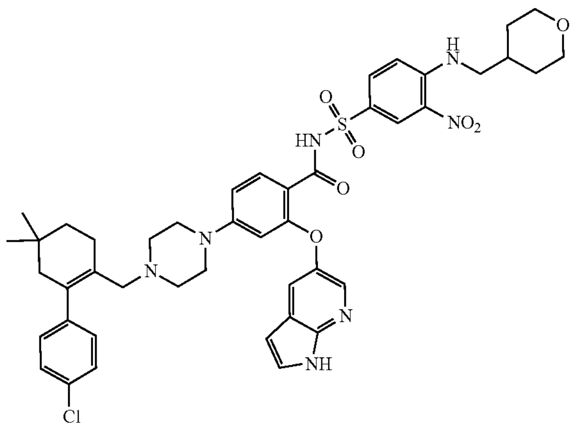 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 $mg/m^2$ (e.g., 350-375, 375-400, 400-425, 425-450, 450-475, or 475-500 $mg/m^2$), e.g., intravenously, e.g., monthly.

In some embodiments, the combination described herein, e.g., a mesothelin CAR-expressing cell and a PD-L1 inhibitor, is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following: Group B Oncolytic Adenovirus (ColoAdl) (PsiOxus Therapeutics Ltd.) (see, e.g., Clinical Trial Identifier: NCT02053220); ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129); VCN-01, which is a genetically modified oncolytic human adenovirus encoding human PH20 hyaluronidase (VCN Biosciences, S.L.) (see, e.g., Clinical Trial Identifiers: NCT02045602 and NCT02045589); Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Catala d'Oncologia) (see, e.g., Clinical Trial Identifier: NCT01864759); Celyvir, which comprises bone marrow-derived autologous mesenchymal stem cells (MSCs) infected with ICOVIR5, an oncolytic adenovirus (Hospital Infantil Universitario Nino Jesns, Madrid, Spain/Ramon Alemany) (see, e.g., Clinical Trial Identifier: NCT01844661); CG0070, which is a conditionally replicating oncolytic serotype 5 adenovirus (Ad5) in which human E2F-1 promoter drives expression of the essential Ela viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intraarterial, intravenous, intramuscular, intrathecal, or intraperitoneal injection. In embodiments, an oncolytic virus described herein is administered intratumorally, transdermally, transmucosally, orally, intranasally, or via pulmonary administration. In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, the combination described herein, e.g., a mesothelin CAR-expressing cell and a PD-L1 inhibitor, is administered to a subject in combination with a molecule targeting GITR and/or modulating GITR functions, such as a GITR agonist and/or a GITR antibody that depletes regulatory T cells (Tregs). In one embodiment, the GITR binding molecules and/or molecules modulating GITR functions (e.g., GITR agonist and/or Treg depleting GITR antibodies) are administered prior to the CAR-expressing cell. For example, in one embodiment, the GITR agonist can be administered prior to apheresis of the cells. In one embodiment, the subject has CLL. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the combination described herein, e.g., a mesothelin CAR-expressing cell and a PD-L1 inhibitor, is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells. In one embodiment, the subject has CLL.

In one embodiment, the combination described herein, e.g., a mesothelin CAR-expressing cell and a PD-L1 inhibitor, is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

In one embodiment, the combination described herein, e.g., a mesothelin CAR-expressing cell and a PD-L1 inhibitor, is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d]pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, the combination described herein, e.g., a mesothelin CAR-expressing cell and a PD-L1 inhibitor, is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

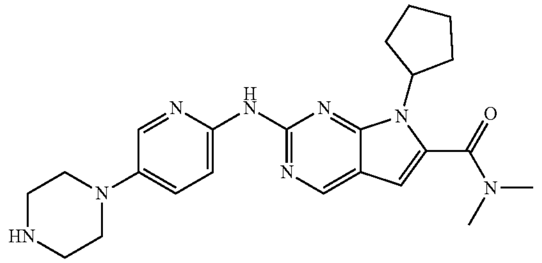 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

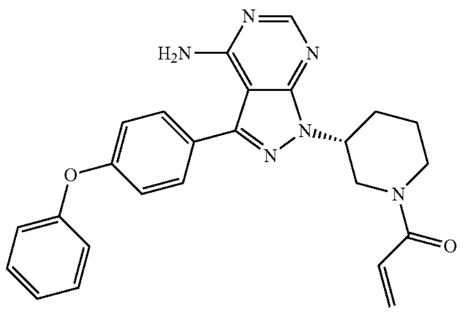 [SMILES: C=CC(=O)N1CCC[C@@H](n2nc(-c3ccc(Oc4ccccc4)cc3)c3c(N)ncnc32)C1]

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

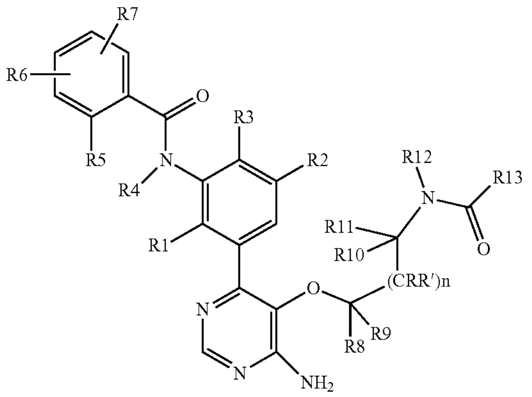

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2- methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.04'9]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 613), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d]pyrimidine (CGP57380);

cercosporamide; ETC-1780445-2; and 4-amino-5-(4-fluoroanilino)-pyrazolo [3,4-d]pyrimidine.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF-04691502); N-[4-[[4-(Dimethylamino)-1-piperidinyl]carbonyl]phenyl]-V-[4-(4,6-di-4-morpholinyl-1,3,5-triazin-2-yl)phenyl]urea (PF-05212384, PKI-587); 2-Methyl-2-[14-[3-methyl-2-oxo-8-(quinolin-3-yl)-2,3-dihydro-1H-imidazo[4,5-c]quinolin-1-yl]phenyl] propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2 (3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d]pyrimidine (CGP57380); cercosporamide; ETC-1780445-2; and 4-amino-5-(4-fluoroanilino)-pyrazolo [3,4-d]pyrimidine.

In embodiments, the combination described herein, e.g., a mesothelin CAR-expressing cell and a PD-L1 inhibitor, is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

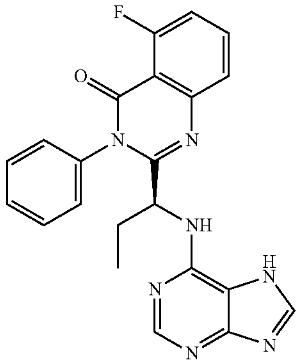 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

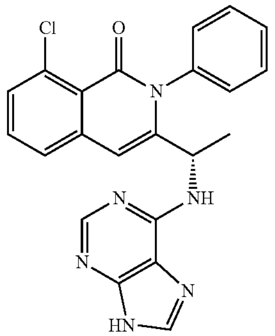 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 $mg/m^2$ (e.g., 350-375, 375-400, 400-425, 425-450, 450-475, or 475-500 $mg/m^2$), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-N2-[2-isopropoxy-5-methyl-4-(4-piperidinyl)phenyl]-N4-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-N2-{4-[4-(dimethylamino)-1-piperidinyl]-2-methoxyphenyl}-$N^4$-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present disclosure may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

In embodiments, the combination described herein, e.g., a mesothelin CAR-expressing cell and a PD-L1 inhibitor, is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, the combination described herein, e.g., a mesothelin CAR-expressing cell and a PD-L1 inhibitor, is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19(2013): 1264-72. The structure of BLZ945 is shown below.

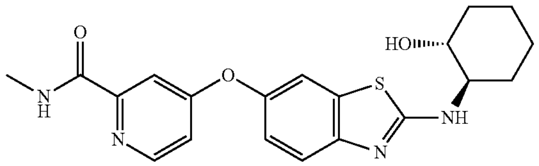 [SMILES: CNC(=O)c1cc(Oc2ccc3nc(N[C@@H]4CCCC[C@H]4O)sc3c2)ccn1]

In embodiments, the combination described herein, e.g., a mesothelin CAR-expressing cell and a PD-L1 inhibitor, herein is administered to a subject in combination with an agent that inhibits or reduces the activity of immunosuppressive plasma cells. Immunosuppressive plasma cells have been shown to impede T cell-dependent immunogenic chemotherapy, such as oxaliplatin (Shalapour et al., *Nature* 2015, 521:94-101). In an embodiment, immunosuppressive plasma cells can express one or more of IgA, interleukin (IL)-10, and PD-L1. In an embodiment, the agent is a CD19 CAR-expressing cell or a BCMA CAR-expressing cell.

In some embodiments, the combination described herein, e.g., a mesothelin CAR-expressing cell and a PD-L1 inhibitor, is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In embodiments, a subject having a disease described herein is administered a combination described herein, e.g., a mesothelin CAR-expressing cell and a PD-L1 inhibitor, in combination with an agent, e.g., cytotoxic or chemotherapy agent, a biologic therapy (e.g., antibody, e.g., monoclonal antibody, or cellular therapy), or an inhibitor (e.g., kinase inhibitor). In embodiments, the subject is administered a CAR-expressing cell described herein in combination with a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In embodiments, the subject is administered a CAR-expressing cell described herein in combination with a hypomethylating agent, e.g., a DNA methyltransferase inhibitor, e.g., azacitidine or decitabine. In embodiments, the subject is administered a CAR-expressing cell described herein in combination with a biologic therapy, e.g., an antibody or cellular therapy, e.g., 225Ac-lintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). SGN-CD33A is an antibody-drug conjugate (ADC) comprising a pyrrolobenzodiazepine dimer that is attached to an anti-CD33 antibody. Actimab-A is an anti-CD33 antibody (lintuzumab) labeled with actinium. IPH2102 is a monoclonal antibody that targets killer immunoglobulin-like receptors (KIRs). In embodiments, the subject is administered a CAR-expressing cell described herein in combination a FLT3 inhibitor, e.g., sorafenib (Bayer), midostaurin (Novartis), quizartinib (Daiichi Sankyo), crenolanib (Arog Pharmaceuticals), PLX3397 (Daiichi Sankyo), AKN-028 (Akinion Pharmaceuticals), or ASP2215 (Astellas). In embodiments, the subject is administered a CAR-expressing cell described herein in combination with an isocitrate dehydrogenase (IDH) inhibitor, e.g., AG-221 (Celgene/Agios) or AG-120 (Agios/Celgene). In embodiments, the subject is administered a CAR-expressing cell described herein in combination with a cell cycle regulator, e.g., inhibitor of polo-like kinase 1 (Plk1), e.g., volasertib (Boehringer Ingelheim); or an inhibitor of cyclin-dependent kinase 9 (Cdk9), e.g., alvocidib (Tolero Pharmaceuticals/Sanofi Aventis). In embodiments, the subject is administered a CAR-expressing cell described herein in combination with a B cell receptor signaling network inhibitor, e.g., an inhibitor of B-cell lymphoma 2 (Bcl-2), e.g., venetoclax (Abbvie/Roche); or an inhibitor of Bruton's tyrosine kinase (Btk), e.g., ibrutinib (Pharmacyclics/Johnson & Johnson Janssen Pharmaceutical). In embodiments, the subject is administered a CAR-expressing cell described herein in combination with an inhibitor of M1 aminopeptidase, e.g., tosedostat (CTI BioPharma/Vernalis); an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineRx).

Some patients may experience allergic reactions to the compounds of the present disclosure and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present disclosure and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid). The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present disclosure, can be prepared and administered as described in the art, such as in the documents cited above.

In one embodiment, the present disclosure provides pharmaceutical compositions comprising at least one compound of the present disclosure (e.g., a compound of the present disclosure) or a pharmaceutically acceptable salt thereof together with a pharmaceutically acceptable carrier suitable for administration to a human or animal subject, either alone or together with other anti-cancer agents.

In one embodiment, the present disclosure provides methods of treating human or animal subjects suffering from a cellular proliferative disease, such as cancer. The present disclosure provides methods of treating a human or animal subject in need of such treatment, comprising administering to the subject a therapeutically effective amount of a compound of the present disclosure (e.g., a compound of the present disclosure) or a pharmaceutically acceptable salt thereof, either alone or in combination with other anti-cancer agents.

In particular, compositions will either be formulated together as a combination therapeutic or administered separately.

In combination therapy, the compound of the present disclosure and other anti-cancer agent(s) may be administered either simultaneously, concurrently or sequentially with no specific time limits, wherein such administration provides therapeutically effective levels of the two compounds in the body of the patient.

In a preferred embodiment, the compound of the present disclosure and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present disclosure and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present disclosure, kits that include one or more compound of the present disclosure and a combination partner as disclosed herein are provided. Representative kits include (a) a compound of the present disclosure or a pharmaceutically acceptable salt thereof, (b) at least one combination partner, e.g., as indicated above, whereby such kit may comprise a package insert or other labeling including directions for administration.

A compound of the present disclosure may also be used to advantage in combination with known therapeutic processes, for example, the administration of hormones or especially radiation. A compound of the present disclosure may in particular be used as a radiosensitizer, especially for the treatment of tumors which exhibit poor sensitivity to radiotherapy. In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hyperfibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

In one embodiment, the subject can be administered an agent which enhances the activity or fitness of a CAR-expressing cell. For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., Programmed Death 1 (PD-1), can, in some embodiments, decrease the ability of a CAR-expressing cell to mount an immune effector response. Examples of inhibitory molecules include PD-1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of a molecule that modulates or regulates, e.g., inhibits, T cell function, e.g., by inhibition at the DNA, RNA or protein level, can optimize a CAR-expressing cell performance. In embodiments, an agent, e.g., an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CAR-expressing cell. In an embodiment, the inhibitor is an shRNA.

In an embodiment, the agent that modulates or regulates, e.g., inhibits, T-cell function is inhibited within a CAR-expressing cell. In these embodiments, a dsRNA molecule that inhibits expression of a molecule that modulates or regulates, e.g., inhibits, T-cell function is linked to the nucleic acid that encodes a component, e.g., all of the components, of the CAR. In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, NY, USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. Configurations of exemplary vectors for expressing a component, e.g., all of the components, of the CAR with a dsRNA molecule that inhibits expression of the molecule that modulates or regulates, e.g., inhibits, T-cell function, is provided, e.g., in FIG. 47 of International Publication WO2015/090230, filed Dec. 19, 2014, which is herein incorporated by reference.

Examples of dsRNA molecules useful for inhibiting expression of a molecule that modulates or regulates, e.g., inhibits, T-cell function, wherein the molecule that modulates or regulates, e.g., inhibits, T-cell function is PD-1 include RNAi agents that target PD-1, as described, e.g., in paragraph [00489] and Tables 16 and 17 of International Publication WO2015/090230, filed Dec. 19, 2014, which is incorporated by reference in its entirety.

In one embodiment, the agent that modulates or regulates, e.g., inhibits, T-cell function can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present disclosure described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

In one embodiment, the anti-PD-1 antibody or fragment thereof is an anti-PD-1 antibody molecule as described in US 2015/0210769, entitled "Antibody Molecules to PD-1 and Uses Thereof," incorporated by reference in its entirety. In one embodiment, the anti-PD-1 antibody molecule includes at least one, two, three, four, five or six CDRs (or collectively all of the CDRs) from a heavy and light chain variable region from an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1, or a sequence substantially identical (e.g., at least 80%, 85%, 90%, 92%, 95%, 97%, 98%, 99% or higher identical) to any of the aforesaid sequences; or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1; or a sequence substantially identical (e.g., at least 80%, 85%, 90%, 92%, 95%, 97%, 98%, 99% or higher identical) to any of the aforesaid sequences.

TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In one embodiment, the anti-TIM3 antibody or fragment thereof is an anti-TIM3 antibody molecule as described in US 2015/0218274, entitled "Antibody Molecules to TIM3 and Uses Thereof," incorporated by reference in its entirety. In one embodiment, the anti-TIM3 antibody molecule includes at least one, two, three, four, five or six CDRs (or collectively all of the CDRs) from a heavy and light chain variable region from an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-TIM3 antibody molecule comprises at least one, two, three or four variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. Cancer *Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAG3. IMP701 (Immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In one embodiment, the anti-LAG3 antibody or fragment thereof is an anti-LAG3 antibody molecule as described in US 2015/0259420, entitled "Antibody Molecules to LAG3 and Uses Thereof," incorporated by reference in its entirety. In one embodiment, the anti-LAG3 antibody molecule includes at least one, two, three, four, five or six CDRs (or collectively all of the CDRs) from a heavy and light chain variable region from an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Table 1; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-LAG3 antibody molecule comprises at least one, two, three or four variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Tables 1; or a sequence substantially identical (e.g., at least 80%, 85%, 90%, 92%, 95%, 97%, 98%, 99% or higher identical) to any of the aforesaid sequences. In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a CAR of the present disclosure.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with the combination described herein, e.g., a mesothelin CAR-expressing cell and a PD-L1 inhibitor. The cytokine can be administered simultaneously or concurrently with the CAR-expressing cells, e.g., administered on the same day. The cytokine may be prepared in the same pharmaceutical composition as the CAR-expressing cells, or may be prepared in a separate pharmaceutical composition. Alternatively, the cytokine can be administered shortly after administration of the CAR-expressing cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing cells, or the first day of the cytokine dosing regimen can be 1 day, 2 days, 3 days, 4 days, 5 days, 6 days, or 7 days after administration of the CAR-expressing cells. In one embodiment, on the first day, the CAR-expressing cells are administered to the subject, and on the second day, a cytokine is administered once a day for the next 7 days. In a preferred embodiment, the cytokine to be administered in combination with CAR-expressing cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CART therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-tumor activity. In a preferred embodiment, the cytokine administered after administration of CAR-expressing cells is IL-7.

Combination with a Low Dose of an mTOR Inhibitor

In one embodiment, the combination described herein, e.g., a mesothelin CAR-expressing cell and a PD-L1 inhibitor, is administered in combination with a low, immune enhancing dose of an mTOR inhibitor.

In another embodiment, administration of a low, immune enhancing, dose of an mTOR inhibitor results in increased or prolonged proliferation of CAR-expressing cells, e.g., in culture or in a subject, e.g., as compared to non-treated CAR-expressing cells or a non-treated subject. In embodiments, increased proliferation is associated with in an increase in the number of CAR-expressing cells. Methods for measuring increased or prolonged proliferation are described in the Examples herein. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

(A)

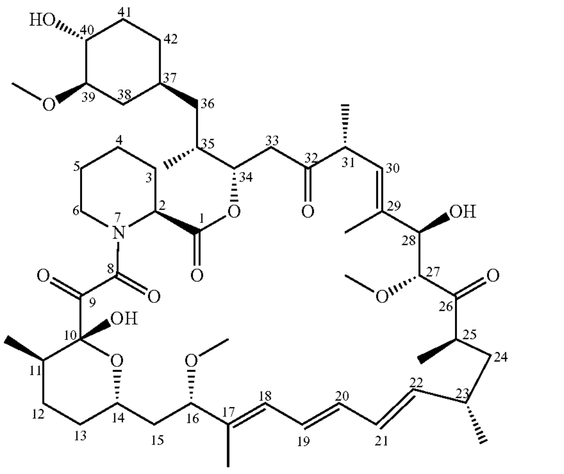

Other suitable rapamycin analogs include, but are not limited to, RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone, sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). b Other examples of allosteric mTor inhibitors include zotarolimus (ABT578) and umirolimus as described in US2005/0101624 the contents of which are incorporated by reference. Other suitable mTOR inhibitors are described in paragraphs 946 to 964 of International Publication WO2015/142675, filed Mar. 13, 2015, which is incorporated by reference in its entirety. Low, immune enhancing doses of an mTOR inhibitor, suitable levels of mTOR inhibition associated with low doses of an mTOR inhibitor, methods for detecting the level of mTOR inhibition, and suitable pharmaceutical compositions thereof are further described in paragraphs 936 to 945 and 965 to 1003 of International Publication WO2015/142675, filed Mar. 13, 2015, which is incorporated by reference in its entirety.

Pharmaceutical Compositions

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

Methods of Treating

When "an immunologically effective amount," "an effective dose", "an anti-cancer effective amount," "a cancer-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject).

The dosage of the above treatments to be administered to a subject will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

The administration of the compositions described herein may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the compositions described herein, e.g., comprising a CAR-expressing cell and/or PD-L1 inhibitor, are administered to a patient by intradermal or subcutaneous injection. In one embodiment, the compositions described herein, e.g., comprising a CAR-expressing cell and/or PD-L1 inhibitor, are administered by i.v. injection. The compositions described herein, e.g., comprising a CAR-expressing cell and/or PD-L1 inhibitor, may be injected directly into a tumor, lymph node, or site of infection.

It can generally be stated that a pharmaceutical composition comprising the immune effector cells described herein may be administered at a dosage of $10^4$ to $10^9$ cells/kg body weight, in some instances $10^5$ to $10^6$ cells/kg body weight, including all integer values within those ranges. The immune effector cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells to a subject and then subsequently redraw blood (or have an apheresis performed), activate the cells therefrom according to the present invention, and reinfuse the patient with these activated and expanded cells. This process can be carried out multiple times every few weeks. In certain aspects, the cells can be activated from blood draws of from 10 cc to 400 cc. In certain aspects, the cells are activated from blood draws of 20 cc, 30 cc, 40 cc, 50 cc, 60 cc, 70 cc, 80 cc, 90 cc, or 100 cc.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR expressing cells of the present invention. In an additional aspect, expanded cells are administered before or following surgery.

In one embodiment, the CAR is introduced into immune effector cells, e.g., using in vitro transcription, and the subject (e.g., human) receives an initial administration of CAR-expressing cells of the invention, and one or more subsequent administrations of the CAR-expressing cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing cells of the invention are administered to the subject (e.g., human) per week, e.g., 2, 3, or 4 administrations of the CAR-expressing cells of the invention are administered per week. In one embodiment, the subject (e.g., human subject) receives more than one administration of the CAR-expressing cells per week (e.g., 2, 3 or 4 administrations per week) (also referred to herein as a cycle), followed by a week of no CAR-expressing cells administration, and then one or more additional administration of the CAR-expressing cells (e.g., more than one administration of the CAR-expressing cells per week) is administered to the subject. In another embodiment, the subject (e.g., human subject) receives more than one cycle of CAR-expressing cells, and the time between each cycle is less than 10, 9, 8, 7, 6, 5, 4, or 3 days. In one embodiment, the CAR-expressing cells are administered every other day for 3 administrations per week. In one embodiment, the CAR-expressing cells of the invention are administered for at least two, three, four, five, six, seven, eight or more weeks.

In some embodiments, a dose of CAR-expressing cells described herein (e.g., mesothelin CAR-expressing cell) comprises about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, $3\times10^8$, or $5\times10^8$ cells/kg. In some embodiments, a dose of CAR cells (e.g., mesothelin CAR-expressing cell) comprises at least about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, $3\times10^8$, or $5\times10^8$ cells/kg. In some embodiments, a dose of CAR cells (e.g., mesothelin CAR-expressing cell) comprises up to about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, $3\times10^8$, or $5\times10^8$ cells/kg. In some embodiments, a dose of CAR cells (e.g., mesothelin CAR-expressing cell) comprises about $1.1\times10^6$-$1.8\times10^7$ cells/kg. In some embodiments, a dose of CAR cells (e.g., mesothelin CAR-expressing cell) comprises about $1\times10^7$, $2\times10^7$, $5\times10^7$, $1\times10^8$, $2\times10^8$, $3\times10^8$, $5\times10^8$, $1\times10^9$, $2\times10^9$, or $5\times10^9$ cells. In some embodiments, a dose of CAR cells (e.g., e.g., mesothelin CAR-expressing cell) comprises at least about $1\times10^7$, $2\times10^7$, $5\times10^7$, $1\times10^8$, $2\times10^8$, $3\times10^8$, $5\times10^8$, $1\times10^9$, $2\times10^9$, or $5\times10^9$ cells. In some embodiments, a dose of CAR cells (e.g., e.g., mesothelin CAR-expressing cell) comprises up to about $1\times10^7$, $2\times10^7$, $5\times10^7$, $1\times10^8$, $2\times10^8$, $3\times10^8$, $5\times10^8$, $1\times10^9$, $2\times10^9$, or $5\times10^9$ cells.

In some embodiments, a dose of CAR cells (e.g., mesothelin CAR-expressing cell) comprises up to about $1\times10^7$, $1.5\times10^7$, $2\times10^7$, $2.5\times10^7$, $3\times10^7$, $3.5\times10^7$, $4\times10^7$, $5\times10^7$, $1\times10^8$, $1.5\times10^8$, $2\times10^8$, $2.5\times10^8$, $3\times10^8$, $3.5\times10^8$, $4\times10^8$, $5\times10^8$, $1\times10^9$, $2\times10^9$, or $5\times10^9$ cells. In some embodiments, a dose of CAR cells (e.g., mesothelin CAR-expressing cell) comprises up to about $1$-$3\times10^7$ to $1$-$3\times10^8$. In some embodiments, the subject is administered about $1$-$3\times10^7$ of mesothelin CAR-expressing cells. In other embodiments, the subject is administered about $1$-$3\times10^8$ of mesothelin-CAR-expressing cells.

In one aspect, mesothelin CAR-expressing cells are generated using lentiviral viral vectors, such as lentivirus. CAR-expressing cells generated that way will have stable CAR expression.

In one aspect, the CAR-expressing cells transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR-expressing cells (particularly with murine scFv bearing CAR-expressing cells) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cell infusion breaks should not last more than ten to fourteen days.

Using CARs with human (instead of murine) scFvs can reduce the likelihood and intensity of a patient having an anti-CAR response.

Dosages and therapeutic regimens of the PD-L1 inhibitor, e.g., anti-PD-L1 antibody molecule, can be determined by a skilled artisan.

In certain embodiments where the PD-L1 inhibitor is an anti-PD-L1 antibody molecule, the anti-PD-L1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-L1 antibody molecule is administered at a dose from about 10 to 20 mg/kg every other week. In one embodiment, the anti-PD-L1 antibody molecule is administered, alone or in combination (e.g., in combination with an anti-LAG-3 antibody molecule), at a dose of less than, or about, 5 mg/kg; less than, or about, 4 mg/kg; less than, or about, 3 mg/kg; less than, or about, 2 mg/kg; less than, or about, 1 mg/kg, every other week. In one embodiment, the anti-PD-L1 antibody molecule is administered at a dose of 1 to 5 mg/kg every other week; 1 to 4 mg/kg every other week, 1 to 3 mg/kg every other week, or 1 to 2 mg/kg every other week. In one embodiment, the anti-PD-L1 antibody molecule is administered, alone or in combination (e.g., in combination with an anti-PD-L1 antibody molecule) at a dose of 1 to 5 mg/kg every other week; 1 to 4 mg/kg every other week, 1 to 3 mg/kg every other week, or 1 to 2 mg/kg every other week.

The antibody molecules can be administered by a variety of methods known in the art, although for many therapeutic applications, the preferred route/mode of administration is intravenous injection or infusion. For example, the antibody molecule can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min. The antibody molecule can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Figure 1B:
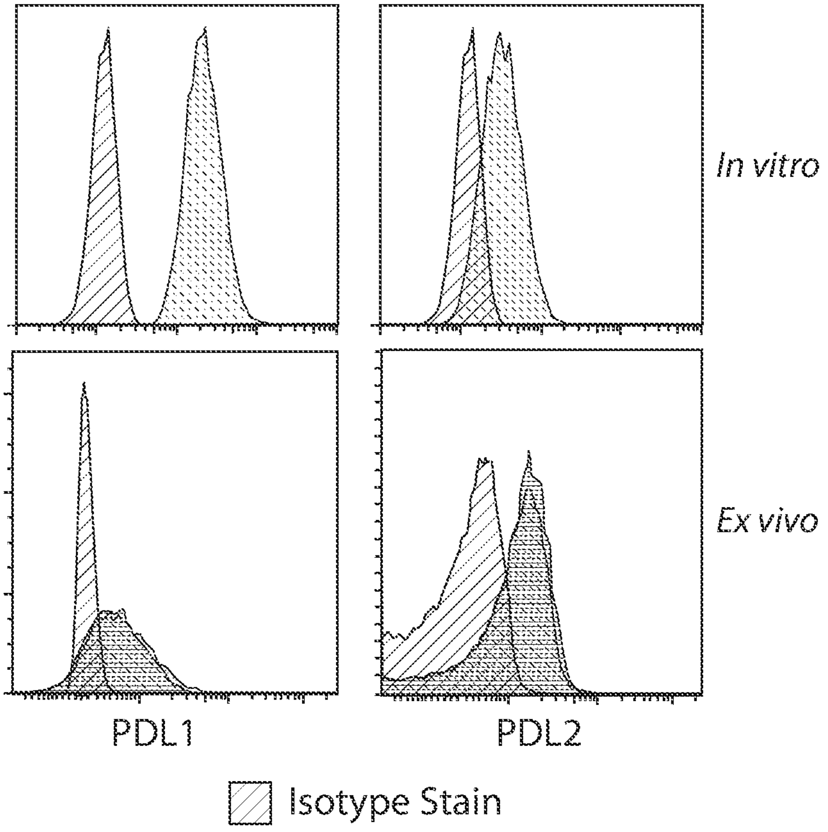
FIG. 1B shows flow cytometric analysis of the expression of PDL1 and PDL2 on Panc02.03 cancer cells. Shown is the expression of both PDL1 and PDL2 by Panc02.03 cancer cells when analyzed both in vitro and ex vivo, from the same tumors analyzed in FIG. 1A. Cancer cells were stained with anti-PDL1 (Biolegend, 29E.2A3) and anti-PDL2 (Biolegend, 24F.10C12).

Example 1: Efficacy of MSLN CART and PD-L1 Inhibitor Combination Therapy in Pancreatic Cancer The anti-tumor activity of mesothelin CART therapy in combination with PD-L1 antibodies was assessed in a mouse model of pancreatic cancer, PANC02.03. Previous studies with mesothelin CAR therapy in the PANC02.03 mouse model showed that mesothelin CAR T cells expanded and infiltrated the tumors. Analysis of these tumor-infiltrating CAR T cells by flow cytometry revealed expression of PD-1 (see FIG. 1A) and PD-L1. Additionally, the PAN02.03 cancer cells expressed express PD-L1 and PD-L2 when tested both in vitro and in vivo (see FIG. 1B).

In a subsequent experiment to test the synergy between mesothelin CAR T cells and PDL1 inhibition, $5\times10^6$ PANC02.03 pancreatic tumor cells were implanted subcutaneously into the flank of immunocompromised NSG mice. PANC02.03 mice were treated with CART therapy alone, PD-L1 therapy alone, or the combination of CART and PD-L1 inhibitor therapy. The effect of the order of administering PD-L1 inhibitor therapy with respect to the CART therapy on anti-tumor activity was assessed with the experiments described below.

Antibody Treatment Prior to CART Therapy

T cells were engineered to express the M5 mesothelin CAR construct (e.g., SEQ ID NO: 67 in Table 2) by lentiviral transduction. Control CAR T cells were engineered to express a CD19 CAR. Mice were divided into 9 groups and treated according to the dosage and treatment schedule below. Two doses of $4\times10^6$ CART cells were injected intravenously on day 23 and 28 after tumor implantation. PD-L1 antibody was injected intraperitoneally at day 21 after tumor implantation, e.g., 48 hours prior to CART therapy.

TABLE 7

| Group | Name | N | CART cells per dose | Schedule CAR T cells | Antibody Dose | Antibody Schedule | Route |
|---|---|---|---|---|---|---|---|
| 1 | PBS | 8 | N/A | N/A | N/A | N/A | IV |
| 2 | CAR 19 | 8 | $4\times10^6$ | Matched to antibody groups | N/A | N/A | IV |
| 3 | M5 | 8 | $4\times10^6$ | Matched to antibody groups | N/A | N/A | IV |
| 4 | CAR19 + PD-LI | 8 | $4\times10^6$ | 2 days post antibody dose; 2$^{nd}$ dose 4 days after 1$^{st}$ dose | 10 mg/kg PD-LI | Tumor at 175-200 mm$^3$; q5d | IV |
| 5 | M5 + PD-L1 | 8 | $4\times10^6$ | 2 days post antibody dose; 2$^{nd}$ dose 4 days after 1$^{st}$ dose | 10 mg/kg PD-LI | Tumor at 175-200 mm$^3$; q5d | IV |

Mice were weighed and calipered twice weekly prior to dosing with treatment to monitor tumor growth. After dosing, the mice were calipered twice weekly. At the end of the study, bone marrow (BM), tumor, and spleen will be collected for FACs analysis.

Figure 2:
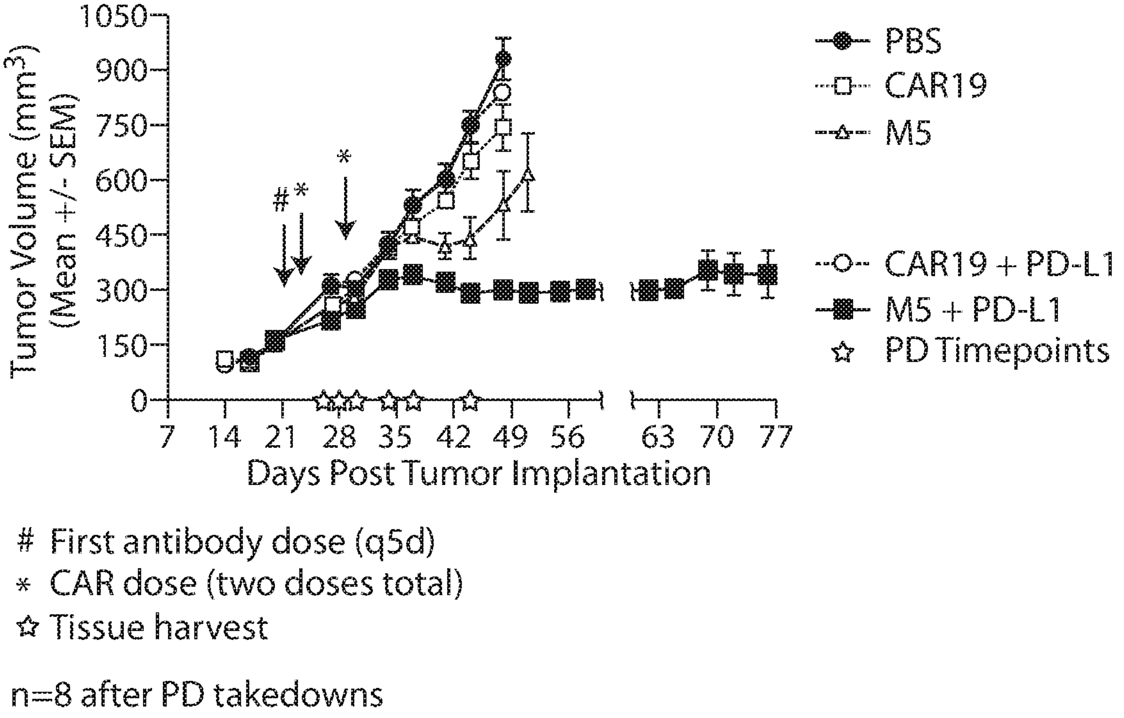
FIG. 2 is a graph showing the tumor progression after various combination treatments with mesothelin CART and a PD-L1 inhibitor, where the PD-L1 inhibitor was administered prior to CAR administration. PD-L1 antibody was administered at the timepoint designated by #. The indicated CAR-expressing cells were administered at the timepoints designated by *. The timepoints where tissues were harvested are designated by the stars on the X-axis.

The results shown in FIG. 2 show that the combination therapy of mesoCART and PD-L1 inhibitor showed transient tumor regression followed by tumor stasis. The combination treatment was shown to be more effective at inhibiting tumor progression than treatment with mesoCART alone. Treatment with CD19 CART alone, or in combination and PD-L1 inhibitor had no effect on tumor progression.

Antibody Treatment after CART Therapy

In the next experiment, PD-L1 inhibitor therapy was administered after mesothelin CART therapy. $4\times10^6$ M5 CART cells were administered 21 days after tumor implantation. PD-1 or PD-L1 antibodies were administered i.v. at 10 mg/kg weekly, with the first dose administered 24 hours after CART administration.

Figure 3:
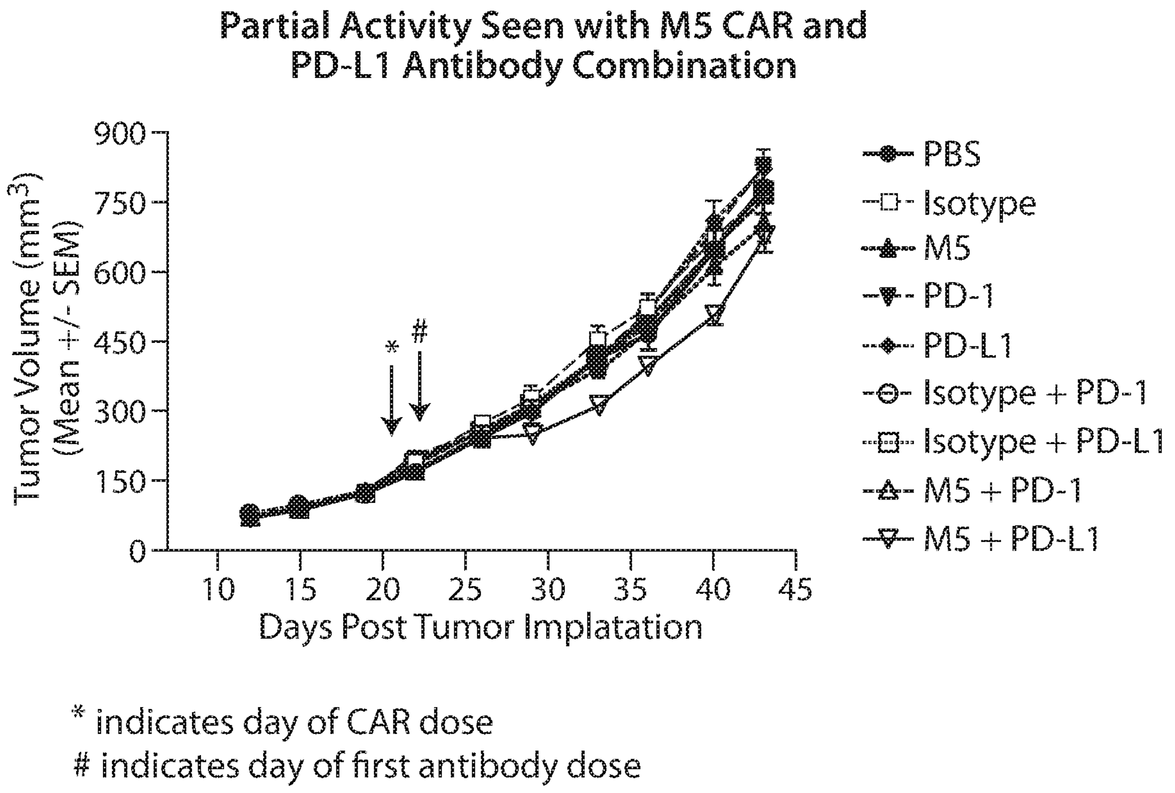
FIG. 3 is a graph the tumor progression after various combination treatments with mesothelin CART and PD-L1 inhibitors, where the PD-L1 inhibitor was administered after CAR administration. PD-L1 antibody was administered at the timepoint designated by #. The indicated CAR-expressing cells were administered at the timepoints designated by *.

The results of treatment on tumor progression are shown in FIG. 3. The combination of M5 CART therapy with PD-L1 antibody treatment only showed minimal and transient anti-tumor activity.

Taking together the data from the two experiments show that administering PD-L1 inhibitor prior to administering the CART therapy has a more robust anti-tumor effect.

Example 2: PD-L1 Expression in Cancer Patients

Further analysis was performed to better characterize the PANC02.03 tumors from NSG mice that were treated with $4\times10^6$ M5 mesothelin CAR positive T cells. PANC02.03 tumor samples were obtained at 35 days from mice that were treated with M5 mesothelin CART. The tumor samples were prepared and serial sections stained to analyze expression of mesothelin and PD-L1 in the tumors, as well as CART infiltration and apoptosis. A mesothelin antibody, anti-PD-L1 antibody (#SP263, Ventana Medical Systems, Tucson, AZ), anti-human CD3 antibody (#2GV6, Vetana Medical Systems), and anti-CC3 antibody (apoptosis marker) (#9661, Cell Signaling Technology, Danvers, MA) were used for immunohistochemical staining, e.g., using immunohistochemical techniques known in the art. In situ hybridization for mesothelin mRNA (#413101, ACDBio, Hayward, CA) was also performed.

Figure 4:
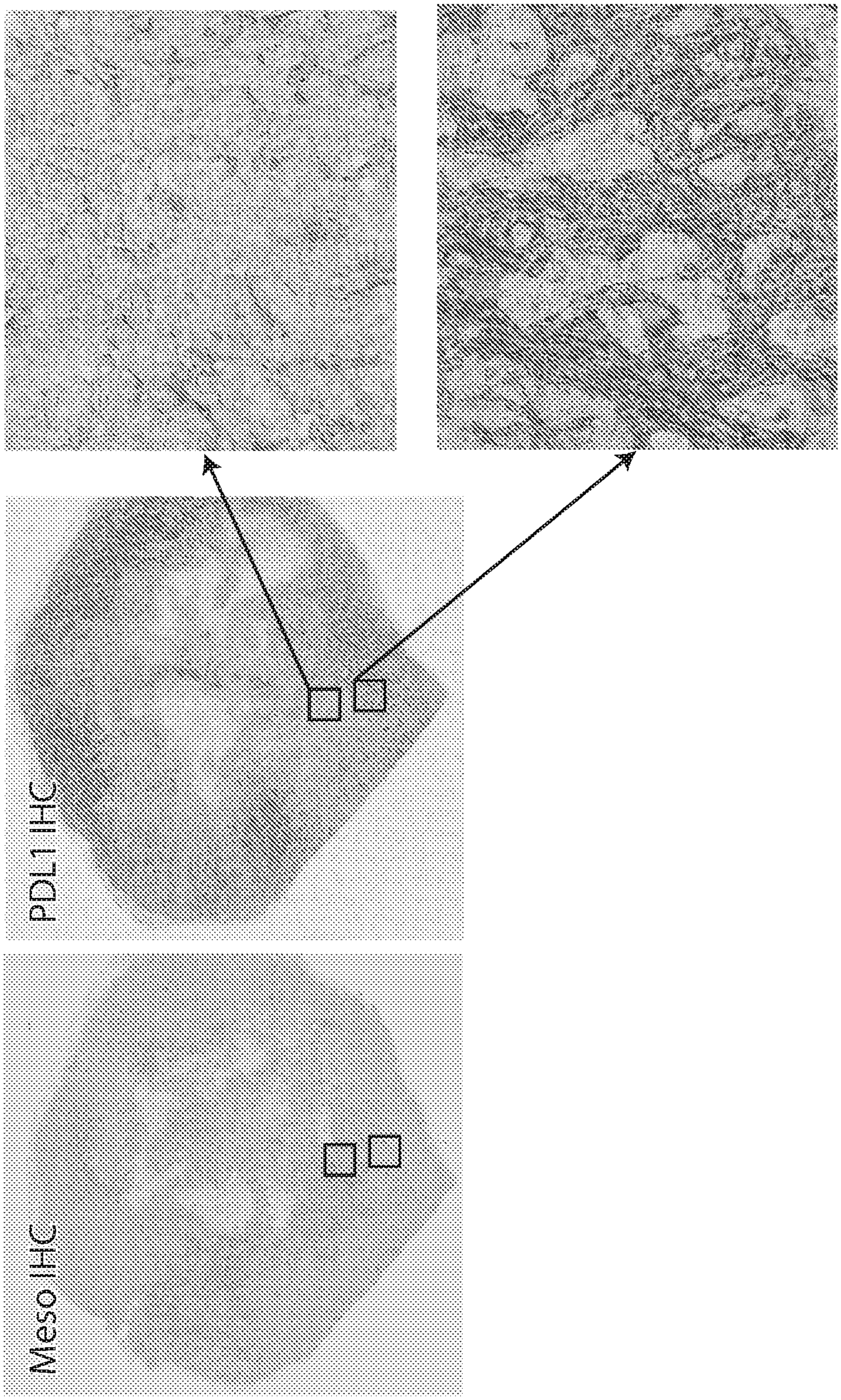
FIG. 4 is a series of images from immunohistochemical analysis of Panc xenograft tissue after treatment with M5 mesothelin CART.
Figure 5:
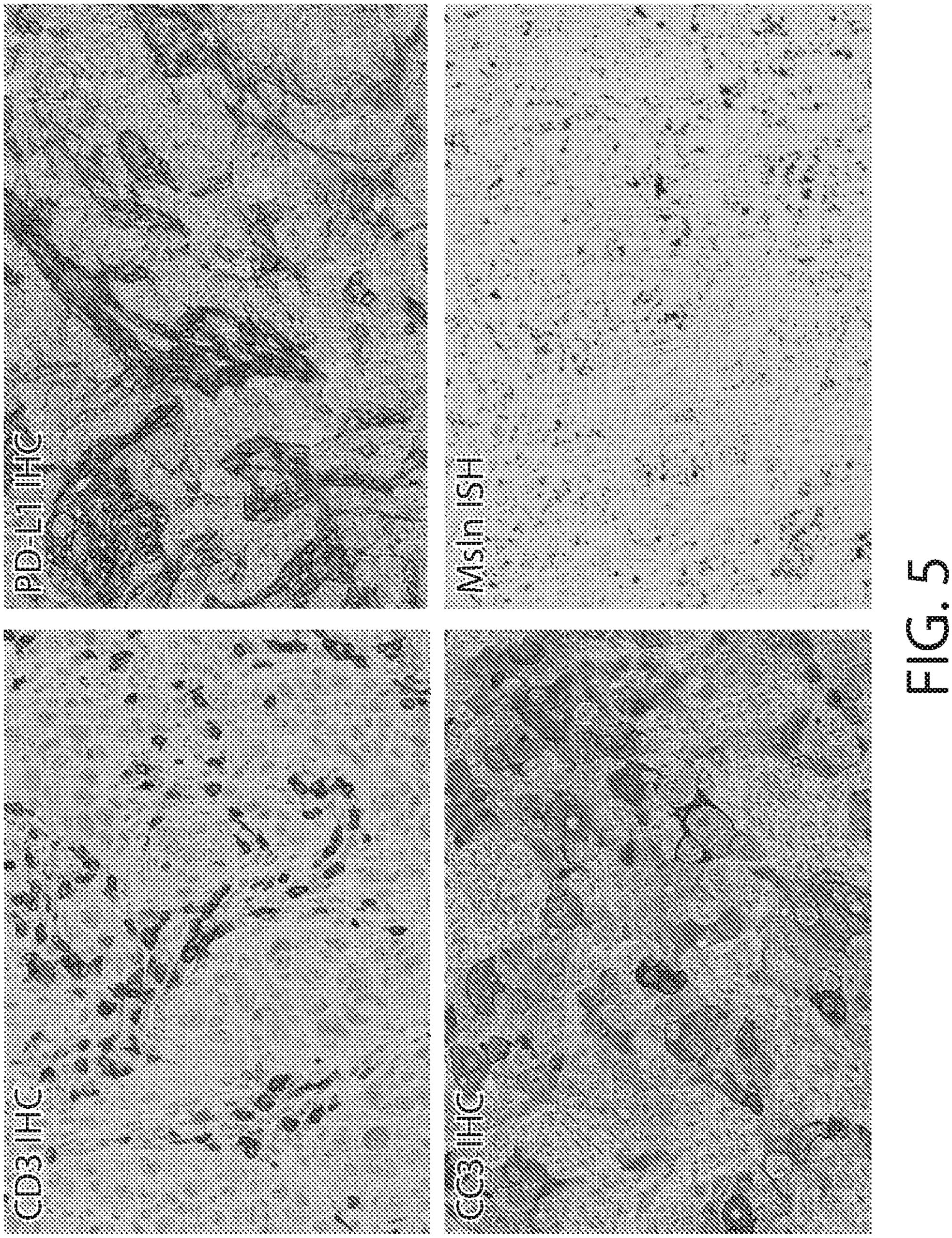
FIG. 5 is a series of images from immunohistochemical analysis of Panc xenograft tissue after treatment with M5 mesothelin CART.

FIG. 4 shows mesothelin expression and PD-L1 expression in the tumor. The tumor has regions of high PD-L1 staining which appear to be inversely correlated with levels of mesothelin protein expression. FIG. 5 shows CAR T cell infiltration (CD3 stained sample, top left panel), apoptosis (CC3 stained sample, bottom left panel), PD-L1 expression (top right panel), and mesothelin mRNA expression (bottom right panel). The results from this expression analysis show that PD-L1 expression is high in tumor regions with low mesothelin protein and mRNA expression (FIG. 4) and yet high CAR T cell infiltration (FIG. 5). These PD-L1-High mesothelin-Low cells are characterized by a spindleloid or mesenchymal morphology and have likely arisen through epithelial mesenchymal transformation. This process is well described in pancreatic tumors and likely contributes to the immunosuppressive tumor microenvironment and disease progression. Thus, these results suggest that a combination treatment using a mesothelin CART and a PD-L1 inhibitor could produce a synergistic effect enhancing efficacy in mesothelin-expressing tumors, where the mesothelin CART targets and kills the mesothelin-expressing tumor cells, while the PD-L1 inhibitor inhibits the immunosuppressive signals from, for example, cancer cells and tumor stromal cells.

Example 3: Low Dose RAD001 Stimulates CART Proliferation in a Cell Culture Model The effect of low doses of RAD001 on CAR T cell proliferation in vitro was evaluated by co-culturing CART-expressing cells with target cells in the presence of different concentrations of RAD001.

Materials and Methods

Generation of CAR-Transduced T Cells

A humanized, anti-human CD19 CAR (huCART19) lentiviral transfer vector was used to produce the genomic material packaged into VSVg pseudotyped lentiviral particles. The amino acid and nucleotide sequence of the humanized anti-human CD19 CAR (huCART19) is CAR 1, ID 104875 described in PCT publication, WO2014/153270, filed Mar. 15, 2014, and is designated SEQ ID NOs. 85 and 31 therein.

Lentiviral transfer vector DNA is mixed with the three packaging components VSVg env, gag/pol and rev in combination with lipofectamine reagent to transfect Lenti-X 293T cells. Medium is changed after 24 h and 30 h thereafter, the virus-containing media is collected, filtered and stored at −80° C. CARTs are generated by transduction of fresh or frozen naïve T cells obtained by negative magnetic selection of healthy donor blood or leukopak. T cells are activated by incubation with anti-CD3/anti-CD28 beads for 24 h, after which viral supernatant or concentrated virus (MOI=2 or 10, respectively) is added to the cultures. The modified T cells are allowed to expand for about 10 days. The percentage of cells transduced (expressing the CARs on the cell surface) and the level of CAR expression (relative fluorescence intensity, Geo Mean) are determined by flow cytometric analysis between days 7 and 9. The combination of slowing growth rate and T cell size approaching ~350 fL determines the state for T cells to be cryopreserved for later analysis.

Evaluating Proliferation of CARTs

To evaluate the functionality of CARTs, the T cells are thawed and counted, and viability is assessed by Cellometer. The number of CAR-positive cells in each culture is normalized using non-transduced T cells (UTD). The impact of RAD001 on CARTs was tested in titrations with RAD001, starting at 50 nM. The target cell line used in all co-culture experiments is Nalm-6, a human pre-B cell acute lymphoblastic leukemia (ALL) cell line expressing CD19 and transduced to express luciferase.

For measuring the proliferation of CARTs, T cells are cultured with target cells at a ratio of 1:1. The assay is run for 4 days, when cells are stained for CD3, CD4, CD8 and CAR expression. The number of T cells is assessed by flow cytometry using counting beads as reference.

Results

Figure 6:
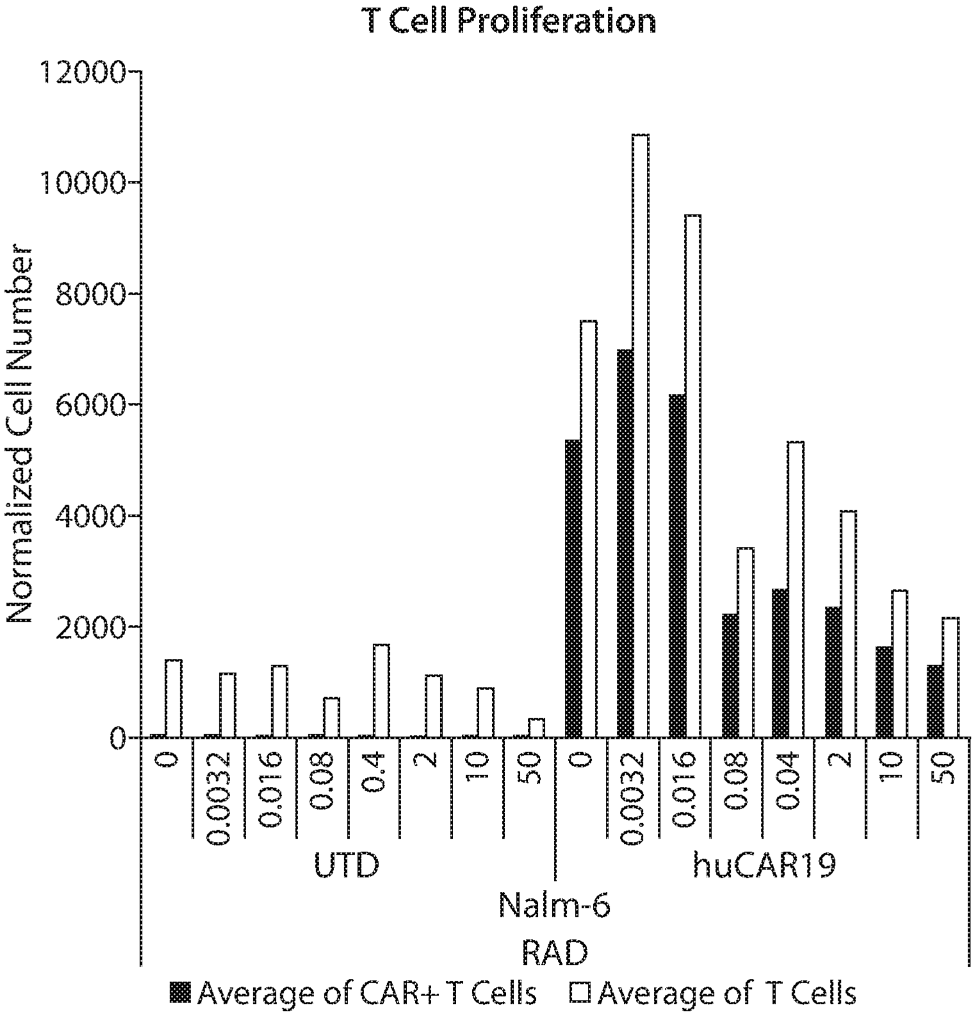
FIG. 6 shows that the proliferation of CAR-expressing, transduced T cells is enhanced by low doses of RAD001 in a cell culture system. CARTs were co-cultured with Nalm-6 cells in the presence of different concentrations of RAD001. The number of CAR-positive CD3-positive T cells (black) and total T cells (gray) was assessed after 4 days of co-culture.

The proliferative capacity of CART cells was tested in a 4 day co-culture assay. The number of CAR-positive CD3-positive T cells (dark bars) and total CD3-positive T cells (light bars) was assessed after culturing the CAR-transduced and non-transduced T cells with Nalm-6 (FIG. 6). huCART19 cells expanded when cultured in the presence of less than 0.016 nM of RAD001, and to a lesser extent at higher concentrations of the compound. Importantly, both at 0.0032 and 0.016 nM RAD001 the proliferation was higher than observed without the addition of RAD001. The non-transduced T cells (UTD) did not show detectable expansion.

Example 4: Low Dose RAD001 Stimulates CART Expansion In Vivo

This example evaluates the ability of huCAR19 cells to proliferate in vivo with different concentrations of RAD001.

Materials and Methods:

NALM6-luc cells: The NALM6 human acute lymphoblastic leukemia (ALL) cell line was developed from the peripheral blood of a patient with relapsed ALL. The cells were then tagged with firefly luciferase. These suspension cells grow in RPMI supplemented with 10% heat inactivated fetal bovine serum.

Mice: 6 week old NSG (NOD.Cg-Prkdc$^{scid}$Il2rg$^{tm1Wjl}$/SzJ) mice were received from the Jackson Laboratory (stock number 005557).

Tumor implantation: NALM6-luc cells were grown and expanded in vitro in RPMI supplemented with 10% heat inactivated fetal bovine serum. The cells were then transferred to a 15 ml conical tube and washed twice with cold sterile PBS. NALM6-luc cells were then counted and resuspended at a concentration of $10\times10^6$ cells per milliliter of PBS. The cells were placed on ice and immediately (within one hour) implanted in the mice. NALM6-luc cells were injected intravenously via the tail vein in a 100 μl volume, for a total of $1\times10^6$ cells per mouse.

CAR T cell dosing: Mice were administered $5\times10^6$ CAR T cells 7 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of $50\times10^6$ CAR T cells per ml of cold PBS and kept on ice until the mice were dosed. The mice were injected intravenously via the tail vein with 100 μl of the CAR T cells for a dose of $5\times10^6$ CAR T cells per mouse. Eight mice per group were treated either with 100 μl of PBS alone (PBS), or humanized CD19 CAR T cells.

RAD001 dosing: A concentrated micro-emulsion of 50 mg equal to 1 mg RAD001 was formulated and then resuspended in D5W (dextrose 5% in water) at the time of dosing. Mice were orally dosed daily (via oral gavage) with 200 μl of the desired doses of RAD001.

PK analysis: Mice were dosed daily with RAD001 starting 7 days post tumor implantation. Dosing groups were as follows: 0.3 mg/kg, 1 mg/kg, 3 mg/kg, and 10 mg/kg. Mice were bled on days 0 and 14 following the first and last dose of RAD001, at the following time points for PK analysis: 15 minutes, 30 minutes, 1 hour, 2 hours, 4 hours, 8 hours, 12 hours, and 24 hours.

Figure 7:
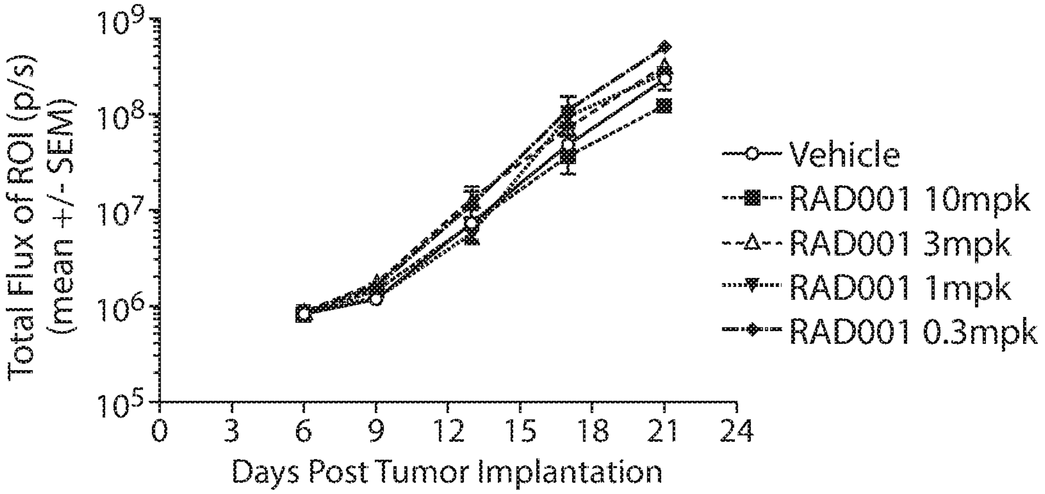
FIG. 7 depicts tumor growth measurements of NALM6-luc cells with daily RAD001 dosing at 0.3, 1, 3, and 10 mg/kg (mpk) or vehicle dosing. Circles denote the vehicle; squares denote the 10 mg/kg dose of RAD001; triangles denote the 3 mg/kg dose of RAD001, inverted triangles denote the 1 mg/kg dose of RAD001; and diamonds denote the 0.3 mg/kg dose of RAD001.
Figure 8A:
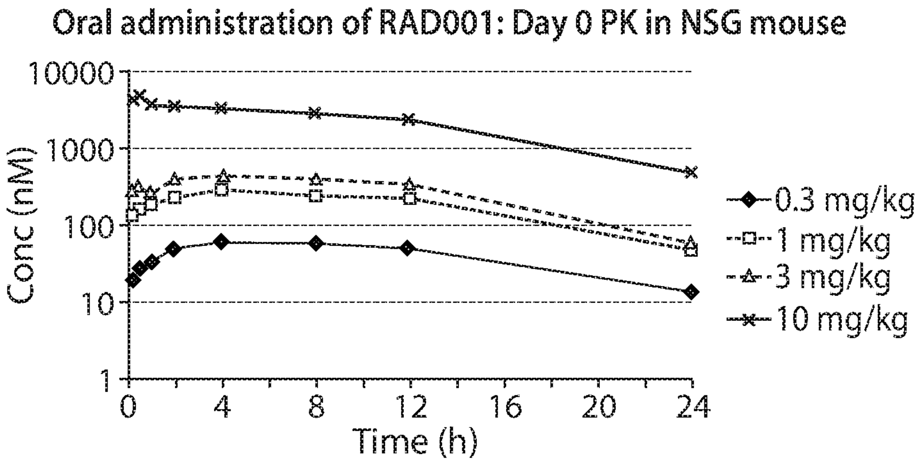
FIGS. 8A and 8B, shows pharmacokinetic curves showing the amount of RAD001 in the blood of NSG mice with NALM6 tumors.
Figure 8B:
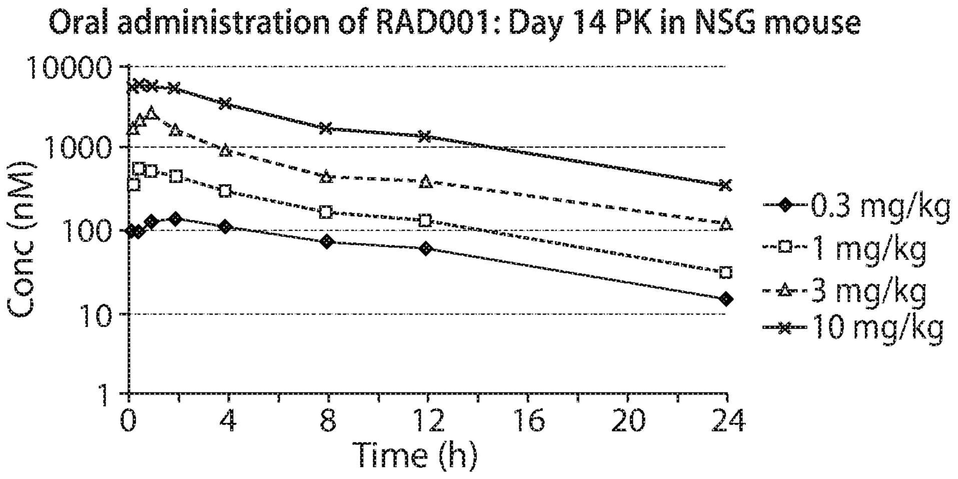

Results:

The expansion and pharmacokinetics of RAD001 was tested in NSG mice with NALM6-luc tumors. Daily oral dosing of RAD001 alone did not have an impact on the growth of NALM6-luc tumors (FIG. 7). The pharmacokinetic analysis of RAD001 shows that it is fairly stable in the blood of tumor bearing mice (FIGS. 8A and 8B). Both the day 0 and day 14 PK analyses show that the RAD001 concentrations in the blood is above 10 nm even 24 hours after dosing at the lowest dose tested (0.3 mg/kg).

Based on these doses, huCAR19 CAR T cells were dosed with and without RAD001 to determine the proliferative ability of these cells. The highest dose used was 3 mg/kg based on the levels of RAD001 in the blood 24 hours after dosing. As the concentration of RAD001 was above 10 nM 24 hours after the final dose of RAD001, several lower doses of RAD001 were used in the in vivo study with CAR T cells. The CAR T cells were dosed IV one day prior to the start of the daily oral RAD001 dosing. Mice were monitored via FACS for T cell expansion.

Figure 9A:
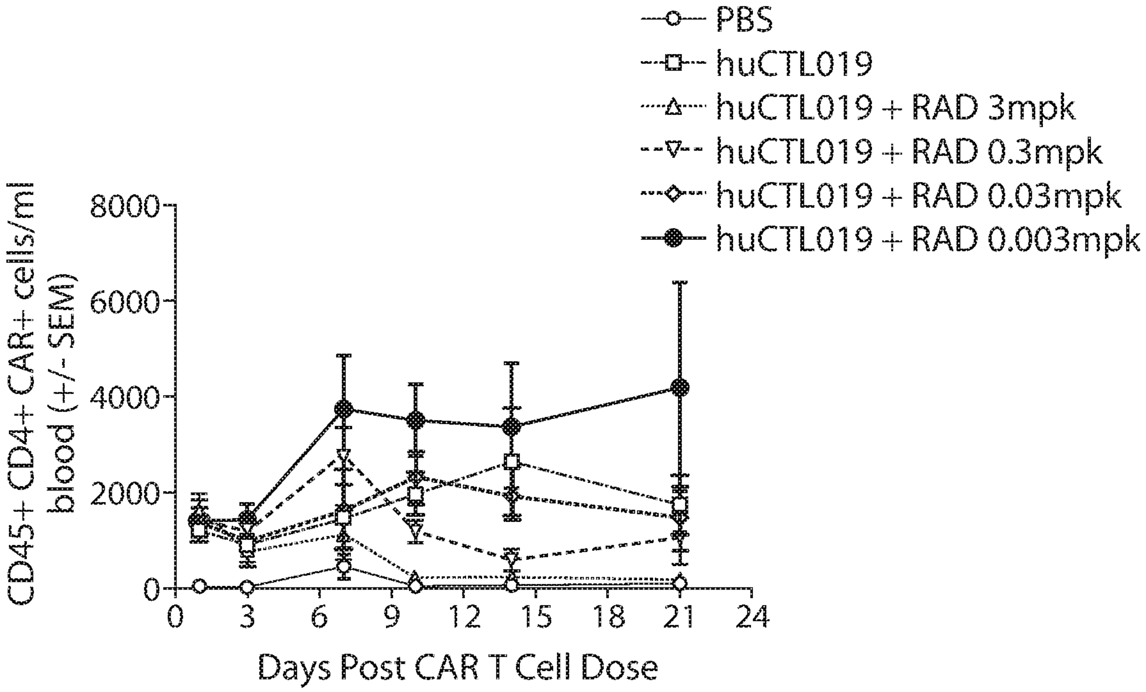
FIGS. 9A and 9B, shows in vivo proliferation of humanized CD19 CART cells with and without RAD001 dosing. Low doses of RAD001 (0.003 mg/kg) daily lead to an enhancement in CAR T cell proliferation, above the normal level of huCAR19 proliferation.
Figure 9B:
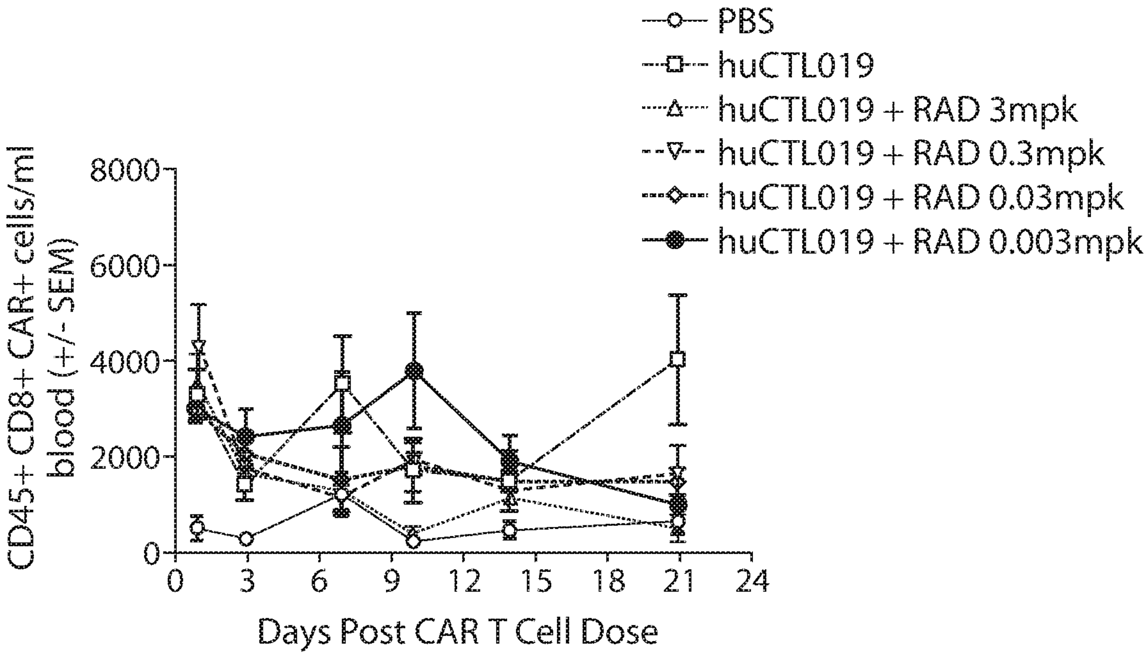

The lowest doses of RAD001 show an enhanced proliferation of the CAR T cells (FIGS. 9A and 9B). This enhanced proliferation is more evident and prolonged with the $CD4^+$ CAR T cells than the $CD8^+$ CAR T cells. However, with the $CD8^+$ CAR T cells, enhanced proliferation can be seen at early time points following the CAR T cell dose. In embodiments, a RNA CART cell can also be used in combination with checkpoint inhibitors.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

SEQUENCE LISTING

```
Sequence total quantity: 613
SEQ ID NO: 1           moltype = AA  length = 21
FEATURE                Location/Qualifiers
REGION                 1..21
                       note = source = /note="Description of Artificial Sequence:
                        Syntheticpeptide"
source                 1..21
                       mol_type = protein
                       organism = synthetic construct
SEQUENCE: 1
MALPVTALLL PLALLLHAAR P                                            21

SEQ ID NO: 2           moltype = AA  length = 45
FEATURE                Location/Qualifiers
REGION                 1..45
                       note = source = /note="Description of Artificial Sequence:
                        Syntheticpolypeptide"
source                 1..45
                       mol_type = protein
                       organism = synthetic construct
SEQUENCE: 2
TTTPAPRPPT PAPTIASQPL SLRPEACRPA AGGAVHTRGL DFACD                  45

SEQ ID NO: 3           moltype = AA  length = 230
FEATURE                Location/Qualifiers
REGION                 1..230
                       note = source = /note="Description of Artificial Sequence:
                        Syntheticpolypeptide"
source                 1..230
                       mol_type = protein
                       organism = synthetic construct
SEQUENCE: 3
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKM             230

SEQ ID NO: 4           moltype = AA  length = 282
FEATURE                Location/Qualifiers
REGION                 1..282
                       note = source = /note="Description of Artificial Sequence:
                        Syntheticpolypeptide"
source                 1..282
                       mol_type = protein
                       organism = synthetic construct
SEQUENCE: 4
RWPESPKAQA SSVPTAQPQA EGSLAKATTA PATTRNTGRG GEEKKKEKEK EEQEERETKT  60
PECPSHTQPL GVYLLTPAVQ DLWLRDKATF TCFVVGSDLK DAHLTWEVAG KVPTGGVEEG  120
LLERHSNGSQ SQHSRLTLPR SLWNAGTSVT CTLNHPSLPP QRLMALREPA AQAPVKLSLN  180
LLASSDPPEA ASWLLCEVSG FSPPNILLMW LEDQREVNTS GFAPARPPPQ PGSTTFWAWS  240
VLRVPAPPSP QPATYTCVVS HEDSRTLLNA SRSLEVSYVT DH                     282

SEQ ID NO: 5           moltype = AA  length = 10
FEATURE                Location/Qualifiers
REGION                 1..10
```

```
                         note = source = /note="Description of Artificial Sequence:
                          Syntheticpeptide"
source                   1..10
                         mol_type = protein
                         organism = synthetic construct
SEQUENCE: 5
GGGGSGGGGS                                                   10

SEQ ID NO: 6             moltype = AA  length = 24
FEATURE                  Location/Qualifiers
REGION                   1..24
                         note = source = /note="Description of Artificial Sequence:
                          Syntheticpeptide"
source                   1..24
                         mol_type = protein
                         organism = synthetic construct
SEQUENCE: 6
IYIWAPLAGT CGVLLLSLVI TLYC                                   24

SEQ ID NO: 7             moltype = AA  length = 42
FEATURE                  Location/Qualifiers
REGION                   1..42
                         note = source = /note="Description of Artificial Sequence:
                          Syntheticpolypeptide"
source                   1..42
                         mol_type = protein
                         organism = synthetic construct
SEQUENCE: 7
KRGRKKLLYI FKQPFMRPVQ TTQEEDGCSC RFPEEEEGGC EL               42

SEQ ID NO: 8             moltype = AA  length = 48
FEATURE                  Location/Qualifiers
REGION                   1..48
                         note = source = /note="Description of Artificial Sequence:
                          Syntheticpolypeptide"
source                   1..48
                         mol_type = protein
                         organism = synthetic construct
SEQUENCE: 8
QRRKYRSNKG ESPVEPAEPC RYSCPREEEG STIPIQEDYR KPEPACSP         48

SEQ ID NO: 9             moltype = AA  length = 112
FEATURE                  Location/Qualifiers
REGION                   1..112
                         note = source = /note="Description of Artificial Sequence:
                          Syntheticpolypeptide"
source                   1..112
                         mol_type = protein
                         organism = synthetic construct
SEQUENCE: 9
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 10            moltype = AA  length = 112
FEATURE                  Location/Qualifiers
source                   1..112
                         mol_type = protein
                         organism = Homo sapiens
SEQUENCE: 10
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 11            moltype = DNA  length = 1184
FEATURE                  Location/Qualifiers
misc_feature             1..1184
                         note = source = /note="Description of Artificial Sequence:
                          Syntheticpolynucleotide"
source                   1..1184
                         mol_type = other DNA
                         organism = synthetic construct
SEQUENCE: 11
cgtgaggctc cggtgcccgt cagtgggcag agcgcacatc gcccacagtc cccgagaagt  60
tgggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctg cagtacgtga ttcttgatcc cgagcttcgg gttggaagtg  360
ggtgggagag ttcgaggcct tgcgcttaag gagccccttc gcctcgtgct tgagttgagg  420
cctggcctgg gcgctggggc cgccgcgtgc gaatctggtg gcaccttcgc gcctgtctcg  480
```

```
ctgctttcga taagtctcta gccatttaaa atttttgatg acctgctgcg acgctttttt  540
tctggcaaga tagtcttgta aatgcgggcc aagatctgca cactggtatt tcggtttttg  600
gggccgcggg cggcgacggg gcccgtgcgt cccagcgcac atgttcggcg aggcggggcc  660
tgcgagcgcg gccaccgaga atcggacggg ggtagtctca agctggccgg cctgctctgg  720
tgcctggcct cgcgccgccg tgtatcgccc cgccctgggc ggcaaggctg gcccggtcgg  780
caccagttgc gtgagcggaa agatggccgc ttcccggccc tgctgcaggg agctcaaaat  840
ggaggacgcg gcgctcggga gagcgggcgg gtgagtcacc cacacaaagg aaaagggcct  900
ttccgtcctc agccgtcgct tcatgtgact ccacggagta ccgggcgccg tccaggcacc  960
tcgattagtt ctcgagcttt tggagtacgt cgtctttagg ttggggggag gggttttatg  1020
cgatggagtt tccccacact gagtgggtgg agactgaagt taggccagct tggcacttga  1080
tgtaattctc cttggaattt gcccttttttg agtttggatc ttggttcatt ctcaagcctc  1140
agacagtggt tcaaagtttt tttcttccat ttcaggtgtc gtga                  1184

SEQ ID NO: 12           moltype = DNA  length = 63
FEATURE                 Location/Qualifiers
misc_feature            1..63
                        note = source = /note="Description of Artificial Sequence:
                         Syntheticoligonucleotide"
source                  1..63
                        mol_type = other DNA
                        organism = synthetic construct
SEQUENCE: 12
atggccctgc ctgtgacagc cctgctgctg cctctggctc tgctgctgca tgccgctaga  60
ccc                                                                63

SEQ ID NO: 13           moltype = DNA  length = 135
FEATURE                 Location/Qualifiers
misc_feature            1..135
                        note = source = /note="Description of Artificial Sequence:
                         Syntheticpolynucleotide"
source                  1..135
                        mol_type = other DNA
                        organism = synthetic construct
SEQUENCE: 13
accacgacgc cagcgccgcg accaccaaca ccggcgccca ccatcgcgtc gcagcccctg  60
tccctgcgcc cagaggcgtg ccggccagcg gcggggggcg cagtgcacac gagggggctg  120
gacttcgcct gtgat                                                   135

SEQ ID NO: 14           moltype = DNA  length = 690
FEATURE                 Location/Qualifiers
misc_feature            1..690
                        note = source = /note="Description of Artificial Sequence:
                         Syntheticpolynucleotide"
source                  1..690
                        mol_type = other DNA
                        organism = synthetic construct
SEQUENCE: 14
gagagcaagt acggccctcc ctgcccccct tgccctgccc ccgagttcct gggcggaccc  60
agcgtgttcc tgttcccccc caagcccaag gacaccctga tgatcagccg gacccccgag  120
gtgacctgtg tggtggtgga cgtgtcccag gaggaccccg aggtccagtt caactggtac  180
gtggacggcg tggaggtgca caacgccaag accaagcccc gggaggagca gttcaatagc  240
acctaccggg tggtgtccgt gctgaccgtg ctgcaccagg actggctgaa cggcaaggaa  300
tacaagtgta aggtgtccaa caagggcctg cccagcagca tcgagaaaac catcagcaag  360
gccaagggcc agcctcggga gccccaggtg tacaccctgc cccctagcca agaggagatg  420
accaagaacc aggtgtccct gacctgcctg gtgaagggct tctaccccag cgacatcgcc  480
gtggagtggg agagcaacgg ccagcccgag aacaactaca agaccacccc ccctgtgctg  540
gacagcgacg gcagcttctt cctgtacagc cggctgaccg tggacaagag ccggtggcag  600
gagggcaacg tctttagctg ctccgtgatg cacgaggccc tgcacaacca ctacacccag  660
aagagcctga gcctgtccct gggcaagatg                                   690

SEQ ID NO: 15           moltype = DNA  length = 847
FEATURE                 Location/Qualifiers
misc_feature            1..847
                        note = source = /note="Description of Artificial Sequence:
                         Syntheticpolynucleotide"
source                  1..847
                        mol_type = other DNA
                        organism = synthetic construct
SEQUENCE: 15
aggtggcccg aaagtcccaa ggcccaggca tctagtgttc ctactgcaca gccccaggca  60
gaaggcagcc tagccaaagc tactactgca cctgccacta cgcgcaatac tggccgtggc  120
ggggaggaga agaaaaagga gaaagagaaa gaagaacagg aagagaggga gaccaagacc  180
cctgaatgtc catcccatac ccagccgctg ggcgtctatc tcttgactcc cgcagtacag  240
gacttgtggc ttagagataa ggccaccttt acatgtttcg tcgtgggctc tgacctgaag  300
gatgcccatt tgacttggga ggttgccgga aaggtaccca caggggggt tgaggaaggg  360
ttgctggagc gccattccaa tggctctcag agccagcact caagactcac ccttccgaga  420
tccctgtgga acgccgggac ctctgtcaca tgtactctaa atcatcctag cctgccccca  480
cagcgtctga tggcccttag agagccagcc gcccaggcac cagttaagct tagcctgaat  540
ctgctcgcca gtagtgatcc cccagaggcc gccagctggc tcttatgcga agtgtccggc  600
```

```
tttagcccgc ccaacatctt gctcatgtgg ctggaggacc agcgagaagt gaacaccagc  660
ggcttcgctc cagcccggcc cccaccccag ccgggttcta ccacattctg ggcctggagt  720
gtcttaaggg tcccagcacc acctagcccc cagccagcca catacacctg tgttgtgtcc  780
catgaagata gcaggaccct gctaaatgct tctaggagtc tggaggtttc ctacgtgact  840
gaccatt                                                            847

SEQ ID NO: 16          moltype = DNA  length = 30
FEATURE                Location/Qualifiers
misc_feature           1..30
                       note = source = /note="Description of Artificial Sequence:
                        Syntheticoligonucleotide"
source                 1..30
                       mol_type = other DNA
                       organism = synthetic construct
SEQUENCE: 16
ggtggcggag gttctggagg tggaggttcc                                   30

SEQ ID NO: 17          moltype = DNA  length = 72
FEATURE                Location/Qualifiers
misc_feature           1..72
                       note = source = /note="Description of Artificial Sequence:
                        Syntheticoligonucleotide"
source                 1..72
                       mol_type = other DNA
                       organism = synthetic construct
SEQUENCE: 17
atctacatct gggcgccctt ggccgggact tgtggggtcc ttctcctgtc actggttatc  60
accctttact gc                                                      72

SEQ ID NO: 18          moltype = DNA  length = 126
FEATURE                Location/Qualifiers
misc_feature           1..126
                       note = source = /note="Description of Artificial Sequence:
                        Syntheticpolynucleotide"
source                 1..126
                       mol_type = other DNA
                       organism = synthetic construct
SEQUENCE: 18
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 19          moltype = DNA  length = 123
FEATURE                Location/Qualifiers
misc_feature           1..123
                       note = source = /note="Description of Artificial Sequence:
                        Syntheticpolynucleotide"
source                 1..123
                       mol_type = other DNA
                       organism = synthetic construct
SEQUENCE: 19
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123

SEQ ID NO: 20          moltype = DNA  length = 336
FEATURE                Location/Qualifiers
misc_feature           1..336
                       note = source = /note="Description of Artificial Sequence:
                        Syntheticpolynucleotide"
source                 1..336
                       mol_type = other DNA
                       organism = synthetic construct
SEQUENCE: 20
agagtgaagt tcagcaggag cgcagacgcc cccgcgtaca agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 21          moltype = DNA  length = 336
FEATURE                Location/Qualifiers
source                 1..336
                       mol_type = other DNA
                       organism = Homo sapiens
SEQUENCE: 21
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
```

-continued

```
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 22          moltype = AA  length = 373
FEATURE                Location/Qualifiers
REGION                 1..373
                       note = source = /note="Description of Artificial Sequence:
                        Syntheticpolypeptide"
source                 1..373
                       mol_type = protein
                       organism = synthetic construct
SEQUENCE: 22
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV TTTPAPRPPT PAPTIASQPL SLRPEACRPA  180
AGGAVHTRGL DFACDIYIWA PLAGTCGVLL LSLVITLYCK RGRKKLLYIF KQPFMRPVQT  240
TQEEDGCSCR FPEEEEGGCE LRVKFSRSAD APAYKQGQNQ LYNELNLGRR EEYDVLDKRR  300
GRDPEMGGKP RRKNPQEGLY NELQKDKMAE AYSEIGMKGE RRRGKGHDGL YQGLSTATKD  360
TYDALHMQAL PPR                                                     373

SEQ ID NO: 23          moltype = DNA  length = 1182
FEATURE                Location/Qualifiers
misc_feature           1..1182
                       note = source = /note="Description of Artificial Sequence:
                        Syntheticpolynucleotide"
source                 1..1182
                       mol_type = other DNA
                       organism = synthetic construct
SEQUENCE: 23
atggccctcc ctgtcactgc cctgcttctc cccctcgcac tcctgctcca cgccgctaga  60
ccacccggat ggtttctgga ctctccggat cgcccgtgga atcccccaac cttctcaccg  120
gcactcttgg ttgtgactga gggcgataat gcgaccttca cgtgctcgtt ctccaacacc  180
tccgaatcat tcgtgctgaa ctggtaccgc atgagcccgt caaaccagac cgacaagctc  240
gccgcgtttc cggaagatcg gtcgcaaccg ggacaggatt gtcggttccg cgtgactcaa  300
ctgccgaatg gcagagactt ccacatgagc gtggtccgcg ctaggcgaaa cgactccggg  360
acctacctgt gcggagccat ctcgctggcg cctaaggccc aaatcaaaga gagcttgagg  420
gccgaactga gagtgaccga gcgcagagct gaggtgccaa ctgcacatcc atccccatcg  480
cctcggcctg cggggcagtt tcagaccctg gtcacgacca ctccggcgcc gcgcccaccg  540
actccggccc caactatcgc gagccagccc ctgtcgctga ggccggaagc atgccgccct  600
gccgccggag gtgctgtgca tacccgggga ttggacttcg catgcgacat ctacatttgg  660
gctcctctcg ccggaacttg tggcgtgctc cttctgtccc tggtcatcac cctgtactgc  720
aagcggggtc ggaaaaagct tctgtacatt ttcaagcagc ccttcatgag gcccgtgcaa  780
accacccagg aggaggacgg ttgctcctgc cggttccccg aagaggaaga aggaggttgc  840
gagctgcgcg tgaagttctc ccggagcgcc gacgcccccg cctataagca gggccagaac  900
cagctgtaca acgaactgaa cctgggacgg cgggaagagt acgatgtgct ggacaagcgg  960
cgcggccggg accccgaaat gggcgggaag cctagaagaa agaaccctca ggaaggcctg  1020
tataacgagc tgcagaagga caagatggcc gaggcctact ccgaaattgg gatgaaggga  1080
gagcggcgga ggggaaaggg gcacgacggc ctgtaccaag gactgtccac cgccaccaag  1140
gacacatacg atgccctgca catgcaggcc cttccccctc gc                     1182

SEQ ID NO: 24          moltype = AA  length = 394
FEATURE                Location/Qualifiers
REGION                 1..394
                       note = source = /note="Description of Artificial Sequence:
                        Syntheticpolypeptide"
source                 1..394
                       mol_type = protein
                       organism = synthetic construct
SEQUENCE: 24
MALPVTALLL PLALLLHAAR PPGWFLDSPD RPWNPPTFSP ALLVVTEGDN ATFTCSFSNT  60
SESFVLNWYR MSPSNQTDKL AAFPEDRSQP GQDCRFRVTQ LPNGRDFHMS VVRARRNDSG  120
TYLCGAISLA PKAQIKESLR AELRVTERRA EVPTAHPSPS PRPAGQFQTL VTTTPAPRPP  180
TPAPTIASQP LSLRPEACRP AAGGAVHTRG LDFACDIYIW APLAGTCGVL LLSLVITLYC  240
KRGRKKLLYI FKQPFMRPVQ TTQEEDGCSC RFPEEEEGGC ELRVKFSRSA DAPAYKQGQN  300
QLYNELNLGR REEYDVLDKR RGRDPEMGGK PRRKNPQEGL YNELQKDKMA EAYSEIGMKG  360
ERRRGKGHDG LYQGLSTATK DTYDALHMQA LPPR                              394

SEQ ID NO: 25          moltype = AA  length = 5
FEATURE                Location/Qualifiers
REGION                 1..5
                       note = source = /note="Description of Artificial Sequence:
                        Syntheticpeptide"
source                 1..5
                       mol_type = protein
                       organism = synthetic construct
SEQUENCE: 25
GGGGS                                                              5
```

```
SEQ ID NO: 26           moltype = AA  length = 30
FEATURE                 Location/Qualifiers
REGION                  1..30
                        note = MISC_FEATURE - /note="This sequence may encompass
                         1-6"Gly Gly Gly Gly Ser" repeating units"
REGION                  1..30
                        note = source = /note="Description of Artificial Sequence:
                         Syntheticpolypeptide"
source                  1..30
                        mol_type = protein
                        organism = synthetic construct
SEQUENCE: 26
GGGGSGGGGS GGGGSGGGGS GGGGSGGGGS                                    30

SEQ ID NO: 27           moltype = AA  length = 20
FEATURE                 Location/Qualifiers
REGION                  1..20
                        note = source = /note="Description of Artificial Sequence:
                         Syntheticpeptide"
source                  1..20
                        mol_type = protein
                        organism = synthetic construct
SEQUENCE: 27
GGGGSGGGGS GGGGSGGGGS                                               20

SEQ ID NO: 28           moltype = AA  length = 15
FEATURE                 Location/Qualifiers
REGION                  1..15
                        note = source = /note="Description of Artificial Sequence:
                         Syntheticpeptide"
source                  1..15
                        mol_type = protein
                        organism = synthetic construct
SEQUENCE: 28
GGGGSGGGGS GGGGS                                                    15

SEQ ID NO: 29           moltype = AA  length = 4
FEATURE                 Location/Qualifiers
REGION                  1..4
                        note = source = /note="Description of Artificial Sequence:
                         Syntheticpeptide"
source                  1..4
                        mol_type = protein
                        organism = synthetic construct
SEQUENCE: 29
GGGS                                                                4

SEQ ID NO: 30           moltype = DNA  length = 5000
FEATURE                 Location/Qualifiers
misc_feature            1..5000
                        note = /note="This sequence may encompass 50-5000
                         nucleotides"
misc_feature            1..5000
                        note = source = /note="Description of Artificial Sequence:
                         Syntheticpolynucleotide"
misc_feature            1..5000
                        note = source = /note="See specification as filed for
                         detailed description ofsubstitutions and preferred
                         embodiments"
source                  1..5000
                        mol_type = other DNA
                        organism = synthetic construct
SEQUENCE: 30
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
```

-continued

```
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaaaaa aaaaaaaaaa aaaaaaaaaa aaaaaaaaaa aaaaaaaaaa aaaaaaaaaa  2220
aaaaaaaaaa aaaaaaaaaa aaaaaaaaaa aaaaaaaaaa aaaaaaaaaa aaaaaaaaaa  2280
aaaaaaaaaa aaaaaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaaaaaaaa aaaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa aaaaaaaaaa aaaaaaaaaa aaaaaaaaaa aaaaaaaaaa  2580
aaaaaaaaaa aaaaaaaaaa aaaaaaaaaa aaaaaaaaaa aaaaaaaaaa aaaaaaaaaa  2640
aaaaaaaaaa aaaaaaaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaaa aaaaaaaaaa aaaaaaaaaa aaaaaaaaaa aaaaaaaaaa aaaaaaaaaa  2820
aaaaaaaaaa aaaaaaaaaa aaaaaaaaaa aaaaaaaaaa aaaaaaaaaa aaaaaaaaaa  2880
aaaaaaaaaa aaaaaaaaaa aaaaaaaaaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000
aaaaaaaaaa aaaaaaaaaa aaaaaaaaaa aaaaaaaaaa aaaaaaaaaa aaaaaaaaaa  3060
aaaaaaaaaa aaaaaaaaaa aaaaaaaaaa aaaaaaaaaa aaaaaaaaaa aaaaaaaaaa  3120
aaaaaaaaaa aaaaaaaaaa aaaaaaaaaa aaaaaaaaaa aaaaaaaaaa aaaaaaaaaa  3180
aaaaaaaaaa aaaaaaaaaa aaaaaaaaaa aaaaaaaaaa aaaaaaaaaa aaaaaaaaaa  3240
aaaaaaaaaa aaaaaaaaaa aaaaaaaaaa aaaaaaaaaa aaaaaaaaaa aaaaaaaaaa  3300
aaaaaaaaaa aaaaaaaaaa aaaaaaaaaa aaaaaaaaaa aaaaaaaaaa aaaaaaaaaa  3360
aaaaaaaaaa aaaaaaaaaa aaaaaaaaaa aaaaaaaaaa aaaaaaaaaa aaaaaaaaaa  3420
aaaaaaaaaa aaaaaaaaaa aaaaaaaaaa aaaaaaaaaa aaaaaaaaaa aaaaaaaaaa  3480
aaaaaaaaaa aaaaaaaaaa aaaaaaaaaa aaaaaaaaaa aaaaaaaaaa aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaaaa  3660
aaaaaaaaaa aaaaaaaaaa aaaaaaaaaa aaaaaaaaaa aaaaaaaaaa aaaaaaaaaa  3720
aaaaaaaaaa aaaaaaaaaa aaaaaaaaaa aaaaaaaaaa aaaaaaaaaa aaaaaaaaaa  3780
aaaaaaaaaa aaaaaaaaaa aaaaaaaaaa aaaaaaaaaa aaaaaaaaaa aaaaaaaaaa  3840
aaaaaaaaaa aaaaaaaaaa aaaaaaaaaa aaaaaaaaaa aaaaaaaaaa aaaaaaaaaa  3900
aaaaaaaaaa aaaaaaaaaa aaaaaaaaaa aaaaaaaaaa aaaaaaaaaa aaaaaaaaaa  3960
aaaaaaaaaa aaaaaaaaaa aaaaaaaaaa aaaaaaaaaa aaaaaaaaaa aaaaaaaaaa  4020
aaaaaaaaaa aaaaaaaaaa aaaaaaaaaa aaaaaaaaaa aaaaaaaaaa aaaaaaaaaa  4080
aaaaaaaaaa aaaaaaaaaa aaaaaaaaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaaaa aaaaaaaaaa aaaaaaaaaa  4260
aaaaaaaaaa aaaaaaaaaa aaaaaaaaaa aaaaaaaaaa aaaaaaaaaa aaaaaaaaaa  4320
aaaaaaaaaa aaaaaaaaaa aaaaaaaaaa aaaaaaaaaa aaaaaaaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaaaa aaaaaaaaaa aaaaaaaaaa  4620
aaaaaaaaaa aaaaaaaaaa aaaaaaaaaa aaaaaaaaaa aaaaaaaaaa aaaaaaaaaa  4680
aaaaaaaaaa aaaaaaaaaa aaaaaaaaaa aaaaaaaaaa aaaaaaaaaa aaaaaaaaaa  4740
aaaaaaaaaa aaaaaaaaaa aaaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaaaaa aaaaaaaaaa aaaaaaaaaa aaaaaaaaaa  4920
aaaaaaaaaa aaaaaaaaaa aaaaaaaaaa aaaaaaaaaa aaaaaaaaaa aaaaaaaaaa  4980
aaaaaaaaaa aaaaaaaaaa                                              5000
```

```
SEQ ID NO: 31          moltype = DNA  length = 100
FEATURE                Location/Qualifiers
misc_feature           1..100
                       note = source = /note="Description of Artificial Sequence:
                        Syntheticpolynucleotide"
source                 1..100
                       mol_type = other DNA
                       organism = synthetic construct
SEQUENCE: 31
```

```
tttttttttt tttttttttt tttttttttt tttttttttt tttttttttt tttttttttt  60
tttttttttt tttttttttt tttttttttt tttttttttt                        100

SEQ ID NO: 32          moltype = DNA  length = 5000
FEATURE                Location/Qualifiers
misc_feature           1..5000
                       note = /note="This sequence may encompass 50-5000
                        nucleotides"
misc_feature           1..5000
                       note = source = /note="Description of Artificial Sequence:
                        Syntheticpolynucleotide"
misc_feature           1..5000
                       note = source = /note="See specification as filed for
                        detailed description ofsubstitutions and preferred
                        embodiments"
source                 1..5000
                       mol_type = other DNA
                       organism = synthetic construct
SEQUENCE: 32
tttttttttt tttttttttt tttttttttt tttttttttt tttttttttt tttttttttt  60
tttttttttt tttttttttt tttttttttt tttttttttt tttttttttt tttttttttt  120
tttttttttt tttttttttt tttttttttt tttttttttt tttttttttt tttttttttt  180
tttttttttt tttttttttt tttttttttt tttttttttt tttttttttt tttttttttt  240
tttttttttt tttttttttt tttttttttt tttttttttt tttttttttt tttttttttt  300
tttttttttt tttttttttt tttttttttt tttttttttt tttttttttt tttttttttt  360
tttttttttt tttttttttt tttttttttt tttttttttt tttttttttt tttttttttt  420
tttttttttt tttttttttt tttttttttt tttttttttt tttttttttt tttttttttt  480
tttttttttt tttttttttt tttttttttt tttttttttt tttttttttt tttttttttt  540
tttttttttt tttttttttt tttttttttt tttttttttt tttttttttt tttttttttt  600
tttttttttt tttttttttt tttttttttt tttttttttt tttttttttt tttttttttt  660
tttttttttt tttttttttt tttttttttt tttttttttt tttttttttt tttttttttt  720
tttttttttt tttttttttt tttttttttt tttttttttt tttttttttt tttttttttt  780
tttttttttt tttttttttt tttttttttt tttttttttt tttttttttt tttttttttt  840
tttttttttt tttttttttt tttttttttt tttttttttt tttttttttt tttttttttt  900
tttttttttt tttttttttt tttttttttt tttttttttt tttttttttt tttttttttt  960
tttttttttt tttttttttt tttttttttt tttttttttt tttttttttt tttttttttt  1020
tttttttttt tttttttttt tttttttttt tttttttttt tttttttttt tttttttttt  1080
tttttttttt tttttttttt tttttttttt tttttttttt tttttttttt tttttttttt  1140
tttttttttt tttttttttt tttttttttt tttttttttt tttttttttt tttttttttt  1200
tttttttttt tttttttttt tttttttttt tttttttttt tttttttttt tttttttttt  1260
tttttttttt tttttttttt tttttttttt tttttttttt tttttttttt tttttttttt  1320
tttttttttt tttttttttt tttttttttt tttttttttt tttttttttt tttttttttt  1380
tttttttttt tttttttttt tttttttttt tttttttttt tttttttttt tttttttttt  1440
tttttttttt tttttttttt tttttttttt tttttttttt tttttttttt tttttttttt  1500
tttttttttt tttttttttt tttttttttt tttttttttt tttttttttt tttttttttt  1560
tttttttttt tttttttttt tttttttttt tttttttttt tttttttttt tttttttttt  1620
tttttttttt tttttttttt tttttttttt tttttttttt tttttttttt tttttttttt  1680
tttttttttt tttttttttt tttttttttt tttttttttt tttttttttt tttttttttt  1740
tttttttttt tttttttttt tttttttttt tttttttttt tttttttttt tttttttttt  1800
tttttttttt tttttttttt tttttttttt tttttttttt tttttttttt tttttttttt  1860
tttttttttt tttttttttt tttttttttt tttttttttt tttttttttt tttttttttt  1920
tttttttttt tttttttttt tttttttttt tttttttttt tttttttttt tttttttttt  1980
tttttttttt tttttttttt tttttttttt tttttttttt tttttttttt tttttttttt  2040
tttttttttt tttttttttt tttttttttt tttttttttt tttttttttt tttttttttt  2100
tttttttttt tttttttttt tttttttttt tttttttttt tttttttttt tttttttttt  2160
tttttttttt tttttttttt tttttttttt tttttttttt tttttttttt tttttttttt  2220
tttttttttt tttttttttt tttttttttt tttttttttt tttttttttt tttttttttt  2280
tttttttttt tttttttttt tttttttttt tttttttttt tttttttttt tttttttttt  2340
tttttttttt tttttttttt tttttttttt tttttttttt tttttttttt tttttttttt  2400
tttttttttt tttttttttt tttttttttt tttttttttt tttttttttt tttttttttt  2460
tttttttttt tttttttttt tttttttttt tttttttttt tttttttttt tttttttttt  2520
tttttttttt tttttttttt tttttttttt tttttttttt tttttttttt tttttttttt  2580
tttttttttt tttttttttt tttttttttt tttttttttt tttttttttt tttttttttt  2640
tttttttttt tttttttttt tttttttttt tttttttttt tttttttttt tttttttttt  2700
tttttttttt tttttttttt tttttttttt tttttttttt tttttttttt tttttttttt  2760
tttttttttt tttttttttt tttttttttt tttttttttt tttttttttt tttttttttt  2820
tttttttttt tttttttttt tttttttttt tttttttttt tttttttttt tttttttttt  2880
tttttttttt tttttttttt tttttttttt tttttttttt tttttttttt tttttttttt  2940
tttttttttt tttttttttt tttttttttt tttttttttt tttttttttt tttttttttt  3000
tttttttttt tttttttttt tttttttttt tttttttttt tttttttttt tttttttttt  3060
tttttttttt tttttttttt tttttttttt tttttttttt tttttttttt tttttttttt  3120
tttttttttt tttttttttt tttttttttt tttttttttt tttttttttt tttttttttt  3180
tttttttttt tttttttttt tttttttttt tttttttttt tttttttttt tttttttttt  3240
tttttttttt tttttttttt tttttttttt tttttttttt tttttttttt tttttttttt  3300
tttttttttt tttttttttt tttttttttt tttttttttt tttttttttt tttttttttt  3360
tttttttttt tttttttttt tttttttttt tttttttttt tttttttttt tttttttttt  3420
tttttttttt tttttttttt tttttttttt tttttttttt tttttttttt tttttttttt  3480
tttttttttt tttttttttt tttttttttt tttttttttt tttttttttt tttttttttt  3540
tttttttttt tttttttttt tttttttttt tttttttttt tttttttttt tttttttttt  3600
```

```
tttttttttt tttttttttt tttttttttt tttttttttt tttttttttt tttttttttt  3660
tttttttttt tttttttttt tttttttttt tttttttttt tttttttttt tttttttttt  3720
tttttttttt tttttttttt tttttttttt tttttttttt tttttttttt tttttttttt  3780
tttttttttt tttttttttt tttttttttt tttttttttt tttttttttt tttttttttt  3840
tttttttttt tttttttttt tttttttttt tttttttttt tttttttttt tttttttttt  3900
tttttttttt tttttttttt tttttttttt tttttttttt tttttttttt tttttttttt  3960
tttttttttt tttttttttt tttttttttt tttttttttt tttttttttt tttttttttt  4020
tttttttttt tttttttttt tttttttttt tttttttttt tttttttttt tttttttttt  4080
tttttttttt tttttttttt tttttttttt tttttttttt tttttttttt tttttttttt  4140
tttttttttt tttttttttt tttttttttt tttttttttt tttttttttt tttttttttt  4200
tttttttttt tttttttttt tttttttttt tttttttttt tttttttttt tttttttttt  4260
tttttttttt tttttttttt tttttttttt tttttttttt tttttttttt tttttttttt  4320
tttttttttt tttttttttt tttttttttt tttttttttt tttttttttt tttttttttt  4380
tttttttttt tttttttttt tttttttttt tttttttttt tttttttttt tttttttttt  4440
tttttttttt tttttttttt tttttttttt tttttttttt tttttttttt tttttttttt  4500
tttttttttt tttttttttt tttttttttt tttttttttt tttttttttt tttttttttt  4560
tttttttttt tttttttttt tttttttttt tttttttttt tttttttttt tttttttttt  4620
tttttttttt tttttttttt tttttttttt tttttttttt tttttttttt tttttttttt  4680
tttttttttt tttttttttt tttttttttt tttttttttt tttttttttt tttttttttt  4740
tttttttttt tttttttttt tttttttttt tttttttttt tttttttttt tttttttttt  4800
tttttttttt tttttttttt tttttttttt tttttttttt tttttttttt tttttttttt  4860
tttttttttt tttttttttt tttttttttt tttttttttt tttttttttt tttttttttt  4920
tttttttttt tttttttttt tttttttttt tttttttttt tttttttttt tttttttttt  4980
tttttttttt tttttttttt                                              5000

SEQ ID NO: 33          moltype = DNA  length = 5000
FEATURE                Location/Qualifiers
misc_feature           1..5000
                       note = /note="This sequence may encompass 100-5000
                        nucleotides"
misc_feature           1..5000
                       note = source = /note="Description of Artificial Sequence:
                        Syntheticpolynucleotide"
misc_feature           1..5000
                       note = source = /note="See specification as filed for
                        detailed description ofsubstitutions and preferred
                        embodiments"
source                 1..5000
                       mol_type = other DNA
                       organism = synthetic construct
SEQUENCE: 33
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaaaaa aaaaaaaaaa aaaaaaaaaa aaaaaaaaaa aaaaaaaaaa aaaaaaaaaa  2220
aaaaaaaaaa aaaaaaaaaa aaaaaaaaaa aaaaaaaaaa aaaaaaaaaa aaaaaaaaaa  2280
```

```
aaaaaaaaaa aaaaaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaaaaaaaa aaaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa aaaaaaaaaa aaaaaaaaaa aaaaaaaaaa aaaaaaaaaa  2580
aaaaaaaaaa aaaaaaaaaa aaaaaaaaaa aaaaaaaaaa aaaaaaaaaa aaaaaaaaaa  2640
aaaaaaaaaa aaaaaaaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaaa aaaaaaaaaa aaaaaaaaaa aaaaaaaaaa aaaaaaaaaa aaaaaaaaaa  2820
aaaaaaaaaa aaaaaaaaaa aaaaaaaaaa aaaaaaaaaa aaaaaaaaaa aaaaaaaaaa  2880
aaaaaaaaaa aaaaaaaaaa aaaaaaaaaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000
aaaaaaaaaa aaaaaaaaaa aaaaaaaaaa aaaaaaaaaa aaaaaaaaaa aaaaaaaaaa  3060
aaaaaaaaaa aaaaaaaaaa aaaaaaaaaa aaaaaaaaaa aaaaaaaaaa aaaaaaaaaa  3120
aaaaaaaaaa aaaaaaaaaa aaaaaaaaaa aaaaaaaaaa aaaaaaaaaa aaaaaaaaaa  3180
aaaaaaaaaa aaaaaaaaaa aaaaaaaaaa aaaaaaaaaa aaaaaaaaaa aaaaaaaaaa  3240
aaaaaaaaaa aaaaaaaaaa aaaaaaaaaa aaaaaaaaaa aaaaaaaaaa aaaaaaaaaa  3300
aaaaaaaaaa aaaaaaaaaa aaaaaaaaaa aaaaaaaaaa aaaaaaaaaa aaaaaaaaaa  3360
aaaaaaaaaa aaaaaaaaaa aaaaaaaaaa aaaaaaaaaa aaaaaaaaaa aaaaaaaaaa  3420
aaaaaaaaaa aaaaaaaaaa aaaaaaaaaa aaaaaaaaaa aaaaaaaaaa aaaaaaaaaa  3480
aaaaaaaaaa aaaaaaaaaa aaaaaaaaaa aaaaaaaaaa aaaaaaaaaa aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaaaa  3660
aaaaaaaaaa aaaaaaaaaa aaaaaaaaaa aaaaaaaaaa aaaaaaaaaa aaaaaaaaaa  3720
aaaaaaaaaa aaaaaaaaaa aaaaaaaaaa aaaaaaaaaa aaaaaaaaaa aaaaaaaaaa  3780
aaaaaaaaaa aaaaaaaaaa aaaaaaaaaa aaaaaaaaaa aaaaaaaaaa aaaaaaaaaa  3840
aaaaaaaaaa aaaaaaaaaa aaaaaaaaaa aaaaaaaaaa aaaaaaaaaa aaaaaaaaaa  3900
aaaaaaaaaa aaaaaaaaaa aaaaaaaaaa aaaaaaaaaa aaaaaaaaaa aaaaaaaaaa  3960
aaaaaaaaaa aaaaaaaaaa aaaaaaaaaa aaaaaaaaaa aaaaaaaaaa aaaaaaaaaa  4020
aaaaaaaaaa aaaaaaaaaa aaaaaaaaaa aaaaaaaaaa aaaaaaaaaa aaaaaaaaaa  4080
aaaaaaaaaa aaaaaaaaaa aaaaaaaaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaaaa aaaaaaaaaa aaaaaaaaaa  4260
aaaaaaaaaa aaaaaaaaaa aaaaaaaaaa aaaaaaaaaa aaaaaaaaaa aaaaaaaaaa  4320
aaaaaaaaaa aaaaaaaaaa aaaaaaaaaa aaaaaaaaaa aaaaaaaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaaaa aaaaaaaaaa aaaaaaaaaa  4620
aaaaaaaaaa aaaaaaaaaa aaaaaaaaaa aaaaaaaaaa aaaaaaaaaa aaaaaaaaaa  4680
aaaaaaaaaa aaaaaaaaaa aaaaaaaaaa aaaaaaaaaa aaaaaaaaaa aaaaaaaaaa  4740
aaaaaaaaaa aaaaaaaaaa aaaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaaaaa aaaaaaaaaa aaaaaaaaaa aaaaaaaaaa  4920
aaaaaaaaaa aaaaaaaaaa aaaaaaaaaa aaaaaaaaaa aaaaaaaaaa aaaaaaaaaa  4980
aaaaaaaaaa aaaaaaaaaa                                              5000

SEQ ID NO: 34          moltype = DNA  length = 400
FEATURE                Location/Qualifiers
misc_feature           1..400
                       note = /note="This sequence may encompass 100-400
                        nucleotides"
misc_feature           1..400
                       note = source = /note="Description of Artificial Sequence:
                        Syntheticpolynucleotide"
misc_feature           1..400
                       note = source = /note="See specification as filed for
                        detailed description ofsubstitutions and preferred
                        embodiments"
source                 1..400
                       mol_type = other DNA
                       organism = synthetic construct
SEQUENCE: 34
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa                        400

SEQ ID NO: 35          moltype = DNA  length = 2000
FEATURE                Location/Qualifiers
misc_feature           1..2000
                       note = /note="This sequence may encompass 50-2000
                        nucleotides"
misc_feature           1..2000
                       note = source = /note="Description of Artificial Sequence:
                        Syntheticpolynucleotide"
```

```
misc_feature          1..2000
                      note = source = /note="See specification as filed for
                       detailed description ofsubstitutions and preferred
                       embodiments"
source                1..2000
                      mol_type = other DNA
                      organism = synthetic construct
SEQUENCE: 35
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa                                              2000

SEQ ID NO: 36         moltype = AA  length = 41
FEATURE               Location/Qualifiers
REGION                1..41
                      note = source = /note="Description of Artificial Sequence:
                       Syntheticpolypeptide"
source                1..41
                      mol_type = protein
                      organism = synthetic construct
SEQUENCE: 36
RSKRSRLLHS DYMNMTPRRP GPTRKHYQPY APPRDFAAYR S                      41

SEQ ID NO: 37         moltype = DNA  length = 123
FEATURE               Location/Qualifiers
misc_feature          1..123
                      note = source = /note="Description of Artificial Sequence:
                       Syntheticpolynucleotide"
source                1..123
                      mol_type = other DNA
                      organism = synthetic construct
SEQUENCE: 37
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123

SEQ ID NO: 38         moltype = AA  length = 35
FEATURE               Location/Qualifiers
REGION                1..35
                      note = source = /note="Description of Artificial Sequence:
                       Syntheticpolypeptide"
source                1..35
                      mol_type = protein
                      organism = synthetic construct
SEQUENCE: 38
TKKKYSSSVH DPNGEYMFMR AVNTAKKSRL TDVTL                             35

SEQ ID NO: 39         moltype = AA  length = 244
```

-continued

```
FEATURE                 Location/Qualifiers
REGION                  1..244
                        note = source = /note="Description of Artificial Sequence:
                         Syntheticpolypeptide"
source                  1..244
                        mol_type = protein
                        organism = synthetic construct
SEQUENCE: 39
QVQLQQSGAE VKKPGASVKV SCKASGYTFT GYYMHWVRQA PGQGLEWMGR INPNSGGTNY  60
AQKFQGRVTM TRDTSISTAY MELSRLRSED TAVYYCARGR YYGMDVWGQG TMVTVSSGGG  120
GSGGGGSGGG GSGGGGSEIV LTQSPATLSL SPGERATISC RASQSVSSNF AWYQQRPGQA  180
PRLLIYDASN RATGIPPRFS GSGSGTDFTL TISSLEPEDF AAYYCHQRSN WLYTFGQGTK  240
VDIK                                                               244

SEQ ID NO: 40           moltype = AA  length = 253
FEATURE                 Location/Qualifiers
REGION                  1..253
                        note = source = /note="Description of Artificial Sequence:
                         Syntheticpolypeptide"
source                  1..253
                        mol_type = protein
                        organism = synthetic construct
SEQUENCE: 40
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCARDL RRTVVTPRAY YGMDVWGQGT  120
TVTVSSGGGG SGGGGSGGGG SGGGGSDIQL TQSPSTLSAS VGDRVTITCQ ASQDISNSLN  180
WYQQKAGKAP KLLIYDASTL ETGVPSRFSG SGSGTDFSFT ISSLQPEDIA TYYCQQHDNL  240
PLTFGQGTKV EIK                                                     253

SEQ ID NO: 41           moltype = AA  length = 246
FEATURE                 Location/Qualifiers
REGION                  1..246
                        note = source = /note="Description of Artificial Sequence:
                         Syntheticpolypeptide"
source                  1..246
                        mol_type = protein
                        organism = synthetic construct
SEQUENCE: 41
QVQLVQSGAE VKKPGAPVKV SCKASGYTFT GYYMHWVRQA PGQGLEWMGW INPNSGGTNY  60
AQKFQGRVTM TRDTSISTAY MELSRLRSDD TAVYYCARGE WDGSYYYDYW GQGTLVTVSS  120
GGGGSGGGGS GGGGSGGGGS DIVLTQTPSS LSASVGDRVT ITCRASQSIN TYLNWYQHKP  180
GKAPKLLIYA ASSLQSGVPS RFSGSGSGTD FTLTISSLQP EDFATYYCQQ SFSPLTFGGG  240
TKLEIK                                                             246

SEQ ID NO: 42           moltype = AA  length = 242
FEATURE                 Location/Qualifiers
REGION                  1..242
                        note = source = /note="Description of Artificial Sequence:
                         Syntheticpolypeptide"
source                  1..242
                        mol_type = protein
                        organism = synthetic construct
SEQUENCE: 42
QVQLVESGGG LVQPGGSLRL SCAASGFTFS SYWMHWVRQV PGKGLVWVSR INTDGSTTTY  60
ADSVEGRFTI SRDNAKNTLY LQMNSLRDDD TAVYYCVGGH WAVWGQGTTV TVSSGGGGSG  120
GGGSGGGGSG GGGSDIQMTQ SPSTLSASVG DRVTITCRAS QSISDRLAWY QQKPGKAPKL  180
LIYKASSLES GVPSRFSGSG SGTEFTLTIS SLQPDDFAVY YCQQYGHLPM YTFGQGTKVE  240
IK                                                                 242

SEQ ID NO: 43           moltype = AA  length = 241
FEATURE                 Location/Qualifiers
REGION                  1..241
                        note = source = /note="Description of Artificial Sequence:
                         Syntheticpolypeptide"
source                  1..241
                        mol_type = protein
                        organism = synthetic construct
SEQUENCE: 43
QVQLVQSGAE VEKPGASVKV SCKASGYTFT DYYMHWVRQA PGQGLEWMGW INPNSGGTNY  60
AQKFQGRVTM TRDTSISTAY MELSRLRSDD TAVYYCASGW DFDYWGQGTL VTVSSGGGGS  120
GGGGSGGGGS GGGGSDIVMT QSPSSLSASV GDRVTITCRA SQSIRYYLSW YQQKPGKAPK  180
LLIYTASILQ NGVPSRFSGS GSGTDFTLTI SSLQPEDFAT YYCLQTYTTP DFGPGTKVEI  240
K                                                                  241

SEQ ID NO: 44           moltype = AA  length = 253
FEATURE                 Location/Qualifiers
REGION                  1..253
                        note = source = /note="Description of Artificial Sequence:
                         Syntheticpolypeptide"
```

```
source                  1..253
                        mol_type = protein
                        organism = synthetic construct
SEQUENCE: 44
QVQLVQSGAE VKKPGASVKV SCKASGYTFT SYYMHWVRQA PGQGLEWMGI INPSGGSTSY  60
AQKFQGRVTM TRDTSTSTVY MELSSLRSED TAVYYCARYR LIAVAGDYYY YGMDVWGQGT  120
MVTVSSGGGG SGGGGSGGGG SGGGGSDIQM TQSPSSVSAS VGDRVTITCR ASQGVGRWLA  180
WYQQKPGTAP KLLIYAASTL QSGVPSRFSG SGSGTDFTLT INNLQPEDFA TYYCQQANSF  240
PLTFGGGTRL EIK                                                      253

SEQ ID NO: 45           moltype = AA  length = 250
FEATURE                 Location/Qualifiers
REGION                  1..250
                        note = source = /note="Description of Artificial Sequence:
                         Syntheticpolypeptide"
source                  1..250
                        mol_type = protein
                        organism = synthetic construct
SEQUENCE: 45
QVQLVQSGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARWK VSSSSPAFDY WGQGTLVTVS  120
SGGGGSGGGG SGGGGSGGGG SEIVLTQSPA TLSLSPGERA ILSCRASQSV YTKYLGWYQQ  180
KPGQAPRLLI YDASTRATGI PDRFSGSGSG TDFTLTINRL EPEDFAVYYC QHYGGSPLIT  240
FGQGTRLEIK                                                          250

SEQ ID NO: 46           moltype = AA  length = 246
FEATURE                 Location/Qualifiers
REGION                  1..246
                        note = source = /note="Description of Artificial Sequence:
                         Syntheticpolypeptide"
source                  1..246
                        mol_type = protein
                        organism = synthetic construct
SEQUENCE: 46
QVQLQQSGAE VKKPGASVKV SCKTSGYPFT GYSLHWVRQA PGQGLEWMGW INPNSGGTNY  60
AQKFQGRVTM TRDTSISTAY MELSRLRSDD TAVYYCARDH YGGNSLFYWG QGTLVTVSSG  120
GGGSGGGGSG GGGSGGGGSD IQLTQSPSSI SASVGDTVSI TCRASQDSGT WLAWYQQKPG  180
KAPNLLMYDA STLEDGVPSR FSGSASGTEF TLTVNRLQPE DSATYYCQQY NSYPLTFGGG  240
TKVDIK                                                              246

SEQ ID NO: 47           moltype = AA  length = 248
FEATURE                 Location/Qualifiers
REGION                  1..248
                        note = source = /note="Description of Artificial Sequence:
                         Syntheticpolypeptide"
source                  1..248
                        mol_type = protein
                        organism = synthetic construct
SEQUENCE: 47
QVQLVQSGAE VKKPGASVEV SCKASGYTFT SYYMHWVRQA PGQGLEWMGI INPSGGSTGY  60
AQKFQGRVTM TRDTSTSTVH MELSSLRSED TAVYYCARGG YSSSSDAFDI WGQGTMVTVS  120
SGGGGSGGGG SGGGGSGGGG SDIQMTQSPP SLSASVGDRV TITCRASQDI SSALAWYQQK  180
PGTPPKLLIY DASSLESGVP SRFSGSGSGT DFTLTISSLQ PEDFATYYCQ QFSSYPLTFG  240
GGTRLEIK                                                            248

SEQ ID NO: 48           moltype = AA  length = 255
FEATURE                 Location/Qualifiers
REGION                  1..255
                        note = source = /note="Description of Artificial Sequence:
                         Syntheticpolypeptide"
source                  1..255
                        mol_type = protein
                        organism = synthetic construct
SEQUENCE: 48
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARVA GGIYYYYGMD VWGQGTTITV  120
SSGGGGSGGG GSGGGGSGGG GSDIVMTQTP DSLAVSLGER ATISCKSSHS VLYNRNNKNY  180
LAWYQQKPGQ PPKLLFYWAS TRKSGVPDRF SGSGSGTDFT LTISSLQPED FATYFCQQTQ  240
TFPLTFGQGT RLEIN                                                    255

SEQ ID NO: 49           moltype = AA  length = 241
FEATURE                 Location/Qualifiers
REGION                  1..241
                        note = source = /note="Description of Artificial Sequence:
                         Syntheticpolypeptide"
source                  1..241
                        mol_type = protein
                        organism = synthetic construct
SEQUENCE: 49
```

-continued

```
QVQLQQSGAE VKKPGASVKV SCKASGYTFT GYYMHWVRQA PGQGLEWMGW INPNSGGTNY  60
AQNFQGRVTM TRDTSISTAY MELRRLRSDD TAVYYCASGW DFDYWGQGTL VTVSSGGGGS  120
GGGGSGGGGS GGGGSDIRMT QSPSSLSASV GDRVTITCRA SQSIRYYLSW YQQKPGKAPK  180
LLIYTASILQ NGVPSRFSGS GSGTDFTLTI SSLQPEDFAT YYCLQTYTTP DFGPGTKVEI  240
K                                                                  241

SEQ ID NO: 50          moltype = AA  length = 246
FEATURE                Location/Qualifiers
REGION                 1..246
                       note = source = /note="Description of Artificial Sequence:
                        Syntheticpolypeptide"
source                 1..246
                       mol_type = protein
                       organism = synthetic construct
SEQUENCE: 50
QVQLVQSGAE VKKPGASVKV SCKASGYTFT GYYMHWVRQA PGQGLEWMGR INPNSGGTNY  60
AQKFQGRVTM TTDTSTSTAY MELRSLRSDD TAVYYCARTT TSYAFDIWGQ GTMVTVSSGG  120
GGSGGGGSGG GGSGGGGSDI QLTQSPSTLS ASVGDRVTIT CRASQSISTW LAWYQQKPGK  180
APNLLIYKAS TLESGVPSRF SGSGSGTEFT LTISSLQPDD FATYYCQQYN TYSPYTFGQG  240
TKLEIK                                                             246

SEQ ID NO: 51          moltype = AA  length = 249
FEATURE                Location/Qualifiers
REGION                 1..249
                       note = source = /note="Description of Artificial Sequence:
                        Syntheticpolypeptide"
source                 1..249
                       mol_type = protein
                       organism = synthetic construct
SEQUENCE: 51
QVQLVQSGGG LVKPGGSLRL SCEASGFIFS DYYMGWIRQA PGKGLEWVSY IGRSGSSMYY  60
ADSVKGRFTF SRDNAKNSLY LQMNSLRAED TAVYYCAASP VVAATEDFQH WGQGTLVTVS  120
SGGGGSGGGG SGGGGSGGGG SDIVMTQTPA TLSLSPGERA TLSCRASQSV TSNYLAWYQQ  180
KPGQAPRLLL FGASTRATGI PDRFSGSGSG TDFTLTINRL EPEDFAMYYC QQYGSAPVTF  240
GQGTKLEIK                                                          249

SEQ ID NO: 52          moltype = AA  length = 249
FEATURE                Location/Qualifiers
REGION                 1..249
                       note = source = /note="Description of Artificial Sequence:
                        Syntheticpolypeptide"
source                 1..249
                       mol_type = protein
                       organism = synthetic construct
SEQUENCE: 52
QVQLVQSGAE VRAPGASVKI SCKASGFTFR GYYIHWVRQA PGQGLEWMGI INPSGGSRAY  60
AQKFQGRVTM TRDTSTSTVY MELSSLRSDD TAMYYCARTA SCGGDCYYLD YWGQGTLVTV  120
SSGGGGSGGG GSGGGGSGGG GSDIQMTQSP PTLSASVGDR VTITCRASEN VNIWLAWYQQ  180
KPGKAPKLLI YKSSSLASGV PSRFSGSGSG AEFTLTISSL QPDDFATYYC QQYQSYPLTF  240
GGGTKVDIK                                                          249

SEQ ID NO: 53          moltype = AA  length = 244
FEATURE                Location/Qualifiers
REGION                 1..244
                       note = source = /note="Description of Artificial Sequence:
                        Syntheticpolypeptide"
source                 1..244
                       mol_type = protein
                       organism = synthetic construct
SEQUENCE: 53
QVQLVQSGGG LVQPGRSLRL SCAASGFTFD DYAMHWVRQA PGKGLEWVSG ISWNSGSIGY  60
ADSVKGRFTI SRDNAKNSLY LQMNSLRAED TAVYYCAKDG SSSWSWGYFD YWGQGTLVTV  120
SSGGGGSGGG GSGGGGSSSE LTQDPAVSVA LGQTVRTTCQ GDALRSYYAS WYQQKPGQAP  180
MLVIYGKNNR PSGIPDRFSG SDSGDTASLT ITGAQAEDEA DYYCNSRDSS GYPVFGTGTK  240
VTVL                                                               244

SEQ ID NO: 54          moltype = AA  length = 246
FEATURE                Location/Qualifiers
REGION                 1..246
                       note = source = /note="Description of Artificial Sequence:
                        Syntheticpolypeptide"
source                 1..246
                       mol_type = protein
                       organism = synthetic construct
SEQUENCE: 54
EVQLVESGGG LVQPGRSLRL SCAASGFTFD DYAMHWVRQA PGKGLEWVSG ISWNSGSTGY  60
ADSVKGRFTI SRDNAKNSLY LQMNSLRAED TALYYCAKDS SSWYGGGSAF DIWGQGTMVT  120
VSSGGGGSGG GGSGGGGSSS ELTQEPAVSV ALGQTVRITC QGDSLRSYYA SWYQQKPGQA  180
PVLVIFGRSR RPSGIPDRFS GSSSGNTASL IITGAQAEDE ADYYCNSRDN TANHYVFGTG  240
```

```
TKLTVL                                                          246

SEQ ID NO: 55           moltype = AA  length = 246
FEATURE                 Location/Qualifiers
REGION                  1..246
                        note = source = /note="Description of Artificial Sequence:
                         Syntheticpolypeptide"
source                  1..246
                        mol_type = protein
                        organism = synthetic construct
SEQUENCE: 55
EVQLVESGGG LVQPGRSLRL SCAASGFTFD DYAMHWVRQA PGKGLEWVSG ISWNSGSTGY  60
ADSVKGRFTI SRDNAKNSLY LQMNSLRAED TALYYCAKDS SSWYGGGSAF DIWGQGTMVT  120
VSSGGGGSGG GGSGGGGSSS ELTQDPAVSV ALGQTVRITC QGDSLRSYYA SWYQQKPGQA  180
PVLVIYGKNN RPSGIPDRFS GSSSGNTASL TITGAQAEDE ADYYCNSRGS SGNHYVFGTG  240
TKVTVL                                                          246

SEQ ID NO: 56           moltype = AA  length = 251
FEATURE                 Location/Qualifiers
REGION                  1..251
                        note = source = /note="Description of Artificial Sequence:
                         Syntheticpolypeptide"
source                  1..251
                        mol_type = protein
                        organism = synthetic construct
SEQUENCE: 56
QVQLVQSGGG LVQPGGSLRL SCAASGFTFS SYWMHWVRQA PGKGLVWVSR INSDGSSTSY  60
ADSVKGRFTI SRDNAKNTLY LQMNSLRAED TAVYYCVRTG WVGSYYYYMD VWGKGTTVTV  120
SSGGGGSGGG GSGGGGSGGG GSEIVLTQSP GTLSLSPGER ATLSCRASQS VSSNYLAWYQ  180
QKPGQPPRLL IYDVSTRATG IPARFSGGGS GTDFTLTISS LEPEDFAVYY CQQRSNWPPW  240
TFGQGTKVEI K                                                     251

SEQ ID NO: 57           moltype = AA  length = 250
FEATURE                 Location/Qualifiers
REGION                  1..250
                        note = source = /note="Description of Artificial Sequence:
                         Syntheticpolypeptide"
source                  1..250
                        mol_type = protein
                        organism = synthetic construct
SEQUENCE: 57
QVQLVQSGGG VVQPGRSLRL SCAASGFTFS SYGMHWVRQA PGKGLEWVAV ISYDGSNKYY  60
ADSVKGRFTI SRDNSKNTLY LQMNSLRAED TAVYYCAKGY SRYYYYGMDV WGQGTTVTVS  120
SGGGGSGGGG SGGGGSGGGG SEIVMTQSPA TLSLSPGERA ILSCRASQSV YTKYLGWYQQ  180
KPGQAPRLLI YDASTRATGI PDRFSGSGSG TDFTLTINRL EPEDFAVYYC QHYGGSPLIT  240
FGQGTKVDIK                                                      250

SEQ ID NO: 58           moltype = AA  length = 249
FEATURE                 Location/Qualifiers
REGION                  1..249
                        note = source = /note="Description of Artificial Sequence:
                         Syntheticpolypeptide"
source                  1..249
                        mol_type = protein
                        organism = synthetic construct
SEQUENCE: 58
QVQLVQSGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKRE AAAGHDWYFD LWGRGTLVTV  120
SSGGGGSGGG GSGGGGSGGG GSDIRVTQSP SSLSASVGDR VTITCRASQS ISSYLNWYQQ  180
KPGKAPKLLI YAASSLQSGV PSRFSGSGSG TDFTLTISSL QPEDFATYYC QQSYSIPLTF  240
GQGTKVEIK                                                       249

SEQ ID NO: 59           moltype = AA  length = 247
FEATURE                 Location/Qualifiers
REGION                  1..247
                        note = source = /note="Description of Artificial Sequence:
                         Syntheticpolypeptide"
source                  1..247
                        mol_type = protein
                        organism = synthetic construct
SEQUENCE: 59
QVQLVQSWAE VKKPGASVKV SCKASGYTFT SYYMHWVRQA PGQGLEWMGI INPSGGSTSY  60
AQKFQGRVTM TRDTSTSTVY MELSNLRSED TAVYYCARSP RVTTGYFDYW GQGTLVTVSS  120
GGGGSGGGGS GGGGSGGGGS DIQLTQSPST LSASVGDRVT ITCRASQSIS SWLAWYQQKP  180
GKAPKLLIYK ASSLESGVPS RFSGSGSGTE FTLTISSLQP DDFATYYCQQ YSSYPLTFGG  240
GTRLEIK                                                         247

SEQ ID NO: 60           moltype = AA  length = 253
FEATURE                 Location/Qualifiers
```

-continued

```
REGION                  1..253
                        note = source = /note="Description of Artificial Sequence:
                         Syntheticpolypeptide"
source                  1..253
                        mol_type = protein
                        organism = synthetic construct
SEQUENCE: 60
QVQLVQSGAE VRRPGASVKI SCRASGDTST RHYIHWLRQA PGQGPEWMGV INPTTGPATG  60
SPAYAQMLQG RVTMTRDTST RTVYMELRSL RFEDTAVYYC ARSVVGRSAP YYFDYWGQGT  120
LVTVSSGGGG SGGGGSGGGG SGGGGSDIQM TQSPSSLSAS VGDRVTITCR ASQGISDYSA  180
WYQQKPGKAP KLLIYAASTL QSGVPSRFSG SGSGTDFTLT ISYLQSEDFA TYYCQQYYSY  240
PLTFGGGTKV DIK                                                    253

SEQ ID NO: 61           moltype = AA  length = 249
FEATURE                 Location/Qualifiers
REGION                  1..249
                        note = source = /note="Description of Artificial Sequence:
                         Syntheticpolypeptide"
source                  1..249
                        mol_type = protein
                        organism = synthetic construct
SEQUENCE: 61
QVQLQQSGAE VKKPGASVKV SCKASGYTFT NYYMHWVRQA PGQGLEWMGI INPSGGYTTY  60
AQKFQGRLTM TRDTSTSTVY MELSSLRSED TAVYYCARIR SCGGDCYYFD NWGQGTLVTV  120
SSGGGGSGGG GSGGGGSGGG GSDIQLTQSP STLSASVGDR VTITCRASEN VNIWLAWYQQ  180
KPGKAPKLLI YKSSSLASGV PSRFSGSGSG AEFTLTISSL QPDDFATYYC QQYQSYPLTF  240
GGGTKVDIK                                                         249

SEQ ID NO: 62           moltype = AA  length = 246
FEATURE                 Location/Qualifiers
REGION                  1..246
                        note = source = /note="Description of Artificial Sequence:
                         Syntheticpolypeptide"
source                  1..246
                        mol_type = protein
                        organism = synthetic construct
SEQUENCE: 62
QITLKESGPA LVKPTQTLTL TCTFSGFSLS TAGVHVGWIR QPPGKALEWL ALISWADDKR  60
YRPSLRSRLD ITRVTSKDQV VLSMTNMQPE DTATYYCALQ GFDGYEANWG PGTLVTVSSG  120
GGGSGGGGSG GGGSGGGGSD IVMTQSPSSL SASAGDRVTI TCRASRGISS ALAWYQQKPG  180
KPPKLLIYDA SSLESGVPSR FSGSGSGTDF TLTIDSLEPE DFATYYCQQS YSTPWTFGQG  240
TKVDIK                                                            246

SEQ ID NO: 63           moltype = AA  length = 488
FEATURE                 Location/Qualifiers
REGION                  1..488
                        note = source = /note="Description of Artificial Sequence:
                         Syntheticpolypeptide"
source                  1..488
                        mol_type = protein
                        organism = synthetic construct
SEQUENCE: 63
MALPVTALLL PLALLLHAAR PQVQLQQSGA EVKKPGASVK VSCKASGYTF TGYYMHWVRQ  60
APGQGLEWMG RINPNSGGTN YAQKFQGRVT MTRDTSISTA YMELSRLRSE DTAVYYCARG  120
RYYGMDVWGQ GTMVTVSSGG GGSGGGGSGG GGSGGGGSEI VLTQSPATLS LSPGERATIS  180
CRASQSVSSN FAWYQQRPGQ APRLLIYDAS NRATGIPPRF SGSGSGTDFT LTISSLEPED  240
FAAYYCHQRS NWLYTFGQGT KVDIKTTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYK QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                          488

SEQ ID NO: 64           moltype = AA  length = 497
FEATURE                 Location/Qualifiers
REGION                  1..497
                        note = source = /note="Description of Artificial Sequence:
                         Syntheticpolypeptide"
source                  1..497
                        mol_type = protein
                        organism = synthetic construct
SEQUENCE: 64
MALPVTALLL PLALLLHAAR PQVQLVQSGA EVKKPGASVK VSCKASGYTF TGYYMHWVRQ  60
APGQGLEWMG WINPNSGGTN YAQKFQGRVT MTRDTSISTA YMELSRLRSD DTAVYYCARD  120
LRRTVVTPRA YYGMDVWGQG TTVTVSSGGG GSGGGGSGGG GSGGGGSDIQ LTQSPSTLSA  180
SVGDRVTITC QASQDISNSL NWYQQKAGKA PKLLIYDAST LETGVPSRFS GSGSGTDFSF  240
TISSLQPEDI ATYYCQQHDN LPLTFGQGTK VEIKTTTPAP RPPTPAPTIA SQPLSLRPEA  300
CRPAAGGAVH TRGLDFACDI YIWAPLAGTC GVLLLSLVIT LYCKRGRKKL LYIFKQPFMR  360
PVQTTQEEDG CSCRFPEEEE GGCELRVKFS RSADAPAYKQ GQNQLYNELN LGRREEYDVL  420
DKRRGRDPEM GGKPRRKNPQ EGLYNELQKD KMAEAYSEIG MKGERRRGKG HDGLYQGLST  480
```

```
ATKDTYDALH MQALPPR                                                497

SEQ ID NO: 65          moltype = AA  length = 490
FEATURE                Location/Qualifiers
REGION                 1..490
                       note = source = /note="Description of Artificial Sequence:
                        Syntheticpolypeptide"
source                 1..490
                       mol_type = protein
                       organism = synthetic construct
SEQUENCE: 65
MALPVTALLL PLALLLHAAR PQVQLVQSGA EVKKPGAPVK VSCKASGYTF TGYYMHWVRQ  60
APGQGLEWMG WINPNSGGTN YAQKFQGRVT MTRDTSISTA YMELSRLRSD DTAVYYCARG  120
EWDGSYYYDY WGQGTLVTVS SGGGGSGGGG SGGGGSGGGG SDIVLTQTPS SLSASVGDRV  180
TITCRASQSI NTYLNWYQHK PGKAPKLLIY AASSLQSGVP SRFSGSGSGT DFTLTISSLQ  240
PEDFATYYCQ QSFSPLTFGG GTKLEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490

SEQ ID NO: 66          moltype = AA  length = 486
FEATURE                Location/Qualifiers
REGION                 1..486
                       note = source = /note="Description of Artificial Sequence:
                        Syntheticpolypeptide"
source                 1..486
                       mol_type = protein
                       organism = synthetic construct
SEQUENCE: 66
MALPVTALLL PLALLLHAAR PQVQLVESGG GLVQPGGSLR LSCAASGFTF SSYWMHWVRQ  60
VPGKGLVWVS RINTDGSTTT YADSVEGRFT ISRDNAKNTL YLQMNSLRDD DTAVYYCVGG  120
HWAVWGQGTT VTVSSGGGGS GGGGSGGGGS GGGGSDIQMT QSPSTLSASV GDRVTITCRA  180
SQSISDRLAW YQQKPGKAPK LLIYKASSLE SGVPSRFSGS GSGTEFTLTI SSLQPDDFAV  240
YYCQQYGHLP MYTFGQGTKV EIKTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 67          moltype = AA  length = 485
FEATURE                Location/Qualifiers
REGION                 1..485
                       note = source = /note="Description of Artificial Sequence:
                        Syntheticpolypeptide"
source                 1..485
                       mol_type = protein
                       organism = synthetic construct
SEQUENCE: 67
MALPVTALLL PLALLLHAAR PQVQLVQSGA EVEKPGASVK VSCKASGYTF TDYYMHWVRQ  60
APGQGLEWMG WINPNSGGTN YAQKFQGRVT MTRDTSISTA YMELSRLRSD DTAVYYCASG  120
WDFDYWGQGT LVTVSSGGGG SGGGGSGGGG SGGGGSDIVM TQSPSSLSAS VGDRVTITCR  180
ASQSIRYYLS WYQQKPGKAP KLLIYTASIL QNGVPSRFSG SGSGTDFTLT ISSLQPEDFA  240
TYYCLQTYTT PDFGPGTKVE IKTTTPAPRP PTPAPTIASQ PLSLRPEACR PAAGGAVHTR  300
GLDFACDIYI WAPLAGTCGV LLLSLVITLY CKRGRKKLLY IFKQPFMRPV QTTQEEDGCS  360
CRFPEEEEGG CELRVKFSRS ADAPAYKQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                             485

SEQ ID NO: 68          moltype = AA  length = 497
FEATURE                Location/Qualifiers
REGION                 1..497
                       note = source = /note="Description of Artificial Sequence:
                        Syntheticpolypeptide"
source                 1..497
                       mol_type = protein
                       organism = synthetic construct
SEQUENCE: 68
MALPVTALLL PLALLLHAAR PQVQLVQSGA EVKKPGASVK VSCKASGYTF TSYYMHWVRQ  60
APGQGLEWMG IINPSGGSTS YAQKFQGRVT MTRDTSTSTV YMELSSLRSE DTAVYYCARY  120
RLIAVAGDYY YYGMDVWGQG TMVTVSSGGG GSGGGGSGGG GSGGGGSDIQ MTQSPSSVSA  180
SVGDRVTITC RASQGVGRWL AWYQQKPGTA PKLLIYAAST LQSGVPSRFS GSGSGTDFTL  240
TINNLQPEDF ATYYCQQANS FPLTFGGGTR LEIKTTTPAP RPPTPAPTIA SQPLSLRPEA  300
CRPAAGGAVH TRGLDFACDI YIWAPLAGTC GVLLLSLVIT LYCKRGRKKL LYIFKQPFMR  360
PVQTTQEEDG CSCRFPEEEE GGCELRVKFS RSADAPAYKQ GQNQLYNELN LGRREEYDVL  420
DKRRGRDPEM GGKPRRKNPQ EGLYNELQKD KMAEAYSEIG MKGERRRGKG HDGLYQGLST  480
ATKDTYDALH MQALPPR                                                497

SEQ ID NO: 69          moltype = AA  length = 494
```

-continued

```
FEATURE               Location/Qualifiers
REGION                1..494
                      note = source = /note="Description of Artificial Sequence:
                       Syntheticpolypeptide"
source                1..494
                      mol_type = protein
                      organism = synthetic construct
SEQUENCE: 69
MALPVTALLL PLALLLHAAR PQVQLVQSGG GVVQPGRSLR LSCAASGFTF SSYAMHWVRQ  60
APGKGLEWVA VISYDGSNKY YADSVKGRFT ISRDNSKNTL YLQMNSLRAE DTAVYYCARW  120
KVSSSSPAFD YWGQGTLVTV SSGGGGSGGG GSGGGGSGGG GSEIVLTQSP ATLSLSPGER  180
AILSCRASQS VYTKYLGWYQ QKPGQAPRLL IYDASTRATG IPDRFSGSGS GTDFTLTINR  240
LEPEDFAVYY CQHYGGSPLI TFGQGTRLEI KTTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYKQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                  494

SEQ ID NO: 70         moltype = AA  length = 490
FEATURE               Location/Qualifiers
REGION                1..490
                      note = source = /note="Description of Artificial Sequence:
                       Syntheticpolypeptide"
source                1..490
                      mol_type = protein
                      organism = synthetic construct
SEQUENCE: 70
MALPVTALLL PLALLLHAAR PQVQLQQSGA EVKKPGASVK VSCKTSGYPF TGYSLHWVRQ  60
APGQGLEWMG WINPNSGGTN YAQKFQGRVT MTRDTSISTA YMELSRLRSD DTAVYYCARD  120
HYGGNSLFYW GQGTLVTVSS GGGGSGGGGS GGGGSGGGGS DIQLTQSPSS ISASVGDTVS  180
ITCRASQDSG TWLAWYQQKP GKAPNLLMYD ASTLEDGVPS RFSGSASGTE FTLTVNRLQP  240
EDSATYYCQQ YNSYPLTFGG GTKVDIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                       490

SEQ ID NO: 71         moltype = AA  length = 492
FEATURE               Location/Qualifiers
REGION                1..492
                      note = source = /note="Description of Artificial Sequence:
                       Syntheticpolypeptide"
source                1..492
                      mol_type = protein
                      organism = synthetic construct
SEQUENCE: 71
MALPVTALLL PLALLLHAAR PQVQLVQSGA EVKKPGASVE VSCKASGYTF TSYYMHWVRQ  60
APGQGLEWMG IINPSGGSTG YAQKFQGRVT MTRDTSTSTV HMELSSLRSE DTAVYYCARG  120
GYSSSSDAFD IWGQGTMVTV SSGGGGSGGG GSGGGGSGGG GSDIQMTQSP PSLSASVGDR  180
VTITCRASQD ISSALAWYQQ KPGTPPKLLI YDASSLESGV PSRFSGSGSG TDFTLTISSL  240
QPEDFATYYC QQFSSYPLTF GGGTRLEIKT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYKQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                    492

SEQ ID NO: 72         moltype = AA  length = 499
FEATURE               Location/Qualifiers
REGION                1..499
                      note = source = /note="Description of Artificial Sequence:
                       Syntheticpolypeptide"
source                1..499
                      mol_type = protein
                      organism = synthetic construct
SEQUENCE: 72
MALPVTALLL PLALLLHAAR PQVQLVQSGA EVKKPGASVK VSCKASGYTF TSYGISWVRQ  60
APGQGLEWMG WISAYNGNTN YAQKLQGRVT MTTDTSTSTA YMELRSLRSD DTAVYYCARV  120
AGGIYYYYGM DVWGQGTTIT VSSGGGGSGG GGSGGGGSGG GGSDIVMTQT PDSLAVSLGE  180
RATISCKSSH SVLYNRNNKN YLAWYQQKPG QPPKLLFYWA STRKSGVPDR FSGSGSGTDF  240
TLTISSLQPE DFATYFCQQT QTFPLTFGQG TRLEINTTTP APRPPTPAPT IASQPLSLRP  300
EACRPAAGGA VHTRGLDFAC DIYIWAPLAG TCGVLLLSLV ITLYCKRGRK KLLYIFKQPF  360
MRPVQTTQEE DGCSCRFPEE EEGGCELRVK FSRSADAPAY KQGQNQLYNE LNLGRREEYD  420
VLDKRRGRDP EMGGKPRRKN PQEGLYNELQ KDKMAEAYSE IGMKGERRRG KGHDGLYQGL  480
STATKDTYDA LHMQALPPR                                             499

SEQ ID NO: 73         moltype = AA  length = 485
FEATURE               Location/Qualifiers
REGION                1..485
                      note = source = /note="Description of Artificial Sequence:
```

```
                          Syntheticpolypeptide"
source                    1..485
                          mol_type = protein
                          organism = synthetic construct
SEQUENCE: 73
MALPVTALLL PLALLLHAAR PQVQLQQSGA EVKKPGASVK VSCKASGYTF TGYYMHWVRQ  60
APGQGLEWMG WINPNSGGTN YAQNFQGRVT MTRDTSISTA YMELRRLRSD DTAVYYCASG  120
WDFDYWGQGT LVTVSSGGGG SGGGGSGGGG SGGGGSDIRM TQSPSSLSAS VGDRVTITCR  180
ASQSIRYYLS WYQQKPGKAP KLLIYTASIL QNGVPSRFSG SGSGTDFTLT ISSLQPEDFA  240
TYYCLQTYTT PDFGPGTKVE IKTTTPAPRP PTPAPTIASQ PLSLRPEACR PAAGGAVHTR  300
GLDFACDIYI WAPLAGTCGV LLLSLVITLY CKRGRKKLLY IFKQPFMRPV QTTQEEDGCS  360
CRFPEEEEGG CELRVKFSRS ADAPAYKQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                             485

SEQ ID NO: 74             moltype = AA  length = 490
FEATURE                   Location/Qualifiers
REGION                    1..490
                          note = source = /note="Description of Artificial Sequence:
                          Syntheticpolypeptide"
source                    1..490
                          mol_type = protein
                          organism = synthetic construct
SEQUENCE: 74
MALPVTALLL PLALLLHAAR PQVQLVQSGA EVKKPGASVK VSCKASGYTF TGYYMHWVRQ  60
APGQGLEWMG RINPNSGGTN YAQKFQGRVT MTTDTSTSTA YMELRSLRSD DTAVYYCART  120
TTSYAFDIWG QGTMVTVSSG GGGSGGGGSG GGGSGGGGSD IQLTQSPSTL SASVGDRVTI  180
TCRASQSIST WLAWYQQKPG KAPNLLIYKA STLESGVPSR FSGSGSGTEF TLTISSLQPD  240
DFATYYCQQY NTYSPYTFGQ GTKLEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490

SEQ ID NO: 75             moltype = AA  length = 493
FEATURE                   Location/Qualifiers
REGION                    1..493
                          note = source = /note="Description of Artificial Sequence:
                          Syntheticpolypeptide"
source                    1..493
                          mol_type = protein
                          organism = synthetic construct
SEQUENCE: 75
MALPVTALLL PLALLLHAAR PQVQLVQSGG GLVKPGGSLR LSCEASGFIF SDYYMGWIRQ  60
APGKGLEWVS YIGRSGSSMY YADSVKGRFT FSRDNAKNSL YLQMNSLRAE DTAVYYCAAS  120
PVVAATEDFQ HWGQGTLVTV SSGGGGSGGG GSGGGGSGGG GSDIVMTQTP ATLSLSPGER  180
ATLSCRASQS VTSNYLAWYQ QKPGQAPRLL LFGASTRATG IPDRFSGSGS GTDFTLTINR  240
LEPEDFAMYY CQQYGSAPVT FGQGTKLEIK TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 76             moltype = AA  length = 493
FEATURE                   Location/Qualifiers
REGION                    1..493
                          note = source = /note="Description of Artificial Sequence:
                          Syntheticpolypeptide"
source                    1..493
                          mol_type = protein
                          organism = synthetic construct
SEQUENCE: 76
MALPVTALLL PLALLLHAAR PQVQLVQSGA EVRAPGASVK ISCKASGFTF RGYYIHWVRQ  60
APGQGLEWMG IINPSGGSRA YAQKFQGRVT MTRDTSTSTV YMELSSLRSD DTAMYYCART  120
ASCGGDCYYL DYWGQGTLVT VSSGGGGSGG GGSGGGGSGG GGSDIQMTQS PPTLSASVGD  180
RVTITCRASE NVNIWLAWYQ QKPGKAPKLL IYKSSSLASG VPSRFSGSGS GAEFTLTISS  240
LQPDDFATYY CQQYQSYPLT FGGGTKVDIK TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 77             moltype = AA  length = 488
FEATURE                   Location/Qualifiers
REGION                    1..488
                          note = source = /note="Description of Artificial Sequence:
                          Syntheticpolypeptide"
source                    1..488
                          mol_type = protein
```

```
                          organism = synthetic construct
SEQUENCE: 77
MALPVTALLL PLALLLHAAR PQVQLVQSGG GLVQPGRSLR LSCAASGFTF DDYAMHWVRQ  60
APGKGLEWVS GISWNSGSIG YADSVKGRFT ISRDNAKNSL YLQMNSLRAE DTAVYYCAKD  120
GSSSWSWGYF DYWGQGTLVT VSSGGGGSGG GGSGGGGSSS ELTQDPAVSV ALGQTVRTTC  180
QGDALRSYYA SWYQQKPGQA PMLVIYGKNN RPSGIPDRFS GSDSGDTASL TITGAQAEDE  240
ADYYCNSRDS SGYPVFGTGT KVTVLTTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYK QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                           488

SEQ ID NO: 78             moltype = AA  length = 490
FEATURE                   Location/Qualifiers
REGION                    1..490
                          note = source = /note="Description of Artificial Sequence:
                           Syntheticpolypeptide"
source                    1..490
                          mol_type = protein
                          organism = synthetic construct
SEQUENCE: 78
MALPVTALLL PLALLLHAAR PEVQLVESGG GLVQPGRSLR LSCAASGFTF DDYAMHWVRQ  60
APGKGLEWVS GISWNSGSTG YADSVKGRFT ISRDNAKNSL YLQMNSLRAE DTALYYCAKD  120
SSSWYGGGSA FDIWGQGTMV TVSSGGGGSG GGGSGGGGSS SELTQEPAVS VALGQTVRIT  180
CQGDSLRSYY ASWYQQKPGQ APVLVIFGRS RRPSGIPDRF SGSSSGNTAS LIITGAQAED  240
EADYYCNSRD NTANHYVFGT GTKLTVLTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 79             moltype = AA  length = 490
FEATURE                   Location/Qualifiers
REGION                    1..490
                          note = source = /note="Description of Artificial Sequence:
                           Syntheticpolypeptide"
source                    1..490
                          mol_type = protein
                          organism = synthetic construct
SEQUENCE: 79
MALPVTALLL PLALLLHAAR PEVQLVESGG GLVQPGRSLR LSCAASGFTF DDYAMHWVRQ  60
APGKGLEWVS GISWNSGSTG YADSVKGRFT ISRDNAKNSL YLQMNSLRAE DTALYYCAKD  120
SSSWYGGGSA FDIWGQGTMV TVSSGGGGSG GGGSGGGGSS SELTQDPAVS VALGQTVRIT  180
CQGDSLRSYY ASWYQQKPGQ APVLVIYGKN NRPSGIPDRF SGSSSGNTAS LTITGAQAED  240
EADYYCNSRG SSGNHYVFGT GTKVTVLTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 80             moltype = AA  length = 495
FEATURE                   Location/Qualifiers
REGION                    1..495
                          note = source = /note="Description of Artificial Sequence:
                           Syntheticpolypeptide"
source                    1..495
                          mol_type = protein
                          organism = synthetic construct
SEQUENCE: 80
MALPVTALLL PLALLLHAAR PQVQLVQSGG GLVQPGGSLR LSCAASGFTF SSYWMHWVRQ  60
APGKGLVWVS RINSDGSSTS YADSVKGRFT ISRDNAKNTL YLQMNSLRAE DTAVYYCVRT  120
GWVGSYYYYM DVWGKGTTVT VSSGGGGSGG GGSGGGGSGG GGSEIVLTQS PGTLSLSPGE  180
RATLSCRASQ SVSSNYLAWY QQKPGQPPRL LIYDVSTRAT GIPARFSGGG SGTDFTLTIS  240
SLEPEDFAVY YCQQRSNWPP WTFGQGTKVE IKTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYKQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 81             moltype = AA  length = 494
FEATURE                   Location/Qualifiers
REGION                    1..494
                          note = source = /note="Description of Artificial Sequence:
                           Syntheticpolypeptide"
source                    1..494
                          mol_type = protein
                          organism = synthetic construct
SEQUENCE: 81
MALPVTALLL PLALLLHAAR PQVQLVQSGG GVVQPGRSLR LSCAASGFTF SSYGMHWVRQ  60
```

```
APGKGLEWVA VISYDGSNKY YADSVKGRFT ISRDNSKNTL YLQMNSLRAE DTAVYYCAKG  120
YSRYYYYGMD VWGQGTTVTV SSGGGGSGGG GSGGGGSGGG GSEIVMTQSP ATLSLSPGER  180
AILSCRASQS VYTKYLGWYQ QKPGQAPRLL IYDASTRATG IPDRFSGSGS GTDFTLTINR  240
LEPEDFAVYY CQHYGGSPLI TFGQGTKVDI KTTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYKQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                   494

SEQ ID NO: 82          moltype = AA  length = 493
FEATURE                Location/Qualifiers
REGION                 1..493
                       note = source = /note="Description of Artificial Sequence:
                        Syntheticpolypeptide"
source                 1..493
                       mol_type = protein
                       organism = synthetic construct
SEQUENCE: 82
MALPVTALLL PLALLLHAAR PQVQLVQSGG GLVQPGGSLR LSCAASGFTF SSYAMSWVRQ  60
APGKGLEWVS AISGSGGSTY YADSVKGRFT ISRDNSKNTL YLQMNSLRAE DTAVYYCAKR  120
EAAAGHDWYF DLWGRGTLVT VSSGGGGSGG GGSGGGGSGG GGSDIRVTQS PSSLSASVGD  180
RVTITCRASQ SISSYLNWYQ QKPGKAPKLL IYAASSLQSG VPSRFSGSGS GTDFTLTISS  240
LQPEDFATYY CQQSYSIPLT FGQGTKVEIK TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 83          moltype = AA  length = 491
FEATURE                Location/Qualifiers
REGION                 1..491
                       note = source = /note="Description of Artificial Sequence:
                        Syntheticpolypeptide"
source                 1..491
                       mol_type = protein
                       organism = synthetic construct
SEQUENCE: 83
MALPVTALLL PLALLLHAAR PQVQLVQSWA EVKKPGASVK VSCKASGYTF TSYYMHWVRQ  60
APGQGLEWMG IINPSGGSTS YAQKFQGRVT MTRDTSTSTV YMELSNLRSE DTAVYYCARS  120
PRVTTGYFDY WGQGTLVTVS SGGGGSGGGG SGGGGSGGGG SDIQLTQSPS TLSASVGDRV  180
TITCRASQSI SSWLAWYQQK PGKAPKLLIY KASSLESGVP SRFSGSGSGT EFTLTISSLQ  240
PDDFATYYCQ QYSSYPLTFG GGTRLEIKTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYKQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 84          moltype = AA  length = 497
FEATURE                Location/Qualifiers
REGION                 1..497
                       note = source = /note="Description of Artificial Sequence:
                        Syntheticpolypeptide"
source                 1..497
                       mol_type = protein
                       organism = synthetic construct
SEQUENCE: 84
MALPVTALLL PLALLLHAAR PQVQLVQSGA EVRRPGASVK ISCRASGDTS TRHYIHWLRQ  60
APGQGPEWMG VINPTTGPAT GSPAYAQMLQ GRVTMTRDTS TRTVYMELRS LRFEDTAVYY  120
CARSVVGRSA PYYFDYWGQG TLVTVSSGGG GSGGGGSGGG GSGGGGSDIQ MTQSPSSLSA  180
SVGDRVTITC RASQGISDYS AWYQQKPGKA PKLLIYAAST LQSGVPSRFS GSGSGTDFTL  240
TISYLQSEDF ATYYCQQYYS YPLTFGGGTK VDIKTTTPAP RPPTPAPTIA SQPLSLRPEA  300
CRPAAGGAVH TRGLDFACDI YIWAPLAGTC GVLLLSLVIT LYCKRGRKKL LYIFKQPFMR  360
PVQTTQEEDG CSCRFPEEEE GGCELRVKFS RSADAPAYKQ GQNQLYNELN LGRREEYDVL  420
DKRRGRDPEM GGKPRRKNPQ EGLYNELQKD KMAEAYSEIG MKGERRRGKG HDGLYQGLST  480
ATKDTYDALH MQALPPR                                                497

SEQ ID NO: 85          moltype = AA  length = 493
FEATURE                Location/Qualifiers
REGION                 1..493
                       note = source = /note="Description of Artificial Sequence:
                        Syntheticpolypeptide"
source                 1..493
                       mol_type = protein
                       organism = synthetic construct
SEQUENCE: 85
MALPVTALLL PLALLLHAAR PQVQLQQSGA EVKKPGASVK VSCKASGYTF TNYYMHWVRQ  60
APGQGLEWMG IINPSGGYTT YAQKFQGRLT MTRDTSTSTV YMELSSLRSE DTAVYYCARI  120
RSCGGDCYYF DNWGQGTLVT VSSGGGGSGG GGSGGGGSGG GGSDIQLTQS PSTLSASVGD  180
RVTITCRASE NVNIWLAWYQ QKPGKAPKLL IYKSSSLASG VPSRFSGSGS GAEFTLTISS  240
```

```
LQPDDFATYY CQQYQSYPLT FGGGTKVDIK TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 86          moltype = AA  length = 490
FEATURE                Location/Qualifiers
REGION                 1..490
                       note = source = /note="Description of Artificial Sequence:
                        Syntheticpolypeptide"
source                 1..490
                       mol_type = protein
                       organism = synthetic construct
SEQUENCE: 86
MALPVTALLL PLALLLHAAR PQITLKESGP ALVKPTQTLT LTCTFSGFSL STAGVHVGWI  60
RQPPGKALEW LALISWADDK RYRPSLRSRL DITRVTSKDQ VVLSMTNMQP EDTATYYCAL  120
QGFDGYEANW GPGTLVTVSS GGGGSGGGGS GGGGSGGGGS DIVMTQSPSS LSASAGDRVT  180
ITCRASRGIS SALAWYQQKP GKPPKLLIYD ASSLESGVPS RFSGSGSGTD FTLTIDSLEP  240
EDFATYYCQQ SYSTPWTFGQ GTKVDIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YKQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490

SEQ ID NO: 87          moltype = DNA  length = 732
FEATURE                Location/Qualifiers
misc_feature           1..732
                       note = source = /note="Description of Artificial Sequence:
                        Syntheticpolynucleotide"
source                 1..732
                       mol_type = other DNA
                       organism = synthetic construct
SEQUENCE: 87
caagtccaac tgcagcagtc aggagcggaa gtgaagaaac caggagcgtc agtcaaagtg  60
tcgtgcaagg ctagcggcta caccttcacc ggctactaca tgcactgggt tcgacaggct  120
ccagggcagg gtctggagtg gatgggccgc atcaacccga attccggtgg gactaactac  180
gcccagaagt tccagggaag agtgaccatg actagggaca cgtcgatcag cactgcgtac  240
atggaactga gccgcctgcg gtccgaggat actgccgtct actactgcgc acgcggaagg  300
tactatggaa tggacgtgtg gggccaaggg actatggtga ctgtgagctc gggaggggga  360
ggctccggtg gcgggggatc aggaggagga ggatcagggg gaggaggttc cgaaattgtc  420
ctcacccaga gcccggcaac cctctcactt tccccgggag agcgcgcaac catctcttgc  480
cgggctagcc aatccgtgtc gtccaatttc gcctggtacc agcaacggcc gggacaagcc  540
cctagactcc tgatctacga cgccagcaac agagcgactg gaattcctcc acgcttttcg  600
ggatcaggct ccggtaccga cttcaccctg actatctcgt cgctcgaacc cgaggatttc  660
gccgcctact actgtcatca gcggtcgaac tggttgtata cgtttggcca gggcaccaag  720
gtggatatca ag                                                     732

SEQ ID NO: 88          moltype = DNA  length = 759
FEATURE                Location/Qualifiers
misc_feature           1..759
                       note = source = /note="Description of Artificial Sequence:
                        Syntheticpolynucleotide"
source                 1..759
                       mol_type = other DNA
                       organism = synthetic construct
SEQUENCE: 88
caagtccaac tcgtccagtc aggagcagaa gtcaagaaac caggtgctag cgtgaaagtg  60
tcgtgcaagg cgtcgggata cactttcacc ggatactaca tgcactgggt ccgccaggcc  120
cccggacaag gactggaatg gatgggctgg atcaacccga atagcggggg aactaattac  180
gcccagaagt ttcagggacg agtgaccatg acccgcgata cctctatctc gaccgcctac  240
atggagctct ccagactgcg ctccgacgat actgcagtgt actactgcgc ccgggacctg  300
aggcggactg tggttactcc tcgcgcctat tatggcatgg acgtgtgggg ccaaggaact  360
actgtgactg tgagctcggg aggcggtggg tcaggcggag gagggtcggg cggtggtggc  420
tcgggagggg gaggaagcga cattcaactt acgcagagcc cgtcaaccct gtcagcgtca  480
gtgggagatc gggtgaccat cacgtgtcag gccagccagg atatctccaa ctcgctcaac  540
tggtaccagc aaaaggcggg taaagctccg aagctgctga tctacgacgc ttccaccctc  600
gagactggag tcccatccag atttccgggg tcaggaagcg gcaccgattt ctccttcacc  660
atttcgtcct tgcaaccgga ggacatcgca acctactact gccagcagca tgacaacttg  720
cctctgacgt tcgggcaggg caccaaggtg gaaatcaag                        759

SEQ ID NO: 89          moltype = DNA  length = 738
FEATURE                Location/Qualifiers
misc_feature           1..738
                       note = source = /note="Description of Artificial Sequence:
                        Syntheticpolynucleotide"
source                 1..738
                       mol_type = other DNA
                       organism = synthetic construct
```

SEQUENCE: 89
caagtccaac tcgtccaatc aggagcggaa gtcaaaaagc ccggagctcc agtgaaagtg 60
tcatgcaagg cctccggcta caccttcacc ggttactata tgcactgggt gcggcaggcc 120
ccgggccagg ggttggaatg gatgggatgg atcaatccaa actcgggtgg gactaactac 180
gcccagaagt tccaaggacg ggtgaccatg actagggaca cctcgatctc caccgcatac 240
atggagctta gcagactccg ctccgacgat accgcagtct actattgcgc gcggggagag 300
tgggacggat cgtactacta cgattactgg ggccagggaa ctctggtgac tgtttcctcg 360
ggtggaggag gttcaggcgg aggcggctcg ggcgggggag gatctggagg aggagggtcc 420
gacattgtgc tgacccaaac tccttcgtcc ctgtcggcca gcgtgggcga ccgcgtgacg 480
attacgtgca gagctagcca atccatcaat acttacctca actggtacca gcataagccg 540
gggaaagcac caaagctgct gatctacgcc gcctcatcct tgcagagcgg tgtgccttca 600
cgctttagcg gatcgggatc gggaacggat ttcaccctga ctatcagctc cctccagccg 660
gaggattttg cgacctacta ctgtcagcag agcttctcac cgctgacttt cggcggcggg 720
accaagctgg aaatcaag 738

SEQ ID NO: 90 moltype = DNA length = 726
FEATURE Location/Qualifiers
misc_feature 1..726
note = source = /note="Description of Artificial Sequence: Syntheticpolynucleotide"
source 1..726
mol_type = other DNA
organism = synthetic construct
SEQUENCE: 90
caagtgcaac tcgttgaatc aggtggaggt ttggtgcaac ccggaggatc tctcagactg 60
tcgtgtgcgg cgtccgggtt caccttttcg tcctactgga tgcactgggt gcgccaggtg 120
ccgggaaaag gactggtgtg ggtgtccaga atcaacaccg acgggtcaac gactacctac 180
gcagatagcg tggaaggtcg gttcaccatt tcgcgggaca acgctaaaaa cactctgtac 240
cttcagatga attcactgcg cgatgacgac accgcagtct actactgcgt cggtggacac 300
tgggcggtct ggggacaggg aactacggtg actgtgtcca gcggcggggg aggaagcggc 360
ggagggggga gcggaggcgg aggatcagga ggaggcggct ccgatatcca gatgacccag 420
tcgccatcga ccctctccgc tagcgtgggg gatagggtca ctatcacttg ccgagccagc 480
caatccatta gcgaccggct tgcctggtac caacagaaac ctggaaaggc cccgaagctg 540
ctcatctaca aggcctcgtc actggagtcg ggagtcccgt cccgcttttc cggctcgggc 600
tcaggcaccg agttcactct gaccatctcg agcctgcagc cggacgattt cgccgtgtat 660
tactgccagc aatacggaca tctcccaatg tacacgttcg gtcagggcac caaggtcgaa 720
atcaag 726

SEQ ID NO: 91 moltype = DNA length = 723
FEATURE Location/Qualifiers
misc_feature 1..723
note = source = /note="Description of Artificial Sequence: Syntheticpolynucleotide"
source 1..723
mol_type = other DNA
organism = synthetic construct
SEQUENCE: 91
caagtccaac tcgttcaatc aggcgcagaa gtcgaaaagc ccggagcatc agtcaaagtc 60
tcttgcaagg cttccggcta caccttcacg gactactaca tgcactgggt gcgccaggct 120
ccaggccagg gactggagtg gatgggatgg atcaacccga attccggggg aactaactac 180
gcccagaagt ttcagggccg ggtgactatg actcgcgata cctcgatctc gactgcgtac 240
atggagctca gccgcctccg gtcggacgat accgccgtgt actattgtgc gtcgggatgg 300
gacttcgact actgggggca gggcactctg gtcactgtgt caagcggagg aggtggatca 360
ggtggaggtg gaagcggggg aggaggttcc ggcggcggag gatcagatat cgtgatgacg 420
caatcgcctt cctcgttgtc cgcatccgtg ggagacaggg tgaccattac ttgcagagcg 480
tcccagtcca ttcggtacta cctgtcgtgg taccagcaga agccggggaa agccccaaaa 540
ctgcttatct atactgcctc gatcctccaa aacggcgtgc catcaagatt cagcggttcg 600
ggcagcggga ccgactttac cctgactatc agcagcctgc agccggaaga tttcgccacg 660
tactactgcc tgcaaaccta caccaccccg gacttcggac ctggaaccaa ggtggagatc 720
aag 723

SEQ ID NO: 92 moltype = DNA length = 759
FEATURE Location/Qualifiers
misc_feature 1..759
note = source = /note="Description of Artificial Sequence: Syntheticpolynucleotide"
source 1..759
mol_type = other DNA
organism = synthetic construct
SEQUENCE: 92
caagtgcaac tcgtccagtc aggtgcagaa gtgaagaaac ccggagcgtc agtcaaagtg 60
tcatgcaagg cgtcaggcta caccttcacc agctactaca tgcactgggt gcggcaggcc 120
ccaggccaag gcttggagtg gatgggaatc attaacccgt caggaggctc cacctcctac 180
gcccagaagt ttcagggaag agtgacgatg actcgggata cgtcgacctc gaccgtgtac 240
atggaactga gctcgctgcg ctccgaggac actgctgtgt actactgcgc acggtacaga 300
ctcattgccg tggcaggaga ctactactac tatggcatgg acgtctgggg gcagggcact 360
atggtcactg tgtcgtccgg cggaggaggc tcgggtggag gaggtagcgg aggaggggga 420
agcggagggg ggggctccga tatccagatg actcagtcgc cttcctccgt gtcggcctcg 480
gttggagatc gcgtcaccat cacttgtcga gcttcccaag gagtcggtag gtggctggcg 540

-continued

```
tggtaccagc aaaagccggg aactgccccg aagctcctga tctacgcggc tagcaccctg  600
cagtcgggag tgccatcccg cttcagcgga tctgggtcag gtaccgactt cacccttacg  660
atcaacaatc tccagccgga ggactttgcc acctattact gccaacaggc caacagcttc  720
cctctgactt tcggaggggg cactcgcctg gaaatcaag                         759

SEQ ID NO: 93          moltype = DNA  length = 750
FEATURE                Location/Qualifiers
misc_feature           1..750
                       note = source = /note="Description of Artificial Sequence:
                        Syntheticpolynucleotide"
source                 1..750
                       mol_type = other DNA
                       organism = synthetic construct
SEQUENCE: 93
caagtgcaat tggttcaatc aggaggagga gtggtgcaac ctggaagatc tctcagactg  60
tcgtgtgcgg catcgggatt cactttctca tcatacgcaa tgcactgggt ccgccaggcc  120
ccgggcaaag gcttggaatg ggtggcggtc atttcatacg acggctcgaa caagtactac  180
gctgacagcg tgaagggacg ctttactatt tcccgggaca attcgaagaa cactctgtac  240
ctccagatga actcccttag ggctgaggac accgccgtct actactgcgc acgctggaaa  300
gtgtcgtcca gctccccagc ttttgactac tggggacagg gaacccttgt gaccgtgtcg  360
tccggtggag gggaagcgg cggaggggga tcaggtggcg gcggatcggg aggcgggga  420
tcagaaatcg tgctgactca gtccccggcc acgctgtctc tcagcccggg agagagagcg  480
atcctgtcct gccgcgcctc gcagagcgtg tacactaagt acctggggtg gtaccagcag  540
aaaccgggtc aagcgcctcg gctgctgatc tacgatgcct ccacccgggc caccggaatc  600
cccgatcggt tctccggcag cggctcggga actgatttca cgctgaccat caatcgcctg  660
gagccggaag atttcgccgt ctattactgc cagcattacg gcgggagccc actcatcacc  720
ttcggtcaag gaacccgact cgaaatcaag                                   750

SEQ ID NO: 94          moltype = DNA  length = 738
FEATURE                Location/Qualifiers
misc_feature           1..738
                       note = source = /note="Description of Artificial Sequence:
                        Syntheticpolynucleotide"
source                 1..738
                       mol_type = other DNA
                       organism = synthetic construct
SEQUENCE: 94
caagtccaac tccagcagtc aggtgcagaa gtcaaaaagc caggagcatc cgtgaaggtt  60
tcgtgcaaga cttccggcta cccttttacc gggtactccc tccattgggt gagacaagca  120
ccgggccagg gactggagtg gatgggatgg atcaacccaa attcgggcgg caccaactat  180
gcgcagaagt tccagggacg ggtgaccatg actcgcgaca cttcgatctc cactgcctac  240
atggagctgt cccgcttgag atctgacgac acggccgtct actactgcgc ccgggatcac  300
tacggaggta attcgctgtt ctactggggg cagggaaccc ttgtgactgt gtcctcgggt  360
ggtggagggt caggaggcgg aggctcaggg ggaggaggta gcggaggagg cggatcagac  420
atccaactga cccagtcacc atcctccatc tcggctagcg tcggagacac cgtgtcgatt  480
acttgtaggg cctcccaaga ctcagggacg tggctggcgt ggtatcagca aaaaccgggc  540
aaagctccga acctgttgat gtacgacgcc agcaccctcg aagatggagt gcctagccgc  600
ttcagcggaa gcgcctcggg cactgaattc acgctgactg tgaatcggct ccagccggag  660
gattcggcga cctactactg ccagcagtac aacagctacc ccctgacctt tggaggcggg  720
accaaggtgg atatcaag                                                738

SEQ ID NO: 95          moltype = DNA  length = 744
FEATURE                Location/Qualifiers
misc_feature           1..744
                       note = source = /note="Description of Artificial Sequence:
                        Syntheticpolynucleotide"
source                 1..744
                       mol_type = other DNA
                       organism = synthetic construct
SEQUENCE: 95
caagtgcaac tcgtccagtc aggtgcagaa gtgaagaaac caggagcgtc cgtcgaagtg  60
tcgtgtaagg cgtccggcta cactttcacc tcgtactaca tgcactgggt gcggcaggcc  120
ccgggacaag gcctcgaatg gatgggaatc atcaacccga gcggaggctc gactggttac  180
gcccagaagt tccagggaag ggtgacgatg acccgcgata cctcgacttc gaccgttcat  240
atggagctct cgtccctgcg gagcgaggac actgctgtct actattgcgc gcggggagga  300
tactctagct cctccgatgc atttgacatt tggggccagg gaactatggt gaccgtgtca  360
tcaggcggag gtggatcagg aggaggaggg tcgggagggg gaggcagcgg cgggggtggg  420
tcggacattc agatgacgca gtcccctcct agcctgagcg cctcggtggg tgacagagtg  480
accatcactt gcagagcctc gcaagacatc tcctccgcat tggcttggta ccagcaaaag  540
ccgggcactc cgccgaaact gctcatctac gatgcctcct cactggagtc aggagtccca  600
tctcgcttct cggggtcagg aagcggcacc gattttaccc ttaccatctc cagcctgcag  660
cccgaggact tcgccacgta ctactgccaa cagttcagct cctacccact gaccttcggg  720
ggcggaactc gcctggaaat caag                                         744

SEQ ID NO: 96          moltype = DNA  length = 765
FEATURE                Location/Qualifiers
misc_feature           1..765
                       note = source = /note="Description of Artificial Sequence:
                        Syntheticpolynucleotide"
```

```
source                 1..765
                       mol_type = other DNA
                       organism = synthetic construct
SEQUENCE: 96
caagtgcaac tcgtccagag cggagcagaa gtcaagaagc caggagcgtc agtgaaagtg  60
tcatgcaagg ccagcggcta tacctttact tcgtatggga tctcctgggt gcggcaggca  120
ccgggccaag gactggagtg gatgggatgg atctcagcct acaacggtaa caccaactac  180
gcccagaagc tgcaaggacg cgtgaccatg actactgata cgagcacctc cactgcctac  240
atggaattgc ggtcccttcg gtcggacgat actgctgtgt actactgcgc aagagtcgcc  300
ggagggatct actactacta cggcatggac gtctggggac agggaaccac cattacggtg  360
tcgagcggag ggggaggctc gggggggagga ggaagcggag gtggcggctc cgggggcggc  420
ggatcggaca ttgtgatgac ccagactcct gactccctgg ctgtttcgtt gggagagcgc  480
gcgactatct cgtgtaagtc cagccactca gtcctgtaca atcgcaataa caagaactac  540
ctcgcgtggt accagcaaaa accgggtcag ccgcctaaac tcctgttcta ctgggcctcc  600
accagaaaga gcggggtgcc agatcgattc tctggatcag gatcaggtac cgactttacg  660
ctgaccatct cgtccctgca gccggaggat ttcgcgactt acttctgcca gcagactcag  720
actttccccc tcaccttcgg tcaaggcacc aggctggaaa tcaat                  765

SEQ ID NO: 97          moltype = DNA  length = 723
FEATURE                Location/Qualifiers
misc_feature           1..723
                       note = source = /note="Description of Artificial Sequence:
                        Syntheticpolynucleotide"
source                 1..723
                       mol_type = other DNA
                       organism = synthetic construct
SEQUENCE: 97
caagtccaat tgcagcagag cggagcagaa gtgaagaagc caggagcgtc agtcaaagtg  60
tcgtgtaagg cgtcaggata caccttcacg ggatactaca tgcactgggt gcgccaggcc  120
ccgggccaag gactcgagtg gatgggctgg atcaacccta actctggagg caccaactac  180
gcccagaatt tccaaggcag agtgaccatg acccgggaca cctccatctc gactgcctat  240
atggaactgc ggcggctgcg ctcggacgat actgctgtgt attactgcgc cagcggctgg  300
gactttgact actggggaca gggtactctg gtgactgttt cctcgggagg aggcggatcg  360
ggtggaggag gtagcggggg aggggggtcg ggaggcggag gcagcgatat tcgcatgact  420
caatcgccgt cctccctgag cgctagcgtg ggagatcgag tcaccatcac ttgcagagcg  480
tcacagtcga ttcgctacta cctgtcctgg taccagcaga aaccgggaaa ggcaccaaag  540
cttctgatct acacggcctc catcctgcaa aatggtgtcc catcaaggtt ctccgggtca  600
gggagcggca ctgacttcac tctcaccatc tcctcactcc agcccgagga ctttgcaacc  660
tactactgcc tccagacgta caccaccccg gatttcggtc ctggaaccaa ggtggaaatc  720
aaa                                                                723

SEQ ID NO: 98          moltype = DNA  length = 738
FEATURE                Location/Qualifiers
misc_feature           1..738
                       note = source = /note="Description of Artificial Sequence:
                        Syntheticpolynucleotide"
source                 1..738
                       mol_type = other DNA
                       organism = synthetic construct
SEQUENCE: 98
caagtccaac tcgtccaaag cggagcagaa gtcaaaaagc caggagcgtc ggtgaaagtg  60
tcttgcaaag ccagcggcta caccttcacg ggttactaca tgcactgggt gcgccaggcg  120
ccgggccagg ggctggagtg gatgggccgg attaacccta acagcggggg aactaattac  180
gctcagaagt tccagggtag agtcaccatg actacggaca cttccacttc caccgcctat  240
atggaactgc gctccctccg ctcagatgat actgccgtgt attactgcgc gcggactacc  300
acgtcatacg catttgacat ctggggccag ggaactatgg tgaccgtgag ctcgggcgga  360
ggcggttcag gggaggaggg aagcggagga ggaggatcgg gaggaggtgg ctccgatatc  420
cagctgactc agtccccgag caccctgtcg gcgtcggtgg gggacagggt taccatcacc  480
tgtagagctt cccaatccat ttcgacttgg ctggcctggt accagcaaaa gccgggaaag  540
gcccctaatt tgcttatcta caaggcatcg accctcgaaa gcggtgtgcc ctcccggttt  600
tcgggatcag gatcagggac cgagttcacc ctgaccatct catccctcca gccggacgac  660
ttcgccactt actactgcca gcagtacaac acctactcgc catacacttt cggccaaggc  720
accaagctgg agatcaag                                                738

SEQ ID NO: 99          moltype = DNA  length = 747
FEATURE                Location/Qualifiers
misc_feature           1..747
                       note = source = /note="Description of Artificial Sequence:
                        Syntheticpolynucleotide"
source                 1..747
                       mol_type = other DNA
                       organism = synthetic construct
SEQUENCE: 99
caagttcaac tcgtgcaatc aggtggagga ctcgtcaaac ccggaggatc attgagactg  60
tcatgcgaag cgagcggttt tatcttctcc gattactata tgggatggat tcggcaggcc  120
ccgggaaagg gactcgaatg ggtgtcatac atcggaaggt caggctcgtc catgtactac  180
gcagactcgg tgaaaggcag attcaccttt agccgggaca acgccaagaa ttccctctac  240
ttgcagatga acagcctgcg agccgaggat actgctgtct actactgtgc cgcgtcgccg  300
gtggtggcag ctactgaaga tttccagcac tggggacagg gaactctggt cacggtgtcg  360
```

```
agcggtgggg gcggaagcgg aggcggagga tcgggcggcg gaggttcggg ggggggaggg  420
tctgacatcg tgatgaccca aaccccagcc accctgagcc tctcccctgg agagcgcgcg  480
actctttcgt gccgcgcttc ccagtcagtg accagcaatt acttggcttg gtaccaacag  540
aagccgggac aggcgccacg gctgctgctt tttggtgcca gcactcgcgc caccggaatc  600
ccggatcgct tctcgggctc agggtccggg acggacttca ccctgactat caaccggctg  660
gaacctgagg acttcgcgat gtactactgc cagcagtacg gctccgcacc agtcactttc  720
ggacaaggca ccaagctgga gatcaag                                      747

SEQ ID NO: 100         moltype = DNA  length = 747
FEATURE                Location/Qualifiers
misc_feature           1..747
                       note = source = /note="Description of Artificial Sequence:
                        Syntheticpolynucleotide"
source                 1..747
                       mol_type = other DNA
                       organism = synthetic construct
SEQUENCE: 100
caagtccaac tcgtccagtc gggagcagaa gttagagcac caggagcgtc agtgaaaatc  60
tcatgcaagg cctcgggctt cacgttccgc ggatactaca tccactgggt gcgccaagcc  120
ccgggtcagg gattggagtg gatgggaatc attaacccat caggagggag ccgggcttac  180
gcgcagaagt tccagggacg cgtcactatg acccgagata cttccacctc gactgtgtac  240
atggaactct cgtccctgag gtccgacgac actgcgatgt attactgtgc tcggactgcc  300
agctgcggtg ggactgttta ctacctcgat tactggggcc agggaactct ggtgaccgtg  360
tccagcggag gtggcgggtc aggggggtggc ggaagcggag gcggcggttc aggcggagga  420
ggctcggaca tccaaatgac gcaatcgccg cctaccctga gcgcttccgt gggagatcgg  480
gtgaccatta cttgcagagc atccgagaac gtcaatatct ggctggcctg gtaccaacag  540
aagccgggga aggcccctaa actgctgatc tacaagtcga gcagccttgc ctctggagtg  600
ccctcccgct tctcgggctc gggatcagga gcggaattca ccctcaccat ctcctccctg  660
cagccagatg actttgccac ctactactgc cagcagtacc agagctatcc gttgaccttt  720
gggggaggca ctaaagtgga catcaag                                      747

SEQ ID NO: 101         moltype = DNA  length = 732
FEATURE                Location/Qualifiers
misc_feature           1..732
                       note = source = /note="Description of Artificial Sequence:
                        Syntheticpolynucleotide"
source                 1..732
                       mol_type = other DNA
                       organism = synthetic construct
SEQUENCE: 101
caagttcaac tcgttcaatc aggtggagga ctcgtgcaac caggaagatc actcagactc  60
agctgcgccg cgtcgggatt cactttcgat gactacgcaa tgcactgggt gcggcaggcc  120
ccgggcaaag gactggaatg ggtgagcgga attagctgga actcggggtc catcgggtac  180
gccgactcgg tgaagggacg ctttacgatc tcccgggaca atgccaagaa ctccctgtat  240
ttgcagatga actccttgag ggctgaggac accgccgtgt actactgcgc taaagatgga  300
tcatcgtcct ggtcctgggg atacttcgat tactggggcc agggcactct ggtgaccgtg  360
tcgtcaggcg gtggagggtc gggcggagga ggtagcggag gcggagggag cagctctgaa  420
ctgacccaag acccggcggt gtcggtcgcc cttggtcaga ctgtgcggac tacctgtcag  480
gggacgcgc tgcgctcgta ctacgcttca tggtaccagc agaagcccgg acaggcacct  540
atgctggtca tctacggaaa gaataaccgc ccatccggca tcccggatcg cttctcgggt  600
tcggacagcg gcgacaccgc atccctgacg atcactggag cgcaggccga ggatgaagcc  660
gactactact gcaattcccg agattcaagc ggctaccctg tgtttgggac cggaactaag  720
gtcaccgtcc tg                                                      732

SEQ ID NO: 102         moltype = DNA  length = 738
FEATURE                Location/Qualifiers
misc_feature           1..738
                       note = source = /note="Description of Artificial Sequence:
                        Syntheticpolynucleotide"
source                 1..738
                       mol_type = other DNA
                       organism = synthetic construct
SEQUENCE: 102
gaagtgcaac tcgtggaatc tggtggagga cttgtgcaac ctggaagatc gttgagactc  60
tcatgtgctg cctccgggtt cacctttgac gactacgcca tgcactgggt gcgccaggca  120
ccaggaaagg gtctggagtg ggtttcgggt atctcgtgga actccgggag cactggctac  180
gctgattcgg tgaaaggccg gtttaccatc tcccgagaca atgcgaagaa ttccctctat  240
ctgcagatga acagcctccg ggccgaggat actgccctgt actactgcgc caaggatagc  300
tcatcatggt acgggaggtgg atcggctttc gatatctggg gccagggcac gatggtcacc  360
gtgtcctcgg ggggcggagg ctccgggggga ggaggtagcg gaggaggagg atcgagctca  420
gagttgactc aagaacccgc agtgtccgtg gcactgggcc aaaccgtcag gatcacttgc  480
cagggagaca gcctgaggtc gtactacgcg tcctggtacc agcagaagcc gggacaggcc  540
ccggtcctgg tcattttcgg acgctcaaga cgcccatcgg gcatcccgga ccggttcagc  600
ggaagctcct cgggaaacac cgcgtcactt atcattaccg gcgcacaggc tgaggacgaa  660
gcggattact actgcaactc ccgcgacaat actgccaacc attacgtgtt cgggaccgga  720
acgaaactga ctgtcctg                                                738

SEQ ID NO: 103         moltype = DNA  length = 738
FEATURE                Location/Qualifiers
```

```
misc_feature            1..738
                        note = source = /note="Description of Artificial Sequence:
                         Syntheticpolynucleotide"
source                  1..738
                        mol_type = other DNA
                        organism = synthetic construct
SEQUENCE: 103
gaagttcaat tggtggaatc tggaggagga cttgtgcaac ccggtagatc tctgagactg  60
tcctgtgcgg catcgggatt caccttcgac gactacgcta tgcactgggt gagacaagcc  120
cctggaaaag gactggagtg ggtgtcaggc atctcctgga atagcgggtc cactggatac  180
gccgattcgg tcaagggtcg cttcaccatt tcccgggaca atgccaagaa ctccctgtac  240
cttcaaatga actccctccg ggccgaggat accgccctct actactgcgc caaagacagc  300
tcgtcatggt atggcggagg gtcggcattt gacatctggg gacagggaac tatggtgact  360
gtgtcatcag gaggcggcgg aagcggcggc ggcgggtccg gcggaggagg gtcgtccagc  420
gaactcaccc aagatccagc agtgagcgtc gcgctgggcc agaccgtcag gatcacgtgc  480
cagggagatt cactgcgctc atactacgcg tcctggtacc agcagaagcc ggggcaggcc  540
ccggtcctcg tgatctacgg aaagaacaac cgcccgtcgg gtatcccaga ccgcttttcg  600
ggtagctcca gcggaaatac ggctagcctg accatcactg gagcacaggc tgaggatgaa  660
gcggactact actgcaattc gcggggctca tcggggaacc attacgtgtt cggaactggt  720
accaaggtga ctgtcctg                                                738

SEQ ID NO: 104          moltype = DNA  length = 753
FEATURE                 Location/Qualifiers
misc_feature            1..753
                        note = source = /note="Description of Artificial Sequence:
                         Syntheticpolynucleotide"
source                  1..753
                        mol_type = other DNA
                        organism = synthetic construct
SEQUENCE: 104
caagtgcagc tcgttcaatc aggcggagga ctcgttcaac caggaggatc attgcgactc  60
tcatgtgcgg cctctggatt cacgtttagc tcatattgga tgcactgggt gcggcaggcg  120
ccggggaaag gtctggtgtg ggtcagccgc atcaactcag acggctcctc gacttcgtac  180
gccgactccg tgaagggacg ctttaccatt tcccgcgaca acgccaagaa taccctttac  240
cttcagatga actccctccg cgctgaggat accgccgtgt actactgcgt gaggactggc  300
tgggtcggca gctactacta ctacatggac gtgtggggca aaggaactac tgtcaccgtg  360
tcaagcggcg gtggaggttc cggcgggggga ggatcggggg ggggcggatc gggtggcgga  420
ggatcggaga tcgtgttgac ccagtcgccg ggaaccctgt cgctgtcgcc tggggagaga  480
gcaactctgt cctgccgggc ttcccagtcg gtgtcgagca attacctggc atggtaccaa  540
cagaagccgg gacagccgcc acgcctgctg atctatgacg tgtcaactcg ggcaactgga  600
atccctgcgc ggttcagcgg cggagggagc ggtaccgatt tcaccctgac tatttcctcc  660
ctcgaaccag aagatttcgc cgtctactac tgccagcaga gaagcaactg gccgccctgg  720
acgttcggac aaggaaccaa ggtcgaaatc aag                               753

SEQ ID NO: 105          moltype = DNA  length = 750
FEATURE                 Location/Qualifiers
misc_feature            1..750
                        note = source = /note="Description of Artificial Sequence:
                         Syntheticpolynucleotide"
source                  1..750
                        mol_type = other DNA
                        organism = synthetic construct
SEQUENCE: 105
caagtgcaat tggttcaatc aggaggagga gtcgtgcagc ccggaagatc gttgagactg  60
tcatgtgccg cgagcggctt tactttctca agctacggaa tgcattgggt gcgacaggct  120
ccgggaaaag gactggaatg ggtcgcagtg atctcatacg acggctcgaa caagtactac  180
gccgactccg tcaagggtcg gttcacgatt tcgcgcgata attccaagaa cactctgtac  240
ctccaaatga acagcctccg ggcagaggac accgccgtct actactgcgc taagggatac  300
tcgcgctact actactatgg aatggatgtg tggggccagg gaactaccgt gacggtgtcg  360
tccggcggcg gtgggtcggg cggaggcgga tcaggtggag gtggaagcgg aggaggaggg  420
agcgaaatcg tcatgactca gtcccctgct accctttctc tgtcgccggg agaaagagcc  480
atcctgagct gccgggcctc ccagagcgtg tacaccaaat acctgggatg gtaccagcag  540
aagccggggc aggcaccaag gctcctgatc tacgatgcgt ccacccgcgc gactggtatc  600
ccagaccgct tttccggctc ggggtcaggg actgacttca cccttactat caatcggctc  660
gagcctgagg atttcgccgt gtattactgc cagcactacg gagggtcccc gctgattacc  720
ttcggccaag gcaccaaagt ggacatcaag                                   750

SEQ ID NO: 106          moltype = DNA  length = 747
FEATURE                 Location/Qualifiers
misc_feature            1..747
                        note = source = /note="Description of Artificial Sequence:
                         Syntheticpolynucleotide"
source                  1..747
                        mol_type = other DNA
                        organism = synthetic construct
SEQUENCE: 106
caagtgcaac ttgttcaatc aggaggagga ctcgttcaac ccggaggatc actgcgactc  60
tcatgtgcag cgtcggggtt caccttctcc agctacgcaa tgtcctgggt gcgccaagcc  120
cctggaaaag gcctggagtg ggtgtcggcc atctctggga gcgggggatc aacttactac  180
```

```
gctgactccg tcaagggccg ctttaccatc tcccgggaca acagcaagaa cactctctat  240
ctccagatga actcgctgag agccgaagat accgctgtct actactgcgc gaagagagaa  300
gctgccgcag ggcacgattg gtacttcgac ttgtggggca ggggcaccct tgtgaccgtg  360
tcctccggtg gaggcggatc aggaggtggg ggatcgggtg gaggaggaag cggaggcggc  420
ggttcggaca ttcgcgtcac ccagtcaccg agctccctca gcgcatcggt gggcgaccgg  480
gtcactatca cttgccgggc gtcccagtcg atctcatcgt atctgaattg gtaccagcag  540
aaaccgggaa aggcgccgaa gctgttgatc tacgctgcca gctccctgca gtcgggtgtg  600
ccatcacgct tttccggctc gggatcggga accgatttca ctctgacgat ctctagcctg  660
cagccagaag atttcgccac ttactactgc cagcagtcct acagcatccc tctgactttc  720
ggacaaggga cgaaagtgga gattaag                                     747

SEQ ID NO: 107         moltype = DNA  length = 741
FEATURE                Location/Qualifiers
misc_feature           1..741
                       note = source = /note="Description of Artificial Sequence:
                        Syntheticpolynucleotide"
source                 1..741
                       mol_type = other DNA
                       organism = synthetic construct
SEQUENCE: 107
caagtccaac tcgttcagtc atgggcagaa gtcaagaaac ccggtgcaag cgtcaaagtg  60
tcgtgtaagg cctccggcta cactttcact tcctactaca tgcactgggt gcgccaagcc  120
ccgggacagg gccttgaatg gatgggcatc atcaacccat caggaggttc cacgagctac  180
gcgcagaagt tccaggggag agtgacgatg actagagata cctccacgag caccgtctac  240
atggagctgt cgaatctgcg gtcagaggac actgctgtgt attactgcgc gcgctccccg  300
cgggtgacca ctggctactt tgactactgg ggacaaggga ccctggtgac cgtcagctcg  360
ggaggcggag gatcgggagg tggagggtcc ggtggaggcg gctctggagg aggcgggtcg  420
gacattcaat tgacccagag cccatccacc ctctcagcct cggtggggga tagggtgact  480
atcacttgcc gggcctccca gtcaatttcc agctggctgg cttggtacca gcaaaagcct  540
ggaaaggcac cgaagctcct gatctacaag gcctcatctc tggaatcagg agtgccttcg  600
cgcttcagcg gaagcggctc gggaactgag tttaccctga ccatctcgag cctgcagcca  660
gatgacttcg cgacctatta ctgccagcag tactcgtcct acccgttgac tttcggagga  720
ggtacccgcc tcgaaatcaa a                                           741

SEQ ID NO: 108         moltype = DNA  length = 759
FEATURE                Location/Qualifiers
misc_feature           1..759
                       note = source = /note="Description of Artificial Sequence:
                        Syntheticpolynucleotide"
source                 1..759
                       mol_type = other DNA
                       organism = synthetic construct
SEQUENCE: 108
caagtccaac tcgtccagtc cggtgcagaa gtcagaaggc caggagcaag cgtgaagatc  60
tcgtgtagag cgtcaggaga caccagcact cgccattaca tccactggct gcgccaggct  120
ccgggccaag ggccggagtg gatgggtgtg atcaacccga ctacgggacc ggctaccgga  180
agccctgcgt acgcacagat gctgcaggga cgggtgacta tgacccgcga tactagcact  240
aggaccgtgt acatggaact ccgctcgttg cggttcgaag ataccgccgt ctactactgc  300
gcccggtccg tggtgggccg aagcgcccct tactacttcg attactgggg acagggcact  360
ctggtgaccg ttagctccgg tgggggaggc tcgggtggag gcggatcggg aggaggaggc  420
agcggtggag gggatcgga cattcagatg acccagtcac cctcctccct ctcagcctcg  480
gtcggggacc gggtgaccat tacgtgcaga gcctcacaag ggatctcgga ctactccgcc  540
tggtaccagc agaaaccggg aaaagcgcca aagctcctga tctacgccgc gagcaccctg  600
caatcaggag tgccatcgcg cttttctgga tcgggctcag ggactgactt cacgctgact  660
atctcctacc ttcagtccga ggatttcgct acctactact gccaacagta ttactcctat  720
cccctgacct ttggcggagg cactaaggtg gacatcaag                        759

SEQ ID NO: 109         moltype = DNA  length = 747
FEATURE                Location/Qualifiers
misc_feature           1..747
                       note = source = /note="Description of Artificial Sequence:
                        Syntheticpolynucleotide"
source                 1..747
                       mol_type = other DNA
                       organism = synthetic construct
SEQUENCE: 109
caagtccaac tccagcaatc gggagcagaa gtcaagaaac caggcgcatc ggtgaaagtg  60
tcgtgtaagg cgtcagggta caccttcacc aactactata tgcactgggt gcgccaggct  120
ccaggccagg ggttggagtg gatggggatc atcaatccgt caggtggcta caccacttac  180
gctcagaagt tccagggacg cctcactatg actcgcgata ctagcacctc cacggtgtac  240
atggaactgt catcgctgag gtccgaagat accgccgtct actactgcgc acggatcaga  300
tcctgcggag gagattgtta ctactttgac aactggggac agggcaccct tgttactgtg  360
tcatcgggag gagggggaag cggaggaggt ggatcaggcg gcggtggcag cgggggcgga  420
ggatcggaca ttcagctgac tcagtccccc tccactttgt cggccagcgt gggagacaga  480
gtgaccatca cttgccgggc gtccgagaac gtcaatatct ggctggcctg gtaccagcaa  540
aagcctggaa aagccccgaa gctgctcatc tataagtcat ccagcctggc gtctggtgtg  600
ccgtcgcggt tctccggcag cgggagcgga gccgagttca ctctcaccat ttcgagcctt  660
caaccggacg atttcgccac ctactactgc cagcagtacc aatcctaccc tctgacgttt  720
ggaggtggaa ccaaggtgga catcaag                                     747
```

```
SEQ ID NO: 110          moltype = DNA  length = 738
FEATURE                 Location/Qualifiers
misc_feature            1..738
                        note = source = /note="Description of Artificial Sequence:
                         Syntheticpolynucleotide"
source                  1..738
                        mol_type = other DNA
                        organism = synthetic construct
SEQUENCE: 110
caaatcactc tgaaagaatc tggaccggcc ctggttaagc cgactcaaac gctcaccctt  60
acttgcacct tcagcggatt ctcactcagc actgctggtg tgcacgtcgg atggattaga  120
cagccgcctg gaaaggccct ggaatggctc gccctcatct cctgggccga tgacaagaga  180
tacaggccct cgcttcgatc ccggttggac attacccggg tgacctcgaa agatcaggtg  240
gtgctctcaa tgaccaatat gcagccggag gacaccgcta cgtactactg cgcactgcaa  300
ggatttgacg gctacgaggc taactgggga ccaggtactc tggtcaccgt gagctccggc  360
gggggaggat caggcggggg ggggtcagga ggcggaggct ccggtggagg aggatcggat  420
atcgtcatga cccagtcccc aagctcgctg agcgcgtcag cgggcgaccg cgtgactatc  480
acttgccggg ccagccgcgg catctcctcc gcactggcgt ggtaccagca gaagcctgga  540
aaaccgccaa agctcctgat ctatgatgcc tccagcctgg agtcaggtgt ccccagccgc  600
ttctcgggtt cgggctcggg aaccgacttc actttgacca tcgactcgct ggaaccggaa  660
gatttcgcaa cctactactg tcagcagtcc tactcgaccc cttggacttt tggacaaggg  720
acgaaggtgg acatcaag                                                738

SEQ ID NO: 111          moltype = DNA  length = 1464
FEATURE                 Location/Qualifiers
misc_feature            1..1464
                        note = source = /note="Description of Artificial Sequence:
                         Syntheticpolynucleotide"
source                  1..1464
                        mol_type = other DNA
                        organism = synthetic construct
SEQUENCE: 111
atggccctcc ctgtcaccgc cctgctgctt ccgctggctc ttctgctcca cgccgctcgg  60
ccccaagtcc aactgcagca gtcaggagcg gaagtgaaga aaccaggagc gtcagtcaaa  120
gtgtcgtgca aggctagcgg ctacaccttc accggctact acatgcactg ggttcgacag  180
gctccagggc agggtctgga gtggatgggc cgcatcaacc cgaattccgg tgggactaac  240
tacgcccaga agttccaggg aagagtgacc atgactaggg acacgtcgat cagcactgcg  300
tacatggaac tgagccgcct gcggtccgag gatactgccg tctactactg cgcacgcgga  360
aggtactatg gaatggacgt gtggggccaa gggactatgg tgactgtgag ctcgggaggg  420
ggaggctccg gtggcggggg atcaggagga ggaggatcag gggaggaggg ttccgaaatt  480
gtcctcaccc agagcccggc aaccctctca ctttccccgg gagagcgcgc aaccatctct  540
tgccgggcta gccaatccgt gtcgtccaat ttcgcctggt accagcaacg gccgggacaa  600
gcccctagac tcctgatcta cgacgccagc aacagagcga ctggaattcc tccacgcttt  660
tcgggatcag gctccggtac cgacttcacc ctgactatct cgtcgctcga acccgaggat  720
ttcgccgcct actactgtca tcagcggtcg aactggttgt atacgtttgg ccagggcacc  780
aaggtggata tcaagaccac taccccagca ccgaggccac ccaccccggc tcctaccatc  840
gcctcccagc ctctgtccct gcgtccggag gcatgtagac ccgcagctgg tggggccgtg  900
catacccggg gtcttgactt cgcctgcgat atctacattt gggcccctct ggctggtact  960
tgcggggtcc tgctgctttc actcgtgatc actctttact gtaagcgcgg tcggaagaag  1020
ctgctgtaca tctttaagca acccttcatg aggcctgtgc agactactca agaggaggac  1080
ggctgttcat gccggttccc agaggaggag gaaggcggct gcgaactgcg cgtgaaattc  1140
agccgcagcg cagatgctcc agcctacaag caggggcaga accagctcta caacgaactc  1200
aatcttggtc ggagagagga gtacgacgtg ctggacaagc ggagaggacg ggacccagaa  1260
atgggcggga agccgcgcag aaagaatccc caagagggcc tgtacaacga gctccaaaag  1320
gataagatgg cagaagccta tagcgagatt ggtatgaaag gggaacgcag aagaggcaaa  1380
ggccacgacg gactgtacca gggactcagc accgccacca aggacaccta tgacgctctt  1440
cacatgcagg ccctgccgcc tcgg                                         1464

SEQ ID NO: 112          moltype = DNA  length = 1491
FEATURE                 Location/Qualifiers
misc_feature            1..1491
                        note = source = /note="Description of Artificial Sequence:
                         Syntheticpolynucleotide"
source                  1..1491
                        mol_type = other DNA
                        organism = synthetic construct
SEQUENCE: 112
atggccctcc ctgtcaccgc cctgctgctt ccgctggctc ttctgctcca cgccgctcgg  60
ccccaagtcc aactcgtcca gtcaggagca gaagtcaaga aaccaggtgc tagcgtgaaa  120
gtgtcgtgca aggcgtcggg atacactttc accggatact acatgcactg ggtccgccag  180
gccccccggac aaggactgga atggatgggc tggatcaacc cgaatagcgg gggaactaat  240
tacgcccaga agtttcaggg acgagtgacc atgacccgcg atacctctat ctcgaccgcc  300
tacatggagc tctccagact gcgctccgac gatactgcag tgtactactg cgcccgggac  360
ctgaggcgga ctgtggttac tcctcgcgcc tattatggca tggacgtgtg gggccaagga  420
actactgtga ctgtgagctc gggaggcggt gggtcaggcg gaggagggtc gggcggtggt  480
ggctcgggag ggggaggaag cgacattcaa cttacgcaga gcccgtcaac cctgtcagcg  540
tcagtgggag atcgggtgac catcacgtgt caggccagcc aggatatctc caactcgctc  600
aactggtacc agcaaaaggc gggtaaagct ccgaagctgc tgatctacga cgcttccacc  660
```

```
ctcgagactg gagtcccatc cagattttcc gggtcaggaa gcggcaccga tttctccttc  720
accatttcgt ccttgcaacc ggaggacatc gcaacctact actgccagca gcatgacaac  780
ttgcctctga cgttcgggca gggcaccaag gtggaaatca agaccactac cccagcaccg  840
aggccaccca ccccggctcc taccatcgcc tcccagcctc tgtccctgcg tccggaggca  900
tgtagacccg cagctggtgg ggccgtgcat acccggggtc ttgacttcgc ctgcgatatc  960
tacatttggg cccctctggc tggtacttgc ggggtcctgc tgctttcact cgtgatcact  1020
ctttactgta agcgcggtcg gaagaagctg ctgtacatct ttaagcaacc cttcatgagg  1080
cctgtgcaga ctactcaaga ggaggacggc tgttcatgcc ggttcccaga ggaggaggaa  1140
ggcggctgcg aactgcgcgt gaaattcagc cgcagcgcag atgctccagc ctacaagcag  1200
gggcagaacc agctctacaa cgaactcaat cttggtcgga gagaggagta cgacgtgctg  1260
gacaagcgga gaggacggga cccagaaatg ggcgggaagc cgcgcagaaa gaatccccaa  1320
gagggcctgt acaacgagct ccaaaaggat aagatggcag aagcctatag cgagattggt  1380
atgaaagggg aacgcagaag aggcaaaggc cacgacggac tgtaccaggg actcagcacc  1440
gccaccaagg acacctatga cgctcttcac atgcaggccc tgccgcctcg g           1491
```

```
SEQ ID NO: 113          moltype = DNA  length = 1470
FEATURE                 Location/Qualifiers
misc_feature            1..1470
                        note = source = /note="Description of Artificial Sequence:
                         Syntheticpolynucleotide"
source                  1..1470
                        mol_type = other DNA
                        organism = synthetic construct
SEQUENCE: 113
atggccctcc ctgtcaccgc cctgctgctt ccgctggctc ttctgctcca cgccgctcgg  60
ccccaagtcc aactcgtcca atcaggagcg gaagtcaaaa agcccggagc tccagtgaaa  120
gtgtcatgca aggcctccgg ctacaccttc accggttact atatgcactg ggtgcggcag  180
gccccgggcc aggggttgga atggatggga tggatcaatc caaactcggg tgggactaac  240
tacgcccaga agttccaagg acgggtgacc atgactaggg acacctcgat ctccaccgca  300
tacatggagc ttagcagact ccgctccgac gataccgcag tctactattg cgcgcgggga  360
gagtgggacg gatcgtacta ctacgattac tggggccagg gaactctggt gactgtttcc  420
tcgggtggag gaggttcagg cggaggcggc tcgggcgggg gaggatctgg aggaggaggg  480
tccgacattg tgctgaccca aactccttcg tccctgtcgg ccagcgtggg cgaccgcgtg  540
acgattacgt gcagagctag ccaatccatc aatacttacc tcaactggta ccagcataag  600
ccggggaaag caccaaagct gctgatctac gccgcctcat ccttgcagag cggtgtgcct  660
tcacgcttta gcggatcggg atcgggaacg gatttcaccc tgactatcag ctccctccag  720
ccggaggatt ttgcgaccta ctactgtcag cagagcttct caccgctgac tttcggcggc  780
gggaccaagc tggaaatcaa gaccactacc ccagcaccga ggccacccac cccggctcct  840
accatcgcct cccagcctct gtccctgcgt ccggaggcat gtagacccgc agctggtggg  900
gccgtgcata cccggggtct tgacttcgcc tgcgatatct acatttgggc ccctctggct  960
ggtacttgcg gggtcctgct gctttcactc gtgatcactc tttactgtaa gcgcggtcgg  1020
aagaagctgc tgtacatctt taagcaaccc ttcatgaggc ctgtgcagac tactcaagag  1080
gaggacggct gttcatgccg gttcccagag gaggaggaag gcggctgcga actgcgcgtg  1140
aaattcagcc gcagcgcaga tgctccagcc tacaagcagg ggcagaacca gctctacaac  1200
gaactcaatc ttggtcggag agaggagtac gacgtgctgg acaagcggag aggacgggac  1260
ccagaaatgg gcgggaagcc gcgcagaaag aatccccaag agggcctgta caacgagctc  1320
caaaaggata agatggcaga agcctatagc gagattggta tgaaagggga acgcagaaga  1380
ggcaaaggcc acgacggact gtaccaggga ctcagcaccg ccaccaagga cacctatgac  1440
gctcttcaca tgcaggccct gccgcctcgg                                  1470
```

```
SEQ ID NO: 114          moltype = DNA  length = 1458
FEATURE                 Location/Qualifiers
misc_feature            1..1458
                        note = source = /note="Description of Artificial Sequence:
                         Syntheticpolynucleotide"
source                  1..1458
                        mol_type = other DNA
                        organism = synthetic construct
SEQUENCE: 114
atggccctcc ctgtcaccgc cctgctgctt ccgctggctc ttctgctcca cgccgctcgg  60
ccccaagtgc aactcgttga atcaggtgga ggtttggtgc aacccggagg atctctcaga  120
ctgtcgtgtg cggcgtccgg gttcaccttt tcgtcctact ggatgcactg ggtgcgccag  180
gtgccgggaa aaggactggt gtgggtgtcc agaatcaaca ccgacgggtc aacgactacc  240
tacgcagata gcgtggaagg tcggttcacc atttcgcggg acaacgctaa aaacactctg  300
taccttcaga tgaattcact gcgcgatgac gacaccgcag tctactactg cgtcggtgga  360
cactgggcgg tctggggaca gggaactacg gtgactgtgt ccagcggcgg gggaggaagc  420
ggcggagggg ggagcggagg cggaggatca ggaggaggcg gctccgatat ccagatgacc  480
cagtcgccat cgaccctctc cgctagcgtg gggataggg tcactatcac ttgccgagcc  540
agccaatcca ttagcgaccg gcttgcctgg taccaacaga aacctggaaa ggccccgaag  600
ctgctcatct acaaggcctc gtcactggag tcgggagtcc cgtcccgctt ttccggctcg  660
ggctcaggca ccgagttcac tctgaccatc tcgagcctgc agccggacga tttcgccgtg  720
tattactgcc agcaatacgg acatctccca atgtacacgt tcggtcaggg caccaaggtc  780
gaaatcaaga ccactacccc agcaccgagg ccacccaccc cggctcctac catcgcctcc  840
cagcctctgt ccctgcgtcc ggaggcatgt agacccgcag ctggtggggc cgtgcatacc  900
cggggtcttg acttcgcctg cgatatctac atttgggccc ctctggctgg tacttgcggg  960
gtcctgctgc tttcactcgt gatcactctt tactgtaagc gcggtcggaa gaagctgctg  1020
tacatcttta agcaaccctt catgaggcct gtgcagacta ctcaagagga ggacggctgt  1080
tcatgccggt tcccagagga ggaggaaggc ggctgcgaac tgcgcgtgaa attcagccgc  1140
agcgcagatg ctccagccta caagcagggg cagaaccagc tctacaacga actcaatctt  1200
```

```
ggtcggagag aggagtacga cgtgctggac aagcggagag gacgggaccc agaaatgggc  1260
gggaagccgc gcagaaagaa tccccaagag ggcctgtaca acgagctcca aaaggataag  1320
atggcagaag cctatagcga gattggtatg aaaggggaac gcagaagagg caaaggccac  1380
gacggactgt accagggact cagcaccgcc accaaggaca cctatgacgc tcttcacatg  1440
caggccctgc cgcctcgg                                                1458
```

```
SEQ ID NO: 115         moltype = DNA  length = 1455
FEATURE                Location/Qualifiers
misc_feature           1..1455
                       note = source = /note="Description of Artificial Sequence:
                        Syntheticpolynucleotide"
source                 1..1455
                       mol_type = other DNA
                       organism = synthetic construct
SEQUENCE: 115
atggccctcc ctgtcaccgc cctgctgctt ccgctggctc ttctgctcca cgccgctcgg  60
ccccaagtcc aactcgttca atcaggcgca gaagtcgaaa agcccggagc atcagtcaaa  120
gtctcttgca aggcttccgg ctacaccttc acggactact acatgcactg ggtgcgccag  180
gctccaggcc agggactgga gtggatggga tggatcaacc cgaattccgg gggaactaac  240
tacgcccaga agtttcaggg ccgggtgact atgactcgcg atacctcgat ctcgactgcg  300
tacatggagc tcagccgcct ccggtcggac gataccgccg tgtactattg tgcgtcggga  360
tgggacttcg actactgggg gcagggcact ctggtcactg tgtcaagcgg aggaggtgga  420
tcaggtggag gtggaagcgg gggaggaggt tccggcggcg gaggatcaga tatcgtgatg  480
acgcaatcgc cttcctcgtt gtccgcatcc gtgggagaca gggtgaccat tacttgcaga  540
gcgtcccagt ccattcggta ctacctgtcg tggtaccagc agaagccggg gaaagcccca  600
aaactgctta tctatactgc ctcgatcctc caaaacggcg tgccatcaag attcagcggt  660
tcgggcagcg ggaccgactt taccctgact atcagcagcc tgcagccgga agatttcgcc  720
acgtactact gcctgcaaac ctacaccacc ccggacttcg gacctggaac caaggtggag  780
atcaagacca ctaccccagc accgaggcca cccaccccgg ctcctaccat cgcctcccag  840
cctctgtccc tgcgtccgga ggcatgtaga cccgcagctg gtggggccgt gcatacccgg  900
ggtcttgact tcgcctgcga tatctacatt tgggcccctc tggctggtac ttgcggggtc  960
ctgctgcttt cactcgtgat cactctttac tgtaagcgcg gtcggaagaa gctgctgtac  1020
atctttaagc aacccttcat gaggcctgtg cagactactc aagaggagga cggctgttca  1080
tgccggttcc cagaggagga ggaaggcggc tgcgaactgc gcgtgaaatt cagccgcagc  1140
gcagatgctc cagcctacaa gcaggggcag aaccagctct acaacgaact caatcttggt  1200
cggagagagg agtacgacgt gctggacaag cggagaggac gggacccaga aatgggcggg  1260
aagccgcgca gaaagaatcc ccaagagggc ctgtacaacg agctccaaaa ggataagatg  1320
gcagaagcct atagcgagat tggtatgaaa ggggaacgca gaagaggcaa aggccacgac  1380
ggactgtacc agggactcag caccgccacc aaggacacct atgacgctct tcacatgcag  1440
gccctgccgc ctcgg                                                   1455
```

```
SEQ ID NO: 116         moltype = DNA  length = 1491
FEATURE                Location/Qualifiers
misc_feature           1..1491
                       note = source = /note="Description of Artificial Sequence:
                        Syntheticpolynucleotide"
source                 1..1491
                       mol_type = other DNA
                       organism = synthetic construct
SEQUENCE: 116
atggccctcc ctgtcaccgc cctgctgctt ccgctggctc ttctgctcca cgccgctcgg  60
ccccaagtgc aactcgtcca gtcaggtgca gaagtgaaga aacccggagc gtcagtcaaa  120
gtgtcatgca aggcgtcagg ctacaccttc accagctact acatgcactg ggtgcggcag  180
gcccccaggcc aaggcttgga gtggatggga atcattaacc cgtcaggagg ctccacctcc  240
tacgcccaga agtttcaggg aagagtgacg atgactcggg atacgtcgac ctcgaccgtg  300
tacatggaac tgagctcgct gcgctccgag gacactgctg tgtactactg cgcacggtac  360
agactcattg ccgtggcagg agactactac tactatggca tggacgtctg ggggcagggc  420
actatggtca ctgtgtcgtc cggcggagga ggctcgggtg gaggaggtag cggaggaggg  480
ggaagcggag ggggggctc cgatatccag atgactcagt cgccttcctc cgtgtcggcc  540
tcggttggag atcgcgtcac catcacttgt cgagcttccc aaggagtcgg taggtggctg  600
gcgtggtacc agcaaaagcc gggaactgcc ccgaagctcc tgatctacgc ggctagcacc  660
ctgcagtcgg gagtgccatc ccgcttcagc ggatctgggt caggtaccga cttcaccctt  720
acgatcaaca atctccagcc ggaggacttt gccacctatt actgccaaca ggccaacagc  780
ttccctctga ctttcggagg gggcactcgc ctggaaatca agaccactac cccagcaccg  840
aggccaccca ccccggctcc taccatcgcc tcccagcctc tgtccctgcg tccggaggca  900
tgtagacccg cagctggtgg ggccgtgcat acccggggtc ttgacttcgc ctgcgatatc  960
tacatttggg cccctctggc tggtacttgc ggggtcctgc tgctttcact cgtgatcact  1020
ctttactgta agcgcggtcg gaagaagctg ctgtacatct ttaagcaacc cttcatgagg  1080
cctgtgcaga ctactcaaga ggaggacggc tgttcatgcc ggttcccaga ggaggaggaa  1140
ggcggctgcg aactgcgcgt gaaattcagc cgcagcgcag atgctccagc ctacaagcag  1200
gggcagaacc agctctacaa cgaactcaat cttggtcgga gagaggagta cgacgtgctg  1260
gacaagcgga gaggacggga cccagaaatg ggcgggaagc cgcgcagaaa gaatccccaa  1320
gagggcctgt acaacgagct ccaaaaggat aagatggcag aagcctatag cgagattggt  1380
atgaaagggg aacgcagaag aggcaaaggc cacgacggac tgtaccaggg actcagcacc  1440
gccaccaagg acacctatga cgctcttcac atgcaggccc tgccgcctcg g           1491
```

```
SEQ ID NO: 117         moltype = DNA  length = 1482
FEATURE                Location/Qualifiers
misc_feature           1..1482
```

```
                         note = source = /note="Description of Artificial Sequence:
                          Syntheticpolynucleotide"
source                   1..1482
                         mol_type = other DNA
                         organism = synthetic construct
SEQUENCE: 117
atggccctcc ctgtcaccgc cctgctgctt ccgctggctc ttctgctcca cgccgctcgg  60
ccccaagtgc aattggttca atcaggagga ggagtggtgc aacctggaag atctctcaga  120
ctgtcgtgtg cggcatcggg attcactttc tcatcatacg caatgcactg ggtccgccag  180
gccccgggca aaggcttgga atgggtggcg gtcatttcat acgacggctc gaacaagtac  240
tacgctgaca gcgtgaaggg acgctttact atttcccggg acaattcgaa gaacactctg  300
tacctccaga tgaactccct tagggctgag gacaccgccg tctactactg cgcacgctgg  360
aaagtgtcgt ccagctcccc agcttttgac tactggggac agggaaccct tgtgaccgtg  420
tcgtccggtg gaggggaag cggcggaggg ggatcaggtg gcggcggatc gggaggcggg  480
ggatcagaaa tcgtgctgac tcagtccccg gccacgctgt ctctcagccc gggagagaga  540
gcgatcctgt cctgccgcgc ctcgcagagc gtgtacacta agtacctggg gtggtaccag  600
cagaaaccgg gtcaagcgcc tcggctgctg atctacgatg cctccacccg ggccaccgga  660
atccccgatc ggttctccgg cagcggctcg ggaactgatt tcacgctgac catcaatcgc  720
ctggagccgg aagatttcgc cgtctattac tgccagcatt acggcgggag cccactcatc  780
accttcggtc aaggaacccg actcgaaatc aagaccacta ccccagcacc gaggccaccc  840
accccggctc ctaccatcgc ctcccagcct ctgtccctgc gtccggaggc atgtagaccc  900
gcagctggtg gggccgtgca tacccggggt cttgacttcg cctgcgatat ctacatttgg  960
gcccctctgg ctggtacttg cggggtcctg ctgctttcac tcgtgatcac tctttactgt  1020
aagcgcggtc ggaagaagct gctgtacatc tttaagcaac ccttcatgag gcctgtgcag  1080
actactcaag aggaggacgg ctgttcatgc cggttcccag aggaggagga aggcggctgc  1140
gaactgcgcg tgaaattcag ccgcagcgca gatgctccag cctacaagca ggggcagaac  1200
cagctctaca acgaactcaa tcttggtcgg agagaggagt acgacgtgct ggacaagcgg  1260
agaggacggg acccagaaat gggcgggaag ccgcgcagaa agaatcccca agagggcctg  1320
tacaacgagc tccaaaagga taagatggca gaagcctata gcgagattgg tatgaaaggg  1380
gaacgcagaa gaggcaaagg ccacgacgga ctgtaccagg gactcagcac cgccaccaag  1440
gacacctatg acgctcttca catgcaggcc ctgccgcctc gg                    1482

SEQ ID NO: 118           moltype = DNA  length = 1470
FEATURE                  Location/Qualifiers
misc_feature             1..1470
                         note = source = /note="Description of Artificial Sequence:
                          Syntheticpolynucleotide"
source                   1..1470
                         mol_type = other DNA
                         organism = synthetic construct
SEQUENCE: 118
atggccctcc ctgtcaccgc cctgctgctt ccgctggctc ttctgctcca cgccgctcgg  60
ccccaagtcc aactccagca gtcaggtgca gaagtcaaaa agccaggagc atccgtgaag  120
gtttcgtgca agacttccgg ctaccctttt accgggtact ccctccattg ggtgagacaa  180
gcaccgggcc agggactgga gtggatggga tggatcaacc caaattcggg cggcaccaac  240
tatgcgcaga agttccaggg acgggtgacc atgactcgcg acacttcgat ctccactgcc  300
tacatggagc tgtcccgctt gagatctgac gacacggccg tctactactg cgcccgggat  360
cactacggag gtaattcgct gttctactgg gggcagggaa cccttgtgac tgtgtcctcg  420
ggtggtggag ggtcaggagg cggaggctca gggggaggag gtagcggagg aggcggatca  480
gacatccaac tgacccagtc accatcctcc atctcggcta gcgtcggaga caccgtgtcg  540
attacttgta gggcctccca agactcaggg acgtggctgg cgtggtatca gcaaaaaccg  600
ggcaaagctc cgaacctgtt gatgtacgac gccagcaccc tcgaagatgg agtgcctagc  660
cgcttcagcg gaagcgcctc gggcactgaa ttcacgctga ctgtgaatcg gctccagccg  720
gaggattcgg cgacctacta ctgccagcag tacaacagct accccctgac ctttggaggc  780
gggaccaagg tggatatcaa gaccactacc ccagcaccga ggccacccac cccggctcct  840
accatcgcct cccagcctct gtccctgcgt ccggaggcat gtagacccgc agctggtggg  900
gccgtgcata cccggggtct tgacttcgcc tgcgatatct acatttgggc ccctctggct  960
ggtacttgcg gggtcctgct gctttcactc gtgatcactc tttactgtaa gcgcggtcgg  1020
aagaagctgc tgtacatctt taagcaaccc ttcatgaggc ctgtgcagac tactcaagag  1080
gaggacggct gttcatgccg gttcccagag gaggaggaag gcggctgcga actgcgcgtg  1140
aaattcagcc gcagcgcaga tgctccagcc tacaagcagg ggcagaacca gctctacaac  1200
gaactcaatc ttggtcggag agaggagtac gacgtgctgg acaagcggag aggacgggac  1260
ccagaaatgg gcgggaagcc gcgcagaaag aatccccaag agggcctgta caacgagctc  1320
caaaaggata agatggcaga agcctatagc gagattggta tgaaagggga acgcagaaga  1380
ggcaaaggcc acgacggact gtaccaggga ctcagcaccg ccaccaagga cacctatgac  1440
gctcttcaca tgcaggccct gccgcctcgg                                  1470

SEQ ID NO: 119           moltype = DNA  length = 1476
FEATURE                  Location/Qualifiers
misc_feature             1..1476
                         note = source = /note="Description of Artificial Sequence:
                          Syntheticpolynucleotide"
source                   1..1476
                         mol_type = other DNA
                         organism = synthetic construct
SEQUENCE: 119
atggccctcc ctgtcaccgc cctgctgctt ccgctggctc ttctgctcca cgccgctcgg  60
ccccaagtgc aactcgtcca gtcaggtgca gaagtgaaga aaccaggagc gtccgtcgaa  120
gtgtcgtgta aggcgtccgg ctacactttc acctcgtact acatgcactg ggtgcggcag  180
```

```
gccccgggac aaggcctcga atggatggga atcatcaacc cgagcggagg ctcgactggt  240
tacgcccaga agttccaggg aagggtgacg atgacccgcg atacctcgac ttcgaccgtt  300
catatggagc tctcgtccct gcggagcgag gacactgctg tctactattg cgcgcgggga  360
ggatactcta gctcctccga tgcatttgac atttggggcc agggaactat ggtgaccgtg  420
tcatcaggcg gaggtggatc aggaggagga gggtcgggag ggggaggcag cggcgggggt  480
gggtcggaca ttcagatgac gcagtcccct cctagcctga gcgcctcggt gggtgacaga  540
gtgaccatca cttgcagagc ctcgcaagac atctcctccg cattggcttg gtaccagcaa  600
aagccgggca ctccgccgaa actgctcatc tacgatgcct cctcactgga gtcaggagtc  660
ccatctcgct tctcggggtc aggaagcggc accgatttta cccttaccat ctccagcctg  720
cagcccgagg acttcgccac gtactactgc caacagttca gctcctaccc actgaccttc  780
gggggcggaa ctcgcctgga aatcaagacc actaccccag caccgaggcc acccaccccg  840
gctcctacca tcgcctccca gcctctgtcc ctgcgtccgg aggcatgtag acccgcagct  900
ggtggggccg tgcatacccg gggtcttgac ttcgcctgcg atatctacat ttgggcccct  960
ctggctggta cttgcggggt cctgctgctt tcactcgtga tcactcttta ctgtaagcgc  1020
ggtcggaaga agctgctgta catctttaag caacccttca tgaggcctgt gcagactact  1080
caagaggagg acggctgttc atgccggttc ccagaggagg aggaaggcgg ctgcgaactg  1140
cgcgtgaaat tcagccgcag cgcagatgct ccagcctaca agcaggggca gaaccagctc  1200
tacaacgaac tcaatcttgg tcggagagag gagtacgacg tgctggacaa gcggagagga  1260
cgggacccag aaatgggcgg gaagccgcgc agaaagaatc cccaagaggg cctgtacaac  1320
gagctccaaa aggataagat ggcagaagcc tatagcgaga ttggtatgaa aggggaacgc  1380
agaagaggca aaggccacga cggactgtac cagggactca gcaccgccac caaggacacc  1440
tatgacgctc ttcacatgca ggccctgccg cctcgg                            1476
```

```
SEQ ID NO: 120          moltype = DNA  length = 1497
FEATURE                 Location/Qualifiers
misc_feature            1..1497
                        note = source = /note="Description of Artificial Sequence:
                         Syntheticpolynucleotide"
source                  1..1497
                        mol_type = other DNA
                        organism = synthetic construct
SEQUENCE: 120
atggccctcc ctgtcaccgc cctgctgctt ccgctggctc ttctgctcca cgccgctcgg  60
ccccaagtgc aactcgtcca gagcggagca gaagtcaaga agccaggagc gtcagtgaaa  120
gtgtcatgca aggccagcgg ctataccttt acttcgtatg ggatctcctg ggtgcggcag  180
gcaccgggcc aaggactgga gtggatggga tggatctcag cctacaacgg taacaccaac  240
tacgcccaga agctgcaagg acgcgtgacc atgactactg atacgagcac ctccactgcc  300
tacatggaat tgcggtccct tcggtcggac gatactgctg tgtactactg cgcaagagtc  360
gccggaggga tctactacta ctacggcatg gacgtctggg gacagggaac caccattacg  420
gtgtcgagcg gaggggagg ctcgggggga ggaggaagcg gaggtggcgg ctccgggggc  480
ggcggatcgg acattgtgat gacccagact cctgactccc tggctgtttc gttgggagag  540
cgcgcgacta tctcgtgtaa gtccagccac tcagtcctgt acaatcgcaa taacaagaac  600
tacctcgcgt ggtaccagca aaaaccgggt cagccgccta aactcctgtt ctactgggcc  660
tccaccagaa agagcggggt gccagatcga ttctctggat caggatcagg taccgacttt  720
acgctgacca tctcgtccct gcagccggag gatttcgcga cttacttctg ccagcagact  780
cagactttcc ccctcacctt cggtcaaggc accaggctgg aaatcaatac cactacccca  840
gcaccgaggc cacccacccc ggctcctacc atcgcctccc agcctctgtc cctgcgtccg  900
gaggcatgta gacccgcagc tggtggggcc gtgcataccc ggggtcttga cttcgcctgc  960
gatatctaca tttgggcccc tctggctggt acttgcgggg tcctgctgct ttcactcgtg  1020
atcactcttt actgtaagcg cggtcggaag aagctgctgt acatctttaa gcaacccttc  1080
atgaggcctg tgcagactac tcaagaggag gacggctgtt catgccggtt cccagaggag  1140
gaggaaggcg gctgcgaact gcgcgtgaaa ttcagccgca gcgcagatgc tccagcctac  1200
aagcaggggc agaaccagct ctacaacgaa ctcaatcttg gtcggagaga ggagtacgac  1260
gtgctggaca agcggagagg acgggaccca gaaatgggcg ggaagccgcg cagaaagaat  1320
ccccaagagg gcctgtacaa cgagctccaa aaggataaga tggcagaagc ctatagcgag  1380
attggtatga aaggggaacg cagaagaggc aaaggccacg acggactgta ccagggactc  1440
agcaccgcca ccaaggacac ctatgacgct cttcacatgc aggccctgcc gcctcgg     1497
```

```
SEQ ID NO: 121          moltype = DNA  length = 1455
FEATURE                 Location/Qualifiers
misc_feature            1..1455
                        note = source = /note="Description of Artificial Sequence:
                         Syntheticpolynucleotide"
source                  1..1455
                        mol_type = other DNA
                        organism = synthetic construct
SEQUENCE: 121
atggccctcc ctgtcaccgc cctgctgctt ccgctggctc ttctgctcca cgccgctcgg  60
ccccaagtcc aattgcagca gagcggagca gaagtgaaga agccaggagc gtcagtcaaa  120
gtgtcgtgta aggcgtcagg atacaccttc acgggatact acatgcactg ggtgcgccag  180
gccccgggcc aaggactcga gtggatgggc tggatcaacc ctaactctgg aggcaccaac  240
tacgcccaga atttccaagg cagagtgacc atgacccggg acacctccat ctcgactgcc  300
tatatggaac tgcggcggct gcgctcggac gatactgctg tgtattactg cgccagcggc  360
tgggactttg actactgggg acagggtact ctggtgactg tttcctcggg aggaggcgga  420
tcgggtggag gaggtagcgg gggagggggg tcgggaggcg gaggcagcga tattcgcatg  480
actcaatcgc cgtcctccct gagcgctagc gtgggagatc gagtcaccat cacttgcaga  540
gcgtcacagt cgattcgcta ctacctgtcc tggtaccagc agaaaccggg aaaggcacca  600
aagcttctga tctacacggc ctccatcctg caaaatggtg tcccatcaag gttctccggg  660
tcagggagcg gcactgactt cactctcacc atctcctcac tccagcccga ggactttgca  720
```

```
acctactact gcctccagac gtacaccacc ccggatttcg gtcctggaac caaggtggaa  780
atcaaaacca ctaccccagc accgaggcca cccaccccgg ctcctaccat cgcctcccag  840
cctctgtccc tgcgtccgga ggcatgtaga cccgcagctg gtggggccgt gcatacccgg  900
ggtcttgact tcgcctgcga tatctacatt tgggcccctc tggctggtac ttgcggggtc  960
ctgctgcttt cactcgtgat cactctttac tgtaagcgcg gtcggaagaa gctgctgtac  1020
atctttaagc aacccttcat gaggcctgtg cagactactc aagaggagga cggctgttca  1080
tgccggttcc cagaggagga ggaaggcggc tgcgaactgc gcgtgaaatt cagccgcagc  1140
gcagatgctc cagcctacaa gcaggggcag aaccagctct acaacgaact caatcttggt  1200
cggagagagg agtacgacgt gctggacaag cggagaggac gggacccaga aatgggcggg  1260
aagccgcgca gaaagaatcc ccaagagggc ctgtacaacg agctccaaaa ggataagatg  1320
gcagaagcct atagcgagat tggtatgaaa ggggaacgca gaagaggcaa aggccacgac  1380
ggactgtacc agggactcag caccgccacc aaggacacct atgacgctct tcacatgcag  1440
gccctgccgc ctcgg                                                   1455
```

```
SEQ ID NO: 122         moltype = DNA  length = 1470
FEATURE                Location/Qualifiers
misc_feature           1..1470
                       note = source = /note="Description of Artificial Sequence:
                        Syntheticpolynucleotide"
source                 1..1470
                       mol_type = other DNA
                       organism = synthetic construct
SEQUENCE: 122
atggccctcc ctgtcaccgc cctgctgctt ccgctggctc ttctgctcca cgccgctcgg  60
ccccaagtcc aactcgtcca aagcggagca gaagtcaaaa agccaggagc gtcggtgaaa  120
gtgtcttgca aagccagcgg ctacaccttc acgggttact acatgcactg ggtgcgccag  180
gcgccgggcc aggggctgga gtggatgggc cggattaacc ctaacagcgg gggaactaat  240
tacgctcaga agttccaggg tagagtcacc atgactacgg acacttccac ttccaccgcc  300
tatatggaac tgcgctccct ccgctcagat gatactgccg tgtattactg cgcgcggact  360
accacgtcat acgcatttga catctggggc cagggaacta tggtgaccgt gagctcgggc  420
ggaggcggtt caggggaggg aggaagcgga ggaggaggat cgggaggagg tggctccgat  480
atccagctga ctcagtcccc gagcaccctg tcggcgtcgg tgggggacag ggttaccatc  540
acctgtagag cttcccaatc catttcgact tggctggcct ggtaccagca aaagccggga  600
aaggccccta atttgcttat ctacaaggca tcgaccctcg aaagcggtgt gccctcccgg  660
ttttcgggat caggatcagg gaccgagttc accctgacca tctcatccct ccagccggac  720
gacttcgcca cttactactg ccagcagtac aacacctact cgccatacac tttcggccaa  780
ggcaccaagc tggagatcaa gaccactacc ccagcaccga ggccacccac cccggctcct  840
accatcgcct cccagcctct gtccctgcgt ccggaggcat gtagacccgc agctggtggg  900
gccgtgcata cccggggtct tgacttcgcc tgcgatatct acatttgggc ccctctggct  960
ggtacttgcg gggtcctgct gctttcactc gtgatcactc tttactgtaa gcgcggtcgg  1020
aagaagctgc tgtacatctt taagcaaccc ttcatgaggc ctgtgcagac tactcaagag  1080
gaggacggct gttcatgccg gttcccagag gaggaggaag gcggctgcga actgcgcgtg  1140
aaattcagcc gcagcgcaga tgctccagcc tacaagcagg ggcagaacca gctctacaac  1200
gaactcaatc ttggtcggag agaggagtac gacgtgctgg acaagcggag aggacgggac  1260
ccagaaatgg gcgggaagcc gcgcagaaag aatccccaag agggcctgta caacgagctc  1320
caaaaggata agatggcaga agcctatagc gagattggta tgaaagggga acgcagaaga  1380
ggcaaaggcc acgacggact gtaccaggga ctcagcaccg ccaccaagga cacctatgac  1440
gctcttcaca tgcaggccct gccgcctcgg                                  1470
```

```
SEQ ID NO: 123         moltype = DNA  length = 1479
FEATURE                Location/Qualifiers
misc_feature           1..1479
                       note = source = /note="Description of Artificial Sequence:
                        Syntheticpolynucleotide"
source                 1..1479
                       mol_type = other DNA
                       organism = synthetic construct
SEQUENCE: 123
atggccctcc ctgtcaccgc cctgctgctt ccgctggctc ttctgctcca cgccgctcgg  60
ccccaagttc aactcgtgca atcaggtgga ggactcgtca aacccggagg atcattgaga  120
ctgtcatgcg aagcgagcgg ttttatcttc tccgattact atatgggatg gattcggcag  180
gccccgggaa agggactcga atgggtgtca tacatcggaa ggtcaggctc gtccatgtac  240
tacgcagact cggtgaaagg cagattcacc tttagccggg acaacgccaa gaattccctc  300
tacttgcaga tgaacagcct gcgagccgag gatactgctg tctactactg tgccgcgtcg  360
ccggtggtgg cagctactga agatttccag cactggggac agggaactct ggtcacggtg  420
tcgagcggtg ggggcggaag cggaggcgga ggatcgggcg gcggaggttc gggggggga  480
gggtctgaca tcgtgatgac ccaaacccca gccaccctga gcctctcccc tggagagcgc  540
gcgactcttt cgtgccgcgc ttcccagtca gtgaccagca attacttggc ttggtaccaa  600
cagaagccgg gacaggcgcc acggctgctg ctttttggtg ccagcactcg cgccaccgga  660
atcccggatc gcttctcggg ctcagggtcc gggacggact tcaccctgac tatcaaccgg  720
ctggaacctg aggacttcgc gatgtactac tgccagcagt acggctccgc accagtcact  780
ttcggacaag gcaccaagct ggagatcaag accactaccc cagcaccgag gccacccacc  840
ccggctccta ccatcgcctc ccagcctctg tccctgcgtc cggaggcatg tagacccgca  900
gctggtgggg ccgtgcatac ccggggtctt gacttcgcct gcgatatcta catttgggcc  960
cctctggctg gtacttgcgg ggtcctgctg ctttcactcg tgatcactct ttactgtaag  1020
cgcggtcgga agaagctgct gtacatcttt aagcaaccct tcatgaggcc tgtgcagact  1080
actcaagagg aggacggctg ttcatgccgg ttcccagagg aggaggaagg cggctgcgaa  1140
ctgcgcgtga aattcagccg cagcgcagat gctccagcct acaagcaggg gcagaaccag  1200
ctctacaacg aactcaatct tggtcggaga gaggagtacg acgtgctgga caagcggaga  1260
```

-continued

```
ggacgggacc cagaaatggg cgggaagccg cgcagaaaga atccccaaga gggcctgtac  1320
aacgagctcc aaaaggataa gatggcagaa gcctatagcg agattggtat gaaaggggaa  1380
cgcagaagag gcaaaggcca cgacggactg taccagggac tcagcaccgc caccaaggac  1440
acctatgacg ctcttcacat gcaggccctg ccgcctcgg                          1479

SEQ ID NO: 124          moltype = DNA  length = 1479
FEATURE                 Location/Qualifiers
misc_feature            1..1479
                        note = source = /note="Description of Artificial Sequence:
                         Syntheticpolynucleotide"
source                  1..1479
                        mol_type = other DNA
                        organism = synthetic construct
SEQUENCE: 124
atggccctcc ctgtcaccgc cctgctgctt ccgctggctc ttctgctcca cgccgctcgg  60
ccccaagtcc aactcgtcca gtcgggagca gaagttagag caccaggagc gtcagtgaaa  120
atctcatgca aggcctcggg cttcacgttc cgcggatact acatccactg ggtgcgccaa  180
gccccgggtc agggattgga gtggatggga atcattaacc catcaggagg gagccgggct  240
tacgcgcaga agttccaggg acgcgtcact atgacccgag atacttccac ctcgactgtg  300
tacatggaac tctcgtccct gaggtccgac gacactgcga tgtattactg tgctcggact  360
gccagctgcg gtggggactg ttactacctc gattactggg gccagggaac tctggtgacc  420
gtgtccagcg gaggtggcgg gtcagggggt ggcggaagcg gaggcggcgg ttcaggcgga  480
ggaggctcgg acatccaaat gacgcaatcg ccgcctaccc tgagcgcttc cgtgggagat  540
cgggtgacca ttacttgcag agcatccgag aacgtcaata tctggctggc ctggtaccaa  600
cagaagccgg ggaaggcccc taaactgctg atctacaagt cgagcagcct tgcctctgga  660
gtgccctccc gcttctcggg ctcgggatca ggagcggaat tcaccctcac catctcctcc  720
ctgcagccag atgactttgc cacctactac tgccagcagt accagagcta tccgttgacc  780
tttgggggag gcactaaagt ggacatcaag accactaccc cagcaccgag gccacccacc  840
ccggctccta ccatcgcctc ccagcctctg tccctgcgtc cggaggcatg tagacccgca  900
gctggtgggg ccgtgcatac ccggggtctt gacttcgcct gcgatatcta catttgggcc  960
cctctggctg gtacttgcgg ggtcctgctg ctttcactcg tgatcactct ttactgtaag  1020
cgcggtcgga agaagctgct gtacatcttt aagcaaccct tcatgaggcc tgtgcagact  1080
actcaagagg aggacggctg ttcatgccgg ttcccagagg aggaggaagg cggctgcgaa  1140
ctgcgcgtga aattcagccg cagcgcagat gctccagcct acaagcaggg gcagaaccag  1200
ctctacaacg aactcaatct tggtcggaga gaggagtacg acgtgctgga caagcggaga  1260
ggacgggacc cagaaatggg cgggaagccg cgcagaaaga atccccaaga gggcctgtac  1320
aacgagctcc aaaaggataa gatggcagaa gcctatagcg agattggtat gaaaggggaa  1380
cgcagaagag gcaaaggcca cgacggactg taccagggac tcagcaccgc caccaaggac  1440
acctatgacg ctcttcacat gcaggccctg ccgcctcgg                          1479

SEQ ID NO: 125          moltype = DNA  length = 1464
FEATURE                 Location/Qualifiers
misc_feature            1..1464
                        note = source = /note="Description of Artificial Sequence:
                         Syntheticpolynucleotide"
source                  1..1464
                        mol_type = other DNA
                        organism = synthetic construct
SEQUENCE: 125
atggccctcc ctgtcaccgc cctgctgctt ccgctggctc ttctgctcca cgccgctcgg  60
ccccaagttc aactcgttca atcaggtgga ggactcgtgc aaccaggaag atcactcaga  120
ctcagctgcg ccgcgtcggg attcactttc gatgactacg caatgcactg ggtgcggcag  180
gccccgggca aaggactgga atgggtgagc ggaattagct ggaactcggg gtccatcggg  240
tacgccgact cggtgaaggg acgctttacg atctcccggg acaatgccaa gaactccctg  300
tatttgcaga tgaactcctt gagggctgag gacaccgccg tgtactactg cgctaaagat  360
ggatcatcgt cctggtcctg gggatacttc gattactggg gccagggcac tctggtgacc  420
gtgtcgtcag gcggtggagg gtcgggcgga ggaggtagcg gaggcggagg gagcagctct  480
gaactgaccc aagacccggc ggtgtcggtc gcccttggtc agactgtgcg gactacctgt  540
caggggggacg cgctgcgctc gtactacgct tcatggtacc agcagaagcc cggacaggca  600
cctatgctgg tcatctacgg aaagaataac cgcccatccg gcatcccgga tcgcttctcg  660
ggttcggaca gcggcgacac cgcatccctg acgatcactg gagcgcaggc cgaggatgaa  720
gccgactact actgcaattc ccgagattca agcggctacc ctgtgtttgg gaccggaact  780
aaggtcaccg tcctgaccac taccccagca ccgaggccac ccaccccggc tcctaccatc  840
gcctcccagc ctctgtccct gcgtccggag gcatgtagac ccgcagctgg tggggccgtg  900
catacccggg gtcttgactt cgcctgcgat atctacattt gggcccctct ggctggtact  960
tgcggggtcc tgctgctttc actcgtgatc actctttact gtaagcgcgg tcggaagaag  1020
ctgctgtaca tctttaagca acccttcatg aggcctgtgc agactactca agaggaggac  1080
ggctgttcat gccggttccc agaggaggag gaaggcggct gcgaactgcg cgtgaaattc  1140
agccgcagcg cagatgctcc agcctacaag caggggcaga accagctcta caacgaactc  1200
aatcttggtc ggagagagga gtacgacgtg ctggacaagc ggagaggacg ggacccagaa  1260
atgggcggga agccgcgcag aaagaatccc caagagggcc tgtacaacga gctccaaaag  1320
gataagatgg cagaagccta tagcgagatt ggtatgaaag gggaacgcag aagaggcaaa  1380
ggccacgacg gactgtacca gggactcagc accgccacca aggacaccta tgacgctctt  1440
cacatgcagg ccctgccgcc tcgg                                          1464

SEQ ID NO: 126          moltype = DNA  length = 1470
FEATURE                 Location/Qualifiers
misc_feature            1..1470
                        note = source = /note="Description of Artificial Sequence:
```

```
                         Syntheticpolynucleotide"
source                  1..1470
                        mol_type = other DNA
                        organism = synthetic construct
SEQUENCE: 126
atggccctcc ctgtcaccgc cctgctgctt ccgctggctc ttctgctcca cgccgctcgg  60
cccgaagtgc aactcgtgga atctggtgga ggacttgtgc aacctggaag atcgttgaga  120
ctctcatgtg ctgcctccgg gttcaccttt gacgactacg ccatgcactg ggtgcgccag  180
gcaccaggaa agggtctgga gtgggtttcg ggtatctcgt ggaactccgg gagcactggc  240
tacgctgatt cggtgaaagg ccggtttacc atctcccgag acaatgcgaa gaattccctc  300
tatctgcaga tgaacagcct ccgggccgag gatactgccc tgtactactg cgccaaggat  360
agctcatcat ggtacggagg tggatcggct ttcgatatct ggggccaggg cacgatggtc  420
accgtgtcct cggggggcgg aggctccggg ggaggaggta gcggaggagg aggatcgagc  480
tcagagttga ctcaagaacc cgcagtgtcc gtggcactgg gccaaaccgt caggatcact  540
tgccagggag acagcctgag gtcgtactac gcgtcctggt accagcagaa gccgggacag  600
gccccggtcc tggtcatttt cggacgctca agacgcccat cgggcatccc ggaccggttc  660
agcggaagct cctcgggaaa caccgcgtca cttatcatta ccggcgcaca ggctgaggac  720
gaagcggatt actactgcaa ctcccgcgac aatactgcca accattacgt gttcgggacc  780
ggaacgaaac tgactgtcct gaccactacc ccagcaccga ggccacccac cccggctcct  840
accatcgcct cccagcctct gtccctgcgt ccggaggcat gtagacccgc agctggtggg  900
gccgtgcata cccggggtct tgacttcgcc tgcgatatct acatttgggc ccctctggct  960
ggtacttgcg ggtcctgct gctttcactc gtgatcactc tttactgtaa gcgcggtcgg  1020
aagaagctgc tgtacatctt taagcaaccc ttcatgaggc ctgtgcagac tactcaagag  1080
gaggacggct gttcatgccg gttcccagag gaggaggaag gcggctgcga actgcgcgtg  1140
aaattcagcc gcagcgcaga tgctccagcc tacaagcagg ggcagaacca gctctacaac  1200
gaactcaatc ttggtcggag agaggagtac gacgtgctgg acaagcggag aggacgggac  1260
ccagaaatgg gcgggaagcc gcgcagaaag aatccccaag agggcctgta caacgagctc  1320
caaaaggata agatggcaga agcctatagc gagattggta tgaaagggga acgcagaaga  1380
ggcaaaggcc acgacggact gtaccaggga ctcagcaccg ccaccaagga cacctatgac  1440
gctcttcaca tgcaggccct gccgcctcgg                                   1470

SEQ ID NO: 127          moltype = DNA  length = 1470
FEATURE                 Location/Qualifiers
misc_feature            1..1470
                        note = source = /note="Description of Artificial Sequence:
                         Syntheticpolynucleotide"
source                  1..1470
                        mol_type = other DNA
                        organism = synthetic construct
SEQUENCE: 127
atggccctcc ctgtcaccgc cctgctgctt ccgctggctc ttctgctcca cgccgctcgg  60
cccgaagttc aattggtgga atctggagga ggacttgtgc aacccggtag atctctgaga  120
ctgtcctgtg cggcatcggg attcaccttc gacgactacg ctatgcactg ggtgagacaa  180
gcccctggaa aaggactgga gtgggtgtca ggcatctcct ggaatagcgg gtccactgga  240
tacgccgatt cggtcaaggg tcgcttcacc atttcccggg acaatgccaa gaactccctg  300
taccttcaaa tgaactccct ccgggccgag gataccgccc tctactactg cgccaaagac  360
agctcgtcat ggtatggcgg agggtcggca tttgacatct ggggacaggg aactatggtg  420
actgtgtcat caggaggcgg cggaagcggc ggcggcgggt ccggcggagg agggtcgtcc  480
agcgaactca cccaagatcc agcagtgagc gtcgcgctgg gccagaccgt caggatcacg  540
tgccagggag attcactgcg ctcatactac gcgtcctggt accagcagaa gccggggcag  600
gccccggtcc tcgtgatcta cggaaagaac aaccgcccgt cgggtatccc agaccgcttt  660
tcgggtagct ccagcggaaa tacggctagc ctgaccatca ctggagcaca ggctgaggat  720
gaagcggact actactgcaa ttcgcggggc tcatcgggga accattacgt gttcggaact  780
ggtaccaagg tgactgtcct gaccactacc ccagcaccga ggccacccac cccggctcct  840
accatcgcct cccagcctct gtccctgcgt ccggaggcat gtagacccgc agctggtggg  900
gccgtgcata cccggggtct tgacttcgcc tgcgatatct acatttgggc ccctctggct  960
ggtacttgcg ggtcctgct gctttcactc gtgatcactc tttactgtaa gcgcggtcgg  1020
aagaagctgc tgtacatctt taagcaaccc ttcatgaggc ctgtgcagac tactcaagag  1080
gaggacggct gttcatgccg gttcccagag gaggaggaag gcggctgcga actgcgcgtg  1140
aaattcagcc gcagcgcaga tgctccagcc tacaagcagg ggcagaacca gctctacaac  1200
gaactcaatc ttggtcggag agaggagtac gacgtgctgg acaagcggag aggacgggac  1260
ccagaaatgg gcgggaagcc gcgcagaaag aatccccaag agggcctgta caacgagctc  1320
caaaaggata agatggcaga agcctatagc gagattggta tgaaagggga acgcagaaga  1380
ggcaaaggcc acgacggact gtaccaggga ctcagcaccg ccaccaagga cacctatgac  1440
gctcttcaca tgcaggccct gccgcctcgg                                   1470

SEQ ID NO: 128          moltype = DNA  length = 1485
FEATURE                 Location/Qualifiers
misc_feature            1..1485
                        note = source = /note="Description of Artificial Sequence:
                         Syntheticpolynucleotide"
source                  1..1485
                        mol_type = other DNA
                        organism = synthetic construct
SEQUENCE: 128
atggccctcc ctgtcaccgc cctgctgctt ccgctggctc ttctgctcca cgccgctcgg  60
ccccaagtgc agctcgttca atcaggcgga ggactcgttc aaccaggagg atcattgcga  120
ctctcatgtg cggcctctgg attcacgttt agctcatatt ggatgcactg ggtgcggcag  180
gcgccgggga aaggtctggt gtgggtcagc cgcatcaact cagacggctc ctcgacttcg  240
```

```
tacgccgact ccgtgaaggg acgctttacc atttcccgcg acaacgccaa gaataccctt  300
taccttcaga tgaactccct ccgcgctgag gataccgccg tgtactactg cgtgaggact  360
ggctgggtcg gcagctacta ctactacatg gacgtgtggg gcaaaggaac tactgtcacc  420
gtgtcaagcg gcggtggagg ttccggcggg ggaggatcgg ggggggcgg atcgggtggc  480
ggaggatcgg agatcgtgtt gacccagtcg ccgggaaccc tgtcgctgtc gcctggggag  540
agagcaactc tgtcctgccg ggcttcccag tcggtgtcga gcaattacct ggcatggtac  600
caacagaagc cgggacagcc gccacgcctg ctgatctatg acgtgtcaac tcgggcaact  660
ggaatccctg cgcggttcag cggcggaggg agcggtaccg atttcaccct gactatttcc  720
tccctcgaac cagaagattt cgccgtctac tactgccagc agagaagcaa ctggccgccc  780
tggacgttcg gacaaggaac caaggtcgaa atcaagacca ctaccccagc accgaggcca  840
cccaccccgg ctcctaccat cgcctcccag cctctgtccc tgcgtccgga ggcatgtaga  900
cccgcagctg gtggggccgt gcatacccgg ggtcttgact tcgcctgcga tatctacatt  960
tgggcccctc tggctggtac ttgcggggtc ctgctgcttt cactcgtgat cactctttac  1020
tgtaagcgcg gtcggaagaa gctgctgtac atctttaagc aacccttcat gaggcctgtg  1080
cagactactc aagaggagga cggctgttca tgccggttcc cagaggagga ggaaggcggc  1140
tgcgaactgc gcgtgaaatt cagccgcagc gcagatgctc cagcctacaa gcaggggcag  1200
aaccagctct acaacgaact caatcttggt cggagagagg agtacgacgt gctggacaag  1260
cggagaggac gggacccaga aatgggcggg aagccgcgca gaaagaatcc ccaagagggc  1320
ctgtacaacg agctccaaaa ggataagatg gcagaagcct atagcgagat tggtatgaaa  1380
ggggaacgca gaagaggcaa aggccacgac ggactgtacc agggactcag caccgccacc  1440
aaggacacct atgacgctct tcacatgcag gccctgccgc ctcgg                  1485

SEQ ID NO: 129          moltype = DNA  length = 1482
FEATURE                 Location/Qualifiers
misc_feature            1..1482
                        note = source = /note="Description of Artificial Sequence:
                         Syntheticpolynucleotide"
source                  1..1482
                        mol_type = other DNA
                        organism = synthetic construct
SEQUENCE: 129
atggccctcc ctgtcaccgc cctgctgctt ccgctggctc ttctgctcca cgccgctcgg  60
ccccaagtgc aattggttca atcaggagga ggagtcgtgc agcccggaag atcgttgaga  120
ctgtcatgtg ccgcgagcgg ctttactttc tcaagctacg gaatgcattg ggtgcgacag  180
gctccgggaa aaggactgga atgggtcgca gtgatctcat acgacggctc gaacaagtac  240
tacgccgact ccgtcaaggg tcggttcacg atttcgcgcg ataattccaa gaacactctg  300
tacctccaaa tgaacagcct ccgggcagag gacaccgccg tctactactg cgctaaggga  360
tactcgcgct actactacta tggaatggat gtgtggggcc agggaactac cgtgacggtg  420
tcgtccggcg gcggtgggtc gggcggaggc ggatcaggtg gaggtggaag cggaggagga  480
gggagcgaaa tcgtcatgac tcagtcccct gctacccttt ctctgtcgcc gggagaaaga  540
gccatcctga gctgccgggc ctcccagagc gtgtacacca aatacctggg atggtaccag  600
cagaagccgg ggcaggcacc aaggctcctg atctacgatg cgtccacccg cgcgactggt  660
atcccagacc gcttttccgg ctcggggtca gggactgact tcacccttac tatcaatcgg  720
ctcgagcctg aggatttcgc cgtgtattac tgccagcact acggagggtc cccgctgatt  780
accttcggcc aaggcaccaa agtggacatc aagaccacta ccccagcacc gaggccaccc  840
accccggctc ctaccatcgc ctcccagcct ctgtccctgc gtccggaggc atgtagaccc  900
gcagctggtg gggccgtgca tacccggggt cttgacttcg cctgcgatat ctacatttgg  960
gcccctctgg ctggtacttg cggggtcctg ctgctttcac tcgtgatcac tctttactgt  1020
aagcgcggtc ggaagaagct gctgtacatc tttaagcaac ccttcatgag gcctgtgcag  1080
actactcaag aggaggacgg ctgttcatgc cggttcccag aggaggagga aggcggctgc  1140
gaactgcgcg tgaaattcag ccgcagcgca gatgctccag cctacaagca ggggcagaac  1200
cagctctaca acgaactcaa tcttggtcgg agagaggagt acgacgtgct ggacaagcgg  1260
agaggacggg acccagaaat gggcgggaag ccgcgcagaa agaatcccca agagggcctg  1320
tacaacgagc tccaaaagga taagatggca gaagcctata gcgagattgg tatgaaaggg  1380
gaacgcagaa gaggcaaagg ccacgacgga ctgtaccagg gactcagcac cgccaccaag  1440
gacacctatg acgctcttca catgcaggcc ctgccgcctc gg                     1482

SEQ ID NO: 130          moltype = DNA  length = 1479
FEATURE                 Location/Qualifiers
misc_feature            1..1479
                        note = source = /note="Description of Artificial Sequence:
                         Syntheticpolynucleotide"
source                  1..1479
                        mol_type = other DNA
                        organism = synthetic construct
SEQUENCE: 130
atggccctcc ctgtcaccgc cctgctgctt ccgctggctc ttctgctcca cgccgctcgg  60
ccccaagtgc aacttgttca atcaggagga ggactcgttc aacccggagg atcactgcga  120
ctctcatgtg cagcgtcggg gttcaccttc tccagctacg caatgtcctg ggtgcgccaa  180
gcccctggaa aaggcctgga gtgggtgtcg gccatctctg ggagcggggg atcaacttac  240
tacgctgact ccgtcaaggg ccgctttacc atctcccggg acaacagcaa gaacactctc  300
tatctccaga tgaactcgct gagagccgaa gataccgctg tctactactg cgcgaagaga  360
gaagctgccg cagggcacga ttggtacttc gacttgtggg gcaggggcac ccttgtgacc  420
gtgtcctccg gtggaggcgg atcaggaggt gggggatcgg gtggaggagg aagcggaggc  480
ggcggttcgg acattcgcgt cacccagtca ccgagctccc tcagcgcatc ggtgggcgac  540
cgggtcacta tcacttgccg ggcgtcccag tcgatctcat cgtatctgaa ttggtaccag  600
cagaaaccgg gaaaggcgcc gaagctgttg atctacgctg ccagctccct gcagtcgggt  660
gtgccatcac gcttttccgg ctcgggatcg ggaaccgatt tcactctgac gatctctagc  720
ctgcagccag aagatttcgc cacttactac tgccagcagt cctacagcat ccctctgact  780
```

```
ttcggacaag ggacgaaagt ggagattaag accactaccc cagcaccgag gccacccacc  840
ccggctccta ccatcgcctc ccagcctctg tccctgcgtc cggaggcatg tagacccgca  900
gctggtgggg ccgtgcatac ccggggtctt gacttcgcct gcgatatcta catttgggcc  960
cctctggctg gtacttgcgg ggtcctgctg ctttcactcg tgatcactct ttactgtaag  1020
cgcggtcgga agaagctgct gtacatcttt aagcaaccct tcatgaggcc tgtgcagact  1080
actcaagagg aggacggctg ttcatgccgg ttcccagagg aggaggaagg cggctgcgaa  1140
ctgcgcgtga aattcagccg cagcgcagat gctccagcct acaagcaggg gcagaaccag  1200
ctctacaacg aactcaatct tggtcggaga gaggagtacg acgtgctgga caagcggaga  1260
ggacgggacc cagaaatggg cgggaagccg cgcagaaaga atccccaaga gggcctgtac  1320
aacgagctcc aaaaggataa gatggcagaa gcctatagcg agattggtat gaaaggggaa  1380
cgcagaagag gcaaaggcca cgacggactg taccagggac tcagcaccgc caccaaggac  1440
acctatgacg ctcttcacat gcaggccctg ccgcctcgg                         1479
```

```
SEQ ID NO: 131         moltype = DNA  length = 1473
FEATURE                Location/Qualifiers
misc_feature           1..1473
                       note = source = /note="Description of Artificial Sequence:
                        Syntheticpolynucleotide"
source                 1..1473
                       mol_type = other DNA
                       organism = synthetic construct
SEQUENCE: 131
atggccctcc ctgtcaccgc cctgctgctt ccgctggctc ttctgctcca cgccgctcgg  60
ccccaagtcc aactcgttca gtcatgggca gaagtcaaga aacccggtgc aagcgtcaaa  120
gtgtcgtgta aggcctccgg ctacactttc acttcctact acatgcactg ggtgcgccaa  180
gccccgggac agggccttga atggatgggc atcatcaacc catcaggagg ttccacgagc  240
tacgcgcaga agttccaggg gagagtgacg atgactagag atacctccac gagcaccgtc  300
tacatggagc tgtcgaatct gcggtcagag gacactgctg tgtattactg cgcgcgctcc  360
ccgcgggtga ccactggcta ctttgactac tggggacaag ggaccctggt gaccgtcagc  420
tcgggaggcg gaggatcggg aggtggaggg tccggtggag gcggctctgg aggaggcggg  480
tcggacattc aattgaccca gagcccatcc accctctcag cctcggtggg ggatagggtg  540
actatcactt gccgggcctc ccagtcaatt tccagctggc tggcttggta ccagcaaaag  600
cctggaaagg caccgaagct cctgatctac aaggcctcat ctctggaatc aggagtgcct  660
tcgcgcttca gcggaagcgg ctcgggaact gagtttaccc tgaccatctc gagcctgcag  720
ccagatgact tcgcgaccta ttactgccag cagtactcgt cctacccgtt gactttcgga  780
ggaggtaccc gcctcgaaat caaaaccact accccagcac cgaggccacc caccccggct  840
cctaccatcg cctcccagcc tctgtccctg cgtccggagg catgtagacc cgcagctggt  900
ggggccgtgc atacccgggg tcttgacttc gcctgcgata tctacatttg ggcccctctg  960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg gagaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                               1473
```

```
SEQ ID NO: 132         moltype = DNA  length = 1491
FEATURE                Location/Qualifiers
misc_feature           1..1491
                       note = source = /note="Description of Artificial Sequence:
                        Syntheticpolynucleotide"
source                 1..1491
                       mol_type = other DNA
                       organism = synthetic construct
SEQUENCE: 132
atggccctcc ctgtcaccgc cctgctgctt ccgctggctc ttctgctcca cgccgctcgg  60
ccccaagtcc aactcgtcca gtccggtgca gaagtcagaa ggccaggagc aagcgtgaag  120
atctcgtgta gagcgtcagg agacaccagc actcgccatt acatccactg gctgcgccag  180
gctccgggcc aagggccgga gtggatgggt gtgatcaacc cgactacggg accggctacc  240
ggaagccctg cgtacgcaca gatgctgcag ggacgggtga ctatgacccg cgatactagc  300
actaggaccg tgtacatgga actccgctcg ttgcggttcg aagataccgc cgtctactac  360
tgcgcccggt ccgtggtggg ccgaagcgcc ccttactact tcgattactg gggacagggc  420
actctggtga ccgttagctc cggtggggga ggctcgggtg gaggcggatc gggaggagga  480
ggcagcggtg gaggggggatc ggacattcag atgacccagt caccctcctc cctctcagcc  540
tcggtcgggg accgggtgac cattacgtgc agagcctcac aagggatctc ggactactcc  600
gcctggtacc agcagaaacc gggaaaagcg ccaaagctcc tgatctacgc cgcgagcacc  660
ctgcaatcag gagtgccatc gcgcttttct ggatcgggct cagggactga cttcacgctg  720
actatctcct accttcagtc cgaggatttc gctacctact actgccaaca gtattactcc  780
tatcccctga cctttggcgg aggcactaag gtggacatca agaccactac cccagcaccg  840
aggccaccca ccccggctcc taccatcgcc tcccagcctc tgtccctgcg tccggaggca  900
tgtagacccg cagctggtgg ggccgtgcat acccggggtc ttgacttcgc ctgcgatatc  960
tacatttggg cccctctggc tggtacttgc ggggtcctgc tgctttcact cgtgatcact  1020
ctttactgta agcgcggtcg gaagaagctg ctgtacatct ttaagcaacc cttcatgagg  1080
cctgtgcaga ctactcaaga ggaggacggc tgttcatgcc ggttcccaga ggaggaggaa  1140
ggcggctgcg aactgcgcgt gaaattcagc cgcagcgcag atgctccagc ctacaagcag  1200
gggcagaacc agctctacaa cgaactcaat cttggtcgga gagaggagta cgacgtgctg  1260
gacaagcgga gaggacggga cccagaaatg ggcgggaagc cgcgcagaaa gaatccccaa  1320
```

```
gagggcctgt acaacgagct ccaaaaggat aagatggcag aagcctatag cgagattggt  1380
atgaaagggg aacgcagaag aggcaaaggc cacgacggac tgtaccaggg actcagcacc  1440
gccaccaagg acacctatga cgctcttcac atgcaggccc tgccgcctcg g           1491

SEQ ID NO: 133         moltype = DNA  length = 1479
FEATURE                Location/Qualifiers
misc_feature           1..1479
                       note = source = /note="Description of Artificial Sequence:
                        Syntheticpolynucleotide"
source                 1..1479
                       mol_type = other DNA
                       organism = synthetic construct
SEQUENCE: 133
atggccctcc ctgtcaccgc cctgctgctt ccgctggctc ttctgctcca cgccgctcgg  60
ccccaagtcc aactccagca atcgggagca gaagtcaaga aaccaggcgc atcggtgaaa  120
gtgtcgtgta aggcgtcagg gtacaccttc accaactact atatgcactg ggtgcgccag  180
gctccaggcc aggggttgga gtggatgggg atcatcaatc cgtcaggtgg ctacaccact  240
tacgctcaga agttccaggg acgcctcact atgactcgcg atactagcac ctccacggtg  300
tacatggaac tgtcatcgct gaggtccgaa gataccgccg tctactactg cgcacggatc  360
agatcctgcg gaggagattg ttactacttt gacaactggg gacagggcac ccttgttact  420
gtgtcatcgg gaggaggggg aagcggagga ggtggatcag gcggcggtgg cagcgggggc  480
ggaggatcgg acattcagct gactcagtcc ccctccactt tgtcggccag cgtgggagac  540
agagtgacca tcacttgccg ggcgtccgag aacgtcaata tctggctggc ctggtaccag  600
caaaagcctg gaaaagcccc gaagctgctc atctataagt catccagcct ggcgtctggt  660
gtgccgtcgc ggttctccgg cagcgggagc ggagccgagt tcactctcac catttcgagc  720
cttcaaccgg acgatttcgc cacctactac tgccagcagt accaatccta ccctctgacg  780
tttggaggtg gaaccaaggt ggacatcaag accactaccc cagcaccgag gccacccacc  840
ccggctccta ccatcgcctc ccagcctctg tccctgcgtc cggaggcatg tagacccgca  900
gctggtgggg ccgtgcatac ccggggtctt gacttcgcct gcgatatcta catttgggcc  960
cctctggctg gtacttgcgg ggtcctgctg ctttcactcg tgatcactct ttactgtaag  1020
cgcggtcgga agaagctgct gtacatcttt aagcaaccct tcatgaggcc tgtgcagact  1080
actcaagagg aggacggctg ttcatgccgg ttcccagagg aggaggaagg cggctgcgaa  1140
ctgcgcgtga aattcagccg cagcgcagat gctccagcct acaagcaggg gcagaaccag  1200
ctctacaacg aactcaatct tggtcggaga gaggagtacg acgtgctgga caagcggaga  1260
ggacgggacc cagaaatggg cgggaagccg cgcagaaaga atccccaaga gggcctgtac  1320
aacgagctcc aaaaggataa gatggcagaa gcctatagcg agattggtat gaaaggggaa  1380
cgcagaagag gcaaaggcca cgacggactg taccagggac tcagcaccgc caccaaggac  1440
acctatgacg ctcttcacat gcaggccctg ccgcctcgg                         1479

SEQ ID NO: 134         moltype = DNA  length = 1470
FEATURE                Location/Qualifiers
misc_feature           1..1470
                       note = source = /note="Description of Artificial Sequence:
                        Syntheticpolynucleotide"
source                 1..1470
                       mol_type = other DNA
                       organism = synthetic construct
SEQUENCE: 134
atggccctcc ctgtcaccgc cctgctgctt ccgctggctc ttctgctcca cgccgctcgg  60
ccccaaatca ctctgaaaga atctggaccg gccctggtta agccgactca aacgctcacc  120
cttacttgca ccttcagcgg attctcactc agcactgctg gtgtgcacgt cggatggatt  180
agacagccgc ctggaaaggc cctggaatgg ctcgccctca tctcctgggc cgatgacaag  240
agatacaggc cctcgcttcg atcccggttg gacattaccc gggtgacctc gaaagatcag  300
gtggtgctct caatgaccaa tatgcagccg gaggacaccg ctacgtacta ctgcgcactg  360
caaggatttg acggctacga ggctaactgg ggaccaggta ctctggtcac cgtgagctcc  420
ggcgggggag gatcaggcgg ggggggtca ggaggcggag gctccggtgg aggaggatcg  480
gatatcgtca tgacccagtc cccaagctcg ctgagcgcgt cagcgggcga ccgcgtgact  540
atcacttgcc gggccagccg cggcatctcc tccgcactgg cgtggtacca gcagaagcct  600
ggaaaaccgc caaagctcct gatctatgat gcctccagcc tggagtcagg tgtccccagc  660
cgcttctcgg gttcgggctc gggaaccgac ttcactttga ccatcgactc gctggaaccg  720
gaagatttcg caacctacta ctgtcagcag tcctactcga ccccttggac ttttggacaa  780
gggacgaagg tggacatcaa gaccactacc ccagcaccga ggccacccac cccggctcct  840
accatcgcct cccagcctct gtccctgcgt ccggaggcat gtagacccgc agctggtggg  900
gccgtgcata cccggggtct tgacttcgcc tgcgatatct acatttgggc ccctctggct  960
ggtacttgcg gggtcctgct gctttcactc gtgatcactc tttactgtaa gcgcggtcgg  1020
aagaagctgc tgtacatctt taagcaaccc ttcatgaggc ctgtgcagac tactcaagag  1080
gaggacggct gttcatgccg gttcccagag gaggaggaag gcggctgcga actgcgcgtg  1140
aaattcagcc gcagcgcaga tgctccagcc tacaagcagg ggcagaacca gctctacaac  1200
gaactcaatc ttggtcggag agaggagtac gacgtgctgg acaagcggag aggacgggac  1260
ccagaaatgg gcgggaagcc gcgcagaaag aatccccaag agggcctgta caacgagctc  1320
caaaaggata agatggcaga agcctatagc gagattggta tgaaagggga acgcagaaga  1380
ggcaaaggcc acgacggact gtaccaggga ctcagcaccg ccaccaagga cacctatgac  1440
gctcttcaca tgcaggccct gccgcctcgg                                   1470

SEQ ID NO: 135         moltype = AA  length = 5
FEATURE                Location/Qualifiers
REGION                 1..5
                       note = source = /note="Description of Artificial Sequence:
                        Syntheticpeptide"
```

```
source                  1..5
                        mol_type = protein
                        organism = synthetic construct
SEQUENCE: 135
GGGGS                                                                 5

SEQ ID NO: 136          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 136
GYTFTGYYMH                                                            10

SEQ ID NO: 137          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 137
GFTFSSYWMH                                                            10

SEQ ID NO: 138          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 138
GYTFTDYYMH                                                            10

SEQ ID NO: 139          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 139
GYTFTSYYMH                                                            10

SEQ ID NO: 140          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 140
GFTFSSYAMH                                                            10

SEQ ID NO: 141          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 141
GYPFTGYSLH                                                            10

SEQ ID NO: 142          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
```

```
                         organism = synthetic construct
SEQUENCE: 142
GYTFTSYYMH                                                                 10

SEQ ID NO: 143           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 143
GYTFTSYGIS                                                                 10

SEQ ID NO: 144           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 144
GYTFTGYYMH                                                                 10

SEQ ID NO: 145           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 145
GFIFSDYYMG                                                                 10

SEQ ID NO: 146           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 146
GFTFRGYYIH                                                                 10

SEQ ID NO: 147           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 147
GFTFDDYAMH                                                                 10

SEQ ID NO: 148           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 148
GFTFSSYWMH                                                                 10

SEQ ID NO: 149           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 149
```

-continued

```
GFTFSSYGMH                                                  10

SEQ ID NO: 150         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 150
GFTFSSYAMS                                                  10

SEQ ID NO: 151         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 151
GYTFTSYYMH                                                  10

SEQ ID NO: 152         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 152
GDTSTRHYIH                                                  10

SEQ ID NO: 153         moltype = AA  length = 10
FEATURE                Location/Qualifiers
REGION                 1..10
                       note = source = /note="Description of Artificial Sequence:
                        Syntheticpeptide"
source                 1..10
                       mol_type = protein
                       organism = synthetic construct
SEQUENCE: 153
GYTFTNYYMH                                                  10

SEQ ID NO: 154         moltype = AA  length = 12
FEATURE                Location/Qualifiers
REGION                 1..12
                       note = source = /note="Description of Artificial Sequence:
                        Syntheticpeptide"
source                 1..12
                       mol_type = protein
                       organism = synthetic construct
SEQUENCE: 154
GFSLSTAGVH VG                                               12

SEQ ID NO: 155         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 155
RINPNSGGTN YAQKFQG                                          17

SEQ ID NO: 156         moltype = AA  length = 17
FEATURE                Location/Qualifiers
REGION                 1..17
                       note = source = /note="Description of Artificial Sequence:
                        Syntheticpeptide"
source                 1..17
                       mol_type = protein
                       organism = synthetic construct
SEQUENCE: 156
WINPNSGGTN YAQKFQG                                          17
```

```
SEQ ID NO: 157          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 157
RINTDGSTTT YADSVEG                                                  17

SEQ ID NO: 158          moltype = AA  length = 16
FEATURE                 Location/Qualifiers
REGION                  1..16
                        note = source = /note="Description of Artificial Sequence:
                         Syntheticpeptide"
source                  1..16
                        mol_type = protein
                        organism = synthetic construct
SEQUENCE: 158
IINPSGGSTS YAQKFQ                                                   16

SEQ ID NO: 159          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 159
WINPNSGGTN YAQKFQG                                                  17

SEQ ID NO: 160          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 160
IINPSGGSTG YAQKFQG                                                  17

SEQ ID NO: 161          moltype = AA  length = 16
FEATURE                 Location/Qualifiers
REGION                  1..16
                        note = source = /note="Description of Artificial Sequence:
                         Syntheticpeptide"
source                  1..16
                        mol_type = protein
                        organism = synthetic construct
SEQUENCE: 161
WISAYNGNTN YAQKLQ                                                   16

SEQ ID NO: 162          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 162
WINPNSGGTN YAQNFQG                                                  17

SEQ ID NO: 163          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 163
RINPNSGGTN YAQKFQG                                                  17

SEQ ID NO: 164          moltype = AA  length = 17
FEATURE                 Location/Qualifiers
```

-continued

```
REGION                  1..17
                        note = source = /note="Description of Artificial Sequence:
                         Syntheticpeptide"
source                  1..17
                        mol_type = protein
                        organism = synthetic construct
SEQUENCE: 164
YIGRSGSSMY YADSVKG                                                          17

SEQ ID NO: 165          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 165
IINPSGGSRA YAQKFQG                                                          17

SEQ ID NO: 166          moltype = AA  length = 16
FEATURE                 Location/Qualifiers
REGION                  1..16
                        note = source = /note="Description of Artificial Sequence:
                         Syntheticpeptide"
source                  1..16
                        mol_type = protein
                        organism = synthetic construct
SEQUENCE: 166
GISWNSGSIG YADSVK                                                           16

SEQ ID NO: 167          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 167
GISWNSGSTG YADSVKG                                                          17

SEQ ID NO: 168          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 168
RINSDGSSTS YADSVKG                                                          17

SEQ ID NO: 169          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 169
VISYDGSNKY YADSVKG                                                          17

SEQ ID NO: 170          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 170
AISGSGGSTY YADSVKG                                                          17

SEQ ID NO: 171          moltype = AA  length = 17
FEATURE                 Location/Qualifiers
REGION                  1..17
                        note = source = /note="Description of Artificial Sequence:
```

```
                         Syntheticpeptide"
source                  1..17
                        mol_type = protein
                        organism = synthetic construct
SEQUENCE: 171
IINPSGGSTS YAQKFQG                                                   17

SEQ ID NO: 172          moltype = AA  length = 21
FEATURE                 Location/Qualifiers
REGION                  1..21
                        note = source = /note="Description of Artificial Sequence:
                         Syntheticpeptide"
source                  1..21
                        mol_type = protein
                        organism = synthetic construct
SEQUENCE: 172
VINPTTGPAT GSPAYAQMLQ G                                              21

SEQ ID NO: 173          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 173
IINPSGGYTT YAQKFQG                                                   17

SEQ ID NO: 174          moltype = AA  length = 16
FEATURE                 Location/Qualifiers
REGION                  1..16
                        note = source = /note="Description of Artificial Sequence:
                         Syntheticpeptide"
source                  1..16
                        mol_type = protein
                        organism = synthetic construct
SEQUENCE: 174
LISWADDKRY RPSLRS                                                    16

SEQ ID NO: 175          moltype = AA  length = 8
FEATURE                 Location/Qualifiers
REGION                  1..8
                        note = source = /note="Description of Artificial Sequence:
                         Syntheticpeptide"
source                  1..8
                        mol_type = protein
                        organism = synthetic construct
SEQUENCE: 175
GRYYGMDV                                                             8

SEQ ID NO: 176          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 176
DLRRTVVTPR AYYGMDV                                                   17

SEQ ID NO: 177          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 177
GEWDGSYYYD Y                                                         11

SEQ ID NO: 178          moltype = AA  length = 5
FEATURE                 Location/Qualifiers
REGION                  1..5
                        note = source = /note="Description of Artificial Sequence:
                         Syntheticpeptide"
source                  1..5
```

```
                         mol_type = protein
                         organism = synthetic construct
SEQUENCE: 178
GHWAV                                                                     5

SEQ ID NO: 179           moltype = AA  length = 6
FEATURE                  Location/Qualifiers
REGION                   1..6
                         note = source = /note="Description of Artificial Sequence:
                          Syntheticpeptide"
source                   1..6
                         mol_type = protein
                         organism = synthetic construct
SEQUENCE: 179
GWDFDY                                                                    6

SEQ ID NO: 180           moltype = AA  length = 17
FEATURE                  Location/Qualifiers
REGION                   1..17
                         note = source = /note="Description of Artificial Sequence:
                          Syntheticpeptide"
source                   1..17
                         mol_type = protein
                         organism = synthetic construct
SEQUENCE: 180
YRLIAVAGDY YYYGMDV                                                        17

SEQ ID NO: 181           moltype = AA  length = 12
FEATURE                  Location/Qualifiers
REGION                   1..12
                         note = source = /note="Description of Artificial Sequence:
                          Syntheticpeptide"
source                   1..12
                         mol_type = protein
                         organism = synthetic construct
SEQUENCE: 181
WKVSSSSPAF DY                                                             12

SEQ ID NO: 182           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 182
DHYGGNSLFY                                                                10

SEQ ID NO: 183           moltype = AA  length = 12
FEATURE                  Location/Qualifiers
REGION                   1..12
                         note = source = /note="Description of Artificial Sequence:
                          Syntheticpeptide"
source                   1..12
                         mol_type = protein
                         organism = synthetic construct
SEQUENCE: 183
GGYSSSSDAF DI                                                             12

SEQ ID NO: 184           moltype = AA  length = 13
FEATURE                  Location/Qualifiers
REGION                   1..13
                         note = source = /note="Description of Artificial Sequence:
                          Syntheticpeptide"
source                   1..13
                         mol_type = protein
                         organism = synthetic construct
SEQUENCE: 184
VAGGIYYYYG MDV                                                            13

SEQ ID NO: 185           moltype = AA  length = 6
FEATURE                  Location/Qualifiers
REGION                   1..6
                         note = source = /note="Description of Artificial Sequence:
                          Syntheticpeptide"
source                   1..6
                         mol_type = protein
                         organism = synthetic construct
```

```
SEQUENCE: 185
GWDFDY                                                      6

SEQ ID NO: 186          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 186
TTTSYAFDI                                                   9

SEQ ID NO: 187          moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 187
SPVVAATEDF QH                                               12

SEQ ID NO: 188          moltype = AA  length = 13
FEATURE                 Location/Qualifiers
REGION                  1..13
                        note = source = /note="Description of Artificial Sequence:
                         Syntheticpeptide"
source                  1..13
                        mol_type = protein
                        organism = synthetic construct
SEQUENCE: 188
TASCGGDCYY LDY                                              13

SEQ ID NO: 189          moltype = AA  length = 13
FEATURE                 Location/Qualifiers
REGION                  1..13
                        note = source = /note="Description of Artificial Sequence:
                         Syntheticpeptide"
source                  1..13
                        mol_type = protein
                        organism = synthetic construct
SEQUENCE: 189
DGSSSWSWGY FDY                                              13

SEQ ID NO: 190          moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 190
DSSSWYGGGS AFDI                                             14

SEQ ID NO: 191          moltype = AA  length = 14
FEATURE                 Location/Qualifiers
REGION                  1..14
                        note = source = /note="Description of Artificial Sequence:
                         Syntheticpeptide"
source                  1..14
                        mol_type = protein
                        organism = synthetic construct
SEQUENCE: 191
DSSSWYGGGS AFDI                                             14

SEQ ID NO: 192          moltype = AA  length = 13
FEATURE                 Location/Qualifiers
REGION                  1..13
                        note = source = /note="Description of Artificial Sequence:
                         Syntheticpeptide"
source                  1..13
                        mol_type = protein
                        organism = synthetic construct
SEQUENCE: 192
TGWVGSYYYY MDV                                              13
```

```
SEQ ID NO: 193          moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 193
GYSRYYYYGM DV                                                             12

SEQ ID NO: 194          moltype = AA  length = 13
FEATURE                 Location/Qualifiers
REGION                  1..13
                        note = source = /note="Description of Artificial Sequence:
                         Syntheticpeptide"
source                  1..13
                        mol_type = protein
                        organism = synthetic construct
SEQUENCE: 194
REAAAGHDWY FDL                                                            13

SEQ ID NO: 195          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 195
SPRVTTGYFD Y                                                              11

SEQ ID NO: 196          moltype = AA  length = 13
FEATURE                 Location/Qualifiers
REGION                  1..13
                        note = source = /note="Description of Artificial Sequence:
                         Syntheticpeptide"
source                  1..13
                        mol_type = protein
                        organism = synthetic construct
SEQUENCE: 196
SVVGRSAPYY FDY                                                            13

SEQ ID NO: 197          moltype = AA  length = 13
FEATURE                 Location/Qualifiers
REGION                  1..13
                        note = source = /note="Description of Artificial Sequence:
                         Syntheticpeptide"
source                  1..13
                        mol_type = protein
                        organism = synthetic construct
SEQUENCE: 197
IRSCGGDCYY FDN                                                            13

SEQ ID NO: 198          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 198
QGFDGYEAN                                                                 9

SEQ ID NO: 199          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 199
RASQSVSSNF A                                                              11

SEQ ID NO: 200          moltype = AA  length = 11
```

```
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 200
QASQDISNSL N                                                                11

SEQ ID NO: 201          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 201
RASQSINTYL N                                                                11

SEQ ID NO: 202          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 202
RASQSISDRL A                                                                11

SEQ ID NO: 203          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 203
RASQSIRYYL S                                                                11

SEQ ID NO: 204          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 204
RASQGVGRWL A                                                                11

SEQ ID NO: 205          moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 205
RASQSVYTKY LG                                                               12

SEQ ID NO: 206          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 206
RASQDSGTWL A                                                                11

SEQ ID NO: 207          moltype = AA  length = 11
FEATURE                 Location/Qualifiers
REGION                  1..11
```

```
                        note = source = /note="Description of Artificial Sequence:
                         Syntheticpeptide"
source                  1..11
                        mol_type = protein
                        organism = synthetic construct
SEQUENCE: 207
RASQDISSAL A                                                       11

SEQ ID NO: 208          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 208
KSSHSVLYNR NNKNYLA                                                 17

SEQ ID NO: 209          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 209
RASQSIRYYL S                                                       11

SEQ ID NO: 210          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 210
RASQSISTWL A                                                       11

SEQ ID NO: 211          moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 211
RASQSVTSNY LA                                                      12

SEQ ID NO: 212          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 212
RASENVNIWL A                                                       11

SEQ ID NO: 213          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 213
QGDALRSYYA S                                                       11

SEQ ID NO: 214          moltype = AA  length = 11
FEATURE                 Location/Qualifiers
REGION                  1..11
                        note = source = /note="Description of Artificial Sequence:
                         Syntheticpeptide"
```

```
source                  1..11
                        mol_type = protein
                        organism = synthetic construct
SEQUENCE: 214
QGDSLRSYYA S                                                              11

SEQ ID NO: 215          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 215
QGDSLRSYYA S                                                              11

SEQ ID NO: 216          moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 216
RASQSVSSNY LA                                                             12

SEQ ID NO: 217          moltype = AA  length = 12
FEATURE                 Location/Qualifiers
REGION                  1..12
                        note = source = /note="Description of Artificial Sequence:
                         Syntheticpeptide"
source                  1..12
                        mol_type = protein
                        organism = synthetic construct
SEQUENCE: 217
RASQSVYTKY LG                                                             12

SEQ ID NO: 218          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 218
RASQSISSYL N                                                              11

SEQ ID NO: 219          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 219
RASQSISSWL A                                                              11

SEQ ID NO: 220          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 220
RASQGISDYS                                                                10

SEQ ID NO: 221          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
```

```
                        organism = synthetic construct
SEQUENCE: 221
RASENVNIWL A                                                 11

SEQ ID NO: 222          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 222
RASRGISSAL A                                                 11

SEQ ID NO: 223          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 223
DASNRAT                                                      7

SEQ ID NO: 224          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 224
DASTLET                                                      7

SEQ ID NO: 225          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 225
AASSLQS                                                      7

SEQ ID NO: 226          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 226
KASSLES                                                      7

SEQ ID NO: 227          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 227
TASILQN                                                      7

SEQ ID NO: 228          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 228
```

```
AASTLQS                                                                7

SEQ ID NO: 229          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 229
DASTRAT                                                                7

SEQ ID NO: 230          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 230
DASTLED                                                                7

SEQ ID NO: 231          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 231
DASSLES                                                                7

SEQ ID NO: 232          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 232
WASTRKS                                                                7

SEQ ID NO: 233          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 233
TASILQN                                                                7

SEQ ID NO: 234          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 234
KASTLES                                                                7

SEQ ID NO: 235          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 235
GASTRAT                                                                7
```

```
SEQ ID NO: 236          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 236
KSSSLAS                                                                    7

SEQ ID NO: 237          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 237
GKNNRPS                                                                    7

SEQ ID NO: 238          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 238
GRSRRPS                                                                    7

SEQ ID NO: 239          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 239
GKNNRPS                                                                    7

SEQ ID NO: 240          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 240
DVSTRAT                                                                    7

SEQ ID NO: 241          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 241
DASTRAT                                                                    7

SEQ ID NO: 242          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 242
AASSLQS                                                                    7

SEQ ID NO: 243          moltype = AA  length = 7
FEATURE                 Location/Qualifiers
```

```
REGION                 1..7
                       note = source = /note="Description of Artificial Sequence:
                        Syntheticpeptide"
source                 1..7
                       mol_type = protein
                       organism = synthetic construct
SEQUENCE: 243
KASSLES                                                                    7

SEQ ID NO: 244         moltype = AA  length = 7
FEATURE                Location/Qualifiers
REGION                 1..7
                       note = source = /note="Description of Artificial Sequence:
                        Syntheticpeptide"
source                 1..7
                       mol_type = protein
                       organism = synthetic construct
SEQUENCE: 244
AASTLQS                                                                    7

SEQ ID NO: 245         moltype = AA  length = 7
FEATURE                Location/Qualifiers
REGION                 1..7
                       note = source = /note="Description of Artificial Sequence:
                        Syntheticpeptide"
source                 1..7
                       mol_type = protein
                       organism = synthetic construct
SEQUENCE: 245
KSSSLAS                                                                    7

SEQ ID NO: 246         moltype = AA  length = 7
FEATURE                Location/Qualifiers
REGION                 1..7
                       note = source = /note="Description of Artificial Sequence:
                        Syntheticpeptide"
source                 1..7
                       mol_type = protein
                       organism = synthetic construct
SEQUENCE: 246
DASSLES                                                                    7

SEQ ID NO: 247         moltype = AA  length = 9
FEATURE                Location/Qualifiers
REGION                 1..9
                       note = source = /note="Description of Artificial Sequence:
                        Syntheticpeptide"
source                 1..9
                       mol_type = protein
                       organism = synthetic construct
SEQUENCE: 247
HQRSNWLYT                                                                  9

SEQ ID NO: 248         moltype = AA  length = 9
FEATURE                Location/Qualifiers
REGION                 1..9
                       note = source = /note="Description of Artificial Sequence:
                        Syntheticpeptide"
source                 1..9
                       mol_type = protein
                       organism = synthetic construct
SEQUENCE: 248
QQHDNLPLT                                                                  9

SEQ ID NO: 249         moltype = AA  length = 8
FEATURE                Location/Qualifiers
REGION                 1..8
                       note = source = /note="Description of Artificial Sequence:
                        Syntheticpeptide"
source                 1..8
                       mol_type = protein
                       organism = synthetic construct
SEQUENCE: 249
QQSFSPLT                                                                   8

SEQ ID NO: 250         moltype = AA  length = 10
FEATURE                Location/Qualifiers
REGION                 1..10
                       note = source = /note="Description of Artificial Sequence:
```

```
                         Syntheticpeptide"
source                  1..10
                        mol_type = protein
                        organism = synthetic construct
SEQUENCE: 250
QQYGHLPMYT                                                    10

SEQ ID NO: 251          moltype = AA  length = 8
FEATURE                 Location/Qualifiers
REGION                  1..8
                        note = source = /note="Description of Artificial Sequence:
                         Syntheticpeptide"
source                  1..8
                        mol_type = protein
                        organism = synthetic construct
SEQUENCE: 251
LQTYTTPD                                                      8

SEQ ID NO: 252          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 252
QQANSFPLT                                                     9

SEQ ID NO: 253          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 253
QHYGGSPLIT                                                    10

SEQ ID NO: 254          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 254
QQYNSYPLT                                                     9

SEQ ID NO: 255          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 255
QQFSSYPLT                                                     9

SEQ ID NO: 256          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 256
QQTQTFPLT                                                     9

SEQ ID NO: 257          moltype = AA  length = 8
FEATURE                 Location/Qualifiers
REGION                  1..8
                        note = source = /note="Description of Artificial Sequence:
                         Syntheticpeptide"
source                  1..8
```

```
                         mol_type = protein
                         organism = synthetic construct
SEQUENCE: 257
LQTYTTPD                                                                  8

SEQ ID NO: 258           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 258
QQYNTYSPYT                                                                10

SEQ ID NO: 259           moltype = AA  length = 9
FEATURE                  Location/Qualifiers
REGION                   1..9
                         note = source = /note="Description of Artificial Sequence:
                          Syntheticpeptide"
source                   1..9
                         mol_type = protein
                         organism = synthetic construct
SEQUENCE: 259
QQYGSAPVT                                                                 9

SEQ ID NO: 260           moltype = AA  length = 9
FEATURE                  Location/Qualifiers
REGION                   1..9
                         note = source = /note="Description of Artificial Sequence:
                          Syntheticpeptide"
source                   1..9
                         mol_type = protein
                         organism = synthetic construct
SEQUENCE: 260
QQYQSYPLT                                                                 9

SEQ ID NO: 261           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
SEQUENCE: 261
NSRDSSGYPV                                                                10

SEQ ID NO: 262           moltype = AA  length = 11
FEATURE                  Location/Qualifiers
REGION                   1..11
                         note = source = /note="Description of Artificial Sequence:
                          Syntheticpeptide"
source                   1..11
                         mol_type = protein
                         organism = synthetic construct
SEQUENCE: 262
NSRDNTANHY V                                                              11

SEQ ID NO: 263           moltype = AA  length = 11
FEATURE                  Location/Qualifiers
REGION                   1..11
                         note = source = /note="Description of Artificial Sequence:
                          Syntheticpeptide"
source                   1..11
                         mol_type = protein
                         organism = synthetic construct
SEQUENCE: 263
NSRGSSGNHY V                                                              11

SEQ ID NO: 264           moltype = AA  length = 10
FEATURE                  Location/Qualifiers
REGION                   1..10
                         note = source = /note="Description of Artificial Sequence:
                          Syntheticpeptide"
source                   1..10
                         mol_type = protein
                         organism = synthetic construct
```

```
SEQUENCE: 264
QQRSNWPPWT                                                          10

SEQ ID NO: 265          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 265
QHYGGSPLIT                                                          10

SEQ ID NO: 266          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 266
QQSYSIPLT                                                           9

SEQ ID NO: 267          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 267
QQYSSYPLT                                                           9

SEQ ID NO: 268          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 268
QQYYSYPLT                                                           9

SEQ ID NO: 269          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 269
QQYQSYPLT                                                           9

SEQ ID NO: 270          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 270
QQSYSTPWT                                                           9

SEQ ID NO: 271          moltype =   length =
SEQUENCE: 271
000

SEQ ID NO: 272          moltype =   length =
SEQUENCE: 272
000

SEQ ID NO: 273          moltype =   length =
SEQUENCE: 273
```

```
000

SEQ ID NO: 274          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 274
VISYDGSNKY YADSVKG                                                  17

SEQ ID NO: 275          moltype = AA  length = 239
FEATURE                 Location/Qualifiers
REGION                  1..239
                        note = source = /note="Description of Artificial Sequence:
                         Syntheticpolypeptide"
source                  1..239
                        mol_type = protein
                        organism = synthetic construct
SEQUENCE: 275
QVQLQQSGPE LEKPGASVKI SCKASGYSFT GYTMNWVKQS HGKSLEWIGL ITPYNGASSY  60
NQKFRGKATL TVDKSSSTAY MDLLSLTSED SAVYFCARGG YDGRGFDYWG QGTTVTVSSG  120
GGGSGGGGSG GGGSDIELTQ SPAIMSASPG EKVTMTCSAS SSVSYMHWYQ QKSGTSPKRW  180
IYDTSKLASG VPGRFSGSGS GNSYSLTISS VEAEDDATYY CQQWSGYPLT FGAGTKLEI   239

SEQ ID NO: 276          moltype =   length =
SEQUENCE: 276
000

SEQ ID NO: 277          moltype =   length =
SEQUENCE: 277
000

SEQ ID NO: 278          moltype = AA  length = 383
FEATURE                 Location/Qualifiers
REGION                  1..383
                        note = source = /note="Description of Artificial Sequence:
                         Syntheticpolypeptide"
source                  1..383
                        mol_type = protein
                        organism = synthetic construct
SEQUENCE: 278
MALPVTALLL PLALLLHAAR PQVQLQQSGP ELEKPGASVK ISCKASGYSF TGYTMNWVKQ  60
SHGKSLEWIG LITPYNGASS YNQKFRGKAT LTVDKSSSTA YMDLLSLTSE DSAVYFCARG  120
GYDGRGFDYW GQGTTVTVSS GGGGSGGGGS GGGGSDIELT QSPAIMSASP GEKVTMTCSA  180
SSSVSYMHWY QQKSGTSPKR WIYDTSKLAS GVPGRFSGSG SGNSYSLTIS SVEAEDDATY  240
YCQQWSGYPL TFGAGTKLEI TTTPAPRPPT PAPTIASQPL SLRPEACRPA AGGAVHTRGL  300
DFACDIYIWA PLAGTCGVLL LSLVITLYCK RGRKKLLYIF KQPFMRPVQT TQEEDGCSCR  360
FPEEEEGGCE LRVKFSRSAD APA                                          383

SEQ ID NO: 279          moltype = DNA  length = 717
FEATURE                 Location/Qualifiers
misc_feature            1..717
                        note = source = /note="Description of Artificial Sequence:
                         Syntheticpolynucleotide"
source                  1..717
                        mol_type = other DNA
                        organism = synthetic construct
SEQUENCE: 279
caagtccagc tccagcagtc gggcccagag ttggagaagc ctggggcgag cgtgaagatc  60
tcatgcaaag cctcaggcta ctcctttact ggatacacga tgaattgggt gaaacagtcg  120
catggaaagt cactggaatg gatcggtctg attacgccct acaacggcgc ctccagctac  180
aaccagaagt tcaggggaaa ggcgaccctt actgtcgaca agtcgtcaag caccgcctac  240
atggacctcc tgtccctgac ctccgaagat agcgcggtct acttttgtgc acgcggaggt  300
tacgatggac ggggattcga ctactggggc cagggaacca ctgtcaccgt gtcgagcgga  360
ggcggaggga gcggaggagg aggcagcgga ggtggagggt cggatatcga actcactcag  420
tccccagcaa tcatgtccgc ttcaccggga gaaaaggtga ccatgacttg ctcggcctcc  480
tcgtccgtgt catacatgca ctggtaccaa caaaaatcgg ggacctcccc taagagatgg  540
atctacgata ccagcaaact ggcttcaggc gtgccgggac gcttctcggg ttcggggagc  600
ggaaattcgt attcgttgac catttcgtcc gtggaagccg aggacgacgc aacttattac  660
tgccaacagt ggtcaggcta cccgctcact ttcggagccg gcactaagct ggagatc     717

SEQ ID NO: 280          moltype = DNA  length = 1149
FEATURE                 Location/Qualifiers
misc_feature            1..1149
                        note = source = /note="Description of Artificial Sequence:
                         Syntheticpolynucleotide"
```

```
source                  1..1149
                        mol_type = other DNA
                        organism = synthetic construct
SEQUENCE: 280
atggccctcc ctgtcaccgc cctgctgctt ccgctggctc ttctgctcca cgccgctcgg  60
ccccaagtcc agctccagca gtcgggccca gagttggaga agcctggggc gagcgtgaag  120
atctcatgca aagcctcagg ctactccttt actggataca cgatgaattg ggtgaaacag  180
tcgcatggaa agtcactgga atggatcggt ctgattacgc cctacaacgg cgcctccagc  240
tacaaccaga agttcagggg aaaggcgacc cttactgtcg acaagtcgtc aagcaccgcc  300
tacatggacc tcctgtccct gacctccgaa gatagcgcgg tctacttttg tgcacgcgga  360
ggttacgatg gacggggatt cgactactgg ggccagggaa ccactgtcac cgtgtcgagc  420
ggaggcggag ggagcggagg aggaggcagc ggaggtggag ggtcggatat cgaactcact  480
cagtccccag caatcatgtc cgcttcaccg ggagaaaagg tgaccatgac ttgctcggcc  540
tcctcgtccg tgtcatacat gcactggtac caacaaaaat cggggacctc ccctaagaga  600
tggatctacg ataccagcaa actggcttca ggcgtgccgg gacgcttctc gggttcgggg  660
agcggaaatt cgtattcgtt gaccatttcg tccgtggaag ccgaggacga cgcaacttat  720
tactgccaac agtggtcagg ctacccgctc actttcggag ccggcactaa gctggagatc  780
accactaccc cagcaccgag gccacccacc ccggctccta ccatcgcctc ccagcctctg  840
tccctgcgtc cggaggcatg tagacccgca gctggtgggg ccgtgcatac ccggggtctt  900
gacttcgcct gcgatatcta catttgggcc cctctggctg gtacttgcgg ggtcctgctg  960
ctttcactcg tgatcactct ttactgtaag cgcggtcgga agaagctgct gtacatcttt  1020
aagcaaccct tcatgaggcc tgtgcagact actcaagagg aggacggctg ttcatgccgg  1080
ttcccagagg aggaggaagg cggctgcgaa ctgcgcgtga aattcagccg cagcgcagat  1140
gctccagcc                                                          1149

SEQ ID NO: 281          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 281
GYSFTGYTMN                                                         10

SEQ ID NO: 282          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 282
LITPYNGASS YNQKFRG                                                 17

SEQ ID NO: 283          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 283
GGYDGRGFDY                                                         10

SEQ ID NO: 284          moltype = AA  length = 10
FEATURE                 Location/Qualifiers
REGION                  1..10
                        note = source = /note="Description of Artificial Sequence:
                         Syntheticpeptide"
source                  1..10
                        mol_type = protein
                        organism = synthetic construct
SEQUENCE: 284
SASSSVSYMH                                                         10

SEQ ID NO: 285          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 285
DTSKLAS                                                            7
```

```
SEQ ID NO: 286          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 286
QQWSGYPLT                                                     9

SEQ ID NO: 287          moltype = AA  length = 5
FEATURE                 Location/Qualifiers
REGION                  1..5
                        note = source = /note="Description of Artificial Sequence:
                         Syntheticpeptide"
source                  1..5
                        mol_type = protein
                        organism = synthetic construct
SEQUENCE: 287
SYWMY                                                         5

SEQ ID NO: 288          moltype = AA  length = 17
FEATURE                 Location/Qualifiers
REGION                  1..17
                        note = source = /note="Description of Artificial Sequence:
                         Syntheticpeptide"
source                  1..17
                        mol_type = protein
                        organism = synthetic construct
SEQUENCE: 288
RIDPNSGSTK YNEKFKN                                            17

SEQ ID NO: 289          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 289
DYRKGLYAMD Y                                                  11

SEQ ID NO: 290          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 290
GYTFTSY                                                       7

SEQ ID NO: 291          moltype = AA  length = 6
FEATURE                 Location/Qualifiers
REGION                  1..6
                        note = source = /note="Description of Artificial Sequence:
                         Syntheticpeptide"
source                  1..6
                        mol_type = protein
                        organism = synthetic construct
SEQUENCE: 291
DPNSGS                                                        6

SEQ ID NO: 292          moltype = AA  length = 120
FEATURE                 Location/Qualifiers
REGION                  1..120
                        note = source = /note="Description of Artificial Sequence:
                         Syntheticpolypeptide"
source                  1..120
                        mol_type = protein
                        organism = synthetic construct
SEQUENCE: 292
QVHLQQPGAE LVKPGASVKL SCKASGYTFT SYWMYWVKQG PGRGLEWIGR IDPNSGSTKY  60
NEKFKNKATL TVDKSSSTAY MQLSSLTSED SAVYYCARDY RKGLYAMDYW GQGTSVTVSS  120
```

-continued

```
SEQ ID NO: 293          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 293
caggtccacc tgcagcagcc tggggctgag cttgtgaagc ctggggcttc agtgaagctg  60
tcctgcaagg cttctggcta caccttcacc agttactgga tgtactgggt gaaacagggg  120
cctggacgag gccttgagtg gattggaagg attgatccta atagtgggag tactaagtac  180
aatgagaagt tcaagaacaa ggccacactg actgtagaca aatcctccag cacagcctac  240
atgcagctca gcagcctgac atctgaggac tctgcggtct attattgtgc aagggactat  300
agaaaggggc tctatgctat ggactactgg ggtcaaggaa cctcagtcac cgtctcctca  360

SEQ ID NO: 294          moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 294
DIVMTQSHKF MSTSVGDRVS ITCKASQDVG TAVAWYQQKP GQSPKLLIYW ASTRHTGVPD  60
RFTGSGSGTD FTLTISNVQS EDLADYFCQQ YNSYPLTFGA GSKLELK                107

SEQ ID NO: 295          moltype = AA  length = 11
FEATURE                 Location/Qualifiers
REGION                  1..11
                        note = source = /note="Description of Artificial Sequence:
                         Syntheticpeptide"
source                  1..11
                        mol_type = protein
                        organism = synthetic construct
SEQUENCE: 295
KASQDVGTAV A                                                      11

SEQ ID NO: 296          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 296
WASTRHT                                                           7

SEQ ID NO: 297          moltype = AA  length = 9
FEATURE                 Location/Qualifiers
REGION                  1..9
                        note = source = /note="Description of Artificial Sequence:
                         Syntheticpeptide"
source                  1..9
                        mol_type = protein
                        organism = synthetic construct
SEQUENCE: 297
QQYNSYPLT                                                         9

SEQ ID NO: 298          moltype = AA  length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 298
SQDVGTA                                                           7

SEQ ID NO: 299          moltype =   length =
SEQUENCE: 299
000

SEQ ID NO: 300          moltype = AA  length = 6
FEATURE                 Location/Qualifiers
REGION                  1..6
```

```
                         note = source = /note="Description of Artificial Sequence:
                          Syntheticpeptide"
source                   1..6
                         mol_type = protein
                         organism = synthetic construct
SEQUENCE: 300
YNSYPL                                                                       6

SEQ ID NO: 301           moltype = DNA  length = 321
FEATURE                  Location/Qualifiers
misc_feature             1..321
                         note = source = /note="Description of Artificial Sequence:
                          Syntheticpolynucleotide"
source                   1..321
                         mol_type = other DNA
                         organism = synthetic construct
SEQUENCE: 301
gacattgtga tgacccagtc tcacaaattc atgtccacat cagtaggaga cagggtcagc  60
atcacctgca aggccagtca ggatgtgggt actgctgtag cctggtatca acagaaacca  120
gggcaatctc ctaaactact gatttactgg gcatccaccc ggcacactgg agtccctgat  180
cgcttcacag gcagtggatc tgggacagat ttcactctca ccattagcaa tgtgcagtct  240
gaagacttgg cagattattt ctgtcagcag tataacagct atcctctcac gttcggtgct  300
gggtccaagc tggagctgaa a                                            321

SEQ ID NO: 302           moltype = AA  length = 120
FEATURE                  Location/Qualifiers
REGION                   1..120
                         note = source = /note="Description of Artificial Sequence:
                          Syntheticpolypeptide"
source                   1..120
                         mol_type = protein
                         organism = synthetic construct
SEQUENCE: 302
EVQLQQSGAE LVKPGASVKL SCKASGYTFT SYWMYWVKQG PGRGLEWIGR IDPNSGSTKY  60
NEKFKNKATL TVDKSSSTAY MQLSSLTSED SAVYYCARDY RKGLYAMDYW GQGTTVTVSS  120

SEQ ID NO: 303           moltype = AA  length = 107
FEATURE                  Location/Qualifiers
REGION                   1..107
                         note = source = /note="Description of Artificial Sequence:
                          Syntheticpolypeptide"
source                   1..107
                         mol_type = protein
                         organism = synthetic construct
SEQUENCE: 303
DIMMTQSHKF MSTSVGDRVS ITCKASQDVG TAVAWYQQKP GQSPKLLIYW ASTRHTGVPD  60
RFTGSGSGTD FTLTISNVQS EDLADYFCQQ YNSYPLTFGQ GTKVEIK                107

SEQ ID NO: 304           moltype = AA  length = 120
FEATURE                  Location/Qualifiers
REGION                   1..120
                         note = source = /note="Description of Artificial Sequence:
                          Syntheticpolypeptide"
source                   1..120
                         mol_type = protein
                         organism = synthetic construct
SEQUENCE: 304
QVQLVQSGAE VKKPGASVKV SCKASGYTFT SYWMYWVRQA TGQGLEWMGR IDPNSGSTKY  60
NEKFKNRFTI SRDDSKNTAY LQMNSLKTED TAVYYCARDY RKGLYAMDYW GQGTTVTVSS  120

SEQ ID NO: 305           moltype = DNA  length = 360
FEATURE                  Location/Qualifiers
misc_feature             1..360
                         note = source = /note="Description of Artificial Sequence:
                          Syntheticpolynucleotide"
source                   1..360
                         mol_type = other DNA
                         organism = synthetic construct
SEQUENCE: 305
caggttcagc tggtgcagtc tggagctgag gtgaagaagc ctggggcctc agtgaaggtc  60
tcctgcaagg cttctggcta caccttcacc agttactgga tgtactgggt gcgacaggcc  120
actggacaag ggcttgagtg gatgggtagg attgatccta atagtgggag tactaagtac  180
aatgagaagt tcaagaacag attcaccatc tccagagatg attcaaagaa cacggcgtat  240
ctgcaaatga acagcctgaa aaccgaggac acggccgtgt attactgtgc aagggactat  300
agaaaggggc tctatgctat ggactactgg ggccagggca ccaccgtgac cgtgtcctcc  360

SEQ ID NO: 306           moltype = AA  length = 447
FEATURE                  Location/Qualifiers
REGION                   1..447
```

```
                         note = source = /note="Description of Artificial Sequence:
                          Syntheticpolypeptide"
source                   1..447
                         mol_type = protein
                         organism = synthetic construct
SEQUENCE: 306
QVQLVQSGAE VKKPGASVKV SCKASGYTFT SYWMYWVRQA TGQGLEWMGR IDPNSGSTKY  60
NEKFKNRFTI SRDDSKNTAY LQMNSLKTED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 307           moltype = DNA  length = 1341
FEATURE                  Location/Qualifiers
misc_feature             1..1341
                         note = source = /note="Description of Artificial Sequence:
                          Syntheticpolynucleotide"
source                   1..1341
                         mol_type = other DNA
                         organism = synthetic construct
SEQUENCE: 307
caggttcagc tggtgcagtc tggagctgag gtgaagaagc ctggggcctc agtgaaggtc  60
tcctgcaagg cttctggcta caccttcacc agttactgga tgtactgggt gcgacaggcc  120
actggacaag ggcttgagtg gatgggtagg attgatccta atagtgggag tactaagtac  180
aatgagaagt tcaagaacag attcaccatc tccagagatg attcaaagaa cacggcgtat  240
ctgcaaatga acagcctgaa aaccgaggac acggccgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                            1341

SEQ ID NO: 308           moltype = AA  length = 107
FEATURE                  Location/Qualifiers
REGION                   1..107
                         note = source = /note="Description of Artificial Sequence:
                          Syntheticpolypeptide"
source                   1..107
                         mol_type = protein
                         organism = synthetic construct
SEQUENCE: 308
DIVMTQTPLS LPVTPGEPAS ISCKASQDVG TAVAWYLQKP GQSPQLLIYW ASTRHTGIPA  60
RFSGSGSGTE FTLTISSLQS EDFAVYYCQQ YNSYPLTFGQ GTKVEIK                107

SEQ ID NO: 309           moltype = DNA  length = 321
FEATURE                  Location/Qualifiers
misc_feature             1..321
                         note = source = /note="Description of Artificial Sequence:
                          Syntheticpolynucleotide"
source                   1..321
                         mol_type = other DNA
                         organism = synthetic construct
SEQUENCE: 309
gatattgtga tgacccagac tccactctcc ctgcccgtca cccctggaga gccggcctcc  60
atctcctgca aggccagtca ggatgtgggt actgctgtag cctggtacct gcagaagcca  120
gggcagtctc cacagctcct gatctattgg gcatccaccc ggcacactgg gatcccagcc  180
aggttcagtg gcagtgggtc tgggacagag ttcactctca ccatcagcag cctgcagtct  240
gaagattttg cagtttatta ctgtcagcag tataacagct atcctctcac gttcggccaa  300
gggaccaagg tggaaatcaa a                                            321

SEQ ID NO: 310           moltype = AA  length = 214
FEATURE                  Location/Qualifiers
REGION                   1..214
```

```
                        note = source = /note="Description of Artificial Sequence:
                         Syntheticpolypeptide"
source                  1..214
                        mol_type = protein
                        organism = synthetic construct
SEQUENCE: 310
DIVMTQTPLS LPVTPGEPAS ISCKASQDVG TAVAWYLQKP GQSPQLLIYW ASTRHTGIPA  60
RFSGSGSGTE FTLTISSLQS EDFAVYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 311          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 311
gatattgtga tgacccagac tccactctcc ctgcccgtca cccctggaga gccggcctcc  60
atctcctgca aggccagtca ggatgtgggt actgctgtag cctggtacct gcagaagcca  120
gggcagtctc cacagctcct gatctattgg gcatccaccc ggcacactgg gatcccagcc  180
aggttcagtg gcagtgggtc tgggacagag ttcactctca ccatcagcag cctgcagtct  240
gaagattttg cagtttatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 312          moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 312
DIQMTQSPSS LSASVGDRVT ITCKASQDVG TAVAWYLQKP GQSPQLLIYW ASTRHTGVPS  60
RFSGSGSGTD FTLTISSLQP EDFATYYCQQ YNSYPLTFGQ GTKVEIK               107

SEQ ID NO: 313          moltype = DNA  length = 321
FEATURE                 Location/Qualifiers
misc_feature            1..321
                        note = source = /note="Description of Artificial Sequence:
                         Syntheticpolynucleotide"
source                  1..321
                        mol_type = other DNA
                        organism = synthetic construct
SEQUENCE: 313
gacatccaga tgacccagtc tccatcctcc ctgtctgcat ctgtaggaga cagagtcacc  60
atcacttgca aggccagtca ggatgtgggt actgctgtag cctggtacct gcagaagcca  120
gggcagtctc cacagctcct gatctattgg gcatccaccc ggcacactgg ggtcccatca  180
aggttcagcg gcagtggatc tgggacagat ttcactctca ccatcagcag cctgcagcct  240
gaagattttg caacttatta ctgtcagcag tataacagct atcctctcac gttcggccaa  300
gggaccaagg tggaaatcaa a                                           321

SEQ ID NO: 314          moltype = AA  length = 214
FEATURE                 Location/Qualifiers
REGION                  1..214
                        note = source = /note="Description of Artificial Sequence:
                         Syntheticpolypeptide"
source                  1..214
                        mol_type = protein
                        organism = synthetic construct
SEQUENCE: 314
DIQMTQSPSS LSASVGDRVT ITCKASQDVG TAVAWYLQKP GQSPQLLIYW ASTRHTGVPS  60
RFSGSGSGTD FTLTISSLQP EDFATYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 315          moltype = DNA  length = 642
FEATURE                 Location/Qualifiers
misc_feature            1..642
                        note = source = /note="Description of Artificial Sequence:
                         Syntheticpolynucleotide"
```

```
source                  1..642
                        mol_type = other DNA
                        organism = synthetic construct
SEQUENCE: 315
gacatccaga tgacccagtc tccatcctcc ctgtctgcat ctgtaggaga cagagtcacc  60
atcacttgca aggccagtca ggatgtgggt actgctgtag cctggtacct gcagaagcca  120
gggcagtctc cacagctcct gatctattgg gcatccaccc ggcacactgg ggtcccatca  180
aggttcagcg gcagtggatc tgggacagat ttcactctca ccatcagcag cctgcagcct  240
gaagattttg caacttatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 316          moltype = AA  length = 120
FEATURE                 Location/Qualifiers
REGION                  1..120
                        note = source = /note="Description of Artificial Sequence:
                         Syntheticpolypeptide"
source                  1..120
                        mol_type = protein
                        organism = synthetic construct
SEQUENCE: 316
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120

SEQ ID NO: 317          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 317
gaggtccagc tggtacagtc tggggctgag gtgaagaagc ctggggctac agtgaaaatc  60
tcctgcaagg tttctggcta caccttcacc agttactgga tgtactgggt gcgacaggcc  120
actggacaag ggcttgagtg gatgggtagg attgatccta atagtgggag tactaagtac  180
aatgagaagt tcaagaacag agtcacgatt accgcggaca aatccacgag cacagcctac  240
atggagctga gcagcctgag atctgaggac acggccgtgt attactgtgc aagggactat  300
agaaaggggc tctatgctat ggactactgg ggccagggca ccaccgtgac cgtgtcctcc  360

SEQ ID NO: 318          moltype = AA  length = 447
FEATURE                 Location/Qualifiers
REGION                  1..447
                        note = source = /note="Description of Artificial Sequence:
                         Syntheticpolypeptide"
source                  1..447
                        mol_type = protein
                        organism = synthetic construct
SEQUENCE: 318
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 319          moltype = DNA  length = 1341
FEATURE                 Location/Qualifiers
misc_feature            1..1341
                        note = source = /note="Description of Artificial Sequence:
                         Syntheticpolynucleotide"
source                  1..1341
                        mol_type = other DNA
                        organism = synthetic construct
SEQUENCE: 319
gaggtccagc tggtacagtc tggggctgag gtgaagaagc ctggggctac agtgaaaatc  60
tcctgcaagg tttctggcta caccttcacc agttactgga tgtactgggt gcgacaggcc  120
actggacaag ggcttgagtg gatgggtagg attgatccta atagtgggag tactaagtac  180
aatgagaagt tcaagaacag agtcacgatt accgcggaca aatccacgag cacagcctac  240
atggagctga gcagcctgag atctgaggac acggccgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
```

```
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                            1341

SEQ ID NO: 320         moltype = AA  length = 107
FEATURE                Location/Qualifiers
REGION                 1..107
                       note = source = /note="Description of Artificial Sequence:
                        Syntheticpolypeptide"
source                 1..107
                       mol_type = protein
                       organism = synthetic construct
SEQUENCE: 320
EIVLTQSPDF QSVTPKEKVT ITCKASQDVG TAVAWYLQKP GQSPQLLIYW ASTRHTGVPD  60
RFSGSGSGTD FTLKISRVEA EDVGVYYCQQ YNSYPLTFGQ GTKVEIK                107

SEQ ID NO: 321         moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 321
gaaattgtgc tgactcagtc tccagacttt cagtctgtga ctccaaagga gaaagtcacc  60
atcacctgca aggccagtca ggatgtgggt actgctgtag cctggtacct gcagaagcca  120
gggcagtctc cacagctcct gatctattgg gcatccaccc ggcacactgg ggtcccagac  180
aggttcagtg gcagtgggtc aggcactgat ttcacactga aaatcagcag ggtggaggct  240
gaggatgttg gagtttatta ctgtcagcag tataacagct atcctctcac gttcggccaa  300
gggaccaagg tggaaatcaa a                                            321

SEQ ID NO: 322         moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 322
EIVLTQSPDF QSVTPKEKVT ITCKASQDVG TAVAWYLQKP GQSPQLLIYW ASTRHTGVPD  60
RFSGSGSGTD FTLKISRVEA EDVGVYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 323         moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 323
gaaattgtgc tgactcagtc tccagacttt cagtctgtga ctccaaagga gaaagtcacc  60
atcacctgca aggccagtca ggatgtgggt actgctgtag cctggtacct gcagaagcca  120
gggcagtctc cacagctcct gatctattgg gcatccaccc ggcacactgg ggtcccagac  180
aggttcagtg gcagtgggtc aggcactgat ttcacactga aaatcagcag ggtggaggct  240
gaggatgttg gagtttatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642
```

-continued

```
SEQ ID NO: 324         moltype = AA  length = 120
FEATURE                Location/Qualifiers
REGION                 1..120
                       note = source = /note="Description of Artificial Sequence:
                        Syntheticpolypeptide"
source                 1..120
                       mol_type = protein
                       organism = synthetic construct
SEQUENCE: 324
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120

SEQ ID NO: 325         moltype = DNA  length = 360
FEATURE                Location/Qualifiers
misc_feature           1..360
                       note = source = /note="Description of Artificial Sequence:
                        Syntheticpolynucleotide"
source                 1..360
                       mol_type = other DNA
                       organism = synthetic construct
SEQUENCE: 325
gaagtgcagc tggtgcagtc tggagcagag gtgaaaaagc ccggggagtc tctgaggatc  60
tcctgtaagg gttctggcta caccttcacc agttactgga tgtactgggt gcgacaggcc  120
cctggacaag ggcttgagtg gatgggtagg attgatccta atagtgggag tactaagtac  180
aatgagaagt tcaagaacag agtcaccata tcagtagaca cgtccaagaa ccagttctcc  240
ctgaagctga gctctgtgac cgccgcggac acggctgtgt attactgtgc aagggactat  300
agaaaggggc tctatgctat ggactactgg ggccagggca ccaccgtgac cgtgtcctcc  360

SEQ ID NO: 326         moltype = AA  length = 447
FEATURE                Location/Qualifiers
REGION                 1..447
                       note = source = /note="Description of Artificial Sequence:
                        Syntheticpolypeptide"
source                 1..447
                       mol_type = protein
                       organism = synthetic construct
SEQUENCE: 326
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 327         moltype = DNA  length = 1341
FEATURE                Location/Qualifiers
misc_feature           1..1341
                       note = source = /note="Description of Artificial Sequence:
                        Syntheticpolynucleotide"
source                 1..1341
                       mol_type = other DNA
                       organism = synthetic construct
SEQUENCE: 327
gaagtgcagc tggtgcagtc tggagcagag gtgaaaaagc ccggggagtc tctgaggatc  60
tcctgtaagg gttctggcta caccttcacc agttactgga tgtactgggt gcgacaggcc  120
cctggacaag ggcttgagtg gatgggtagg attgatccta atagtgggag tactaagtac  180
aatgagaagt tcaagaacag agtcaccata tcagtagaca cgtccaagaa ccagttctcc  240
ctgaagctga gctctgtgac cgccgcggac acggctgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                          1341
```

```
SEQ ID NO: 328          moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 328
EIVLTQSPDF QSVTPKEKVT ITCKASQDVG TAVAWYLQKP GQSPQLLIYW ASTRHTGVPS  60
RFSGSGSGTD FTFTISSLQP EDIATYYCQQ YNSYPLTFGQ GTKVEIK                107

SEQ ID NO: 329          moltype = DNA  length = 321
FEATURE                 Location/Qualifiers
misc_feature            1..321
                        note = source = /note="Description of Artificial Sequence:
                         Syntheticpolynucleotide"
source                  1..321
                        mol_type = other DNA
                        organism = synthetic construct
SEQUENCE: 329
gaaattgtgc tgactcagtc tccagacttt cagtctgtga ctccaaagga gaaagtcacc  60
atcacctgca aggccagtca ggatgtgggt actgctgtag cctggtacct gcagaagcca  120
gggcagtctc cacagctcct gatctattgg gcatccaccc ggcacactgg ggtcccatca  180
aggttcagtg gaagtggatc tgggacagat tttactttca ccatcagcag cctgcagcct  240
gaagatattg caacatatta ctgtcagcag tataacagct atcctctcac gttcggccaa  300
gggaccaagg tggaaatcaa a                                            321

SEQ ID NO: 330          moltype = AA  length = 214
FEATURE                 Location/Qualifiers
REGION                  1..214
                        note = source = /note="Description of Artificial Sequence:
                         Syntheticpolypeptide"
source                  1..214
                        mol_type = protein
                        organism = synthetic construct
SEQUENCE: 330
EIVLTQSPDF QSVTPKEKVT ITCKASQDVG TAVAWYLQKP GQSPQLLIYW ASTRHTGVPS  60
RFSGSGSGTD FTFTISSLQP EDIATYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 331          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 331
gaaattgtgc tgactcagtc tccagacttt cagtctgtga ctccaaagga gaaagtcacc  60
atcacctgca aggccagtca ggatgtgggt actgctgtag cctggtacct gcagaagcca  120
gggcagtctc cacagctcct gatctattgg gcatccaccc ggcacactgg ggtcccatca  180
aggttcagtg gaagtggatc tgggacagat tttactttca ccatcagcag cctgcagcct  240
gaagatattg caacatatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 332          moltype = AA  length = 120
FEATURE                 Location/Qualifiers
REGION                  1..120
                        note = source = /note="Description of Artificial Sequence:
                         Syntheticpolypeptide"
source                  1..120
                        mol_type = protein
                        organism = synthetic construct
SEQUENCE: 332
EVQLVQSGAE VKKPGATVKI SCKVSGYTFT SYWMYWIRQS PSRGLEWLGR IDPNSGSTKY  60
NEKFKNRLTI SKDTSKNQVV LTMTNMDPVD TATYYCARDY RKGLYAMDYW GQGTTVTVSS  120

SEQ ID NO: 333          moltype = DNA  length = 360
FEATURE                 Location/Qualifiers
misc_feature            1..360
                        note = source = /note="Description of Artificial Sequence:
```

-continued

```
                         Syntheticpolynucleotide"
source                  1..360
                        mol_type = other DNA
                        organism = synthetic construct
SEQUENCE: 333
gaggtccagc tggtacagtc tggggctgag gtgaagaagc ctggggctac agtgaaaatc  60
tcctgcaagg tttctggcta caccttcacc agttactgga tgtactggat caggcagtcc  120
ccatcgagag gccttgagtg gctgggtagg attgatccta atagtgggag tactaagtac  180
aatgagaagt tcaagaacag actcaccatc tccaaggaca cctccaaaaa ccaggtggtc  240
cttacaatga ccaacatgga ccctgtggac acagccacgt attactgtgc aagggactat  300
agaaaggggc tctatgctat ggactactgg ggccagggca ccaccgtgac cgtgtcctcc  360

SEQ ID NO: 334          moltype = AA  length = 447
FEATURE                 Location/Qualifiers
REGION                  1..447
                        note = source = /note="Description of Artificial Sequence:
                         Syntheticpolypeptide"
source                  1..447
                        mol_type = protein
                        organism = synthetic construct
SEQUENCE: 334
EVQLVQSGAE VKKPGATVKI SCKVSGYTFT SYWMYWIRQS PSRGLEWLGR IDPNSGSTKY  60
NEKFKNRLTI SKDTSKNQVV LTMTNMDPVD TATYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 335          moltype = DNA  length = 1341
FEATURE                 Location/Qualifiers
misc_feature            1..1341
                        note = source = /note="Description of Artificial Sequence:
                         Syntheticpolynucleotide"
source                  1..1341
                        mol_type = other DNA
                        organism = synthetic construct
SEQUENCE: 335
gaggtccagc tggtacagtc tggggctgag gtgaagaagc ctggggctac agtgaaaatc  60
tcctgcaagg tttctggcta caccttcacc agttactgga tgtactggat caggcagtcc  120
ccatcgagag gccttgagtg gctgggtagg attgatccta atagtgggag tactaagtac  180
aatgagaagt tcaagaacag actcaccatc tccaaggaca cctccaaaaa ccaggtggtc  240
cttacaatga ccaacatgga ccctgtggac acagccacgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                           1341

SEQ ID NO: 336          moltype = AA  length = 120
FEATURE                 Location/Qualifiers
REGION                  1..120
                        note = source = /note="Description of Artificial Sequence:
                         Syntheticpolypeptide"
source                  1..120
                        mol_type = protein
                        organism = synthetic construct
SEQUENCE: 336
EVQLVQSGAE VKKPGESLRI SCKGSGYTFT SYWMYWIRQP PGKGLEWIGR IDPNSGSTKY  60
NEKFKNRVTI TADKSTSTAY MELSSLRSED TAVYYCARDY RKGLYAMDYW GQGTTVTVSS  120

SEQ ID NO: 337          moltype = DNA  length = 360
FEATURE                 Location/Qualifiers
misc_feature            1..360
                        note = source = /note="Description of Artificial Sequence:
```

```
                        Syntheticpolynucleotide"
source                  1..360
                        mol_type = other DNA
                        organism = synthetic construct
SEQUENCE: 337
gaagtgcagc tggtgcagtc tggagcagag gtgaaaaagc ccggggagtc tctgaggatc  60
tcctgtaagg gttctggcta caccttcacc agttactgga tgtactggat ccgccagccc  120
ccagggaagg ggctggagtg gattggtagg attgatccta atagtgggag tactaagtac  180
aatgagaagt tcaagaacag agtcacgatt accgcggaca aatccacgag cacagcctac  240
atggagctga gcagcctgag atctgaggac acggccgtgt attactgtgc aagggactat  300
agaaaggggc tctatgctat ggactactgg ggccagggca ccaccgtgac cgtgtcctcc  360

SEQ ID NO: 338          moltype = AA  length = 447
FEATURE                 Location/Qualifiers
REGION                  1..447
                        note = source = /note="Description of Artificial Sequence:
                        Syntheticpolypeptide"
source                  1..447
                        mol_type = protein
                        organism = synthetic construct
SEQUENCE: 338
EVQLVQSGAE VKKPGESLRI SCKGSGYTFT SYWMYWIRQP PGKGLEWIGR IDPNSGSTKY  60
NEKFKNRVTI TADKSTSTAY MELSSLRSED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 339          moltype = DNA  length = 1341
FEATURE                 Location/Qualifiers
misc_feature            1..1341
                        note = source = /note="Description of Artificial Sequence:
                        Syntheticpolynucleotide"
source                  1..1341
                        mol_type = other DNA
                        organism = synthetic construct
SEQUENCE: 339
gaagtgcagc tggtgcagtc tggagcagag gtgaaaaagc ccggggagtc tctgaggatc  60
tcctgtaagg gttctggcta caccttcacc agttactgga tgtactggat ccgccagccc  120
ccagggaagg ggctggagtg gattggtagg attgatccta atagtgggag tactaagtac  180
aatgagaagt tcaagaacag agtcacgatt accgcggaca aatccacgag cacagcctac  240
atggagctga gcagcctgag atctgaggac acggccgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                            1341

SEQ ID NO: 340          moltype = AA  length = 120
FEATURE                 Location/Qualifiers
REGION                  1..120
                        note = source = /note="Description of Artificial Sequence:
                        Syntheticpolypeptide"
source                  1..120
                        mol_type = protein
                        organism = synthetic construct
SEQUENCE: 340
QVQLVQSGAE VKKPGASVKV SCKASGYTFT SYWMYWIRQS PSRGLEWLGR IDPNSGSTKY  60
NEKFKNRFTI SRDDSKNTAY LQMNSLKTED TAVYYCARDY RKGLYAMDYW GQGTTVTVSS  120

SEQ ID NO: 341          moltype = DNA  length = 360
FEATURE                 Location/Qualifiers
misc_feature            1..360
                        note = source = /note="Description of Artificial Sequence:
```

```
                         Syntheticpolynucleotide"
source                  1..360
                        mol_type = other DNA
                        organism = synthetic construct
SEQUENCE: 341
caggttcagc tggtgcagtc tggagctgag gtgaagaagc ctggggcctc agtgaaggtc  60
tcctgcaagg cttctggcta caccttcacc agttactgga tgtactggat caggcagtcc  120
ccatcgagag gccttgagtg gctgggtagg attgatccta atagtgggag tactaagtac  180
aatgagaagt tcaagaacag attcaccatc tccagagatg attcaaagaa cacggcgtat  240
ctgcaaatga acagcctgaa aaccgaggac acggccgtgt attactgtgc aagggactat  300
agaaaggggc tctatgctat ggactactgg ggccagggca ccaccgtgac cgtgtcctcc  360

SEQ ID NO: 342          moltype = AA  length = 447
FEATURE                 Location/Qualifiers
REGION                  1..447
                        note = source = /note="Description of Artificial Sequence:
                         Syntheticpolypeptide"
source                  1..447
                        mol_type = protein
                        organism = synthetic construct
SEQUENCE: 342
QVQLVQSGAE VKKPGASVKV SCKASGYTFT SYWMYWIRQS PSRGLEWLGR IDPNSGSTKY  60
NEKFKNRFTI SRDDSKNTAY LQMNSLKTED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 343          moltype = DNA  length = 1341
FEATURE                 Location/Qualifiers
misc_feature            1..1341
                        note = source = /note="Description of Artificial Sequence:
                         Syntheticpolynucleotide"
source                  1..1341
                        mol_type = other DNA
                        organism = synthetic construct
SEQUENCE: 343
caggttcagc tggtgcagtc tggagctgag gtgaagaagc ctggggcctc agtgaaggtc  60
tcctgcaagg cttctggcta caccttcacc agttactgga tgtactggat caggcagtcc  120
ccatcgagag gccttgagtg gctgggtagg attgatccta atagtgggag tactaagtac  180
aatgagaagt tcaagaacag attcaccatc tccagagatg attcaaagaa cacggcgtat  240
ctgcaaatga acagcctgaa aaccgaggac acggccgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                           1341

SEQ ID NO: 344          moltype = AA  length = 107
FEATURE                 Location/Qualifiers
REGION                  1..107
                        note = source = /note="Description of Artificial Sequence:
                         Syntheticpolypeptide"
source                  1..107
                        mol_type = protein
                        organism = synthetic construct
SEQUENCE: 344
EIVLTQSPAT LSLSPGERAT LSCKASQDVG TAVAWYLQKP GQSPQLLIYW ASTRHTGIPP  60
RFSGSGYGTD FTLTINNIES EDAAYYFCQQ YNSYPLTFGQ GTKVEIK               107

SEQ ID NO: 345          moltype = DNA  length = 321
FEATURE                 Location/Qualifiers
misc_feature            1..321
                        note = source = /note="Description of Artificial Sequence:
```

```
                         Syntheticpolynucleotide"
source                  1..321
                        mol_type = other DNA
                        organism = synthetic construct
SEQUENCE: 345
gaaattgtgt tgacacagtc tccagccacc ctgtctttgt ctccagggga aagagccacc  60
ctctcctgca aggccagtca ggatgtgggt actgctgtag cctggtacct gcagaagcca  120
gggcagtctc cacagctcct gatctattgg gcatccaccc ggcacactgg gatcccacct  180
cgattcagtg gcagcgggta tggaacagat tttaccctca caattaataa catagaatct  240
gaggatgctg catattactt ctgtcagcag tataacagct atcctctcac gttcggccaa  300
gggaccaagg tggaaatcaa a                                            321

SEQ ID NO: 346          moltype = AA  length = 214
FEATURE                 Location/Qualifiers
REGION                  1..214
                        note = source = /note="Description of Artificial Sequence:
                         Syntheticpolypeptide"
source                  1..214
                        mol_type = protein
                        organism = synthetic construct
SEQUENCE: 346
EIVLTQSPAT LSLSPGERAT LSCKASQDVG TAVAWYLQKP GQSPQLLIYW ASTRHTGIPP  60
RFSGSGYGTD FTLTINNIES EDAAYYFCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 347          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 347
gaaattgtgt tgacacagtc tccagccacc ctgtctttgt ctccagggga aagagccacc  60
ctctcctgca aggccagtca ggatgtgggt actgctgtag cctggtacct gcagaagcca  120
gggcagtctc cacagctcct gatctattgg gcatccaccc ggcacactgg gatcccacct  180
cgattcagtg gcagcgggta tggaacagat tttaccctca caattaataa catagaatct  240
gaggatgctg catattactt ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 348          moltype = AA  length = 120
FEATURE                 Location/Qualifiers
REGION                  1..120
                        note = source = /note="Description of Artificial Sequence:
                         Syntheticpolypeptide"
source                  1..120
                        mol_type = protein
                        organism = synthetic construct
SEQUENCE: 348
EVQLVQSGAE VKKPGESLRI SCKGSGYTFT SYWMYWVRQA RGQRLEWIGR IDPNSGSTKY  60
NEKFKNRLTI SKDTSKNQVV LTMTNMDPVD TATYYCARDY RKGLYAMDYW GQGTTVTVSS  120

SEQ ID NO: 349          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 349
gaagtgcagc tggtgcagtc tggagcagag gtgaaaaagc ccggggagtc tctgaggatc  60
tcctgtaagg gttctggcta caccttcacc agttactgga tgtactgggt gcgacaggct  120
cgtggacaac gccttgagtg gataggtagg attgatccta atagtgggag tactaagtac  180
aatgagaagt tcaagaacag actcaccatc tccaaggaca cctccaaaaa ccaggtggtc  240
cttacaatga ccaacatgga ccctgtggac acagccacgt attactgtgc aagggactat  300
agaaaggggc tctatgctat ggactactgg ggccagggca ccaccgtgac cgtgtcctcc  360

SEQ ID NO: 350          moltype = AA  length = 447
FEATURE                 Location/Qualifiers
REGION                  1..447
                        note = source = /note="Description of Artificial Sequence:
```

```
                          Syntheticpolypeptide"
source                   1..447
                         mol_type = protein
                         organism = synthetic construct
SEQUENCE: 350
EVQLVQSGAE VKKPGESLRI SCKGSGYTFT SYWMYWVRQA RGQRLEWIGR IDPNSGSTKY  60
NEKFKNRLTI SKDTSKNQVV LTMTNMDPVD TATYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 351           moltype = DNA  length = 1341
FEATURE                  Location/Qualifiers
misc_feature             1..1341
                         note = source = /note="Description of Artificial Sequence:
                          Syntheticpolynucleotide"
source                   1..1341
                         mol_type = other DNA
                         organism = synthetic construct
SEQUENCE: 351
gaagtgcagc tggtgcagtc tggagcagag gtgaaaaagc ccggggagtc tctgaggatc  60
tcctgtaagg gttctggcta caccttcacc agttactgga tgtactgggt gcgacaggct  120
cgtggacaac gccttgagtg gataggtagg attgatccta atagtgggag tactaagtac  180
aatgagaagt tcaagaacag actcaccatc tccaaggaca cctccaaaaa ccaggtggtc  240
cttacaatga ccaacatgga ccctgtggac acagccacgt attactgtgc aagggactat  300
agaaagggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                            1341

SEQ ID NO: 352           moltype = AA  length = 107
FEATURE                  Location/Qualifiers
REGION                   1..107
                         note = source = /note="Description of Artificial Sequence:
                          Syntheticpolypeptide"
source                   1..107
                         mol_type = protein
                         organism = synthetic construct
SEQUENCE: 352
DVVMTQSPLS LPVTLGQPAS ISCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 353           moltype = DNA  length = 321
FEATURE                  Location/Qualifiers
misc_feature             1..321
                         note = source = /note="Description of Artificial Sequence:
                          Syntheticpolynucleotide"
source                   1..321
                         mol_type = other DNA
                         organism = synthetic construct
SEQUENCE: 353
gatgttgtga tgactcagtc tccactctcc ctgcccgtca cccttggaca gccggcctcc  60
atctcctgca aggccagtca ggatgtgggt actgctgtag cctggtacca gcagaaacct  120
ggccaggctc ccaggctcct catctattgg gcatccaccc ggcacactgg ggtcccatca  180
aggttcagcg gcagtggatc tgggacagaa ttcactctca ccatcagcag cctgcagcct  240
gatgattttg caacttatta ctgtcagcag tataacagct atcctctcac gttcggccaa  300
gggaccaagg tggaaatcaa a                                            321

SEQ ID NO: 354           moltype = AA  length = 214
FEATURE                  Location/Qualifiers
REGION                   1..214
                         note = source = /note="Description of Artificial Sequence:
```

```
                          Syntheticpolypeptide"
source                   1..214
                         mol_type = protein
                         organism = synthetic construct
SEQUENCE: 354
DVVMTQSPLS LPVTLGQPAS ISCKASQDVG TAVAWYQQKP GQAPRLLIYW ASTRHTGVPS  60
RFSGSGSGTE FTLTISSLQP DDFATYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 355           moltype = DNA  length = 642
FEATURE                  Location/Qualifiers
misc_feature             1..642
                         note = source = /note="Description of Artificial Sequence:
                          Syntheticpolynucleotide"
source                   1..642
                         mol_type = other DNA
                         organism = synthetic construct
SEQUENCE: 355
gatgttgtga tgactcagtc tccactctcc ctgcccgtca cccttggaca gccggcctcc  60
atctcctgca aggccagtca ggatgtgggt actgctgtag cctggtacca gcagaaacct  120
ggccaggctc ccaggctcct catctattgg gcatccaccc ggcacactgg ggtcccatca  180
aggttcagcg gcagtggatc tgggacagaa ttcactctca ccatcagcag cctgcagcct  240
gatgattttg caacttatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 356           moltype = AA  length = 120
FEATURE                  Location/Qualifiers
REGION                   1..120
                         note = source = /note="Description of Artificial Sequence:
                          Syntheticpolypeptide"
source                   1..120
                         mol_type = protein
                         organism = synthetic construct
SEQUENCE: 356
QITLKESGPT LVKPTQTLTL TCTFSGYTFT SYWMYWVRQA PGKGLEWVSR IDPNSGSTKY  60
NEKFKNRVTI TADKSTSTAY MELSSLRSED TAVYYCARDY RKGLYAMDYW GQGTTVTVSS  120

SEQ ID NO: 357           moltype = DNA  length = 360
FEATURE                  Location/Qualifiers
misc_feature             1..360
                         note = source = /note="Description of Artificial Sequence:
                          Syntheticpolynucleotide"
source                   1..360
                         mol_type = other DNA
                         organism = synthetic construct
SEQUENCE: 357
cagatcacct tgaaggagtc tggtcctacg ctggtgaaac ccacacagac cctcacgctg  60
acctgcacct tctctggcta caccttcacc agttactgga tgtactgggt ccgccaggct  120
ccagggaagg ggctggagtg ggtcagtagg attgatccta atagtgggag tactaagtac  180
aatgagaagt tcaagaacag agtcacgatt accgcggaca aatccacgag cacagcctac  240
atggagctga gcagcctgag atctgaggac acggccgtgt attactgtgc aagggactat  300
agaaagggc tctatgctat ggactactgg ggccagggca ccaccgtgac cgtgtcctcc  360

SEQ ID NO: 358           moltype = AA  length = 447
FEATURE                  Location/Qualifiers
REGION                   1..447
                         note = source = /note="Description of Artificial Sequence:
                          Syntheticpolypeptide"
source                   1..447
                         mol_type = protein
                         organism = synthetic construct
SEQUENCE: 358
QITLKESGPT LVKPTQTLTL TCTFSGYTFT SYWMYWVRQA PGKGLEWVSR IDPNSGSTKY  60
NEKFKNRVTI TADKSTSTAY MELSSLRSED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 359           moltype = DNA  length = 1341
FEATURE                  Location/Qualifiers
```

-continued

```
misc_feature          1..1341
                      note = source = /note="Description of Artificial Sequence:
                       Syntheticpolynucleotide"
source                1..1341
                      mol_type = other DNA
                      organism = synthetic construct
SEQUENCE: 359
cagatcacct tgaaggagtc tggtcctacg ctggtgaaac ccacacagac cctcacgctg  60
acctgcacct tctctggcta caccttcacc agttactgga tgtactgggt ccgccaggct  120
ccagggaagg ggctggagtg ggtcagtagg attgatccta atagtgggag tactaagtac  180
aatgagaagt tcaagaacag agtcacgatt accgcggaca aatccacgag cacagcctac  240
atggagctga gcagcctgag atctgaggac acggccgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                            1341

SEQ ID NO: 360        moltype = AA  length = 107
FEATURE               Location/Qualifiers
REGION                1..107
                      note = source = /note="Description of Artificial Sequence:
                       Syntheticpolypeptide"
source                1..107
                      mol_type = protein
                      organism = synthetic construct
SEQUENCE: 360
DIQMTQSPSS LSASVGDRVT ITCKASQDVG TAVAWYQQKP GQAPRLLIYW ASTRHTGVPS  60
RFSGSGSGTD FTFTISSLQP EDIATYYCQQ YNSYPLTFGQ GTKVEIK                107

SEQ ID NO: 361        moltype = DNA  length = 321
FEATURE               Location/Qualifiers
misc_feature          1..321
                      note = source = /note="Description of Artificial Sequence:
                       Syntheticpolynucleotide"
source                1..321
                      mol_type = other DNA
                      organism = synthetic construct
SEQUENCE: 361
gacatccaga tgacccagtc tccatcctcc ctgtctgcat ctgtaggaga cagagtcacc  60
atcacttgca aggccagtca ggatgtgggt actgctgtag cctggtacca gcagaaacct  120
ggccaggctc ccaggctcct catctattgg gcatccaccc ggcacactgg ggtcccatca  180
aggttcagtg gaagtggatc tgggacagat tttactttca ccatcagcag cctgcagcct  240
gaagatattg caacatatta ctgtcagcag tataacagct atcctctcac gttcggccaa  300
gggaccaagg tggaaatcaa a                                            321

SEQ ID NO: 362        moltype = AA  length = 214
FEATURE               Location/Qualifiers
REGION                1..214
                      note = source = /note="Description of Artificial Sequence:
                       Syntheticpolypeptide"
source                1..214
                      mol_type = protein
                      organism = synthetic construct
SEQUENCE: 362
DIQMTQSPSS LSASVGDRVT ITCKASQDVG TAVAWYQQKP GQAPRLLIYW ASTRHTGVPS  60
RFSGSGSGTD FTFTISSLQP EDIATYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 363        moltype = DNA  length = 642
FEATURE               Location/Qualifiers
misc_feature          1..642
                      note = source = /note="Description of Artificial Sequence:
                       Syntheticpolynucleotide"
source                1..642
```

```
                        mol_type = other DNA
                        organism = synthetic construct
SEQUENCE: 363
gacatccaga tgacccagtc tccatcctcc ctgtctgcat ctgtaggaga cagagtcacc  60
atcacttgca aggccagtca ggatgtgggt actgctgtag cctggtacca gcagaaacct  120
ggccaggctc ccaggctcct catctattgg gcatccaccc ggcacactgg ggtcccatca  180
aggttcagtg gaagtggatc tgggacagat tttactttca ccatcagcag cctgcagcct  240
gaagatattg caacatatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 364          moltype = AA  length = 120
FEATURE                 Location/Qualifiers
REGION                  1..120
                        note = source = /note="Description of Artificial Sequence:
                         Syntheticpolypeptide"
source                  1..120
                        mol_type = protein
                        organism = synthetic construct
SEQUENCE: 364
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120

SEQ ID NO: 365          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 365
gaggtccagc tggtacagtc tggggctgag gtgaagaagc ctggggctac agtgaaaatc  60
tcctgcaagg tttctggcta caccttcacc agttactgga tgtactgggt gcgacaggct  120
cgtggacaac gccttgagtg gataggtagg attgatccta atagtgggag tactaagtac  180
aatgagaagt tcaagaacag attcaccatc tccagagaca attccaagaa cacgctgtat  240
cttcaaatga acagcctgag agccgaggac acggccgtgt attactgtgc aagggactat  300
agaaaggggc tctatgctat ggactactgg ggccagggca ccaccgtgac cgtgtcctcc  360

SEQ ID NO: 366          moltype = AA  length = 446
FEATURE                 Location/Qualifiers
REGION                  1..446
                        note = source = /note="Description of Artificial Sequence:
                         Syntheticpolypeptide"
source                  1..446
                        mol_type = protein
                        organism = synthetic construct
SEQUENCE: 366
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                       446

SEQ ID NO: 367          moltype = DNA  length = 1341
FEATURE                 Location/Qualifiers
misc_feature            1..1341
                        note = source = /note="Description of Artificial Sequence:
                         Syntheticpolynucleotide"
source                  1..1341
                        mol_type = other DNA
                        organism = synthetic construct
SEQUENCE: 367
gaggtccagc tggtacagtc tggggctgag gtgaagaagc ctggggctac agtgaaaatc  60
tcctgcaagg tttctggcta caccttcacc agttactgga tgtactgggt gcgacaggct  120
cgtggacaac gccttgagtg gataggtagg attgatccta atagtgggag tactaagtac  180
aatgagaagt tcaagaacag attcaccatc tccagagaca attccaagaa cacgctgtat  240
cttcaaatga acagcctgag agccgaggac acggccgtgt attactgtgc aagggactat  300
agaaaggggc tctatgctat ggactactgg ggccagggca ccaccgtgac cgtgtcctcc  360
gcttccacca agggcccatc cgtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
```

-continued

```
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                            1341

SEQ ID NO: 368         moltype = AA  length = 107
FEATURE                Location/Qualifiers
REGION                 1..107
                       note = source = /note="Description of Artificial Sequence:
                        Syntheticpolypeptide"
source                 1..107
                       mol_type = protein
                       organism = synthetic construct
SEQUENCE: 368
AIQLTQSPSS LSASVGDRVT ITCKASQDVG TAVAWYLQKP GQSPQLLIYW ASTRHTGVPS  60
RFSGSGSGTD FTFTISSLEA EDAATYYCQQ YNSYPLTFGQ GTKVEIK                107

SEQ ID NO: 369         moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 369
gccatccagt tgacccagtc tccatcctcc ctgtctgcat ctgtaggaga cagagtcacc  60
atcacttgca aggccagtca ggatgtgggt actgctgtag cctggtacct gcagaagcca  120
gggcagtctc cacagctcct gatctattgg gcatccaccc ggcacactgg ggtcccctcg  180
aggttcagtg gcagtggatc tgggacagat ttcaccttta ccatcagtag cctggaagct  240
gaagatgctg caacatatta ctgtcagcag tataacagct atcctctcac gttcggccaa  300
gggaccaagg tggaaatcaa a                                            321

SEQ ID NO: 370         moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 370
AIQLTQSPSS LSASVGDRVT ITCKASQDVG TAVAWYLQKP GQSPQLLIYW ASTRHTGVPS  60
RFSGSGSGTD FTFTISSLEA EDAATYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 371         moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 371
gccatccagt tgacccagtc tccatcctcc ctgtctgcat ctgtaggaga cagagtcacc  60
atcacttgca aggccagtca ggatgtgggt actgctgtag cctggtacct gcagaagcca  120
gggcagtctc cacagctcct gatctattgg gcatccaccc ggcacactgg ggtcccctcg  180
aggttcagtg gcagtggatc tgggacagat ttcaccttta ccatcagtag cctggaagct  240
gaagatgctg caacatatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 372         moltype = AA  length = 107
```

```
FEATURE                Location/Qualifiers
REGION                 1..107
                       note = source = /note="Description of Artificial Sequence:
                        Syntheticpolypeptide"
source                 1..107
                       mol_type = protein
                       organism = synthetic construct
SEQUENCE: 372
EIVLTQSPDF QSVTPKEKVT ITCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 373         moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 373
gaaattgtgc tgactcagtc tccagacttt cagtctgtga ctccaaagga gaaagtcacc  60
atcacctgca aggccagtca ggatgtgggt actgctgtag cctggtacca gcagaaacct  120
ggccaggctc ccaggctcct catctattgg gcatccaccc ggcacactgg ggtcccatca  180
aggttcagcg gcagtggatc tgggacagaa ttcactctca ccatcagcag cctgcagcct  240
gatgattttg caacttatta ctgtcagcag tataacagct atcctctcac gttcggccaa  300
gggaccaagg tggaaatcaa a                                            321

SEQ ID NO: 374         moltype = AA  length = 214
FEATURE                Location/Qualifiers
REGION                 1..214
                       note = source = /note="Description of Artificial Sequence:
                        Syntheticpolypeptide"
source                 1..214
                       mol_type = protein
                       organism = synthetic construct
SEQUENCE: 374
EIVLTQSPDF QSVTPKEKVT ITCKASQDVG TAVAWYQQKP GQAPRLLIYW ASTRHTGVPS  60
RFSGSGSGTE FTLTISSLQP DDFATYYCQQ YNSYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 375         moltype = DNA  length = 642
FEATURE                Location/Qualifiers
misc_feature           1..642
                       note = source = /note="Description of Artificial Sequence:
                        Syntheticpolynucleotide"
source                 1..642
                       mol_type = other DNA
                       organism = synthetic construct
SEQUENCE: 375
gaaattgtgc tgactcagtc tccagacttt cagtctgtga ctccaaagga gaaagtcacc  60
atcacctgca aggccagtca ggatgtgggt actgctgtag cctggtacca gcagaaacct  120
ggccaggctc ccaggctcct catctattgg gcatccaccc ggcacactgg ggtcccatca  180
aggttcagcg gcagtggatc tgggacagaa ttcactctca ccatcagcag cctgcagcct  240
gatgattttg caacttatta ctgtcagcag tataacagct atcctctcac gttcggccaa  300
gggaccaagg tggaaatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 376         moltype = DNA  length = 360
FEATURE                Location/Qualifiers
misc_feature           1..360
                       note = source = /note="Description of Artificial Sequence:
                        Syntheticpolynucleotide"
source                 1..360
                       mol_type = other DNA
                       organism = synthetic construct
SEQUENCE: 376
gaagtgcagc tggtgcagtc aggcgccgaa gtgaagaagc ccggcgagtc actgagaatt  60
agctgtaaag gttcaggcta caccttcact agctactgga tgtactgggt ccgacaggcc  120
ccagggcaag gcctggagtg gatgggtaga atcgacccta atagcggctc tactaagtat  180
aacgagaagt ttaagaatag agtgactatt agcgtggaca cctctaagaa tcagtttagc  240
ctgaagctgt ctagcgtgac cgccgctgac accgccgtct actactgcgc tagagactat  300
agaaagggcc tgtacgctat ggactactgg ggtcaaggca ctaccgtgac cgtgtcttca  360

SEQ ID NO: 377         moltype = AA  length = 446
```

-continued

```
FEATURE                 Location/Qualifiers
REGION                  1..446
                        note = source = /note="Description of Artificial Sequence:
                         Syntheticpolypeptide"
source                  1..446
                        mol_type = protein
                        organism = synthetic construct
SEQUENCE: 377
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 378          moltype = DNA  length = 1338
FEATURE                 Location/Qualifiers
misc_feature            1..1338
                        note = source = /note="Description of Artificial Sequence:
                         Syntheticpolynucleotide"
source                  1..1338
                        mol_type = other DNA
                        organism = synthetic construct
SEQUENCE: 378
gaagtgcagc tggtgcagtc aggcgccgaa gtgaagaagc ccggcgagtc actgagaatt  60
agctgtaaag gttcaggcta caccttcact agctactgga tgtactgggt ccgacaggcc  120
ccagggcaag gcctggagtg gatgggtaga atcgacccta atagcggctc tactaagtat  180
aacgagaagt ttaagaatag agtgactatt agcgtggaca cctctaagaa tcagtttagc  240
ctgaagctgt ctagcgtgac cgccgctgac accgccgtct actactgcgc tagagactat  300
agaaagggcc tgtacgctat ggactactgg ggtcaaggca ctaccgtgac cgtgtcttca  360
gctagcacta agggcccgtc cgtgttcccc ctggcacctt gtagccggag cactagcgaa  420
tccaccgctg ccctcggctg cctggtcaag gattacttcc cggagcccgt gaccgtgtcc  480
tggaacagcg gagccctgac ctccggagtg cacaccttcc ccgctgtgct gcagagctcc  540
gggctgtact cgctgtcgtc ggtggtcacg gtgccttcat ctagcctggg taccaagacc  600
tacacttgca acgtggacca caagccttcc aacactaagg tggacaagcg cgtcgaatcg  660
aagtacggcc caccgtgccc gccttgtccc gcgccggagt tcctcggcgg tccctcggtc  720
tttctgttcc caccgaagcc caaggacact ttgatgattt cccgcacccc tgaagtgaca  780
tgcgtggtcg tggacgtgtc acaggaagat ccggaggtgc agttcaattg gtacgtggat  840
ggcgtcgagg tgcacaacgc caaaaccaag ccgagggagg agcagttcaa ctccacttac  900
cgcgtcgtgt ccgtgctgac ggtgctgcat caggactggc tgaacgggaa ggagtacaag  960
tgcaaagtgt ccaacaaggg acttcctagc tcaatcgaaa agaccatctc gaaagccaag  1020
ggacagcccc gggaacccca agtgtatacc ctgccaccga gccaggaaga aatgactaag  1080
aaccaagtct cattgacttg ccttgtgaag ggcttctacc catcggatat cgccgtggaa  1140
tgggagtcca acggccagcc ggaaaacaac tacaagacca cccctccggt gctggactca  1200
gacggatcct tcttcctcta ctcgcggctg accgtggata agagcagatg gcaggaggga  1260
aatgtgttca gctgttctgt gatgcatgaa gccctgcaca accactacac tcagaagtcc  1320
ctgtccctct ccctggga                                                1338

SEQ ID NO: 379          moltype = DNA  length = 321
FEATURE                 Location/Qualifiers
misc_feature            1..321
                        note = source = /note="Description of Artificial Sequence:
                         Syntheticpolynucleotide"
source                  1..321
                        mol_type = other DNA
                        organism = synthetic construct
SEQUENCE: 379
gagatcgtcc tgactcagtc acccgacttt cagtcagtga cccctaaaga gaaagtcact  60
atcacctgta aagcctctca ggacgtgggc accgccgtgg cctggtatct gcagaagcct  120
ggtcaatcac ctcagctgct gatctactgg gcctctacta gacacaccgg cgtgccctct  180
aggtttagcg gtagcggtag tggcaccgac ttcaccttca ctatctcttc actgcagccc  240
gaggatatcg ctacctacta ctgtcagcag tataatagct accccctgac cttcggtcaa  300
ggcactaagg tcgagattaa g                                           321

SEQ ID NO: 380          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 380
gagatcgtcc tgactcagtc acccgacttt cagtcagtga cccctaaaga gaaagtcact  60
atcacctgta aagcctctca ggacgtgggc accgccgtgg cctggtatct gcagaagcct  120
ggtcaatcac ctcagctgct gatctactgg gcctctacta gacacaccgg cgtgccctct  180
aggtttagcg gtagcggtag tggcaccgac ttcaccttca ctatctcttc actgcagccc  240
```

```
gaggatatcg ctacctacta ctgtcagcag tataatagct accccctgac cttcggtcaa  300
ggcactaagg tcgagattaa gcgtacggtg gccgctccca gcgtgttcat cttccccccc  360
agcgacgagc agctgaagag cggcaccgcc agcgtggtgt gcctgctgaa caacttctac  420
cccgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                    642

SEQ ID NO: 381          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 381
gaagtgcagc tggtgcagtc aggcgccgaa gtgaagaaac ccggcgctac cgtgaagatt  60
agctgtaaag tctcaggcta caccttcact agctactgga tgtactgggt ccgacaggct  120
accggtcaag gcctggagtg gatgggtaga atcgacccta atagcggctc tactaagtat  180
aacgagaagt ttaagaatag agtgactatc accgccgata agtctactag caccgcctat  240
atggaactgt ctagcctgag atcagaggac accgccgtct actactgcgc tagagactat  300
agaaagggcc tgtacgctat ggactactgg ggtcaaggca ctaccgtgac cgtgtcttca  360

SEQ ID NO: 382          moltype = AA  length = 446
FEATURE                 Location/Qualifiers
REGION                  1..446
                        note = source = /note="Description of Artificial Sequence:
                         Syntheticpolypeptide"
source                  1..446
                        mol_type = protein
                        organism = synthetic construct
SEQUENCE: 382
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 383          moltype = DNA  length = 1338
FEATURE                 Location/Qualifiers
misc_feature            1..1338
                        note = source = /note="Description of Artificial Sequence:
                         Syntheticpolynucleotide"
source                  1..1338
                        mol_type = other DNA
                        organism = synthetic construct
SEQUENCE: 383
gaagtgcagc tggtgcagtc aggcgccgaa gtgaagaaac ccggcgctac cgtgaagatt  60
agctgtaaag tctcaggcta caccttcact agctactgga tgtactgggt ccgacaggct  120
accggtcaag gcctggagtg gatgggtaga atcgacccta atagcggctc tactaagtat  180
aacgagaagt ttaagaatag agtgactatc accgccgata agtctactag caccgcctat  240
atggaactgt ctagcctgag atcagaggac accgccgtct actactgcgc tagagactat  300
agaaagggcc tgtacgctat ggactactgg ggtcaaggca ctaccgtgac cgtgtcttca  360
gctagcacta agggcccgtc cgtgttcccc ctggcacctt gtagccggag cactagcgaa  420
tccaccgctg ccctcggctg cctggtcaag gattacttcc cggagcccgt gaccgtgtcc  480
tggaacagcg gagccctgac ctccggagtg cacaccttcc ccgctgtgct gcagagctcc  540
gggctgtact cgctgtcgtc ggtggtcacg gtgccttcat ctagcctggg taccaagacc  600
tacacttgca acgtggacca caagccttcc aacactaagg tggacaagcg cgtcgaatcg  660
aagtacggcc caccgtgccc gccttgtccc gcgccggagt tcctcggcgg tccctcggtc  720
tttctgttcc caccgaagcc caaggacact ttgatgattt cccgcacccc tgaagtgaca  780
tgcgtggtcg tggacgtgtc acaggaagat ccggaggtgc agttcaattg gtacgtggat  840
ggcgtcgagg tgcacaacgc caaaaccaag ccgagggagg agcagttcaa ctccacttac  900
cgcgtcgtgt ccgtgctgac ggtgctgcat caggactggc tgaacgggaa ggagtacaag  960
tgcaaagtgt ccaacaaggg acttcctagc tcaatcgaaa agaccatctc gaaagccaag  1020
ggacagcccc gggaacccca agtgtatacc ctgccaccga gccaggaaga aatgactaag  1080
aaccaagtct cattgacttg ccttgtgaag ggcttctacc catcggatat cgccgtggaa  1140
tgggagtcca acggccagcc ggaaaacaac tacaagacca cccctccggt gctggactca  1200
gacggatcct tcttcctcta ctcgcggctg accgtggata agagcagatg gcaggaggga  1260
aatgtgttca gctgttctgt gatgcatgaa gccctgcaca accactacac tcagaagtcc  1320
ctgtccctct ccctggga                                                1338

SEQ ID NO: 384          moltype = DNA  length = 321
FEATURE                 Location/Qualifiers
misc_feature            1..321
                        note = source = /note="Description of Artificial Sequence:
```

```
                         Syntheticpolynucleotide"
source                  1..321
                        mol_type = other DNA
                        organism = synthetic construct
SEQUENCE: 384
gacgtcgtga tgactcagtc acccctgagc ctgcccgtga ccctggggca gcccgcctct  60
attagctgta aagcctctca ggacgtgggc accgccgtgg cctggtatca gcagaagcca  120
gggcaagccc ctagactgct gatctactgg gcctctacta gacacaccgg cgtgccctct  180
aggtttagcg gtagcggtag tggcaccgag ttcaccctga ctatctcttc actgcagccc  240
gacgacttcg ctacctacta ctgtcagcag tataatagct accccctgac cttcggtcaa  300
ggcactaagg tcgagattaa g                                            321

SEQ ID NO: 385          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 385
gacgtcgtga tgactcagtc acccctgagc ctgcccgtga ccctggggca gcccgcctct  60
attagctgta aagcctctca ggacgtgggc accgccgtgg cctggtatca gcagaagcca  120
gggcaagccc ctagactgct gatctactgg gcctctacta gacacaccgg cgtgccctct  180
aggtttagcg gtagcggtag tggcaccgag ttcaccctga ctatctcttc actgcagccc  240
gacgacttcg ctacctacta ctgtcagcag tataatagct accccctgac cttcggtcaa  300
ggcactaagg tcgagattaa gcgtacggtg gccgctccca gcgtgttcat cttccccccc  360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 386          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 386
gaagtgcagc tggtgcagtc aggcgccgaa gtgaagaaac ccggcgctac cgtgaagatt  60
agctgtaaag tctcaggcta caccttcact agctactgga tgtactgggt ccgacaggct  120
agagggcaaa gactggagtg gatcggtaga atcgacccta atagcggctc tactaagtat  180
aacgagaagt ttaagaatag gttcactatt agtagggata actctaagaa caccctgtac  240
ctgcagatga atagcctgag agccgaggac accgccgtct actactgcgc tagagactat  300
agaaagggcc tgtacgctat ggactactgg ggtcaaggca ctaccgtgac cgtgtcttca  360

SEQ ID NO: 387          moltype = DNA  length = 1338
FEATURE                 Location/Qualifiers
misc_feature            1..1338
                        note = source = /note="Description of Artificial Sequence:
                         Syntheticpolynucleotide"
source                  1..1338
                        mol_type = other DNA
                        organism = synthetic construct
SEQUENCE: 387
gaagtgcagc tggtgcagtc aggcgccgaa gtgaagaaac ccggcgctac cgtgaagatt  60
agctgtaaag tctcaggcta caccttcact agctactgga tgtactgggt ccgacaggct  120
agagggcaaa gactggagtg gatcggtaga atcgacccta atagcggctc tactaagtat  180
aacgagaagt ttaagaatag gttcactatt agtagggata actctaagaa caccctgtac  240
ctgcagatga atagcctgag agccgaggac accgccgtct actactgcgc tagagactat  300
agaaagggcc tgtacgctat ggactactgg ggtcaaggca ctaccgtgac cgtgtcttca  360
gctagcacta agggcccgtc cgtgttcccc ctggcacctt gtagccggag cactagcgaa  420
tccaccgctg ccctcggctg cctggtcaag gattacttcc cggagcccgt gaccgtgtcc  480
tggaacagcg gagccctgac ctccggagtg cacaccttcc ccgctgtgct gcagagctcc  540
gggctgtact cgctgtcgtc ggtggtcacg gtgccttcat ctagcctggg taccaagacc  600
tacacttgca acgtggacca caagccttcc aacactaagg tggacaagcg cgtcgaatcg  660
aagtacggcc caccgtgccc gccttgtccc gcgccggagt tcctcggcgg tccctcggtc  720
tttctgttcc caccgaagcc caaggacact ttgatgattt cccgcacccc tgaagtgaca  780
tgcgtggtcg tggacgtgtc acaggaagat ccggaggtgc agttcaattg gtacgtggat  840
ggcgtcgagg tgcacaacgc caaaaccaag ccgagggagg agcagttcaa ctccacttac  900
cgcgtcgtgt ccgtgctgac ggtgctgcat caggactggc tgaacgggaa ggagtacaag  960
tgcaaagtgt ccaacaaggg acttcctagc tcaatcgaaa agaccatctc gaaagccaag  1020
ggacagcccc gggaacccca agtgtatacc ctgccaccga gccaggaaga aatgactaag  1080
aaccaagtct cattgacttg ccttgtgaag ggcttctacc catcggatat cgccgtggaa  1140
tgggagtcca acggccagcc ggaaaacaac tacaagacca cccctccggt gctggactca  1200
gacggatcct tcttcctcta ctcgcggctg accgtggata agagcagatg gcaggaggga  1260
```

```
aatgtgttca gctgttctgt gatgcatgaa gccctgcaca accactacac tcagaagtcc  1320
ctgtccctct ccctggga                                                1338

SEQ ID NO: 388          moltype = DNA  length = 321
FEATURE                 Location/Qualifiers
misc_feature            1..321
                        note = source = /note="Description of Artificial Sequence:
                         Syntheticpolynucleotide"
source                  1..321
                        mol_type = other DNA
                        organism = synthetic construct
SEQUENCE: 388
gctattcagc tgactcagtc acctagtagc ctgagcgcta gtgtgggcga tagagtgact  60
atcacctgta aagcctctca ggacgtgggc accgccgtgg cctggtatct gcagaagcct  120
ggtcaatcac ctcagctgct gatctactgg gcctctacta gacacaccgg cgtgccctct  180
aggtttagcg gtagcggtag tggcaccgac ttcaccttca ctatctcttc actggaagcc  240
gaggacgccg ctacctacta ctgtcagcag tataatagct accccctgac cttcggtcaa  300
ggcactaagg tcgagattaa g                                            321

SEQ ID NO: 389          moltype = DNA  length = 642
FEATURE                 Location/Qualifiers
misc_feature            1..642
                        note = source = /note="Description of Artificial Sequence:
                         Syntheticpolynucleotide"
source                  1..642
                        mol_type = other DNA
                        organism = synthetic construct
SEQUENCE: 389
gctattcagc tgactcagtc acctagtagc ctgagcgcta gtgtgggcga tagagtgact  60
atcacctgta aagcctctca ggacgtgggc accgccgtgg cctggtatct gcagaagcct  120
ggtcaatcac ctcagctgct gatctactgg gcctctacta gacacaccgg cgtgccctct  180
aggtttagcg gtagcggtag tggcaccgac ttcaccttca ctatctcttc actggaagcc  240
gaggacgccg ctacctacta ctgtcagcag tataatagct accccctgac cttcggtcaa  300
ggcactaagg tcgagattaa gcgtacggtg gccgctccca gcgtgttcat cttccccccc  360
agcgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcataag gtgtacgcct gcgaggtgac ccaccagggc  600
ctgtccagcc ccgtgaccaa gagcttcaac aggggcgagt gc                     642

SEQ ID NO: 390          moltype =   length =
SEQUENCE: 390
000

SEQ ID NO: 391          moltype = AA  length = 447
FEATURE                 Location/Qualifiers
REGION                  1..447
                        note = source = /note="Description of Artificial Sequence:
                         Syntheticpolypeptide"
source                  1..447
                        mol_type = protein
                        organism = synthetic construct
SEQUENCE: 391
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 392          moltype = DNA  length = 360
FEATURE                 Location/Qualifiers
misc_feature            1..360
                        note = source = /note="Description of Artificial Sequence:
                         Syntheticpolynucleotide"
source                  1..360
                        mol_type = other DNA
                        organism = synthetic construct
SEQUENCE: 392
gaagtgcagc tggtgcagtc tggcgccgaa gtgaagaaac ccggcgctac cgtgaagatc  60
tcctgcaagg tgtccggcta caccttcacc agctactgga tgtactgggt gcgacaggct  120
accggccagg gcctggaatg gatgggcaga atcgacccca actccggctc caccaagtac  180
aacgagaagt tcaagaaccg cgtgaccatc accgccgaca agtccacctc caccgcctac  240
atggaactgt cctccctgcg gagcgaggac accgccgtgt actactgcgc cagagactac  300
cggaagggcc tgtacgccat ggactattgg ggccagggca ccaccgtgac cgtgtcctct  360

SEQ ID NO: 393          moltype = AA  length = 446
```

-continued

```
FEATURE                Location/Qualifiers
REGION                 1..446
                       note = source = /note="Description of Artificial Sequence:
                        Syntheticpolypeptide"
source                 1..446
                       mol_type = protein
                       organism = synthetic construct
SEQUENCE: 393
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                     446

SEQ ID NO: 394         moltype = DNA  length = 1348
FEATURE                Location/Qualifiers
misc_feature           1..1348
                       note = source = /note="Description of Artificial Sequence:
                        Syntheticpolynucleotide"
source                 1..1348
                       mol_type = other DNA
                       organism = synthetic construct
SEQUENCE: 394
gaagtgcagc tggtgcagtc tggcgccgaa gtgaagaaac ccggcgctac cgtgaagatc  60
tcctgcaagg tgtccggcta caccttcacc agctactgga tgtactgggt gcgacaggct  120
accggccagg gcctggaatg gatgggcaga atcgacccca actccggctc caccaagtac  180
aacgagaagt tcaagaaccg cgtgaccatc accgccgaca agtccacctc caccgcctac  240
atggaactgt cctccctgcg gagcgaggac accgccgtgt actactgcgc cagagactac  300
cggaagggcc tgtacgccat ggactattgg ggccagggca ccaccgtgac cgtgtcctct  360
gcttccacca agggcccaag cgtgttcccc ctggcccct gctccagaag caccagcgag  420
agcacagccg ccctgggctg cctggtgaag gactacttcc ccgagcccgt gaccgtgtcc  480
tggaacagcg gagccctgac cagcggcgtg cacaccttcc ccgccgtgct gcagagcagc  540
ggcctgtaca gcctgagcag cgtggtgacc gtgcccagca gcagcctggg caccaagacc  600
tacacctgta acgtggacca caagcccagc aacaccaagg tggacaagag ggtggagagc  660
aagtacggcc caccctgccc cccctgccca gcccccgagt tcctgggcgg acccagcgtg  720
ttcctgttcc cccccaagcc caaggacacc ctgatgatca gcagaacccc cgaggtgacc  780
tgtgtggtgg tggacgtgtc ccaggaggac cccgaggtcc agttcaactg gtacgtggac  840
ggcgtggagg tgcacaacgc caagaccaag cccagagagg agcagtttaa cagcacctac  900
cgggtggtgt ccgtgctgac cgtgctgcac caggactggc tgaacggcaa agagtacaag  960
tgtaaggtct ccaacaaggg cctgccaagc agcatcgaaa agaccatcag caaggccaag  1020
ggccagccta gagagcccca ggtctacacc ctgccaccca gccaagagga gatgaccaag  1080
aaccaggtgt ccctgacctg tctggtgaag ggcttctacc caagcgacat cgccgtggag  1140
tgggagagca acggccagcc cgagaacaac tacaagacca cccccccagt gctggacagc  1200
gacggcagct tcttcctgta cagcaggctg accgtggaca agtccagatg gcaggagggc  1260
aacgtcttta gctgctccgt gatgcacgag gccctgcaca accactacac ccagaagagc  1320
ctgagcctgt ccctgggctg atgaattc                                   1348

SEQ ID NO: 395         moltype = DNA  length = 321
FEATURE                Location/Qualifiers
misc_feature           1..321
                       note = source = /note="Description of Artificial Sequence:
                        Syntheticpolynucleotide"
source                 1..321
                       mol_type = other DNA
                       organism = synthetic construct
SEQUENCE: 395
gagatcgtgc tgacccagtc ccccgacttc cagtccgtga cccccaaaga aaaagtgacc  60
atcacatgca aggcctccca ggacgtgggc accgccgtgg cttggtatct gcagaagcct  120
ggccagtccc ctcagctgct gatctactgg gcctctacca gacacaccgg cgtgcccgac  180
agattctccg gctctggctc tggcaccgac ttcaccctga agatctcccg ggtggaagcc  240
gaggatgtgg gcgtgtacta ctgccagcag tacaactcct accccctgac cttcggccag  300
ggcaccaagg tggaaatcaa g                                          321

SEQ ID NO: 396         moltype = DNA  length = 652
FEATURE                Location/Qualifiers
misc_feature           1..652
                       note = source = /note="Description of Artificial Sequence:
                        Syntheticpolynucleotide"
source                 1..652
                       mol_type = other DNA
                       organism = synthetic construct
SEQUENCE: 396
gagatcgtgc tgacccagtc ccccgacttc cagtccgtga cccccaaaga aaaagtgacc  60
atcacatgca aggcctccca ggacgtgggc accgccgtgg cttggtatct gcagaagcct  120
ggccagtccc ctcagctgct gatctactgg gcctctacca gacacaccgg cgtgcccgac  180
agattctccg gctctggctc tggcaccgac ttcaccctga agatctcccg ggtggaagcc  240
```

gaggatgtgg gcgtgtacta ctgccagcag tacaactcct accccctgac cttcggccag 300
ggcaccaagg tggaaatcaa gcgtacggtg gccgctccca gcgtgttcat cttccccccca 360
agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gctgatgaat tc 652

SEQ ID NO: 397 moltype = DNA length = 360
FEATURE Location/Qualifiers
misc_feature 1..360
note = source = /note="Description of Artificial Sequence: Syntheticpolynucleotide"
source 1..360
mol_type = other DNA
organism = synthetic construct
SEQUENCE: 397
gaagtgcagc tggtgcagtc tggcgccgaa gtgaagaagc ctggcgagtc cctgcggatc 60
tcctgcaagg gctccggcta caccttcacc agctactgga tgtactggat ccggcagccc 120
cctggcaagg gcctggaatg gatcggcaga atcgacccca actccggctc caccaagtac 180
aacgagaagt tcaagaaccg cgtgaccatc accgccgaca agtccacctc caccgcctac 240
atggaactgt cctccctgag atccgaggac accgccgtgt actactgcgc cagagactac 300
cggaagggcc tgtacgccat ggactattgg ggccagggca ccaccgtgac cgtgtcctct 360

SEQ ID NO: 398 moltype = AA length = 446
FEATURE Location/Qualifiers
REGION 1..446
note = source = /note="Description of Artificial Sequence: Syntheticpolypeptide"
source 1..446
mol_type = protein
organism = synthetic construct
SEQUENCE: 398
EVQLVQSGAE VKKPGESLRI SCKGSGYTFT SYWMYWIRQP PGKGLEWIGR IDPNSGSTKY 60
NEKFKNRVTI TADKSTSTAY MELSSLRSED TAVYYCARDY RKGLYAMDYW GQGTTVTVSS 120
ASTKGPSVFP LAPCSRSTSE STAALGCLVK DYFPEPVTVS WNSGALTSGV HTFPAVLQSS 180
GLYSLSSVVT VPSSSLGTKT YTCNVDHKPS NTKVDKRVES KYGPPCPPCP APEFLGGPSV 240
FLFPPKPKDT LMISRTPEVT CVVVDVSQED PEVQFNWYVD GVEVHNAKTK PREEQFNSTY 300
RVVSVLTVLH QDWLNGKEYK CKVSNKGLPS SIEKTISKAK GQPREPQVYT LPPSQEEMTK 360
NQVSLTCLVK GFYPSDIAVE WESNGQPENN YKTTPPVLDS DGSFFLYSRL TVDKSRWQEG 420
NVFSCSVMHE ALHNHYTQKS LSLSLG 446

SEQ ID NO: 399 moltype = DNA length = 1348
FEATURE Location/Qualifiers
misc_feature 1..1348
note = source = /note="Description of Artificial Sequence: Syntheticpolynucleotide"
source 1..1348
mol_type = other DNA
organism = synthetic construct
SEQUENCE: 399
gaagtgcagc tggtgcagtc tggcgccgaa gtgaagaagc ctggcgagtc cctgcggatc 60
tcctgcaagg gctccggcta caccttcacc agctactgga tgtactggat ccggcagccc 120
cctggcaagg gcctggaatg gatcggcaga atcgacccca actccggctc caccaagtac 180
aacgagaagt tcaagaaccg cgtgaccatc accgccgaca agtccacctc caccgcctac 240
atggaactgt cctccctgag atccgaggac accgccgtgt actactgcgc cagagactac 300
cggaagggcc tgtacgccat ggactattgg ggccagggca ccaccgtgac cgtgtcctct 360
gcttctacca agggcccaag cgtgttcccc ctggcccct gctccagaag caccagcgag 420
agcacagccg ccctgggctg cctggtgaag gactacttcc ccgagcccgt gaccgtgtcc 480
tggaacagcg gagccctgac cagcggcgtg cacaccttcc ccgccgtgct gcagagcagc 540
ggcctgtaca gcctgagcag cgtggtgacc gtgcccagca gcagcctggg caccaagacc 600
tacacctgta acgtggacca caagcccagc aacaccaagg tggacaagag ggtggagagc 660
aagtacggcc caccctgccc ccctgccca gcccccgagt tcctgggcgg acccagcgtg 720
ttcctgttcc cccccaagcc caaggacacc ctgatgatca gcagaacccc cgaggtgacc 780
tgtgtggtgg tggacgtgtc ccaggaggac cccgaggtcc agttcaactg gtacgtggac 840
ggcgtggagg tgcacaacgc caagaccaag cccagagagg agcagtttaa cagcacctac 900
cgggtggtgt ccgtgctgac cgtgctgcac caggactggc tgaacggcaa agagtacaag 960
tgtaaggtct ccaacaaggg cctgccaagc agcatcgaaa agaccatcag caaggccaag 1020
ggccagccta gagagcccca ggtctacacc ctgccaccca gccaagagga gatgaccaag 1080
aaccaggtgt ccctgacctg tctggtgaag ggcttctacc caagcgacat cgccgtggag 1140
tgggagagca acggccagcc cgagaacaac tacaagacca cccccccagt gctggacagc 1200
gacggcagct tcttcctgta cagcaggctg accgtggaca agtccagatg gcaggagggc 1260
aacgtcttta gctgctccgt gatgcacgag gccctgcaca accactacac ccagaagagc 1320
ctgagcctgt ccctgggctg atgaattc 1348

SEQ ID NO: 400 moltype = DNA length = 321
FEATURE Location/Qualifiers
misc_feature 1..321
note = source = /note="Description of Artificial Sequence:

```
                         Syntheticpolynucleotide"
source                  1..321
                        mol_type = other DNA
                        organism = synthetic construct
SEQUENCE: 400
gagatcgtgc tgacccagtc ccccgacttc cagtccgtga cccccaaaga aaaagtgacc  60
atcacatgca aggcctccca ggacgtgggc accgccgtgg cttggtatct gcagaagcct  120
ggccagtccc ctcagctgct gatctactgg gcctctacca gacacaccgg cgtgccctcc  180
agattctccg gctctggctc tggcaccgac tttaccttca ccatctccag cctgcagccc  240
gaggatatcg ccacctacta ctgccagcag tacaactcct accccctgac cttcggccag  300
ggcaccaagg tggaaatcaa g                                            321

SEQ ID NO: 401          moltype = DNA  length = 652
FEATURE                 Location/Qualifiers
misc_feature            1..652
                        note = source = /note="Description of Artificial Sequence:
                         Syntheticpolynucleotide"
source                  1..652
                        mol_type = other DNA
                        organism = synthetic construct
SEQUENCE: 401
gagatcgtgc tgacccagtc ccccgacttc cagtccgtga cccccaaaga aaaagtgacc  60
atcacatgca aggcctccca ggacgtgggc accgccgtgg cttggtatct gcagaagcct  120
ggccagtccc ctcagctgct gatctactgg gcctctacca gacacaccgg cgtgccctcc  180
agattctccg gctctggctc tggcaccgac tttaccttca ccatctccag cctgcagccc  240
gaggatatcg ccacctacta ctgccagcag tacaactcct accccctgac cttcggccag  300
ggcaccaagg tggaaatcaa gcgtacggtg gccgctccca gcgtgttcat cttcccccca  360
agcgacgagc agctgaagag cggcaccgcc agcgtggtgt gtctgctgaa caacttctac  420
cccagggagg ccaaggtgca gtggaaggtg gacaacgccc tgcagagcgg caacagccag  480
gagagcgtca ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac aggggcgagt gctgatgaat tc          652

SEQ ID NO: 402          moltype =   length =
SEQUENCE: 402
000

SEQ ID NO: 403          moltype =   length =
SEQUENCE: 403
000

SEQ ID NO: 404          moltype =   length =
SEQUENCE: 404
000

SEQ ID NO: 405          moltype =   length =
SEQUENCE: 405
000

SEQ ID NO: 406          moltype =   length =
SEQUENCE: 406
000

SEQ ID NO: 407          moltype =   length =
SEQUENCE: 407
000

SEQ ID NO: 408          moltype =   length =
SEQUENCE: 408
000

SEQ ID NO: 409          moltype =   length =
SEQUENCE: 409
000

SEQ ID NO: 410          moltype =   length =
SEQUENCE: 410
000

SEQ ID NO: 411          moltype =   length =
SEQUENCE: 411
000

SEQ ID NO: 412          moltype =   length =
SEQUENCE: 412
000

SEQ ID NO: 413          moltype =   length =
SEQUENCE: 413
```

000

SEQ ID NO: 414 moltype = length =
SEQUENCE: 414
000

SEQ ID NO: 415 moltype = length =
SEQUENCE: 415
000

SEQ ID NO: 416 moltype = length =
SEQUENCE: 416
000

SEQ ID NO: 417 moltype = length =
SEQUENCE: 417
000

SEQ ID NO: 418 moltype = length =
SEQUENCE: 418
000

SEQ ID NO: 419 moltype = length =
SEQUENCE: 419
000

SEQ ID NO: 420 moltype = length =
SEQUENCE: 420
000

SEQ ID NO: 421 moltype = length =
SEQUENCE: 421
000

SEQ ID NO: 422 moltype = length =
SEQUENCE: 422
000

SEQ ID NO: 423 moltype = length =
SEQUENCE: 423
000

SEQ ID NO: 424 moltype = length =
SEQUENCE: 424
000

SEQ ID NO: 425 moltype = length =
SEQUENCE: 425
000

SEQ ID NO: 426 moltype = length =
SEQUENCE: 426
000

SEQ ID NO: 427 moltype = length =
SEQUENCE: 427
000

SEQ ID NO: 428 moltype = length =
SEQUENCE: 428
000

SEQ ID NO: 429 moltype = length =
SEQUENCE: 429
000

SEQ ID NO: 430 moltype = length =
SEQUENCE: 430
000

SEQ ID NO: 431 moltype = length =
SEQUENCE: 431
000

SEQ ID NO: 432 moltype = length =
SEQUENCE: 432
000

SEQ ID NO: 433 moltype = length =

SEQUENCE: 433
000

SEQ ID NO: 434 moltype = length =
SEQUENCE: 434
000

SEQ ID NO: 435 moltype = length =
SEQUENCE: 435
000

SEQ ID NO: 436 moltype = length =
SEQUENCE: 436
000

SEQ ID NO: 437 moltype = length =
SEQUENCE: 437
000

SEQ ID NO: 438 moltype = length =
SEQUENCE: 438
000

SEQ ID NO: 439 moltype = length =
SEQUENCE: 439
000

SEQ ID NO: 440 moltype = length =
SEQUENCE: 440
000

SEQ ID NO: 441 moltype = length =
SEQUENCE: 441
000

SEQ ID NO: 442 moltype = length =
SEQUENCE: 442
000

SEQ ID NO: 443 moltype = length =
SEQUENCE: 443
000

SEQ ID NO: 444 moltype = length =
SEQUENCE: 444
000

SEQ ID NO: 445 moltype = length =
SEQUENCE: 445
000

SEQ ID NO: 446 moltype = length =
SEQUENCE: 446
000

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = length =
SEQUENCE: 450
000

SEQ ID NO: 451 moltype = length =
SEQUENCE: 451
000

SEQ ID NO: 452 moltype = length =
SEQUENCE: 452
000

-continued

SEQ ID NO: 453 moltype = length =
SEQUENCE: 453
000

SEQ ID NO: 454 moltype = length =
SEQUENCE: 454
000

SEQ ID NO: 455 moltype = length =
SEQUENCE: 455
000

SEQ ID NO: 456 moltype = length =
SEQUENCE: 456
000

SEQ ID NO: 457 moltype = length =
SEQUENCE: 457
000

SEQ ID NO: 458 moltype = length =
SEQUENCE: 458
000

SEQ ID NO: 459 moltype = length =
SEQUENCE: 459
000

SEQ ID NO: 460 moltype = length =
SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =
SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

SEQ ID NO: 492 moltype = length =
SEQUENCE: 492

000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

SEQ ID NO: 500 moltype = length =
SEQUENCE: 500
000

SEQ ID NO: 501 moltype = length =
SEQUENCE: 501
000

SEQ ID NO: 502 moltype = length =
SEQUENCE: 502
000

SEQ ID NO: 503 moltype = length =
SEQUENCE: 503
000

SEQ ID NO: 504 moltype = length =
SEQUENCE: 504
000

SEQ ID NO: 505 moltype = length =
SEQUENCE: 505
000

SEQ ID NO: 506 moltype = length =
SEQUENCE: 506
000

SEQ ID NO: 507 moltype = length =
SEQUENCE: 507
000

SEQ ID NO: 508 moltype = length =
SEQUENCE: 508
000

SEQ ID NO: 509 moltype = length =
SEQUENCE: 509
000

SEQ ID NO: 510 moltype = length =
SEQUENCE: 510
000

SEQ ID NO: 511 moltype = length =
SEQUENCE: 511
000

SEQ ID NO: 512 moltype = length =

SEQUENCE: 512
000

SEQ ID NO: 513 moltype = length =
SEQUENCE: 513
000

SEQ ID NO: 514 moltype = length =
SEQUENCE: 514
000

SEQ ID NO: 515 moltype = length =
SEQUENCE: 515
000

SEQ ID NO: 516 moltype = length =
SEQUENCE: 516
000

SEQ ID NO: 517 moltype = length =
SEQUENCE: 517
000

SEQ ID NO: 518 moltype = length =
SEQUENCE: 518
000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =
SEQUENCE: 523
000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563
000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

SEQ ID NO: 571 moltype = length =
SEQUENCE: 571

000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =

```
SEQUENCE: 591
000

SEQ ID NO: 592         moltype =    length =
SEQUENCE: 592
000

SEQ ID NO: 593         moltype =    length =
SEQUENCE: 593
000

SEQ ID NO: 594         moltype =    length =
SEQUENCE: 594
000

SEQ ID NO: 595         moltype =    length =
SEQUENCE: 595
000

SEQ ID NO: 596         moltype =    length =
SEQUENCE: 596
000

SEQ ID NO: 597         moltype = DNA   length = 521
FEATURE                Location/Qualifiers
misc_feature           1..521
                       note = source = /note="Description of Unknown:Wild-type PGK
                         promoter sequence"
source                 1..521
                       mol_type = other DNA
                       organism = unidentified
SEQUENCE: 597
acccctctct ccagccacta agccagttgc tccctcggct gacggctgca cgcgaggcct    60
ccgaacgtct tacgccttgt ggcgcgcccg tccttgtccc gggtgtgatg gcggggtgtg   120
gggcggaggg cgtggcgggg aagggccggc gacgagagcc gcgcgggacg actcgtcggc   180
gataaccggt gtcgggtagc gccagccgcg cgacggtaac gagggaccgc gacaggcaga   240
cgctcccatg atcactctgc acgccgaagg caaatagtgc aggccgtgcg gcgcttggcg   300
ttccttggaa gggctgaatc cccgcctcgt ccttcgcagc ggccccccgg gtgttcccat   360
cgccgcttct aggcccactg cgacgcttgc ctgcacttct tacacgctct gggtcccagc   420
cgcggcgacg caaagggcct tggtgcgggt ctcgtcggcg cagggacgcg tttgggtccc   480
gacggaacct tttccgcgtt ggggttgggg caccataagc t                      521

SEQ ID NO: 598         moltype = DNA   length = 118
FEATURE                Location/Qualifiers
misc_feature           1..118
                       note = source = /note="Description of Artificial Sequence:
                         Syntheticpolynucleotide"
source                 1..118
                       mol_type = other DNA
                       organism = synthetic construct
SEQUENCE: 598
acccctctct ccagccacta agccagttgc tccctcggct gacggctgca cgcgaggcct    60
ccgaacgtct tacgccttgt ggcgcgcccg tccttgtccc gggtgtgatg gcggggtg    118

SEQ ID NO: 599         moltype = DNA   length = 221
FEATURE                Location/Qualifiers
misc_feature           1..221
                       note = source = /note="Description of Artificial Sequence:
                         Syntheticpolynucleotide"
source                 1..221
                       mol_type = other DNA
                       organism = synthetic construct
SEQUENCE: 599
acccctctct ccagccacta agccagttgc tccctcggct gacggctgca cgcgaggcct    60
ccgaacgtct tacgccttgt ggcgcgcccg tccttgtccc gggtgtgatg gcggggtgtg   120
gggcggaggg cgtggcgggg aagggccggc gacgagagcc gcgcgggacg actcgtcggc   180
gataaccggt gtcgggtagc gccagccgcg cgacggtaac g                      221

SEQ ID NO: 600         moltype = DNA   length = 324
FEATURE                Location/Qualifiers
misc_feature           1..324
                       note = source = /note="Description of Artificial Sequence:
                         Syntheticpolynucleotide"
source                 1..324
                       mol_type = other DNA
                       organism = synthetic construct
SEQUENCE: 600
acccctctct ccagccacta agccagttgc tccctcggct gacggctgca cgcgaggcct    60
ccgaacgtct tacgccttgt ggcgcgcccg tccttgtccc gggtgtgatg gcggggtgtg   120
```

```
gggcggaggg cgtggcgggg aagggccggc gacgagagcc gcgcgggacg actcgtcggc  180
gataaccggt gtcgggtagc gccagccgcg cgacggtaac gagggaccgc gacaggcaga  240
cgctcccatg atcactctgc acgccgaagg caaatagtgc aggccgtgcg gcgcttggcg  300
ttccttggaa gggctgaatc cccg                                         324

SEQ ID NO: 601         moltype = DNA  length = 422
FEATURE                Location/Qualifiers
misc_feature           1..422
                       note = source = /note="Description of Artificial Sequence:
                        Syntheticpolynucleotide"
source                 1..422
                       mol_type = other DNA
                       organism = synthetic construct
SEQUENCE: 601
acccctctct ccagccacta agccagttgc tccctcggct gacggctgca cgcgaggcct  60
ccgaacgtct tacgccttgt ggcgcgcccg tccttgtccc gggtgtgatg gcggggtgtg  120
gggcggaggg cgtggcgggg aagggccggc gacgagagcc gcgcgggacg actcgtcggc  180
gataaccggt gtcgggtagc gccagccgcg cgacggtaac gagggaccgc gacaggcaga  240
cgctcccatg atcactctgc acgccgaagg caaatagtgc aggccgtgcg gcgcttggcg  300
ttccttggaa gggctgaatc cccgcctcgt ccttcgcagc ggccccccgg gtgttcccat  360
cgccgcttct aggcccactg cgacgcttgc ctgcacttct tacacgctct gggtcccagc  420
cg                                                                 422

SEQ ID NO: 602         moltype = AA  length = 21
FEATURE                Location/Qualifiers
VARIANT                1..3
                       note = /replace=" "
REGION                 1..21
                       note = misc_feature - /note="Variant residues given in the
                        sequence have nopreference with respect to those in the
                        annotationsfor variant positions"
REGION                 1..21
                       note = source = /note="Description of Artificial Sequence:
                        Syntheticpeptide"
source                 1..21
                       mol_type = protein
                       organism = synthetic construct
SEQUENCE: 602
GSGEGRGSLL TCGDVEENPG P                                           21

SEQ ID NO: 603         moltype = AA  length = 22
FEATURE                Location/Qualifiers
VARIANT                1..3
                       note = /replace=" "
REGION                 1..22
                       note = misc_feature - /note="Variant residues given in the
                        sequence have nopreference with respect to those in the
                        annotationsfor variant positions"
REGION                 1..22
                       note = source = /note="Description of Artificial Sequence:
                        Syntheticpeptide"
source                 1..22
                       mol_type = protein
                       organism = synthetic construct
SEQUENCE: 603
GSGATNFSLL KQAGDVEENP GP                                          22

SEQ ID NO: 604         moltype = AA  length = 23
FEATURE                Location/Qualifiers
VARIANT                1..3
                       note = /replace=" "
REGION                 1..23
                       note = misc_feature - /note="Variant residues given in the
                        sequence have nopreference with respect to those in the
                        annotationsfor variant positions"
REGION                 1..23
                       note = source = /note="Description of Artificial Sequence:
                        Syntheticpeptide"
source                 1..23
                       mol_type = protein
                       organism = synthetic construct
SEQUENCE: 604
GSGQCTNYAL LKLAGDVESN PGP                                         23

SEQ ID NO: 605         moltype = AA  length = 25
FEATURE                Location/Qualifiers
VARIANT                1..3
                       note = /replace=" "
REGION                 1..25
```

```
                        note = misc_feature - /note="Variant residues given in the
                         sequence have nopreference with respect to those in the
                         annotationsfor variant positions"
REGION                  1..25
                        note = source = /note="Description of Artificial Sequence:
                         Syntheticpeptide"
source                  1..25
                        mol_type = protein
                        organism = synthetic construct
SEQUENCE: 605
GSGVKQTLNF DLLKLAGDVE SNPGP                                         25

SEQ ID NO: 606          moltype = AA  length = 40
FEATURE                 Location/Qualifiers
REGION                  1..40
                        note = MISC_FEATURE - /note="This sequence may encompass
                         1-10"Gly Gly Gly Ser" repeating units"
REGION                  1..40
                        note = source = /note="Description of Artificial Sequence:
                         Syntheticpolypeptide"
source                  1..40
                        mol_type = protein
                        organism = synthetic construct
SEQUENCE: 606
GGGSGGGSGG GSGGGSGGGS GGGSGGGSGG GSGGGSGGGS                         40

SEQ ID NO: 607          moltype = DNA  length = 105
FEATURE                 Location/Qualifiers
misc_feature            1..105
                        note = source = /note="Description of Artificial Sequence:
                         Syntheticpolynucleotide"
source                  1..105
                        mol_type = other DNA
                        organism = synthetic construct
SEQUENCE: 607
acaaaaaaga agtattcatc cagtgtgcac gaccctaacg gtgaatacat gttcatgaga  60
gcagtgaaca cagccaaaaa atccagactc acagatgtga cccta                  105

SEQ ID NO: 608          moltype = DNA  length = 30
FEATURE                 Location/Qualifiers
misc_feature            1..30
                        note = source = /note="Description of Artificial Sequence:
                         Syntheticoligonucleotide"
source                  1..30
                        mol_type = other DNA
                        organism = synthetic construct
SEQUENCE: 608
ggtggcggag gttctggagg tgggggttcc                                    30

SEQ ID NO: 609          moltype = AA  length = 4
FEATURE                 Location/Qualifiers
REGION                  1..4
                        note = source = /note="Description of Artificial Sequence:
                         Syntheticpeptide"
source                  1..4
                        mol_type = protein
                        organism = synthetic construct
SEQUENCE: 609
GGGS                                                                4

SEQ ID NO: 610          moltype = AA  length = 18
FEATURE                 Location/Qualifiers
REGION                  1..18
                        note = source = /note="Description of Artificial Sequence:
                         Syntheticpeptide"
source                  1..18
                        mol_type = protein
                        organism = synthetic construct
SEQUENCE: 610
GSTSGSGKPG SGEGSTKG                                                 18

SEQ ID NO: 611          moltype = AA  length = 118
FEATURE                 Location/Qualifiers
REGION                  1..118
                        note = source = /note="Description of Artificial Sequence:
                         Syntheticpolypeptide"
source                  1..118
                        mol_type = protein
                        organism = synthetic construct
```

-continued

```
SEQUENCE: 611
EVQLLESGGG LVQPGGSLRL SCAASGFTFS SYIMMWVRQA PGKGLEWVSS IYPSGGITFY  60
ADKGRFTISR DNSKNTLYLQ MNSLRAEDTA VYYCARIKLG TVTTVDYWGQ GTLVTVSS    118

SEQ ID NO: 612          moltype = AA  length = 110
FEATURE                 Location/Qualifiers
REGION                  1..110
                        note = source = /note="Description of Artificial Sequence:
                         Syntheticpolypeptide"
source                  1..110
                        mol_type = protein
                        organism = synthetic construct
SEQUENCE: 612
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL            110

SEQ ID NO: 613          moltype = AA  length = 4
FEATURE                 Location/Qualifiers
REGION                  1..4
                        note = source = /note="Description of Artificial Sequence:
                         Syntheticpeptide"
source                  1..4
                        mol_type = protein
                        organism = synthetic construct
SEQUENCE: 613
RGDS                                                              4
```

What is claimed is:

1. A composition or dosage formulation each comprising:

(a) a cell or a population of immune effector cells expressing a chimeric antigen receptor (CAR), wherein the CAR comprises a mesothelin binding domain, a transmembrane domain, and an intracellular signaling domain; and wherein the mesothelin binding domain comprises:

(i) a heavy chain complementarity determining region 1 (HC CDR1), a heavy chain complementarity determining region 2 (HC CDR2), and a heavy chain complementarity determining region 3 (HC CDR3) of an anti-mesothelin antibody selected from the group consisting of M1, M2, M3, M4, M5, M6, M7, M8, M9, M10 M11, M12, M13, M14, M15, M16, M17, M18, M19, M20, M21, M22, M23, and M24; and (ii) a light chain complementarity determining region 1 (LC CDR1), a light chain complementarity determining region 2 (LC CDR2), and a light chain complementarity determining region 3 (LC CDR3) of an anti-mesothelin antibody selected from the group consisting of M1, M2, M3, M4, M5, M6, M7, M8, M9, M10, M11, M12, M13, M14, M15, M16, M17, M18, M19, M20, M21, M22, M23, and M24; and (b) a PD-L1 inhibitor wherein the PD-L1 inhibitor is an anti-PD-L1 antibody molecule selected from the group consisting of YW243.55.S70, MPDL3280A (atezolizumab), MEDI-4736, MSB-0010718C (avelumab), MDX-1105, and an anti-PD-L1 antibody molecule comprising:

(i) a heavy chain complementarity determining region 1 (HC CDR1) amino acid sequence selected from SEQ ID NO: 287, 290, or 195, a HC CDR2 amino acid sequence of SEQ ID NO: 288, and a HC CDR3 amino acid sequence of SEQ ID NO: 289; and a light chain complementarity determining region 1 (LC CDR1) amino acid sequence of SEQ ID NO: 295, a LC CDR2 amino acid sequence of SEQ ID NO: 296, and a LC CDR3 amino acid sequence of SEQ ID NO: 297; or (ii) a HC CDR1 amino acid sequence selected from SEQ ID NOs: 287, 290, or 195, a HC CDR2 amino acid sequence of SEQ ID NO: 291, and a HC CDR3 amino acid sequence of SEQ ID NO: 292; and a LC CDR1 amino acid sequence of SEQ ID NO: 298, a LC CDR2 amino acid sequence of SEQ ID NO: 299, and a LC CDR3 amino acid sequence of SEQ ID NO: 300;

wherein the cell or the population of immune effector cells expressing the CAR and the PD-L1 inhibitor are in different compositions or dosage formulations or compositions; and wherein the PD-L1 inhibitor is administered to a subject having a disease associated with mesothelin expression at least 2 days prior to administration of the cell or the population of immune effector cells expressing the CAR.

2. The composition or dosage formulation of claim 1, wherein the composition or dosage formulation comprises a single dose of the CAR-expressing cell and a single dose of the PD-L1 inhibitor.

3. The composition or dosage formulation of claim 2, wherein:

(a) the dose of CAR-expressing cells:

(i) comprises at least about 1-3×$10^7$ to 1-3×$10^8$ cells;

(ii) is about 1-3×$10^7$ cells; or (iii) is about 1-3×$10^8$ cells; or (b) the dose of the PD-L1 inhibitor is about 1 to 30 mg/kg, about 5 to 25 mg/kg, about 10 to 20 mg/kg, or about 1 to 5 mg/kg.

4. The composition or dosage formulation of claim 2, wherein the composition or dosage formulation of the CAR-expressing cell is administered:

(a) at least 2 days, 3 days, 4 days, 5 days, 6 days, 7 days, or 2 weeks after the composition or dosage formulation of PDL1 inhibitor is administered; or (b) 2 days after the composition or dosage formulation of the PD-L1 inhibitor is administered.

5. The composition or dosage formulation of claim 2, wherein one or more subsequent doses of a CAR-expressing cell is administered to the subject after the initial dose of the CAR-expressing cell.

6. The composition or dosage formulation of claim 5, wherein the one or more subsequent doses of the CAR-expressing cell are administered:

(a) at least 2 days, 3 days, 4 days, 5 days, 6 days, 7 days or 2 weeks, after the previous dose of the CAR-expressing cell;

(b) at least 5 days after the previous dose of the CAR-expressing cell.

7. The composition or dosage formulation of claim 1, wherein the anti PD-L1 antibody molecule is selected from the group consisting of BAP058-hum01, BAP058-hum02, BAP058-hum03, BAP058-hum04, BAP058-hum05, BAP058-hum06, BAP058-hum07, BAP058-hum08, BAP058-hum09, BAP058-hum010, BAP058-hum011, BAP058-hum012, BAP058-hum013, BAP058-hum014 BAP058-hum015, BAP058-hum016, BAP058-hum017, BAP058-Clone K, BAP058-Clone L, BAP058-Clone M, BAP058-Clone N, and BAP058-Clone O.89.

8. The composition or dosage formulation of claim 1, wherein the anti-PD-L1 antibody molecule comprises:

(a) a heavy chain variable region comprising:

(i) an amino acid sequence of a heavy chain variable region selected from the group consisting of SEQ ID NOs: 304, 306, 316, 318, 324, 326, 332, 334, 336, 338, 340, 342, 348, 350, 356, 358, 364, 366, 377, 382, 391, 393, and 398;

(ii) an amino acid sequence having at least one, two or three modifications but not more than 30, 20 or 10 modifications to the amino acid sequence of a heavy chain variable region selected from the group consisting of SEQ ID NOs: 304, 306, 316, 318, 324, 326, 332, 334, 336, 338, 340, 342, 348, 350, 356, 358, 364, 366, 377, 382, 391, 393, and 398; or (iii) an amino acid sequence with 95-99% identity to the amino acid sequence of a heavy chain variable region selected from the group consisting of SEQ ID NOs: 304, 306, 316, 318, 324, 326, 332, 334, 336, 338, 340, 342, 348, 350, 356, 358, 364, 366, 377, 382, 391, 393, and 398; and (b) a light chain variable region comprising:

(i) an amino acid sequence of a light chain variable region selected from the group consisting of SEQ ID NOs: 308, 310, 312, 314, 320, 322, 330, 328, 344, 346, 352, 354, 360, 362, 368, 370, 372 and 374;

(ii) an amino acid sequence having at least one, two or three modifications but not more than 30, 20 or 10 modifications to the amino acid sequence of any light chain variable region selected from the group consisting of SEQ ID NOs: 308, 310, 312, 314, 320, 322, 330, 328, 344, 346, 352, 354, 360, 362, 368, 370, 372 and 374; or (iii) an amino acid sequence with 95-99% identity to the amino acid sequence of any light chain variable region selected from the group consisting of SEQ ID NOs: 308, 310, 312, 314, 320, 322, 330, 328, 344, 346, 352, 354, 360, 362, 368, 370, 372 and 374.

9. The composition or dosage formulation of claim 1, wherein the anti-PD-L1 antibody molecule comprises:

(a) a heavy chain variable domain comprising the amino acid sequence of SEQ ID NO: 304 and a light chain variable domain comprising the amino acid sequence of SEQ ID NO: 308;

(b) a heavy chain variable domain comprising the amino acid sequence of SEQ ID NO: 304 and a light chain variable domain comprising the amino acid sequence of SEQ ID NO: 312;

(c) a heavy chain variable domain comprising the amino acid sequence of SEQ ID NO: 304 and a light chain variable domain comprising the amino acid sequence of SEQ ID NO: 372;

(d) a heavy chain variable domain comprising the amino acid sequence of SEQ ID NO: 316 and a light chain variable domain comprising the amino acid sequence of SEQ ID NO: 320;

(e) a heavy chain variable domain comprising the amino acid sequence of SEQ ID NO: 316 and a light chain variable domain comprising the amino acid sequence of SEQ ID NO: 352;

(f) a heavy chain variable domain comprising the amino acid sequence of SEQ ID NO: 324 and a light chain variable domain comprising the amino acid sequence of SEQ ID NO: 328;

(g) a heavy chain variable domain comprising the amino acid sequence of SEQ ID NO: 324 and a light chain variable domain comprising the amino acid sequence of SEQ ID NO: 360;

(h) a heavy chain variable domain comprising the amino acid sequence of SEQ ID NO: 332 and a light chain variable domain comprising the amino acid sequence of SEQ ID NO: 328;

(i) a heavy chain variable domain comprising the amino acid sequence of SEQ ID NO: 336 and a light chain variable domain comprising the amino acid sequence of SEQ ID NO: 328;

(j) a heavy chain variable domain comprising the amino acid sequence of SEQ ID NO: 336 and a light chain variable domain comprising the amino acid sequence of SEQ ID NO: 308;

(k) a heavy chain variable domain comprising the amino acid sequence of SEQ ID NO: 336 and a light chain variable domain comprising the amino acid sequence of SEQ ID NO: 372;

(l) a heavy chain variable domain comprising the amino acid sequence of SEQ ID NO: 340 and a light chain variable domain comprising the amino acid sequence of SEQ ID NO: 344;

(m) a heavy chain variable domain comprising the amino acid sequence of SEQ ID NO: 340 and a light chain variable domain comprising the amino acid sequence of SEQ ID NO: 372;

(n) a heavy chain variable domain comprising the amino acid sequence of SEQ ID NO: 348 and a light chain variable domain comprising the amino acid sequence of SEQ ID NO: 352;

(o) a heavy chain variable domain comprising the amino acid sequence of SEQ ID NO: 348 and a light chain variable domain comprising the amino acid sequence of SEQ ID NO: 386;

(p) a heavy chain variable domain comprising the amino acid sequence of SEQ ID NO: 356 and a light chain variable domain comprising the amino acid sequence of SEQ ID NO: 352; or (q) a heavy chain variable domain comprising the amino acid sequence of SEQ ID NO: 364 and a light chain variable domain comprising the amino acid sequence of SEQ ID NO: 368.

10. The composition or dosage formulation of claim 1, wherein the anti-PD-L1 antibody molecule comprises:

(a) a heavy chain comprising the amino acid sequence of SEQ ID NO: 306 and a light chain comprising the amino acid sequence of SEQ ID NO: 310;

(b) a heavy chain comprising the amino acid sequence of SEQ ID NO: 306 and a light chain comprising the amino acid sequence of SEQ ID NO: 314;

(c) a heavy chain comprising the amino acid sequence of SEQ ID NO: 306 and a light chain comprising the amino acid sequence of SEQ ID NO: 374;

(d) a heavy chain comprising the amino acid sequence of SEQ ID NO: 318 and a light chain comprising the amino acid sequence of SEQ ID NO: 322;

(e) a heavy chain comprising the amino acid sequence of SEQ ID NO: 318 and a light chain comprising the amino acid sequence of SEQ ID NO: 354;

(f) a heavy chain comprising the amino acid sequence of SEQ ID NO: 326 and a light chain comprising the amino acid sequence of SEQ ID NO: 330;

(g) a heavy chain comprising the amino acid sequence of SEQ ID NO: 326 and a light chain comprising the amino acid sequence of SEQ ID NO: 362;

(h) a heavy chain comprising the amino acid sequence of SEQ ID NO: 334 and a light chain comprising the amino acid sequence of SEQ ID NO: 330;

(i) a heavy chain comprising the amino acid sequence of SEQ ID NO: 338 and a light chain comprising the amino acid sequence of SEQ ID NO: 330;

(j) a heavy chain comprising the amino acid sequence of SEQ ID NO: 338 and a light chain comprising the amino acid sequence of SEQ ID NO: 310;

(k) a heavy chain comprising the amino acid sequence of SEQ ID NO: 338 and a light chain comprising the amino acid sequence of SEQ ID NO: 374;

(l) a heavy chain comprising the amino acid sequence of SEQ ID NO: 342 and a light chain comprising the amino acid sequence of SEQ ID NO: 346;

(m) a heavy chain comprising the amino acid sequence of SEQ ID NO: 342 and a light chain comprising the amino acid sequence of SEQ ID NO: 374;

(n) a heavy chain comprising the amino acid sequence of SEQ ID NO: 350 and a light chain comprising the amino acid sequence of SEQ ID NO: 354;

(o) a heavy chain comprising the amino acid sequence of SEQ ID NO: 350 and a light chain comprising the amino acid sequence of SEQ ID NO: 374;

(p) a heavy chain comprising the amino acid sequence of SEQ ID NO: 358 and a light chain comprising the amino acid sequence of SEQ ID NO: 354;

(q) a heavy chain comprising the amino acid sequence of SEQ ID NO: 366 and a light chain comprising the amino acid sequence of SEQ ID NO:370;

(r) a heavy chain comprising the amino acid sequence of SEQ ID NO: 393 and a light chain comprising the amino acid sequence of SEQ ID NO: 322;

(s) a heavy chain comprising the amino acid sequence of SEQ ID NO: 377 and a light chain comprising the amino acid sequence of SEQ ID NO: 330; or (t) a heavy chain comprising the amino acid sequence of SEQ ID NO: 382 and a light chain comprising the amino acid sequence of SEQ ID NO: 354.

11. The composition or dosage formulation of claim 1, wherein the mesothelin binding domain comprises:

(a) a heavy chain variable region comprising:

(i) an amino acid sequence of a heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62;

(ii) an amino acid sequence having at least one, two or three modifications but not more than 30, 20 or 10 modifications to the amino acid sequence of any heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62; or (iii) an amino acid sequence with 95-99% identity to the amino acid sequence of a heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62; and (b) a light chain variable region comprising:

(i) the amino acid sequence of a light chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62;

(ii) an amino acid sequence having at least one, two or three modifications but not more than 30, 20 or 10 modifications to the amino acid sequence of a light chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62; or (iii) an amino acid sequence with 95-99% identity to the amino acid sequence of any heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO:

57, SEQ ID NO: 58, SEQ ID NO: 59, SEQ ID NO: 60, SEQ ID NO: 61, and SEQ ID NO: 62.

12. The composition or dosage formulation of claim 1, wherein the mesothelin binding domain comprises:

(i) the amino acid sequence selected from the group consisting of SEQ ID NO: 43, SEQ ID NO: 49, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62;

(ii) an amino acid sequence having at least one, two or three modifications but not more than 30, 20 or 10 modifications to any of SEQ ID NO: 43, SEQ ID NO: 49, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62; or (iii) an amino acid sequence with 95-99% identity to the amino acid sequence to any of SEQ ID NO: 43, SEQ ID NO: 49, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62.

13. The composition or dosage formulation of claim 1, wherein the transmembrane domain comprises:

(a) a transmembrane domain from a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154;

(b) the amino acid sequence of SEQ ID NO: 6, (c) an amino acid sequence comprises at least one, two or three modifications but not more than 20, 10 or 5 modifications of the amino acid sequence of SEQ ID NO:6, or (d) a sequence with 95-99% identity to the amino acid sequence of SEQ ID NO:6.

14. The composition or dosage formulation of claim 1, wherein the intracellular signaling domain comprises a costimulatory signaling comprising:

(a) the amino acid sequence of SEQ ID NO:7;

(b) an amino acid sequence having at least one, two or three modifications but not more than 20, 10 or 5 modifications of the amino acid sequence of SEQ ID NO:7; or (c) an amino acid sequence with 95-99% identity to the amino acid sequence of SEQ ID NO: 7.

15. The composition or dosage formulation of claim 1, wherein the intracellular signaling domain comprises:

(a) a functional signaling domain of 4-1BB and/or a functional signaling domain of CD3 zeta;

(b) the amino acid sequence of SEQ ID NO: 7 and/or the amino acid sequence of SEQ ID NO: 9 or SEQ ID NO:10;

(c) an amino acid sequence having at least one, two or three modifications but not more than 20, 10 or 5 modifications of the amino acid sequence of SEQ ID NO:7 and/or the amino acid sequence of SEQ ID NO:9 or SEQ ID NO: 10; or (d) an amino acid sequence with 95-99% identity to the amino acid sequence of SEQ ID NO: 7 and/or the amino acid sequence of SEQ ID NO:9 or SEQ ID NO:10; or (e) the amino acid sequence of SEQ ID NO:7 and the amino acid sequence of SEQ ID NO: 9 or SEQ ID NO:10, wherein the amino acid sequences comprising the intracellular signaling domain are expressed in the same frame and as a single polypeptide chain.

16. The composition or dosage formulation of claim 1, wherein the CAR comprises:

(a) the amino acid sequence of any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86;

(b) an amino acid sequence having at least one, two or three modifications but not more than 30, 20 or 10 modifications to any of SEQ ID NO: 67, SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86; or (c) an amino acid sequence with 95-99% identity to any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86.

17. The composition or dosage formulation of claim 1, wherein the composition or dosage formulation comprising the CAR-expressing cell and the composition or dosage formulation comprising the PD-L1 inhibitor are administered for a treatment interval.

18. The composition or dosage formulation of claim 17, wherein the treatment interval comprises a single dose of the PD-L1 inhibitor and a single dose of the CAR-expressing cell.

19. The composition or dosage formulation of claim 18, wherein the treatment interval comprises a dose of CAR-expressing cells administered 2 days after the dose of the PD-L1 inhibitor is administered, and wherein the treatment interval is repeated twice, and wherein the treatment intervals are initiated 3 days after the completion of the previous treatment interval.

20. The composition or dosage formulation of claim 19, wherein one or more subsequent doses of the PDL1 inhibitor is administered every 5 days, 7 days, 2 weeks, 3 weeks, or 4 weeks, after the second treatment interval.

21. The composition or dosage formulation of claim 17, wherein the treatment or treatment interval:

(a) is repeated one or more times;

(b) is followed by one or more subsequent treatment intervals wherein the one or more subsequent treatment intervals is administered at least 1 day, 2 days, 3 days, 4 days, 5 days, 6 days, 7 days, or 2 weeks, after the completion of the first or previous treatment interval; or (c) comprises a first and second dose of the PD-L1 inhibitor and a dose of the CAR-expressing cell, and wherein the dose of the CAR-expressing cell is administered after administration of the first dose of the PD-L1 inhibitor but before the administration of the second dose of the PD-L1 inhibitor.

22. The composition or dosage formulation of claim 21, wherein:

(a) the treatment interval is initiated upon administration of the first dose of the PD-L1 inhibitor and completed upon administration of the second dose of the PD-L1 inhibitor;

(b) the second dose of the PD-L1 inhibitor is administered at least 5 days, 7 days, 1 week, 2 weeks, or 3 weeks after administration of the first dose of the PD-L1 inhibitor;

(c) the dose of the CAR-expressing cell is administered at least 2 days, 3 days, 4 days, 5 days, 6 days, 7 days, or 2 weeks after administration of the first dose of the PD-L1 inhibitor; or (d) the second dose of the PD-L1 inhibitor is administered at least 2 days, 3 days, 4 days, 5 days, 6 days, 7 days, or 2 weeks after administration of the dose of the CAR-expressing cell.

23. The composition or dosage formulation of claim 17, wherein the treatment interval:

(a) is initiated upon administration of the dose of the PD-L1 inhibitor and completed upon administration of the dose of the CAR-expressing cell; or (b) further comprises one or more subsequent doses of the PD-L1 inhibitor.

24. The composition or dosage formulation of claim 23, wherein the one or more subsequent doses of the PD-L1 inhibitor are administered:

(a) after the completion of one or more treatment intervals;

(b) after the administration of the single dose of the PD-L1 inhibitor;

(c) at least 5 days, 7 days, 2 weeks, 3 weeks or 4 weeks, after the previous dose of PD-L1 inhibitor;

(d) at least 1, 2, 3, 4, 5, 6, or 7 days, after the initial dose of the CAR-expressing cell; or (e) prior to the first dose of the CAR-expressing cell.

25. The composition or dosage formulation of claim 17, wherein a dose of the PD-L1 inhibitor is administered every 5 days, 7 days, 2 weeks, 3 weeks, or 4 days after the previous dose of PD-L1 inhibitor or after the completion of one or more treatment intervals.

26. The composition or dosage formulation of claim 1, wherein the cell is a T cell, an autologous T cell, an allogeneic T cell, or an NK cell.

27. The composition or dosage formulation of claim 1, wherein the disease associated with mesothelin expression is a cancer selected from the group consisting of mesothelioma, malignant pleural mesothelioma, non-small cell lung cancer, small cell lung cancer, squamous cell lung cancer, or large cell lung cancer, pancreatic cancer, pancreatic ductal adenocarcinoma, pancreatic metastatic, ovarian cancer, or colorectal cancer and bladder cancer, a metastasis thereof, and any combination thereof.

* * * * *